(12) United States Patent
Remiszewski et al.

(10) Patent No.: US 11,459,321 B2
(45) Date of Patent: Oct. 4, 2022

(54) BROAD SPECTRUM ANTIVIRAL COMPOSITIONS AND METHODS

(71) Applicant: Evrys Bio, LLC, Doylestown, PA (US)

(72) Inventors: Stacy Remiszewski, Washington Township, NJ (US); Lillian W. Chiang, Princeton, NJ (US); Eain Anthony Murphy, Doylestown, PA (US); Qun Sun, Princeton, NJ (US); Frank Kayser, San Francisco, CA (US); Sarah Jocelyn Fink, Arlington, MA (US)

(73) Assignee: Evrys Bio, LLC, Doylestown, PA (US)

( * ) Notice: Subject to any disclaimer, the term of this patent is extended or adjusted under 35 U.S.C. 154(b) by 0 days.

(21) Appl. No.: 16/756,734

(22) PCT Filed: Oct. 17, 2018

(86) PCT No.: PCT/US2018/056379
§ 371 (c)(1),
(2) Date: Apr. 16, 2020

(87) PCT Pub. No.: WO2019/079519
PCT Pub. Date: Apr. 25, 2019

(65) Prior Publication Data
US 2021/0139475 A1    May 13, 2021

Related U.S. Application Data

(60) Provisional application No. 62/574,067, filed on Oct. 18, 2017.

(51) Int. Cl.
*C07D 417/14*    (2006.01)
*A61K 45/06*    (2006.01)

(52) U.S. Cl.
CPC ............ *C07D 417/14* (2013.01); *A61K 45/06* (2013.01)

(58) Field of Classification Search
None
See application file for complete search history.

*Primary Examiner* — Heidi Reese
(74) *Attorney, Agent, or Firm* — F. Aaron Dubberley

(57) ABSTRACT

Novel thiazole- and isoquinoline-containing compounds are presented that are useful for treating and/or preventing broad-spectrum viral infections. Methods of treating and/or preventing broad-spectrum viral infections are also presented. These compounds have shown inhibition of HCMV, influenza viruses, Zika virus, BK Virus and RSV replication in cell-based assays.

21 Claims, 3 Drawing Sheets ppm (δ)
¹HNMR (CD₃OD, 500 MHz)

ppm (δ)
¹HNMR (CD₃OD, 500 MHz)

ppm (δ)
¹HNMR (CD₃OD, 500 MHz)

ppm (δ)
¹HNMR (CDCl₃, 500 MHz)

ppm (δ)
¹HNMR (CD₃OD, 500 MHz)

ppm (δ)
¹HNMR (DMSO-d₆, 500 MHz)

BROAD SPECTRUM ANTIVIRAL COMPOSITIONS AND METHODS

CROSS-REFERENCE TO RELATED APPLICATION

This application claims the benefit of U.S. Provisional Patent Application No. 62/574,067, filed Oct. 18, 2017, which is incorporated by reference herein in its entirety.

STATEMENT OF FEDERALLY FUNDED RESEARCH

The U.S. Government has a paid-up license in this invention and the right, in limited circumstances, to require the patent owner to license others on reasonable terms as provided for in the terms of grant number 1R44AI122488-01 awarded by the National Institute of Allergy and Infectious Diseases.

TECHNICAL FIELD

This document relates to compounds useful for preventing, treating or ameliorating viral infection.

BACKGROUND

According to the Viral Disease Branch of the Walter Reed Army Institute of Research, non-adenovirus respiratory infections "cause 25-30% of infectious disease hospitalizations in the military, second only to injury as a cause of DNBI [disease and non-battle injury] among deployed forces".

Influenza A is a case in point. It contributes considerably to the military disease burden, and it also infects a significant portion of the U.S. civilian population each year, causing respiratory illness with serious morbidity and mortality. Every year, 5-20% of the U.S. population is infected with seasonal influenza resulting in >200,000 hospitalizations and 24,000 deaths. Moreover, the inevitable emergence of a lethal pandemic influenza A virus poses a serious threat and recent reports of genetic manipulation illustrate the potential of influenza A as a vehicle for biological warfare. Current influenza vaccines are not a solution; their effectiveness has ranged from 10-60% across the past 12 years. Marketed direct acting antiviral therapies for influenza include viral neuraminidase (NA) inhibitors and M2 channel blockers. Additional anti-influenza drugs are being evaluated in clinical trials, including a repurposed antiprotozoal agent that blocks the maturation of viral hemagglutinin by altering its glycosylation via an unknown mechanism. Current drugs suffer from rapid emergence of resistance, because they interact directly with virus proteins (direct-acting antivirals, DAAs). Replication of the viral RNA genome is highly error prone and this high mutation rate (genetic drift), coupled with reassortment of the segmented viral genome (genetic shift) leads to the rapid evolution of drug-resistant isolates that can be just as infectious as their wild-type counterparts. As a result, significant unmet medical need exists for novel therapeutic strategies that overcome the limitations of existing drugs. Antivirals targeting a broad-range of influenza subtypes, while minimizing the emergence of drug-resistant virus, represent a major unmet public health need.

But the need for new therapeutics to treat respiratory pathogens extends notably beyond influenza. No drugs are available to treat coronaviruses, such as MERS and SARS, parainfluenza viruses or adenoviruses; and RSV infections are treated with ribavirin, which is marginally effective (a virus-specific antibody is also available, but only for prophylactic use). Further, multiple respiratory pathogens present with similar symptoms, referred to as influenza-like illness, so a single broad-spectrum drug with efficacy across a variety of different pathogens would be of great utility. There is a need to develop a single pharmaceutical effective against a broad-spectrum of viruses that can cause respiratory infections—not only influenza, but also coronaviruses, RSV, parainfluenza virus, human cytomegalovirus (HCMV) and adenovirus.

Human cytomegalovirus (HCMV) is a major cause of birth defects and opportunistic infections in immunosuppressed individuals, and a possible cofactor in certain cancers. Organ transplant patients under immunosuppressive therapy are at high risk for viral infections; activation of a latent virus as well as donor or community acquired primary infections can cause significant complications including graft rejection, morbidity, and mortality. Herpesviruses (e.g. HCMV, HSV-1), polyomaviruses (e.g. BKV and JCV), hepatitis viruses (HBV and HCV) and respiratory viruses (e.g. influenza A, adenovirus) are the 4 major viral classes infecting these patients. Cytomegalovirus (HCMV) is the most prevalent post-transplant pathogen; HCMV can infect most organs, and despite the availability of HCMV antivirals such as ganciclovir, nephrotoxic side effects and increasing rates of drug-resistance significantly reduce graft and patient survival. In addition, HCMV-mediated immune modulation can reactivate distinct latent viruses carried by most adults. FORGE Life Science, LLC has previously disclosed thiazole-containing compounds which are active against HCMV replication in published patent applications WO 2016/077232 and WO 2016/077240

SUMMARY

The invention provides compounds having the structure of Formula I:

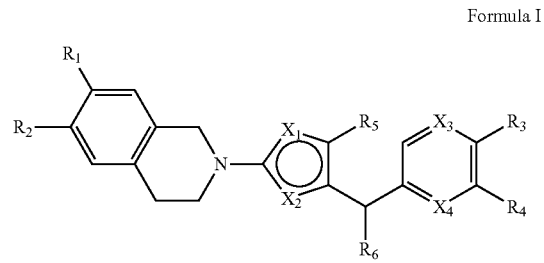

Formula I wherein:
one of X1 and X2 is N and the other is S;
X3 and X4 are independently selected from C and N; and when X3 is C it is optionally substituted with methyl, ethyl, propyl, i-propyl or n-propyl;
one of R1 and R2 is H and the other is a 5- or 6-membered aryl or cylcloalkyl with 0 to 3 ring heteroatoms independently selected from N and O and substituted with 0 to 3 groups independently selected from:
=O, $C_{1-6}$ straight or branched alkyl optionally substituted with —OR12 or NR7R8, $C_{1-6}$ straight or branched alkoxy optionally substituted with NR7R8 or —OR12, and $C_{3-6}$ cycloalkyl optionally substituted with —R12, —OR12 or —NR7R8, or R1 and R2 together form a 5- or 6-membered aryl or cylcloalkyl with 0 to 3 ring heteroatoms independently selected from N and O and substituted with 0 to 3 groups independently selected from:
=O, $C_{1-6}$ straight or branched alkyl optionally substituted with —OR12 or NR7R8, $C_{1-6}$ straight or branched alkoxy optionally substituted with NR7R8 or —OR12, and $C_{3-6}$ cycloalkyl optionally substituted with —R12, —OR12 or —NR7R8;

R3 is selected from H, halo, —C≡CH, —C≡N, —OH, —OCF$_3$, —OCHF$_2$, $C_{1-4}$ straight or branched alkoxy, —SO$_2$($C_{1-6}$ alkyl), —N(CH$_3$)$_2$, —C(O)NH$_2$, —NHSO$_2$R7, —C(O)NR7R8, and a ring structure comprising a 5- or 6-membered aryl or a 4-, 5-, or 6-membered cylcloalkyl with 0 to 3 ring heteroatoms independently selected from N, O and S and substituted with 0 to 2 groups independently selected from =O, halo, $C_{1-6}$ straight or branched alkyl optionally substituted with —OR12 or —NR7R8, $C_{1-6}$ straight or branched alkoxy optionally substituted with —NR7R8 or —OR12, —C(O)—$C_{1-6}$ alkyl and —C(O)O—$C_{1-6}$ alkyl;

R4 is selected from H, halo, —C≡CH, —OH, —OCF$_3$, —OCHF$_2$, $C_{1-4}$ straight or branched alkoxy, —SO$_2$($C_{1-6}$ alkyl), —N(CH$_3$)$_2$, —C(O)NH$_2$, —NHSO$_2$R7, —C(O)NR7R8, a ring structure comprising a 5- or 6-membered aryl or a 4-, 5-, or 6-membered cylcloalkyl with 0 to 3 ring heteroatoms independently selected from N, O and S and substituted with 0 to 2 groups independently selected from =O, halo, $C_{1-6}$ straight or branched alkyl optionally substituted with —OR12 or —NR7R8, $C_{1-6}$ straight or branched alkoxy optionally substituted with —NR7R8 or —OR12, —C(O)—$C_{1-6}$ alkyl and —C(O)O—$C_{1-6}$ alkyl, or the R4 group bonds to X4 to form a 5- or 6-membered aryl or cylcloalkyl with 0 to 3 ring heteroatoms selected from N, O and S and substituted with 0 to 2 groups selected from =O, halo, $C_{1-6}$ straight or branched alkyl optionally substituted with —OR12 or —NR7R8, $C_{1-6}$ straight or branched alkoxy optionally substituted with —NR7R8 or —OR12, —C(O)—$C_{1-6}$ alkyl and —C(O)O—$C_{1-6}$ alkyl;

provided that:
at least one of R3 and R4 is selected from the group consisting of: H, halo, —C≡CH, —C≡N, —OH, —OCF$_3$, —OCHF$_2$, $C_{1-4}$ straight or branched alkoxy, —SO$_2$($C_{1-6}$ alkyl), —N(CH$_3$)$_2$, —C(O)NH$_2$, —NHSO$_2$R7, and —C(O)NR7R8, and
R3 and R4 are not both H;

R5 is selected from the group consisting of H, methyl, ethyl, n-propyl, isopropyl, n-butyl, CF$_3$, CH$_2$CF$_3$ and halo;

R6 is selected from the group consisting of H, methyl, ethyl, n-propyl, isopropyl, n-butyl, CF$_3$, CH$_2$CF$_3$, halo, cyclopropylmethyl and $C_{1-4}$ alkoxy;

R7 and R8 are independently selected, in each instance, from H, $C_{1-6}$ straight or branched alkyl, $C_{3-6}$ cycloalkyl, cyclopropylmethyl and cyclobutylmethyl; and R12 is independently selected, in each instance, from H and $C_{1-4}$ straight or branched alkyl.

or a pharmaceutically acceptable salt or solvate thereof.

The compounds of the invention are useful for treating and/or preventing viral infections. In particular, the compounds of the invention are broad-spectrum antivirals. For example, the compounds of the invention block the replication of two very different human pathogens with comparable potency, influenza A, a rapidly replicating orthomyxovirus with an RNA genome, and HCMV, a slowly replicating herpesvirus with a DNA genome.

The invention also provides methods of preventing, treating and/or ameliorating HCMV infections with compounds of Formula I. The invention also provides methods of preventing, treating and/or ameliorating influenza infections with compounds of Formula I.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
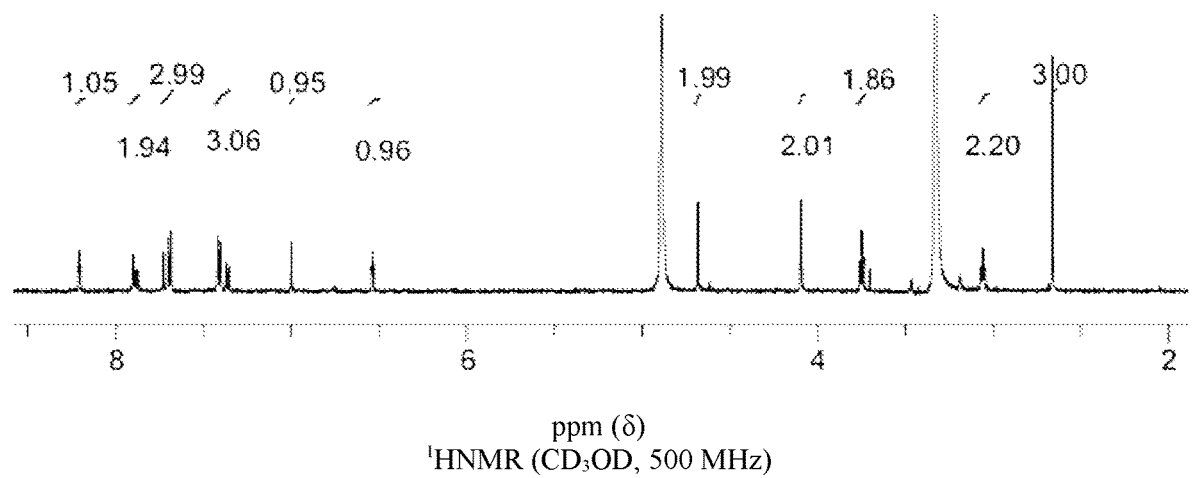
FIG. 1 presents the proton (1H) NMR Spectrum of Example 6 in CD$_3$OD at 500 MHz.

Provided herein are compounds useful in the treatment and/or prevention of a broad spectrum of viral infections.

Provided herein are methods for treating or preventing a viral infection in a subject. In some embodiments, the methods include administering a therapeutically effective amount of one or more of the compounds provided herein. In some embodiments, the compounds provided herein can inhibit virus production in a cell infected with the virus. In such embodiments, the cell is contacted with a virus production inhibiting amount of one or more compounds provided herein.

Provided herein are compounds of the structure of Formula I:

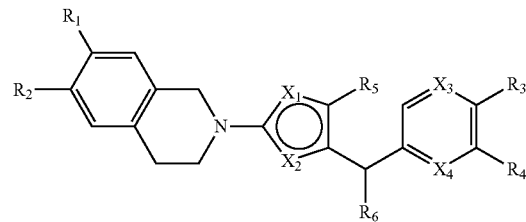

Formula I wherein:
one of X1 and X2 is N and the other is S;
X3 and X4 are independently selected from C and N; and when X3 is C it is optionally substituted with methyl, ethyl, propyl, i-propyl or n-propyl;
one of R1 and R2 is H and the other is a 5- or 6-membered aryl or cylcloalkyl with 0 to 3 ring heteroatoms independently selected from N and O and substituted with 0 to 3 groups independently selected from:
=O, $C_{1-6}$ straight or branched alkyl optionally substituted with —OR12 or NR7R8, $C_{1-6}$ straight or branched alkoxy optionally substituted with NR7R8 or —OR12, and $C_{3-6}$ cycloalkyl optionally substituted with —R12, —OR12 or —NR7R8,
or R1 and R2 together form a 5- or 6-membered aryl or cylcloalkyl with 0 to 3 ring heteroatoms independently selected from N and O and substituted with 0 to 3 groups independently selected from:
=O, $C_{1-6}$ straight or branched alkyl optionally substituted with —OR12 or NR7R8, $C_{1-6}$ straight or branched alkoxy optionally substituted with NR7R8 or —OR12, and $C_{3-6}$ cycloalkyl optionally substituted with —R12, —OR12 or —NR7R8;
R3 is selected from H, halo, —C≡CH, —OH, —OCF$_3$, —OCHF$_2$, $C_{1-4}$ straight or branched alkoxy, —SO$_2$($C_{1-6}$ alkyl), —N(CH$_3$)$_2$, —C(O)NH$_2$, —NHSO$_2$R7, —C(O)NR7R8, and a ring structure comprising a 5- or 6-membered aryl or a 4-, 5-, or 6-membered cylcloalkyl with 0 to 3 ring heteroatoms independently selected from N, O and S and substituted with 0 to 2 groups independently selected from =O, halo, $C_{1-6}$ straight or branched alkyl optionally substituted with —OR12 or —NR7R8, $C_{1-6}$ straight or branched alkoxy optionally substituted with —NR7R8 or —OR12, —C(O)—$C_{1-6}$ alkyl and —C(O)O—$C_{1-6}$ alkyl;
R4 is selected from H, halo, —C≡CH, —OH, —OCF$_3$, —OCHF$_2$, $C_{1-4}$ straight or branched alkoxy, —SO$_2$($C_{1-6}$ alkyl), —N(CH$_3$)$_2$, —C(O)NH$_2$, —NHSO$_2$R7, —C(O)NR7R8, a ring structure comprising a 5- or 6-membered aryl or a 4-, 5-, or 6-membered cylcloalkyl with 0 to 3 ring heteroatoms independently selected from N, O and S and substituted with 0 to 2 groups independently selected from =O, halo, $C_{1-6}$ straight or branched alkyl optionally substituted with —OR12 or —NR7R8, $C_{1-6}$ straight or branched alkoxy optionally substituted with —NR7R8 or —OR12, —C(O)—$C_{1-6}$ alkyl and —C(O)O—$C_{1-6}$ alkyl,
or the R4 group bonds to X4 to form a 5- or 6-membered aryl or cylcloalkyl with 0 to 3 ring heteroatoms selected from N, O and S and substituted with 0 to 2 groups selected from =O, halo, $C_{1-6}$ straight or branched alkyl optionally substituted with —OR12 or —NR7R8, $C_{1-6}$ straight or branched alkoxy optionally substituted with —NR7R8 or —OR12, —C(O)—$C_{1-6}$ alkyl and —C(O)O—$C_{1-6}$ alkyl;
provided that:
at least one of R3 and R4 is selected from the group consisting of: H, halo, —C≡CH, —C≡N, —OH, —OCF$_3$, —OCHF$_2$, $C_{1-4}$ straight or branched alkoxy, —SO$_2$($C_{1-6}$ alkyl), —N(CH$_3$)$_2$, —C(O)NH$_2$, —NHSO$_2$R7, and —C(O)NR7R8, and R3 and R4 are not both H;
R5 is selected from the group consisting of H, methyl, ethyl, n-propyl, isopropyl, n-butyl, CF$_3$, CH$_2$CF$_3$ and halo;
R6 is selected from the group consisting of H, methyl, ethyl, n-propyl, isopropyl, n-butyl, CF$_3$, CH$_2$CF$_3$, halo, cyclopropylmethyl and $C_{1-4}$ alkoxy;

R7 and R8 are independently selected, in each instance, from H, $C_{1-6}$ straight or branched alkyl, $C_{3-6}$ cycloalkyl, cyclopropylmethyl and cyclobutylmethyl; and
R12 is independently selected, in each instance, from H and $C_{1-4}$ straight or branched alkyl.
and pharmaceutically acceptable salts or solvates thereof.

The compounds of Formula I are useful for preventing, treating and/or ameliorating a virus infection. In particular, these compounds are broad-spectrum antivirals able to treat a wide variety of infection caused by viruses, such as influenza, coronaviruses, respiratory syncytial virus (RSV), parainfluenza virus, human cytomegalovirus (HCMV) and adenovirus. In particular, applicants have demonstrated the broad-spectrum antiviral utility of the compound of Formula I by demonstrating these compounds' ability to block the replication of two very different human pathogens with comparable potency, influenza A, a rapidly replicating orthomyxovirus with an RNA genome, and HCMV, a slowly replicating herpesvirus with a DNA genome.

In some embodiments of the of the antiviral compounds of Formula I,
one of R1 and R2 is H and the other is a 5- or 6-membered aryl or cylcloalkyl with 1 to 3 ring heteroatoms independently selected from N and O and substituted with 0 to 2 groups independently selected from:
=O, $C_{1-6}$ straight or branched alkyl optionally substituted with —OR12 or —NR7R8, $C_{1-6}$ straight or branched alkoxy optionally substituted with —NR7R8 or —OR12, cyclopropyl, cyclopropylmethyl, cyclobutyl, cyclopentyl, and cyclohexyl,
or R1 and R2 together form a 5- or 6-membered aryl, cylcloalkyl or cycloalkenyl with 1 to 3 ring heteroatoms independently selected from N and O and substituted with 0 to 2 groups independently selected from:
=O, $C_{1-6}$ straight or branched alkyl optionally substituted with —OR12 or —NR7R8, $C_{1-6}$ straight or branched alkoxy optionally substituted with —NR7R8 or —OR12, cyclopropyl, cyclopropylmethyl, cyclobutyl, cyclopentyl, and cyclohexyl.

In some of the embodiments of the antiviral compounds of formula I, R3 is selected from the group consisting of:

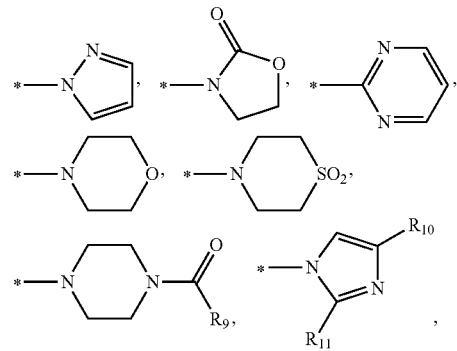

and —SO$_2$($C_{1-6}$ alkyl);
wherein:
R9 is selected from the group consisting of: H, cyclopropyl, cyclopropylmethyl, cyclobutyl, cyclopentyl, cyclohexyl, $C_{1-6}$ straight or branched alkyl optionally substituted with —OR12 or —NR7R8, and $C_{1-6}$ straight or branched alkoxy optionally substituted with —NR7R8; and
R10 and R11 are independently selected from the group consisting of: H, cyclopropyl, cyclopropylmethyl, cyclobutyl, $C_{1-4}$ straight or branched alkyl optionally substituted with —OR12 or —NR7R8, $C_{1-4}$ straight or branched alkoxy optionally substituted with NR7R8.

In some of the embodiments of the antiviral compounds of formula I, R4 is selected from the group consisting of:

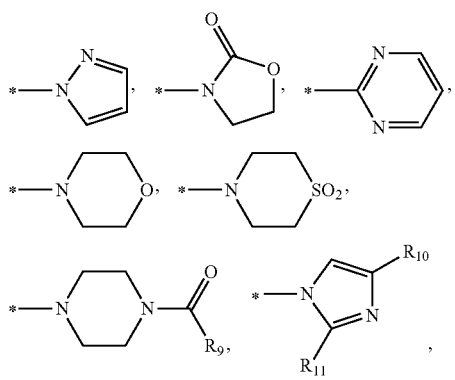

and —SO$_2$(C$_{1-6}$ alkyl);

wherein:

R9 is selected from the group consisting of: H, cyclopropyl, cyclopropylmethyl, cyclobutyl, cyclopentyl, cyclohexyl, $C_{1-6}$ straight or branched alkyl optionally substituted with —OR12 or —NR7R8, and $C_{1-6}$ straight or branched alkoxy optionally substituted with —NR7R8; and R10 and R11 are independently selected from the group consisting of: H, cyclopropyl, cyclopropylmethyl, cyclobutyl, $C_{1-4}$ straight or branched alkyl optionally substituted with —OR12 or —NR7R8, $C_{1-4}$ straight or branched alkoxy optionally substituted with NR7R8.

In some of the embodiments of the antiviral compounds of Formula I, one of R1 and R2 is H and the other is a 5- or 6-membered aryl or cylcloalkyl with at least one N ring heteroatom and 0 to 2 additional ring heteroatoms independently selected from N and O and substituted with 0 to 2 groups independently selected from:

=O, $C_{1-6}$ straight or branched alkyl optionally substituted with —OR12 or NR7R8, $C_{1-6}$ straight or branched alkoxy optionally substituted with NR7R8 or —OR12, and $C_{3-6}$ cycloalkyl optionally substituted with —R12, —OR12 or —NR7R8.

Compounds of this embodiment include, but are not limited to:

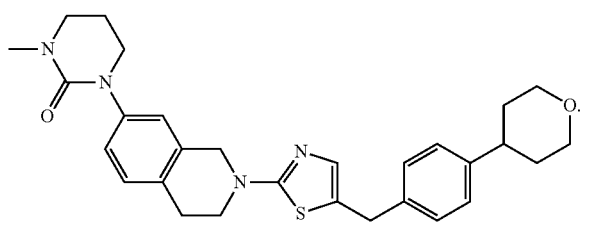

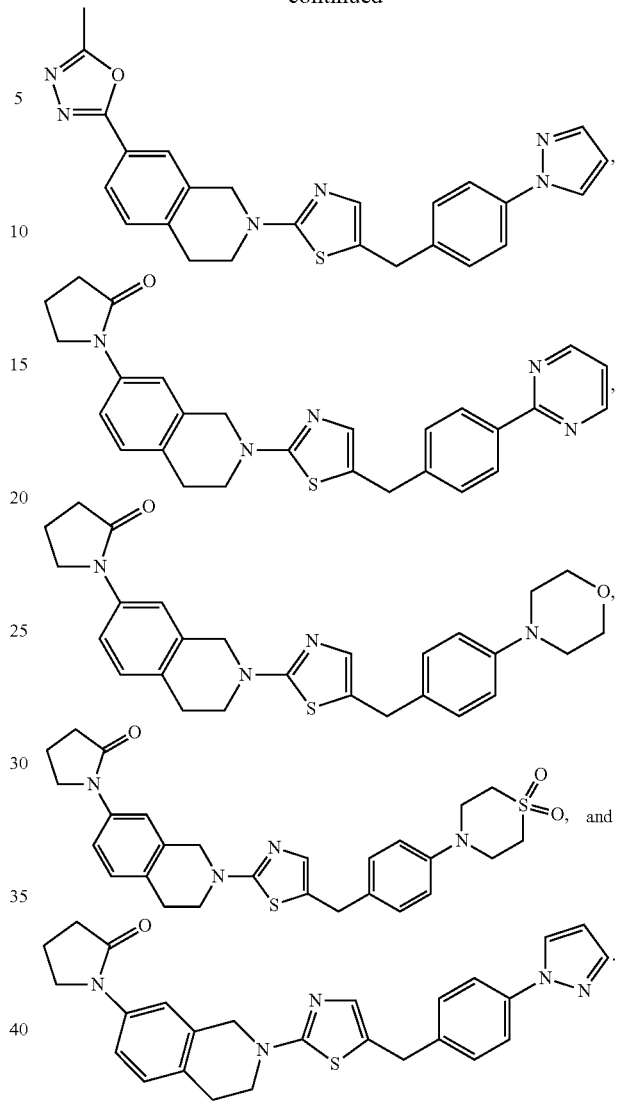

In some embodiments of the compounds of Formula I, one of R1 and R2 is H and the other is selected from the group consisting of:

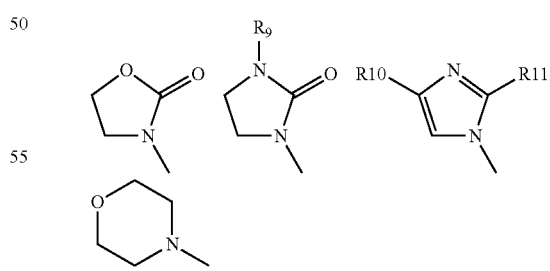

wherein:

R9 is selected from the group consisting of: H, cyclopropyl, cyclopropylmethyl, cyclobutyl, cyclopentyl, cyclohexyl, $C_{1-6}$ straight or branched alkyl optionally substituted with —OR12 or —NR7R8, and $C_{1-6}$ straight or branched alkoxy optionally substituted with —NR7R8; and R10 and R11 are independently selected from the group consisting of: H, cyclopropyl, cyclopropylmethyl, cyclobutyl, $C_{1-4}$ straight or branched alkyl optionally substituted with —OR12 or —NR7R8, $C_{1-4}$ straight or branched alkoxy optionally substituted with NR7R8.
Compounds of this embodiment include, but are not limited to:
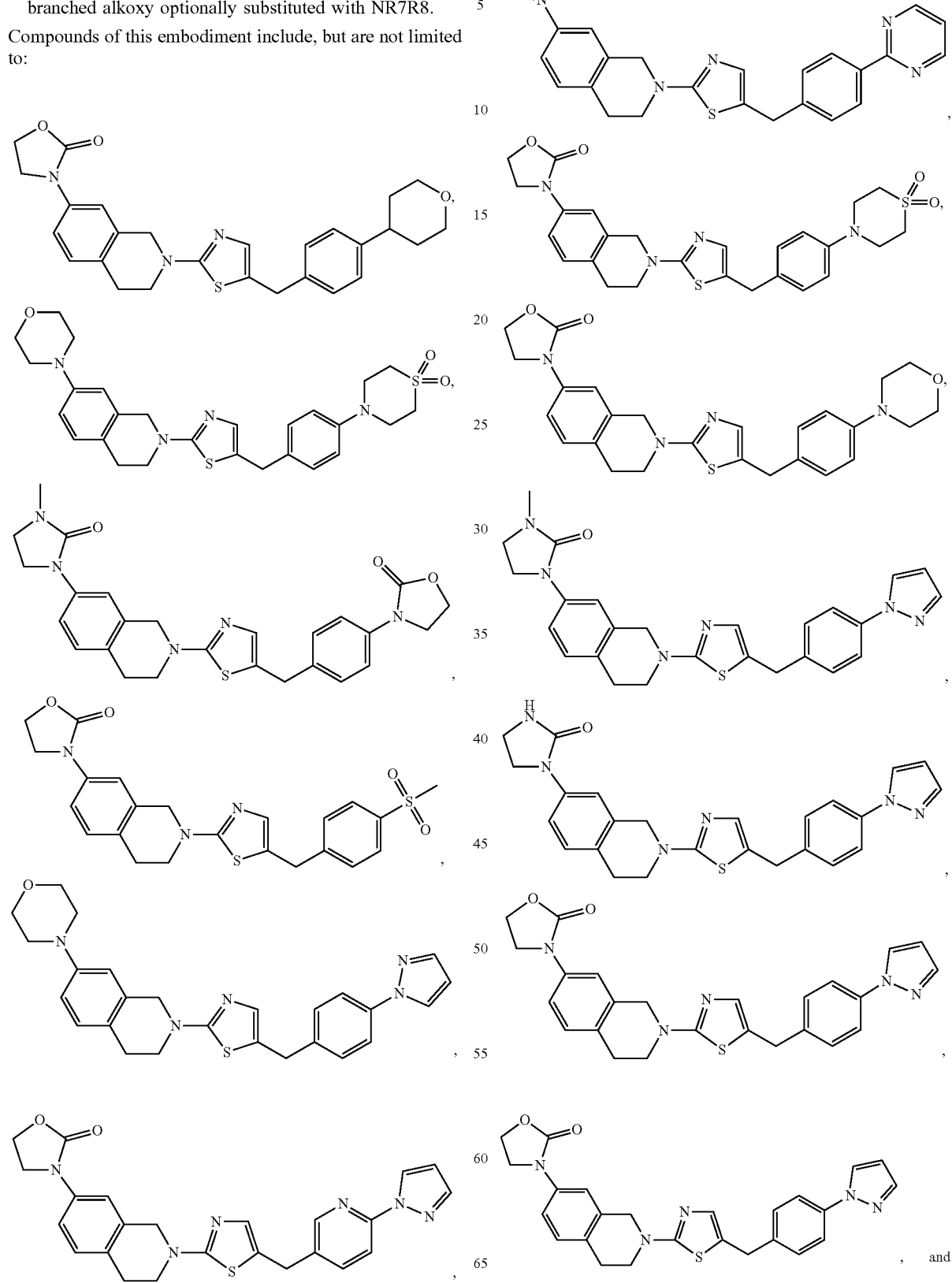

-continued

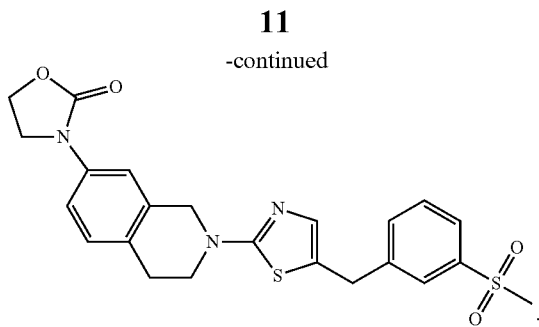

Some embodiments of the compounds of Formula I are compounds of Formula II:

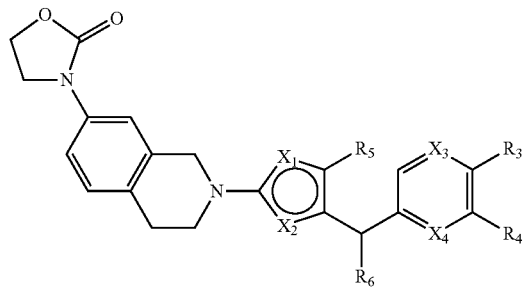

Formula II wherein X1, X2, X3, X4, R3, R4, R5 and R6 are defined as they are for Formula I. In some embodiments of the antiviral compounds of Formula II, R3 is selected from the group consisting of:

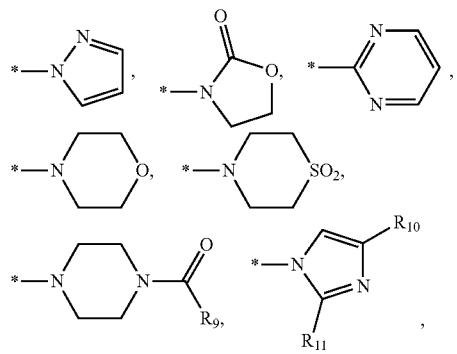

and —SO$_2$(C$_{1-6}$ alkyl);

wherein:

R9 is selected from the group consisting of: H, cyclopropyl, cyclopropylmethyl, cyclobutyl, cyclopentyl, cyclohexyl, C$_{1-6}$ straight or branched alkyl optionally substituted with —OR12 or —NR7R8, and C$_{1-6}$ straight or branched alkoxy optionally substituted with —NR7R8; and R10 and R11 are independently selected from the group consisting of: H, cyclopropyl, cyclopropylmethyl, cyclobutyl, C$_{1-4}$ straight or branched alkyl optionally substituted with —OR12 or —NR7R8, C$_{1-4}$ straight or branched alkoxy optionally substituted with NR7R8.

In some of the embodiments of the antiviral compounds of Formula II, R4 is selected from the group consisting of:

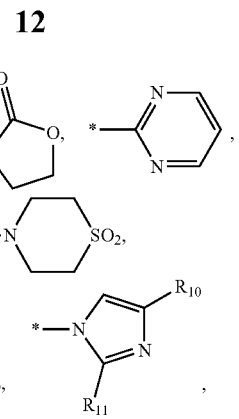

and —SO$_2$(C$_{1-6}$ alkyl);

wherein:

R9 is selected from the group consisting of: H, cyclopropyl, cyclopropylmethyl, cyclobutyl, cyclopentyl, cyclohexyl, C$_{1-6}$ straight or branched alkyl optionally substituted with —OR12 or —NR7R8, and C$_{1-6}$ straight or branched alkoxy optionally substituted with —NR7R8; and R10 and R11 are independently selected from the group consisting of: H, cyclopropyl, cyclopropylmethyl, cyclobutyl, C$_{1-4}$ straight or branched alkyl optionally substituted with —OR12 or —NR7R8, C$_{1-4}$ straight or branched alkoxy optionally substituted with NR7R8.

Some embodiments of the compounds of Formula I are compounds of Formula III:

Formula III

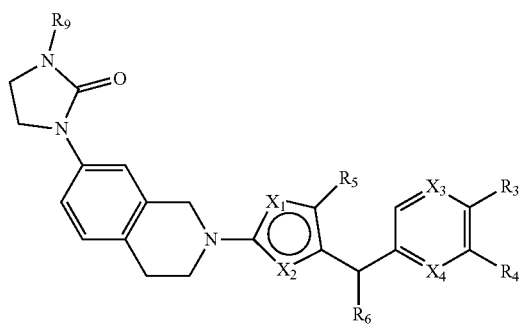

wherein:

R9 is selected from the group consisting of: H, cyclopropyl, cyclopropylmethyl, cyclobutyl, cyclopentyl, cyclohexyl, C$_{1-6}$ straight or branched alkyl optionally substituted with —OR12 or —NR7R8, and C$_{1-6}$ straight or branched alkoxy optionally substituted with —NR7R8, and X1, X2, X3, X4, R3, R4, R5, R6, R7, R8, and R12 are defined as they are for Formula I. In some embodiments of the antiviral compounds of Formula III, R3 is selected from the group consisting of:

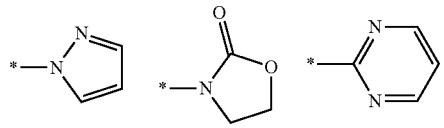

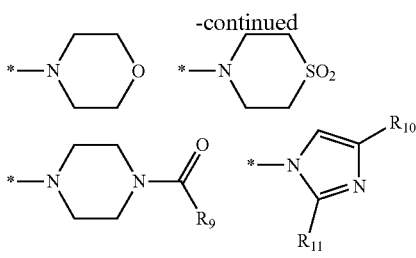

and —SO$_2$(C$_{1-6}$ alkyl);
   wherein: R10 and R11 are independently selected from the group consisting of: H, cyclopropyl, cyclopropylmethyl, cyclobutyl, C$_{1-4}$ straight or branched alkyl optionally substituted with —OR12 or —NR7R8, C$_{1-4}$ straight or branched alkoxy optionally substituted with NR7R8.

In some of the embodiments of the antiviral compounds of Formula III, R4 is selected from the group consisting of:

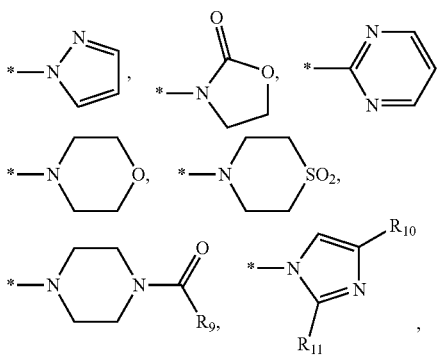

and —SO$_2$(C$_{1-6}$ alkyl);
   wherein: R10 and R11 are independently selected from the group consisting of: H, cyclopropyl, cyclopropylmethyl, cyclobutyl, C$_{1-4}$ straight or branched alkyl optionally substituted with —OR12 or —NR7R8, C$_{1-4}$ straight or branched alkoxy optionally substituted with NR7R8.

Some embodiments of the compounds of Formula I are compounds of Formula IV:

Formula IV

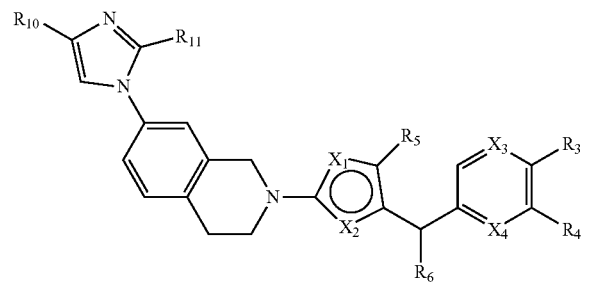

wherein:
   R10 and R11 are independently selected from the group consisting of: H, cyclopropyl, cyclopropylmethyl, cyclobutyl, C$_{1-4}$ straight or branched alkyl optionally substituted with —OR12 or —NR7R8, C$_{1-4}$ straight or branched alkoxy optionally substituted with NR7R8, and X1, X2, X3, X4, R3, R4, R5, R6, R7, R8, and R12 are defined as they are for Formula I. In some embodiments of the antiviral compounds of Formula IV, R3 is selected from the group consisting of:

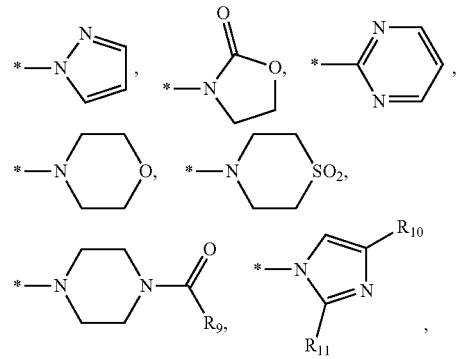

and —SO$_2$(C$_{1-6}$ alkyl);
   wherein: R9 is selected from the group consisting of: H, cyclopropyl, cyclopropylmethyl, cyclobutyl, cyclopentyl, cyclohexyl, C$_{1-6}$ straight or branched alkyl optionally substituted with —OR12 or —NR7R8, and C$_{1-6}$ straight or branched alkoxy optionally substituted with —NR7R8. In some of the embodiments of the antiviral compounds of Formula IV, R4 is selected from the group consisting of:

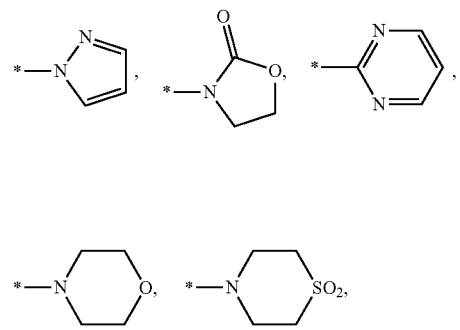

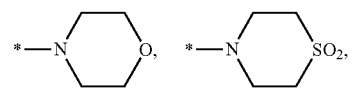

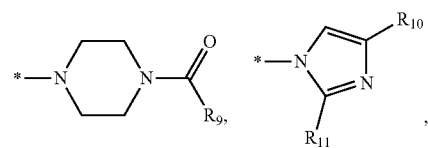

and —SO$_2$(C$_{1-6}$ alkyl);
   wherein: R9 is selected from the group consisting of: H, cyclopropyl, cyclopropylmethyl, cyclobutyl, cyclopentyl, cyclohexyl, C$_{1-6}$ straight or branched alkyl optionally substituted with —OR12 or —NR7R8, and C$_{1-6}$ straight or branched alkoxy optionally substituted with —NR7R8.

Some embodiments of the compounds of Formula I are compounds of Formula V:

Formula V

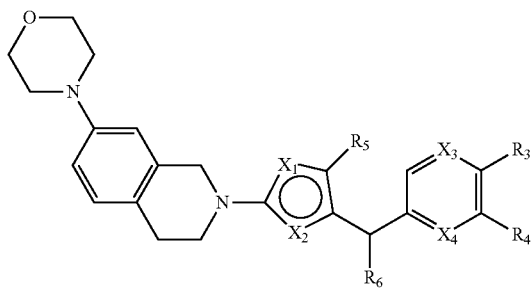

wherein X1, X2, X3, X4, R3, R4, R5 and R6 are defined as they are for Formula I. In some embodiments of the antiviral compounds of Formula V, R3 is selected from the group consisting of:

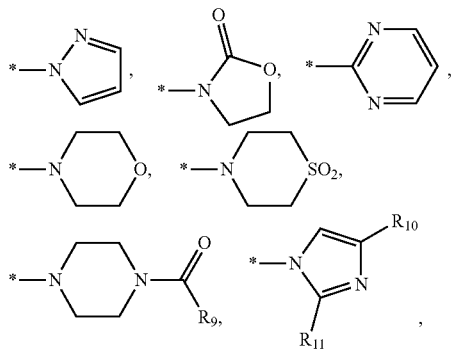

and —SO$_2$(C$_{1-6}$ alkyl);
wherein:
R9 is selected from the group consisting of: H, cyclopropyl, cyclopropylmethyl, cyclobutyl, cyclopentyl, cyclohexyl, C$_{1-6}$ straight or branched alkyl optionally substituted with —OR12 or —NR7R8, and C$_{1-6}$ straight or branched alkoxy optionally substituted with —NR7R8; and
R10 and R11 are independently selected from the group consisting of: H, cyclopropyl, cyclopropylmethyl, cyclobutyl, C$_{1-4}$ straight or branched alkyl optionally substituted with —OR12 or —NR7R8, C$_{1-4}$ straight or branched alkoxy optionally substituted with NR7R8.

In some of the embodiments of the antiviral compounds of Formula V, R4 is selected from the group consisting of:

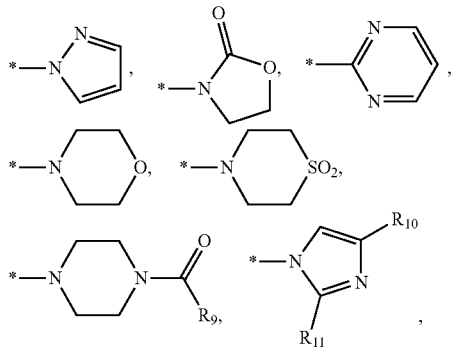

and —SO$_2$(C$_{1-6}$ alkyl);
wherein:
R9 is selected from the group consisting of: H, cyclopropyl, cyclopropylmethyl, cyclobutyl, cyclopentyl, cyclohexyl, C$_{1-6}$ straight or branched alkyl optionally substituted with —OR12 or —NR7R8, and C$_{1-6}$ straight or branched alkoxy optionally substituted with —NR7R8; and
R10 and R11 are independently selected from the group consisting of: H, cyclopropyl, cyclopropylmethyl, cyclobutyl, C$_{1-4}$ straight or branched alkyl optionally substituted with —OR12 or —NR7R8, C$_{1-4}$ straight or branched alkoxy optionally substituted with NR7R8.

Some embodiments of the compounds of Formula I are compounds of Formula VI:

Formula VI

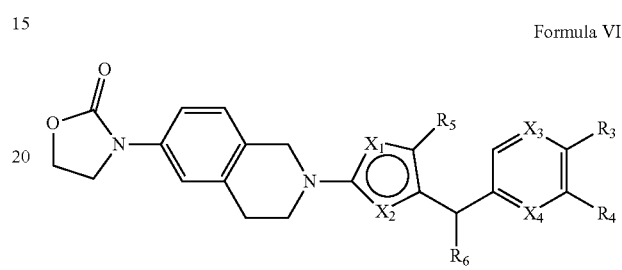

wherein X1, X2, X3, X4, R3, R4, R5 and R6 are defined as they are for Formula I. In some embodiments of the antiviral compounds of Formula VI, R3 is selected from the group consisting of:

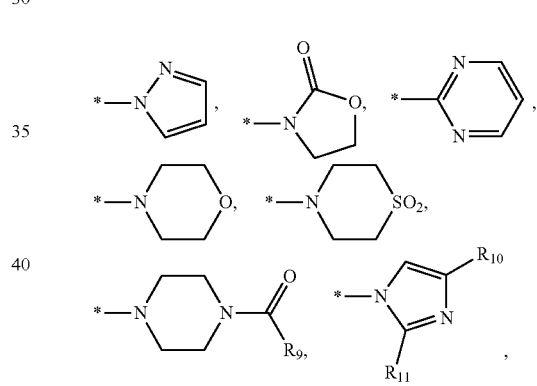

and —SO$_2$(C$_{1-6}$ alkyl);
wherein:
R9 is selected from the group consisting of: H, cyclopropyl, cyclopropylmethyl, cyclobutyl, cyclopentyl, cyclohexyl, C$_{1-6}$ straight or branched alkyl optionally substituted with —OR12 or —NR7R8, and C$_{1-6}$ straight or branched alkoxy optionally substituted with —NR7R8; and
R10 and R11 are independently selected from the group consisting of: H, cyclopropyl, cyclopropylmethyl, cyclobutyl, C$_{1-4}$ straight or branched alkyl optionally substituted with —OR12 or —NR7R8, C$_{1-4}$ straight or branched alkoxy optionally substituted with NR7R8.

In some of the embodiments of the antiviral compounds of Formula VI, R4 is selected from the group consisting of:

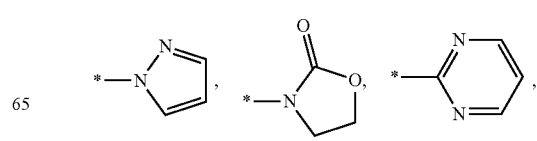

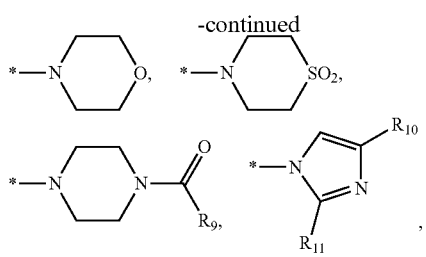

and —SO$_2$(C$_{1-6}$ alkyl);
wherein:
R9 is selected from the group consisting of: H, cyclopropyl, cyclopropylmethyl, cyclobutyl, cyclopentyl, cyclohexyl, C$_{1-6}$ straight or branched alkyl optionally substituted with —OR12 or —NR7R8, and C$_{1-6}$ straight or branched alkoxy optionally substituted with —NR7R8; and
R10 and R11 are independently selected from the group consisting of: H, cyclopropyl, cyclopropylmethyl, cyclobutyl, C$_{1-4}$ straight or branched alkyl optionally substituted with —OR12 or —NR7R8, C$_{1-4}$ straight or branched alkoxy optionally substituted with NR7R8.

Some embodiments of the compounds of Formula I are compounds of Formula VII:

Formula VII

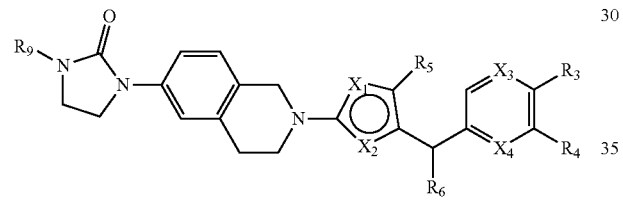

wherein:
R9 is selected from the group consisting of: H, cyclopropyl, cyclopropylmethyl, cyclobutyl, cyclopentyl, cyclohexyl, C$_{1-6}$ straight or branched alkyl optionally substituted with —OR12 or —NR7R8, and C$_{1-6}$ straight or branched alkoxy optionally substituted with —NR7R8, and
X1, X2, X3, X4, R3, R4, R5, R6, R7, R8, and R12 are defined as they are for Formula I. In some embodiments of the antiviral compounds of Formula VII, R3 is selected from the group consisting of:

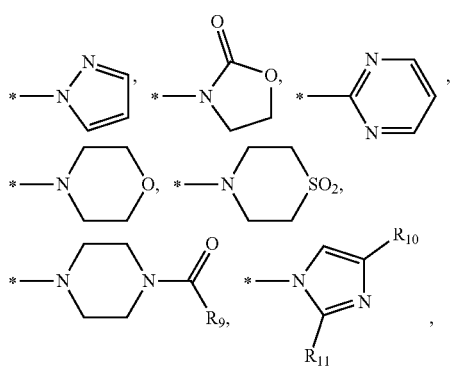

and —SO$_2$(C$_{1-6}$ alkyl);

wherein: R10 and R11 are independently selected from the group consisting of: H, cyclopropyl, cyclopropylmethyl, cyclobutyl, C$_{1-4}$ straight or branched alkyl optionally substituted with —OR12 or —NR7R8, C$_{1-4}$ straight or branched alkoxy optionally substituted with NR7R8.

In some of the embodiments of the antiviral compounds of Formula VII, R4 is selected from the group consisting of:

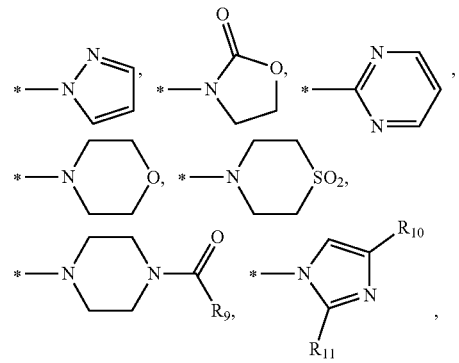

and —SO$_2$(C$_{1-6}$ alkyl);
wherein: R10 and R11 are independently selected from the group consisting of: H, cyclopropyl, cyclopropylmethyl, cyclobutyl, C$_{1-4}$ straight or branched alkyl optionally substituted with —OR12 or —NR7R8, C$_{1-4}$ straight or branched alkoxy optionally substituted with NR7R8.

Some embodiments of the compounds of Formula I are compounds of Formula VIII:

Formula VIII

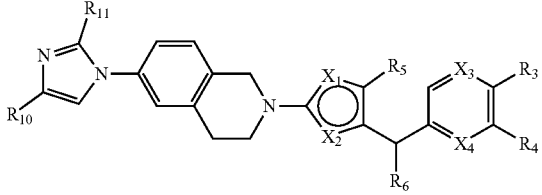

wherein:
R10 and R11 are independently selected from the group consisting of: H, cyclopropyl, cyclopropylmethyl, cyclobutyl, C$_{1-4}$ straight or branched alkyl optionally substituted with —OR12 or —NR7R8, C$_{1-4}$ straight or branched alkoxy optionally substituted with NR7R8, and
X1, X2, X3, X4, R3, R4, R5, R6, R7, R8, and R12 are defined as they are for Formula I. In some embodiments of the antiviral compounds of Formula VIII, R3 is selected from the group consisting of:

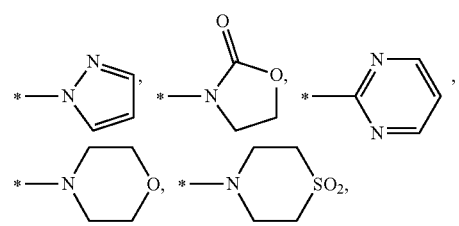

-continued

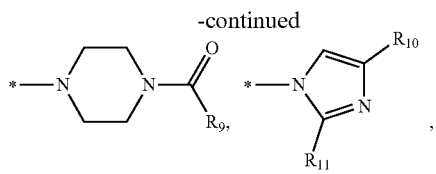 , 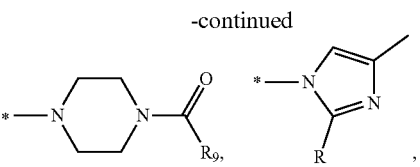 , and —SO$_2$(C$_{1-6}$ alkyl);
wherein: R9 is selected from the group consisting of: H, cyclopropyl, cyclopropylmethyl, cyclobutyl, cyclopentyl, cyclohexyl, C$_{1-6}$ straight or branched alkyl optionally substituted with —OR12 or —NR7R8, and C$_{1-6}$ straight or branched alkoxy optionally substituted with —NR7R8. In some of the embodiments of the antiviral compounds of Formula VIII, R4 is selected from the group consisting of:

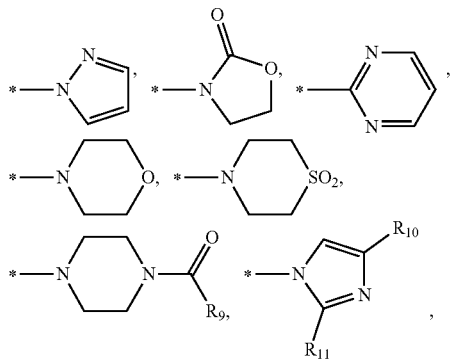

and —SO$_2$(C$_{1-6}$ alkyl);
wherein: R9 is selected from the group consisting of: H, cyclopropyl, cyclopropylmethyl, cyclobutyl, cyclopentyl, cyclohexyl, C$_{1-6}$ straight or branched alkyl optionally substituted with —OR12 or —NR7R8, and C$_{1-6}$ straight or branched alkoxy optionally substituted with —NR7R8.

Some embodiments of the compounds of Formula I are compounds of Formula IX:

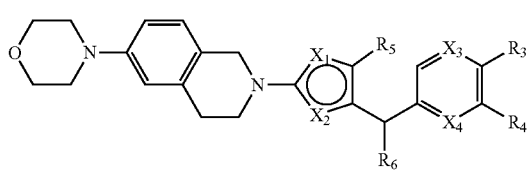

Formula IX wherein X1, X2, X3, X4, R3, R4, R5 and R6 are defined as they are for Formula I. In some embodiments of the antiviral compounds of Formula IX, R3 is selected from the group consisting of:

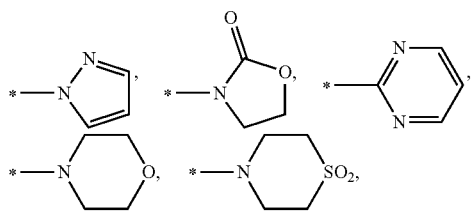

-continued

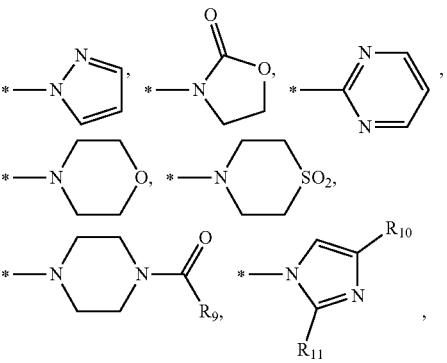

and —SO$_2$(C$_{1-6}$ alkyl);
wherein:
R9 is selected from the group consisting of: H, cyclopropyl, cyclopropylmethyl, cyclobutyl, cyclopentyl, cyclohexyl, C$_{1-6}$ straight or branched alkyl optionally substituted with —OR12 or —NR7R8, and C$_{1-6}$ straight or branched alkoxy optionally substituted with —NR7R8; and
R10 and R11 are independently selected from the group consisting of: H, cyclopropyl, cyclopropylmethyl, cyclobutyl, C$_{1-4}$ straight or branched alkyl optionally substituted with —OR12 or —NR7R8, C$_{1-4}$ straight or branched alkoxy optionally substituted with NR7R8.

In some of the embodiments of the antiviral compounds of Formula IX, R4 is selected from the group consisting of:

and —SO$_2$(C$_{1-6}$ alkyl);
wherein:
R9 is selected from the group consisting of: H, cyclopropyl, cyclopropylmethyl, cyclobutyl, cyclopentyl, cyclohexyl, C$_{1-6}$ straight or branched alkyl optionally substituted with —OR12 or —NR7R8, and C$_{1-6}$ straight or branched alkoxy optionally substituted with —NR7R8; and
R10 and R11 are independently selected from the group consisting of: H, cyclopropyl, cyclopropylmethyl, cyclobutyl, C$_{1-4}$ straight or branched alkyl optionally substituted with —OR12 or —NR7R8, C$_{1-4}$ straight or branched alkoxy optionally substituted with NR7R8.

Also provided herein is a method for treating or preventing a viral infection in a subject comprising administering a therapeutically effective amount of a compound of Formula I, Formula II, Formula III, Formula IV, Formula V, Formula VI, Formula VII, Formula VIII, Formula IX or pharmaceutically acceptable salts or solvates thereof.

Also provided herein is a method of inhibiting virus production comprising contacting a virus-infected cell with a virus production inhibiting amount of a compound of Formula I, Formula II, Formula III, Formula IV, Formula V, Formula VI, Formula VII, Formula VIII, Formula IX or pharmaceutically acceptable salts or solvates thereof.

Also provided herein is a method for treating or preventing an HCMV infection in a subject by administering a therapeutically effective amount of a compound of Formula I, Formula II, Formula III, Formula IV, Formula V, Formula VI, Formula VII, Formula VIII, Formula IX or pharmaceutically acceptable salts or solvates thereof.

Also provided herein is a method of inhibiting HCMV production comprising contacting an HCMV-infected cell with a virus production inhibiting amount of a compound of Formula I, Formula II, Formula III, Formula IV, Formula V, Formula VI, Formula VII, Formula VIII, Formula IX or pharmaceutically acceptable salts or solvates thereof.

Also provided herein is a method for treating or preventing an influenza infection in a subject by administering a therapeutically effective amount of a compound of Formula I, Formula II, Formula III, Formula IV, Formula V, Formula VI, Formula VII, Formula VIII, Formula IX or pharmaceutically acceptable salts or solvates thereof.

Also provided herein is a method of inhibiting influenza production comprising contacting an influenza-infected cell with a virus production inhibiting amount of a compound of Formula I, Formula II, Formula III, Formula IV, Formula V, Formula VI, Formula VII, Formula VIII, Formula IX or pharmaceutically acceptable salts or solvates thereof.

An antiviral agent can also be administered in conjunction with the compounds and the methods described herein. The agent can be any therapeutic agent useful in the treatment of a viral infection, an HCMV infection or an influenza infection. For example, an antiviral agent can include acyclovir, docosanol, ribarivin, interferons, and the like; cellulose acetate, carbopol and carrageenan, pleconaril, amantidine, rimantidine, fomivirsen, zidovudine, lamivudine, zanamivir, oseltamivir, brivudine, abacavir, adefovir, amprenavir, arbidol, atazanavir, atripla, cidofovir, combivir, edoxudine, efavirenz, emtricitabine, enfuvirtide, entecavir, famciclovir, fosamprenavir, foscarnet, fosfonet, ganciclovir, gardasil, ibacitabine, imunovir, idoxuridine, imiquimod, indinavir, inosine, integrase inhibitor, lamivudine, lopinavir, loviride, mk-0518, maraviroc, moroxydine, nelfinavir, nevirapine, nexavir, nucleotide and/or nucleoside analogues, oseltamivir, penciclovir, peramivir, podophyllotoxin, rimantadine, ritonavir, saquinavir, stavudine, tenofovir, tenofovir disoproxil, tipranavir, trifluridine, trizivir, tromantadine, truvada, valaciclovir, valganciclovir, vicriviroc, vidarabine, viramidine, zalcitabine, morpholino oligonucleotides, ribozyme, protease inhibitors, an assembly inhibitor (e.g., rifampicin), zidovudine, brincidofovir, favipiravir, nitoxanide, letermovir, maribavir, CMX157 or a combination or two or more antiviral agents.

In some embodiments, a compound provided herein can be administered before, after, or simultaneously with the administration or one or more antiviral agents.

An antiviral agent provided herein, including a pharmaceutically acceptable salt or solvate thereof, can be purchased commercially or prepared using known organic synthesis techniques.

The methods provided herein include the manufacture and use of pharmaceutical compositions, which include compounds provided herein and one or more pharmaceutically acceptable carriers. Also provided herein are the compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

A pharmaceutical composition is typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., *Remington: The Science and Practice of Pharmacy*, 21st ed., 2005; and the books in the series *Drugs and the Pharmaceutical Sciences: a Series of Textbooks and Monographs* (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates, or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injection can include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. The composition should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin.

Sterile injectable solutions can be prepared by incorporating a compound provided herein in the required amount in an appropriate solvent with one or a combination of ingredients enumerated above, as required, followed by filtered sterilization. Generally, dispersions are prepared by incorporating a compound provided herein into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of a compound provided herein plus any additional desired ingredient from a previously sterile-filtered solution thereof.

Oral compositions generally include an inert diluent or an edible carrier. For the purpose of oral therapeutic administration, a compound provided herein can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the compounds provided herein can be formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

Additionally, intranasal delivery is possible, as described in, inter alia, Hamajima et al., Clin. Immunol. Immunopathol., 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical composition may be administered at once or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Dosage forms or compositions containing a compound as described herein in the range of 0.005% to 100% with the balance made up from non-toxic carrier may be prepared. Methods for preparation of these compositions are known to those skilled in the art. The contemplated compositions may contain 0.001%-100% of a compound provided herein, in one embodiment 0.1-95%, in another embodiment 75-85%.

The pharmaceutical compositions can be included in a container, pack, or dispenser together with instructions for administration.

As described above, the preparations of one or more compounds provided herein may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. In some embodiments, administration is oral.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrastemal injection, and infusion.

Actual dosage levels of the active ingredients in the pharmaceutical compositions provided herein may be varied so as to obtain an amount of the active ingredient which is effective to achieve the desired therapeutic response for a particular patient, composition, and mode of administration, without being toxic to the patient.

The concentration of a compound provided herein in a pharmaceutically acceptable mixture will vary depending on several factors, including the dosage of the compound to be administered, the pharmacokinetic characteristics of the compound(s) employed, and the route of administration. In some embodiments, the compositions provided herein can be provided in an aqueous solution containing about 0.1-10% w/v of a compound disclosed herein, among other substances, for parenteral administration. Typical dose ranges can include from about 0.01 to about 500 mg/kg of body weight per day, given in 1-4 divided doses. Each divided dose may contain the same or different compounds. The dosage will be a therapeutically effective amount depending on several factors including the overall health of a patient, and the formulation and route of administration of the selected compound(s).

Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses. The amount of active ingredient which can be combined with a carrier material to produce a single dosage form will generally be that amount of the compound which produces a therapeutic effect.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the patient and adjusting the dosage and/or timing.

Also provided herein is a conjoint therapy wherein one or more other therapeutic agents are administered with a compound or a pharmaceutical composition comprising a compound provided herein. Such conjoint treatment may be achieved by way of the simultaneous, sequential, or separate dosing of the individual components of the treatment.

Definitions

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about", whether or not the term is explicitly used, unless explicitly stated otherwise. As used herein, the singular forms "a," "an," and "the" include plural referents unless the context clearly dictates otherwise.

A "subject," as used herein, includes both humans and other animals, particularly mammals. Thus, the methods are applicable to both human therapy and veterinary applications. In some embodiments, the patient is a mammal, for example, a primate. In some embodiments, the patient is a human.

A "therapeutically effective" amount of a compound provided herein is typically one which is sufficient to prevent, eliminate, ameliorate or reduce the symptoms of a viral infection, including, but not limited to influenza, coronaviruses, respiratory syncytial virus (RSV), parainfluenza virus, human cytomegalovirus (HCMV) and adenovirus infection. It will be appreciated that different concentrations may be employed for prophylaxis than for treatment of an active disease.

A "virus production inhibiting" amount of a compound provided herein is typically one which is sufficient to achieve a measurable reduction in the amount of virus produced by the cells contacted with the compound. In some embodiments, a "virus production inhibiting" amount is an amount which inhibits a least 30% of the virus production in untreated cells. In some embodiments, a "virus production inhibiting" amount is an amount which inhibits a least 50% of the virus production in untreated cells. In some embodiments, a "virus production inhibiting" amount is an amount which inhibits a least 70% of the virus production in untreated cells. In some embodiments, a "virus production inhibiting" amount is an amount which inhibits a least 90% of the virus production in untreated cells.

The terms "treatment" and "prevention" are art-recognized and include administration of one or more of the compounds or pharmaceutical compositions provided herein. If it is administered prior to clinical manifestation of the unwanted condition (e.g., disease or other unwanted state of the subject) then the treatment is preventative, (i.e., it protects the subject against developing the unwanted condition). As used in this context, the term "prevent" means to slow or prevent the onset of at least one symptom of a disorder as provided herein. For example, such prevention may be prompted by a likelihood of exposure to an infective agent (e.g., a virus) or when a subject exhibits other symptoms that indicate onset of a disorder (e.g., a metabolic disorder or cardiovascular disorder) may be likely. Alternatively, if it is administered after manifestation of the unwanted condition, the treatment is therapeutic, (i.e., it is intended to diminish, ameliorate, or stabilize the existing unwanted condition or side effects thereof). As used in this context, to "treat" means to ameliorate at least one symptom of a disorder as provided herein.

The term, "compound," as used herein is meant to include all stereoisomers, geometric isomers, and tautomers of the structures depicted. Compounds herein identified by name or structure as one particular tautomeric form are intended to include other tautomeric forms unless otherwise specified.

In some embodiments, a compound provided herein, or salt thereof, is substantially isolated. By "substantially isolated" it is meant that the compound is at least partially or substantially separated from the environment in which it was formed or detected. Partial separation can include, for example, a composition enriched in the compound provided herein. Substantial separation can include compositions containing at least about 50%, at least about 60%, at least about 70%, at least about 80%, at least about 90%, at least about 95%, at least about 97%, or at least about 99% by weight of the compound provided herein, or salt thereof. Methods for isolating compounds and their salts are routine in the art.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salt" refers to the relatively non-toxic, inorganic and organic acid addition salts of a compound provided herein. These salts can be prepared in situ during the final isolation and purification of a compound provided herein, or by separately reacting the compound in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", *J. Pharm. Sci.* 66: 1-19.)

In some embodiments, a compound provided herein may contain one or more acidic functional groups and, thus, is capable of forming pharmaceutically acceptable salts with pharmaceutically acceptable bases. The term "pharmaceutically acceptable salts" in these instances refers to the relatively non-toxic inorganic and organic base addition salts of a compound provided herein. These salts can likewise be prepared in situ during the final isolation and purification of the compound, or by separately reacting the purified compound in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

The term "solvate" means a compound that further includes a stoichiometric or non-stoichiometric amount of solvent bound by non-covalent intermolecular forces. Where the solvent is water, the solvate is a hydrate. The term "pharmaceutically acceptable solvate" refers to the relatively non-toxic solvates of a compound provided herein, using a solvent which is, within the sound scope of medical judgement, suitable for use in contact with the tissues of human beings and animals without excessive toxicity, irritation, allergic response or other problem or complication, commensurate with a reasonable benefit/risk ratio.

The term "alkyl" as employed herein refers to straight and branched chain aliphatic groups having from 1 to 12 carbon atoms, preferably 1-8 carbon atoms, and more preferably 1-6 carbon atoms, which is optionally substituted with one, two or three substituents. Preferred alkyl groups include, without limitation, methyl, ethyl, propyl, isopropyl, butyl, isobutyl, secbutyl, tertbutyl, pentyl, and hexyl. A "$C_0$" alkyl (as in "$C_0$-$C_3$-alkyl") is a covalent bond (like "$C_0$" hydrocarbyl). The term "lower alkyl" refers to straight and branched chain aliphatic groups having from 1 to 6 carbon atoms. Unless otherwise specified, the term "alkyl" includes alkenyl, alkynyl and cyclic alkyl groups.

The term "alkenyl" as used herein means an unsaturated straight or branched chain aliphatic group with one or more carbon-carbon double bonds, having from 2 to 12 carbon atoms, preferably 2-8 carbon atoms, and more preferably 2-6 carbon atoms, which is optionally substituted with one, two or three substituents. Preferred alkenyl groups include, without limitation, ethenyl, propenyl, butenyl, pentenyl, and hexenyl.

The term "alkynyl" as used herein means an unsaturated straight or branched chain aliphatic group with one or more carbon-carbon triple bonds, having from 2 to 12 carbon atoms, preferably 2-8 carbon atoms, and more preferably 2-6 carbon atoms, which is optionally substituted with one, two or three substituents. Preferred alkynyl groups include, without limitation, ethynyl, propynyl, butynyl, pentynyl, and hexynyl.

The term "heteroalkyl" refers to an alkyl group, as defined herein above, wherein one or more carbon atoms in the chain are replaced by a heteroatom selected from the group consisting of O, S, and N.

An "aryl" group is a $C_6$-$C_{14}$ aromatic moiety comprising one to three aromatic rings, which is optionally substituted. Preferably, the aryl group is a $C_6$-$C_{10}$ aryl group. Preferred aryl groups include, without limitation, phenyl, naphthyl, anthracenyl, and fluorenyl.

A "heterocyclyl" or "heterocyclic" group is a ring structure having from about 3 to about 8 atoms, wherein one or more atoms are selected from the group consisting of N, O, and S. The heterocyclic group is optionally substituted on carbon at one or more positions. The heterocyclic group is also independently optionally substituted on nitrogen with alkyl, aryl, aralkyl, alkylcarbonyl, alkyl sulfonyl, arylcarbonyl, aryl sulfonyl, alkoxycarbonyl, aralkoxycarbonyl, or on sulfur with oxo or lower alkyl. Preferred heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholino. In certain preferred embodiments, the heterocyclic group is fused to an aryl, heteroaryl, or cycloalkyl group. Examples of such fused heterocyles include, without limitation, tetrahydroquinoline and dihydrobenzofuran. Specifically excluded from the scope of this term are compounds having adjacent annular O and/or S atoms.

As used herein, the term "heteroaryl" refers to groups having 5 to 14 ring atoms, preferably 5, 6, 9, or 10 ring atoms; having 6, 10, or 14 π electrons shared in a cyclic array; and having, in addition to carbon atoms, from one to three heteroatoms per ring selected from the group consisting of N, O, and S. A "heteroaralkyl" or "heteroarylalkyl" group comprises a heteroaryl group covalently linked to an alkyl group, either of which is independently optionally substituted or unsubstituted. Preferred heteroalkyl groups comprise a C1-C6 alkyl group and a heteroaryl group having 5, 6, 9, or 10 ring atoms. Specifically excluded from the scope of this term are compounds having adjacent annular O and/or S atoms. Examples of preferred heteroaralkyl groups include pyridylmethyl, pyridylethyl, pyrrolylmethyl, pyrrolylethyl, imidazolylmethyl, imidazolylethyl, thiazolylmethyl, and thiazolylethyl. Specifically excluded from the scope of this term are compounds having adjacent annular O and/or S atoms.

Embodiments of heterocyclyls and heteroaryls include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

As employed herein, when a moiety (e.g., cycloalkyl, hydrocarbyl, aryl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—), nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups.

The term "halogen" or "halo" as employed herein refers to chlorine, bromine, fluorine, or iodine. As herein employed, the term "acyl" refers to an alkylcarbonyl or arylcarbonyl substituent. The term "acylamino" refers to an amide group attached at the nitrogen atom (i.e., R—CO—NH—). The term "carbamoyl" refers to an amide group attached at the carbonyl carbon atom (i.e., NH$_2$—CO—). The nitrogen atom of an acylamino or carbamoyl substituent is optionally additionally substituted. The term "sulfonamido" refers to a sulfonamide substituent attached by either the sulfur or the nitrogen atom. The term "amino" is meant to include NH$_2$, alkylamino, arylamino, and cyclic amino groups. The term "ureido" as employed herein refers to a substituted or unsubstituted urea moiety.

A moiety that is substituted is one in which one or more hydrogens have been independently replaced with another chemical substituent. As a non-limiting example, substituted phenyls include 2-flurophenyl, 3,4-dichlorophenyl, 3-chloro-4-fluoro-phenyl, 2-fluor-3-propylphenyl. As another non-limiting example, substituted n-octyls include 2,4 dimethyl-5-ethy-octyl and 3-cyclopentyl-octyl. Included within this definition are methylenes (—CH$_2$—) substituted with oxygen to form carbonyl-CO—).

An "unsubstituted" moiety as defined above (e.g., unsubstituted cycloalkyl, unsubstituted heteroaryl, etc.) means that moiety as defined above that does not have any of the optional substituents for which the definition of the moiety (above) otherwise provides. Thus, for example, while an "aryl" includes phenyl and phenyl substituted with a halo, "unsubstituted aryl" does not include phenyl substituted with a halo.

Synthesis of Compounds of the Invention

The compounds in the present invention (compounds of Formula I) can be prepared using the general reaction scheme set out in the schemes below. The following abbreviations are used:

NMP, N-methyl-2-pyrrolidone; RT, room temperature; DCM, dichloromethane; DMF, N,N-Dimethylformamide; THF, tetrahydrofuran; DCE, 1,2-dichloroethane; TES or TES-H, triethylsilane; TES, triethoxysilane; TFA, trifluoroacetic acid; EtOAc or EA, ethyl acetate; M, molar; TBAF, tetrabutylammonium fluoride; t-BuOH, t-butanol; MeI, methyl iodide; DMSO, dimethylsulfoxide; MeCN, acetonitrile; XPhos, 2-dicyclohexylphosphino-2',4',6'-triisopropylbiphenyl; MeOH, methanol; h or hrs, hours; aq., aqueous; DMF, 1,2-dimethoxyethane; sat., saturated; atm, atmosphere; Ac$_2$O, acetic anhydride; conc., concentrated; eq., equivalents; DIEA, N,N-diisopropylethylamine; HATU, N-[(Dimethylamino)-1H-1,2,3-triazolo-[4,5-b]pyridin-1-yl-methylene]-N-methylmethanaminium hexafluorophosphate N-oxide; DMA, N,N-Dimethylacetamide; Pd$_2$(dba)$_3$, tris(dibenzylideneacetone)dipalladium(0); S-Phos, dicyclohexyl(2',6'-dimethoxy-[1,1'-biphenyl]-2-yl)phosphine; PE, petroleum ether; AcOK, potassium acetate; Pd(dppf)Cl$_2$, [1,1'-Bis(diphenylphosphino)ferrocene]dichloropalladium (II); DMI, 1,3-dimethyl-2-imidazolidinone; Prep-TLC, preperative thin layer chromatography; t-BuONa, sodium t-butoxide; t-BuOK, potassium t-butoxide; HMDS, hexamethyldisilazane; (Pd(OAc)$_2$, palladium (II) acetate; EtOH, ethanol; DEA, diethylamine; AcOH, acetic acid; BOC$_2$O, di-tert-butyl dicarbonate; Et$_3$N, triethylamine; Prep-HPLC, preparative HPLC; TsOH, p-toluenesulfonic acid; TBAB, Tetra-n-butylammonium bromide.

Scheme 1

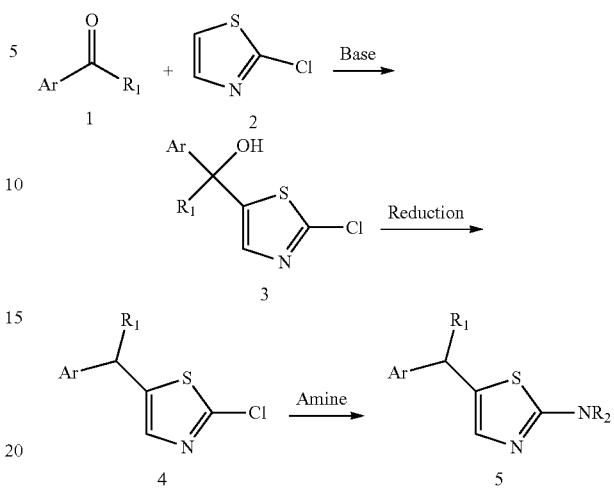

A base, e.g., n-BuLi or sec-BuLi can be reacted with 2-chloro-1,3-thiazole (2) and a suitable aromatic or heteroaromatic aldehyde or ketone of general formula 1 to afford compounds of general structure 3. Compounds of general structure 3 can be treated with a suitable reducing agent, e.g., a silane such as triethylsilane and an acid such as trifluoroacetic acid to provide compounds of general structure 4. Compounds of general structure 4 can be treated with a suitable amine, e.g., a substituted or unsubstituted 1,2,3,4-tetrahydroisoquinoline to afford compounds of general structure 5. It will be recognized that compounds of general structure 5 are identical to compounds of Formula I.

Scheme 2

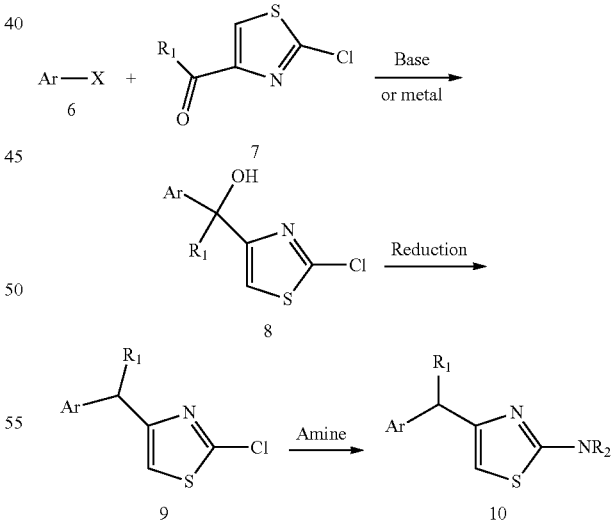

A base, e.g., n-BuLi or sec-BuLi or a metal, e.g., Mg or Li, can be reacted with a suitable halogenated aromatic or heteroaromatic of general formula 6, where X is Cl, Br or I, and compounds of general structure 7 to afford compounds of general structure 8. Compounds of general structure 8 can be treated with a suitable reducing agent, e.g., a silane such as triethylsilane and an acid such as trifluoroacetic acid to provide compounds of general structure 9. Compounds of general structure 9 can be treated with a suitable amine, e.g., a substituted or unsubstituted 1,2,3,4-tetrahydroisoquinoline to afford compounds of general structure 10. It will be recognized that compounds of general structure 10 are identical to compounds of Formula I.

Those skilled in the art will recognize there may be alternate synthetic paths to provide compounds of Formula I. The following Schemes describe examples of such alternate synthetic paths but are not to be considered limiting.

Scheme 3

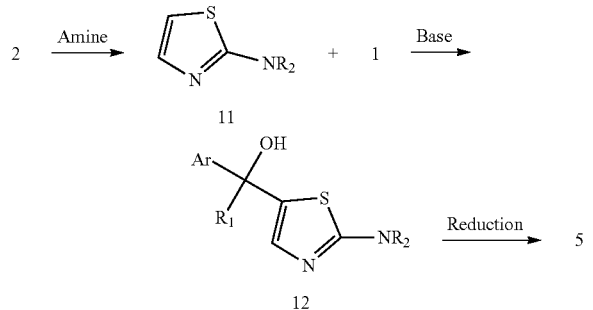

In some instances, a suitable amine, e.g., a substituted or unsubstituted 1,2,3,4-tetrahydroisoquinoline can be reacted with 2-chloro-1,3-thiazole (2) to afford compounds of general structure 11. Compounds of general structure 11 can be reacted with base, e.g., n-BuLi or sec-BuLi and compounds of general structure 1 to afford compounds of general structure 12. Compounds of general structure 12 can be treated with a suitable reducing agent, e.g., a silane such as triethylsilane and an acid such as trifluoroacetic acid to provide compounds of general structure 5.

Scheme 4

In some instances, compounds of general structure 3 can be treated with a suitable amine, e.g., a substituted or unsubstituted 1,2,3,4-tetrahydroisoquinoline to afford compounds of general structure 12. Compounds of general formula 12 can be treated as described above to provide compound of general formula 5.

Scheme 5

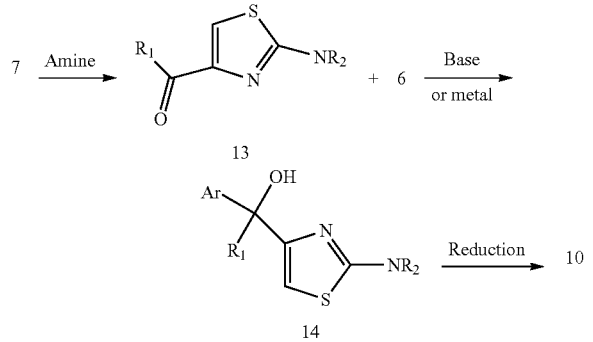

In some instances, a suitable amine, e.g., a substituted or unsubstituted 1,2,3,4-tetrahydroisoquinoline can be reacted with compounds of general structure 7 to afford compounds of general structure 13. A base, e.g., n-BuLi or sec-BuLi or a metal, e.g., Mg or Li, can be reacted with a suitable halogenated aromatic or heteroaromatic compounds of general formula 6, where X is Cl, Br or I, and compounds of general formula 13 to afford compounds of general formula 14. Compounds of general formula 12 can be treated as described above to provide compound of general formula 10.

Scheme 6

In some instances, compounds of general formula 8 can be reacted with a suitable amine, e.g., a substituted or unsubstituted 1,2,3,4-tetrahydroisoquinoline to afford compounds of general formula 14. Compounds of general formula 14 can be treated as described above to provide compound of general formula 10.

Methods to perform the above described reactions and processes would be apparent to those of ordinary skill in the art based on the present disclosure, or can be deduced in analogy from the examples. Starting materials are commercially available or can be made by methods analogous to those described in the Examples below.

Preparation of Intermediates

Preparation of Intermediate 1

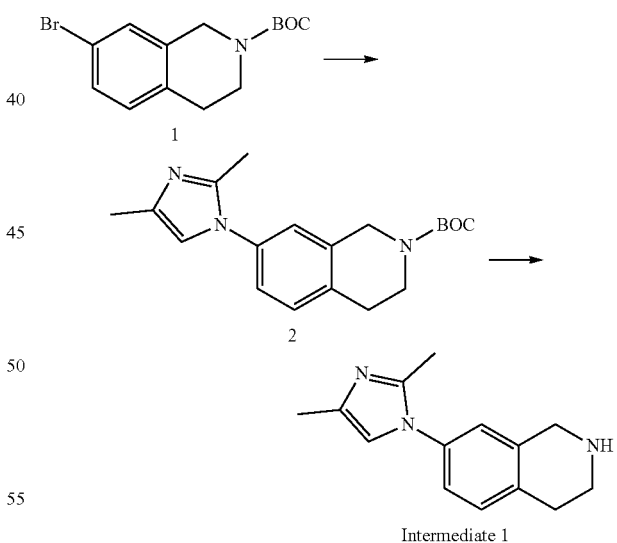

1. A mixture of 1 (Key Organics, 15 g, 48.08 mmol), 2,4-dimethyl-1H-imidazole (13.8 g, 144.23 mmol), (S,S)—N,N'-dimethyl-1,2-diaminocyclohexane (1.37 g, 9.62 mmol), t-BuOK (16.15 g, 144.23 mmol) and CuI (4.58 g, 24.04 mmol) in NMP (150 mL) was stirred at 160° C. overnight under $N_2$. The mixture was cooled to RT, sat. aq. NaHCO$_3$ (50 mL) and Boc$_2$O (26.2 g, 120 mmol) were added and the resulting mixture was stirred at RT overnight. The mixture was concentrated, and the residue was purified by chromatography on silica gel to give a material which was purified by Prep-HPLC to give 2 (6 g, 38% yield) as a pale-yellow oil. MS (ESI): mass calcd. for $C_{19}H_{25}N_3O_2$ 327.43, m/z found 327.9 $[M+H]^+$.

2. To a solution of 2 (6 g, 18.35 mmol) in DCM (50 mL) was added TFA (50 mL). The resulting mixture was stirred at RT overnight, concentrated and the residue was diluted with water, basified with $K_2CO_3$ to pH=10, extracted with DCM, the combined organic phase was washed with brine, dried over $Na_2SO_4$, filtered, and the filtrate concentrated to give Intermediate 1 (3.4 g, 81.5% yield) as a pale-yellow oil. MS (ESI): mass calcd. for $C_{14}H_{17}N_3$ 227.31, m/z found 227.9 $[M+H]^+$.

Preparation of Intermediate 2

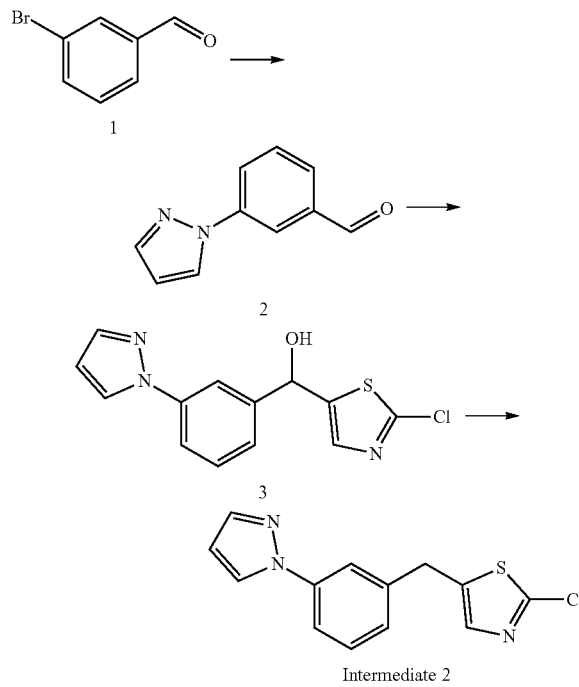

Intermediate 2

1. To a solution of 1 (30 g, 163 mmol) in dry DMF (250 mL) were added pyrazole (11.1 g, 163 mmol), $Cs_2CO_3$ (79.2 g, 243 mmol) and CuI (3 g, 15.8 mmol). The resulting mixture was stirred at 120° C. overnight. After cooling to RT, the residue was treated with water and extracted with EtOAc. The organic extracts were washed with water, brine, dried over anhydrous $Na_2SO_4$, filtered and concentrated to give a crude oil. The crude product was purified by silica gel chromatography to afford 2 as yellow oil (12 g, 43%).

2. To a solution of 2-chlorothiazole (8.3 g, 70 mmol) in dry THF (100 mL) at −78° C. under $N_2$ was added n-BuLi (28 mL, 70 mmol) dropwise. After 1 h solution of 2 (12 g, 70 mmol) in THF (30 mL) was added dropwise. The resulting solution was slowly warmed to RT. The reaction was diluted with $NH_4Cl$ solution and extracted with EtOAc. The organic extracts were concentrated to give a crude oil which was purified by silica gel chromatography to afford 3 as brown semi-solid (12.8 g, 63%).

3. To a solution of 3 (12.8 g, 44 mmol) in DCE (150 mL) was added TES-H (15.3 g, 132 mmol), the mixture cooled to 0° C. and TFA (50 g, 0.44 mol) was added dropwise. The resulting solution was stirred at 60° C. for 4 h. The residue was concentrated and purified by silica gel chromatography to afford Intermediate 2 as yellow oil (9.2 g, 76%).

Alternate Preparation of Intermediate 2

1. A mixture of 1 (18.5 g, 100 mmol), 1H-pyrazole (6.8 g, 100 mmol), $Cs_2CO_3$ (35.9 g, 110 mmol), 18-crown-6 (1.9 g, 7.2 mmol), CuI (1.9 g, 10 mmol) in DMF (200 mL) was stirred at 80° C. for 16 hrs. The resulting mixture was cooled, filtered and concentrated, diluted with EA, washed with water, brine, dried over $Na_2SO_4$, concentrated and purified by Combi-Flash to obtain 2 (9 g, 52% yield) as a yellow oil. MS (ESI): mass calcd. for $C_{10}H_8N_2O$ 172, m/z found 173 $[M+H]^+$.

2. To a solution of 2-chlorothiazole (6.5 g, 55 mmol) in THF (250 ml) at −78° C., n-BuLi (25 mL, 60 mmol, 2.4 M in hexane) was added slowly, the resulting mixture was stirred at −78° C. for 1 h. A solution of 2 (8.5 g, 50 mmol) in THF (40 ml) was added slowly at −78° C., after a stirring 1 h, the reaction mixture was warmed to RT slowly and stirred for 20 min. Then it was quenched with saturated $NH_4Cl$. The mixture was extracted with EA and the combined extracts washed with brine, dried over $Na_2SO_4$, filtered, concentrated and the residue purified by Combi-Flash to obtain 3 (4.2 g, 29% yield) as a yellow solid. MS (ESI): mass calcd. for $C_{13}H_{10}ClN_3OS$ 291, m/z found 292 $[M+H]^+$.

3. To a mixture of 3 (4.2 g, 14.4 mmol), TFA (16.4 g, 144 mmol) in DCE (200 mL), TES (7.1 g, 43.3 mmol) was added at 0° C., and the mixture was heated to 100° C. for 16 hrs. The resulting mixture was cooled to RT, washed with water, brine, dried over $Na_2SO_4$, filtered, concentrated and purified by Combi-Flash to obtain product Intermediate 2 (2.2 g, 55% yield) as a yellow oil. MS (ESI): mass calcd. for $C_{13}H_{10}ClN_3S$ 275.0, m/z found 276 $[M+H]^+$.

Preparation of Intermediate 3

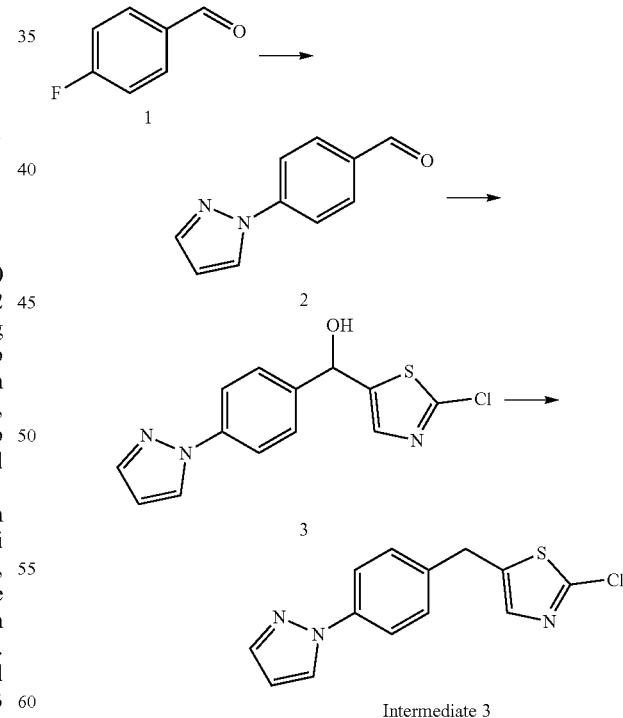

Intermediate 3

1. To a solution of 1 (10 g, 80.6 mmol) in dry DMF (100 mL) were added pyrazole (5.5 g, 80.6 mmol) and $K_2CO_3$ (12.2 g, 88.7 mmol). The resulting mixture was stirred at 100° C. overnight. After cooling to RT, the mixture was treated with water and extracted with EA. The organic extracts were washed with water, brine, dried over anhydrous $Na_2SO_4$, filtered and the filtrate concentrated to give a crude oil. The crude product was purified by recrystallization to afford 2 (4 g, 29%). $^1$HNMR (CDCl$_3$, 300 MHz) δ: 6.5-6.6 (s, 1H), 7.7-7.8 (s, 1H), 7.9-8.0 (d, 2H), 8.0-8.1 (d, 2H), 8.1-8.2 (s, 1H), 10.0-10.1 (s, 1H).

2. To a solution of 2-chlorothiazole (1.45 g, 12.1 mmol) in dry THF (10 mL) at −78° C. under $N_2$ was added n-BuLi (5 mL, 12.1 mmol) dropwise. After 1 h a solution of 2 (1.6 g, 9.3 mmol) was added dropwise at −78° C. The resulting solution was slowly warmed to RT. The reaction was diluted with $NH_4Cl$ solution and extracted with EA. The organic extracts were concentrated to give a crude oil. The crude product was purified by silica gel chromatography to afford 3 (1.2 g, 50%). $^1$HNMR (CDCl$_3$, 300 MHz) δ: 6.1-6.2 (s, 1H), 6.5-6.6 (s, 1H), 7.2-7.3 (s, 1H), 7.4-7.5 (d, 2H), 7.6-7.7 (d, 2H), 7.7-7.8 (s, 1H), 7.9-8.0 (s, 1H).

3. To a solution of 3 (1.2 g, 4.1 mmol) in DCE (20 mL) was added TES-H (1.4 g, 12.8 mmol), the mixture cooled to 0° C. and TFA (4.7 g, 41 mmol) was added dropwise. The resulting solution was stirred at 60° C. for 4 h. The residue was concentrated and purified by silica gel chromatography to afford Intermediate 3 (1 g, 91%). $^1$HNMR (CDCl$_3$, 300 MHz) δ: 4.1-4.2 (s, 2H), 6.4-6.5 (s, 1H), 7.2-7.4 (m, 3H), 7.6-7.8 (m, 3H), 7.9-8.0 (s, 1H).

Alternate Preparation of Intermediate 3

1. To a solution of 2-chlorothiazole (3.85 g, 32.3 mmol) in dry THF (80 mL) at −78° C. under $N_2$ was added n-BuLi (14.3 mL, 35.5 mmol) dropwise. After 1 h a solution of 2 (5.0 g, 29.1 mmol) in THF (40 mL) was added dropwise at −78° C. The resulting solution was slowly warmed to RT. The reaction was diluted with $NH_4Cl$ solution and extracted with EtOAc. The organic extracts were concentrated to give a crude oil. The crude product was purified by silica gel chromatography to afford 3 as light brown oil (5.9 g, 69.7%).

2. To a solution of 3 (5.9 g, 20.3 mmol) in DCE (20 mL) was added TES-H (7.06 g, 60.9 mmol), the mixture cooled to 0° C. and TFA (22.8 g, 0.2 mol) was added dropwise. The resulting solution was stirred at 60° C. for 4 h. The residue was concentrated and purified by silica gel chromatography to afford Intermediate 3 as white solid (4.84 g, 86.9%).

Alternate Preparation of Intermediate 3

1. A mixture of 4-bromobenzaldehyde (100.0 g, 540 mmol), 1H-pyrazole (37 g, 540 mmol), $Cs_2CO_3$ (194 g, 594 mmol), CuI (10.3 g, 54 mmol), 18-Crown-6 (11 g, 41 mmol) in DMF (500 mL) was stirred under e at 80° C. for 24 hours. After cooling to room temperature, ice-water was added to the mixture which was extracted with EA. The organic extracts were washed with water, brine and dried over $Na_2SO_4$, filtered and concentrated. The resulting residue was purified by column chromatography on silica gel to afford 2 (76 g, 81.7% yield) as a white solid. MS (ESI): mass calcd. for $C_{10}H_8N_2O$ 172.18, m/z found 173.0 [M+H]$^+$.

2. To a solution of 2-chlorothiazole (54.2 g, 0.45 mol) in dry (550 mL) at −78° C. was added n-BuLi (187.5 mL, 2.4 M, 0.45 mol) dropwise. The mixture was stirred for 1 hour at −78° C. and a solution of 2 (65 g, 0.38 mol) in THF (700 mL) was added dropwise at −78° C. The resulting solution was allowed to slowly warm to room temperature. The reaction mixture was quenched with sat. aq. $NH_4Cl$ and extracted with EA. The organic extracts were washed with brine and dried over s$Na_2SO_4$, filtered and concentrated. The resulting residue was purified by column chromatography on silica gel to give 3 (90 g, 82.6% yield) as a yellow solid. MS (ESI): mass calcd. for $C_{13}H_{10}ClN_3OS$ 291.76, m/z found 291.7 [M+H]$^+$.

3. To a solution of 3 (66 g, 0.23 mol) in TFA (330 mL) was added TES (148 g, 0.9 mol) at room temperature. The reaction mixture was stirred at reflux for 1 h. The mixture was evaporated and the mixture was diluted with EA. The resulting mixture was washed with sat. $NaHCO_3$, brine and dried over $Na_2SO_4$, filtered and concentrated. The resulting residue was purified by column chromatography on silica gel to give Intermediate 3 (55 g, 88.7% yield) as a yellow solid. MS (ESI): mass calcd. for C13H10ClN3S 275.76, m/z found 275.8 [M+H]$^+$.

Preparation of Intermediate 4

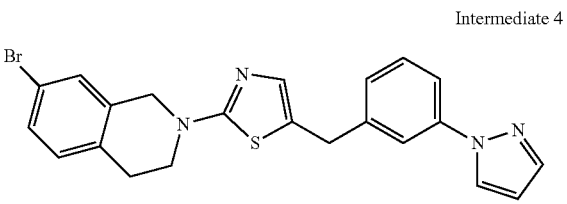 [SMILES: Brc1ccc2c(c1)CN(c1ncc(Cc3cccc(-n4cccn4)c3)s1)CC2]

Intermediate 4

1. A mixture of 7-bromo-1,2,3,4-tetrahydroisoquinoline hydrochloride (Key Organics, 250 mg, 1 mmol), Intermediate 2 (276 mg, 1 mmol) and $K_2CO_3$ (414 mg, 3 mmol) in DMSO (5 mL) was stirred at 140° C. for 2 hrs. Then it was cooled to RT, poured into water, neutralized with 3N HCl, extracted with EtOAc. The combined organic phase was washed with brine, dried over $Na_2SO_4$, filtered, concentrated and the resulting residue purified by chromatography on silica gel to give Intermediate 4 (200 mg, 44% yield) as a yellow-white solid. MS (ESI): mass calcd. for $C_{22}H_{19}BrN_4S$ 451.39, m/z found 450.7 452.7 [M+H]$^+$.

Preparation of Intermediate 5

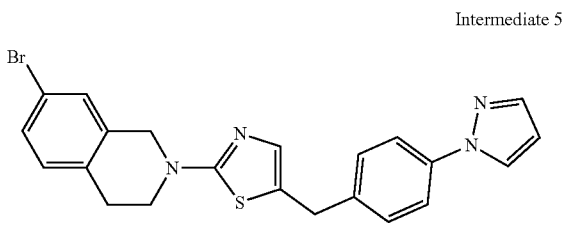 [SMILES: Brc1ccc2c(c1)CN(c1ncc(Cc3ccc(-n4cccn4)cc3)s1)CC2]

Intermediate 5

1. A mixture of Intermediate 3 (1.0 g, 3.6 mmol), $Cs_2CO_3$ (3.5 g, 10.8 mmol) and 7-bromo-1,2,3,4-tetrahydroisoquinoine (Key Organics, 848 mg, 4.0 mmol) in DMSO (25 mL) was stirred under nitrogen atmosphere at 140° C. for 2 h. After cooling to RT, ice-water was added to the mixture which was then extracted with EtOAc. The organic extracts were washed with water, brine and dried over $Na_2SO_4$, filtered, concentrated. The resulting residue was purified by column chromatography on silica gel to give Intermediate 5 (1.0 g, 61.3% yield) as a yellow solid. MS (ESI): mass calcd. for C22H19BrN4S 451.38, m/z found 450.7 [M+H]$^+$.

Preparation of Intermediate 6

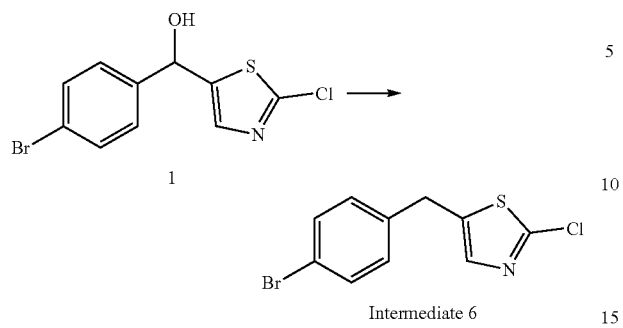

Intermediate 6

1. To a solution of 2-chlorothiazole (5.76 g, 48 mmol) in dry THF (40 mL) at −78° C. under $N_2$ was added n-BuLi (2.4M, 20.0 mL, 48 mmol) dropwise. After 1 h, a solution of 4-bromobenzaldehyde (7.40 g, 40 mmol) in THF (40 mL) was added dropwise. The mixture was slowly warmed to RT and stirred overnight. The mixture was quenched with sat. aq. $NH_4Cl$ and extracted with EtOAc. The combined extracts were washed with brine, dried over $Na_2SO_4$, filtered, concentrated and the resulting residue purified by chromatography on silica gel to give 1 (8.00 g, 66% yield) as a yellow oil. MS (ESI): mass calcd. for $C_{10}H_7BrClNOS$ 304.59, m/z found 305.7 $[M+H]^+$.

2. A mixture of 1 (8.00 g, 26.4 mmol) and TES (18 mL) in TFA (50 mL) was stirred at RT for 2 hrs, concentrated and the residue was diluted with sat. aq. $NaHCO_3$. The mixture was extracted with DCM and the combined organic extracts were washed with brine, dried over $Na_2SO_4$, filtered, concentrated and the residue purified by chromatography on silica gel to give Intermediate 6 (7.20 g, 94.7% yield) as a brown oil. MS (ESI): mass calcd. for $C_{10}H_7BrClNS$ 288.59, m/z found 289.6 $[M+H]^+$.

Preparation of Intermediate 7

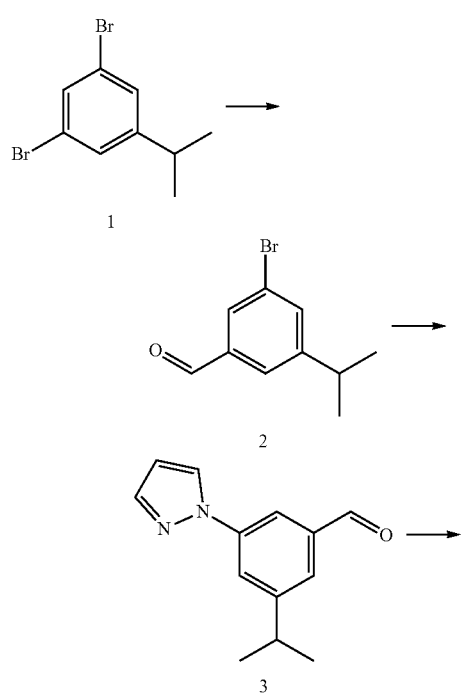

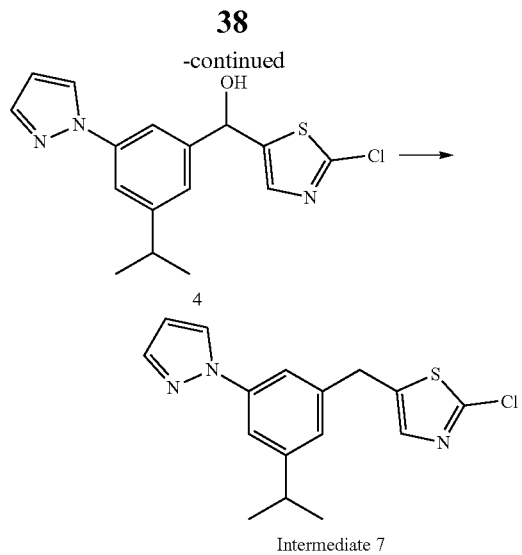

Intermediate 7

1. To a solution of 1 (20 g, 71.9 mmol) in dry THF (100 mL) at −78° C. was added n-BuLi (31.7 mL, 79.1 mmol) dropwise under $N_2$. After 1 h DMF (1.66 g, 79.1 mmol) was added dropwise at −78° C. The resulting solution was allowed to slowly warm to RT. The reaction was quenched with $NH_4Cl$ solution and extracted with EA. The combined extracts were concentrated to give a crude oil. The crude product was purified by silica gel chromatography to afford 2 (12 g, 73.5%).

2. To a solution of 2 (12 g, 52.9 mmol) in dry DMF (200 mL) were added 1H-pyrazole (4.0 g, 58.1 mmol), $Cs_2CO_3$ (19 g, 58.1 mmol), CuI (1.2 g), 18-Crown-6 (1.2 g) and the resulting mixture was stirred at 80° C. for 24 h. The mixture was cooled to RT, diluted with with water and extracted with EA. The combined organic layer was washed with water, brine, dried over anhydrous $Na_2SO_4$, filtered and concentrated to give a crude oil. The crude product was purified by recrystallization to afford 3 (7.3 g, 64.5%).

3. To a solution of 2-chlorothiazole (4.47 g, 37.5 mmol) in dry THF (100 mL) at −78° C. under $N_2$ was added n-BuLi (15 mL, 37.5 mmol) dropwise. After 1 h a solution of 3 (7.3 g, 34.1 mmol) was added dropwise at −78° C. The resulting mixture was allowed to slowly warm to RT. The reaction was quenched with $NH_4Cl$ solution and extracted with EA. The organic layer was concentrated to give a crude oil. The crude product was purified by silica gel chromatography to afford 4 (4.6 g, 40.3%).

4. To a solution of 4 (4.6 g, 13.8 mmol) in DCE (40 mL) at 0° C. was added TFA (10.4 mL, 138 mmol), TES (6.6 mL, 41.3 mmol) slowly. The resulting solution was stirred at RT for 3 h. The reaction was quenched with $H_2O$ and extracted with DCM. The combined extracts were concentrated to give a crude oil and which was purified by silica gel chromatography to afford Intermediate 7 (1.8 g, 41.1%). $^1$HNMR (CDCl$_3$, 300 MHz) δ: 1.2-1.3 (d, 6H), 2.9-3.0 (m, 1H), 4.1-4.2 (s, 2H), 6.4-6.5 (s, 1H), 7.0 (s, 1H), 7.3-7.4 (d, 2H), 7.4-7.5 (s, 1H), 7.7-7.8 (s, 1H), 7.9-8.0 (s, 1H).

Preparation of Intermediate 9

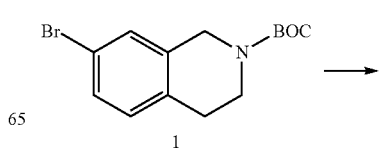

39
-continued

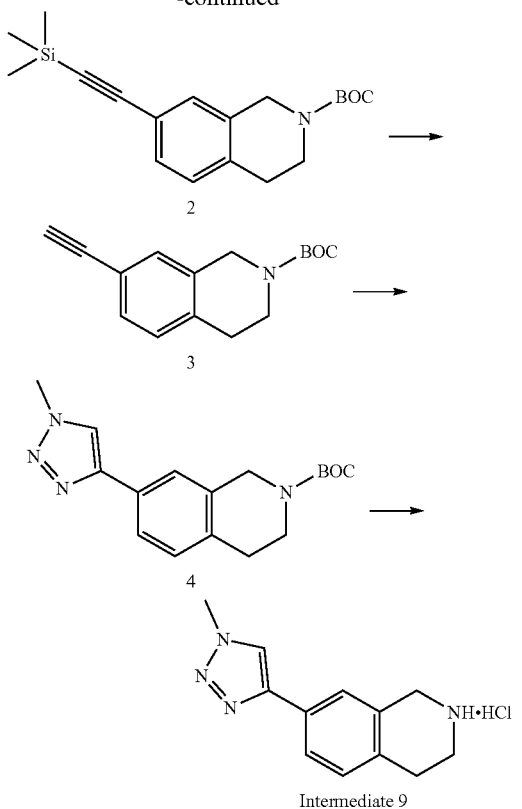

Intermediate 9

1. A mixture of 1 (Key Organics, 500 mg, 1.60 mmol), ethynyltrimethylsilane (236 mg, 2.40 mmol), Pd(PPh₃)₂Cl₂ (140 mg, 0.20 mmol), CuI (60.8 mg, 0.32 mmol) and Et₃N (485 mg, 4.80 mmol) in dry DMF (5.00 mL) was stirred at 60° C. for 1 h. The reaction was quenched with water and extracted with EtOAc. The combined organic layers were washed with water and brine, dried over Na₂SO₄ and concentrated to give a crude product which was purified by silica gel chromatography to afford 2 (494 mg, 94% yield) as a yellow oil.

2. To a solution of 2 (494 mg, 1.50 mmol) in THF was added TBAF (1 M in THF, 10 mL) and stirred at RT for 6 h. The mixture was poured into water and extracted with EtOAc. The combined organic layers were washed with water and brine, dried over Na₂SO₄ and concentrated. The residue was purified by silica gel column chromatography (petrol ether/EtOAc=20/1) to give 3 (280 mg, 73%) as a yellow solid.

3. A mixture of 3 (280 mg, 1.09 mmol), iodomethane (155 mg, 1.09 mmol), NaN₃ (84.5 mg, 1.30 mmol), CuI (207 mg, 1.09 mmol), t-BuOH (658 mg, 8.89 mmol) and H₂O (1.96 g, 109 mmol) was stirred in sealed tube at 100° C. overnight. The mixture was cooled, quenched with water and extracted with EtOAc. The combined organic layers were washed with water and brine, dried over Na₂SO₄ and concentrated to give a crude product, which was purified by silica gel column chromatography to afford 4 (171 mg, 50% yield) as a colorless solid.

4. A mixture of 4 (171 mg, 0.54 mmol), HCl-dioxane (4 M, 3.00 mL, 12.0 mmol) and DCM (3.00 mL) was stirred at RT for 2 h. The mixture was concentrated to give Intermediate 9 (100 mg, 74% yield) as an off-white solid.

40
Alternate Preparation of Intermediate 9

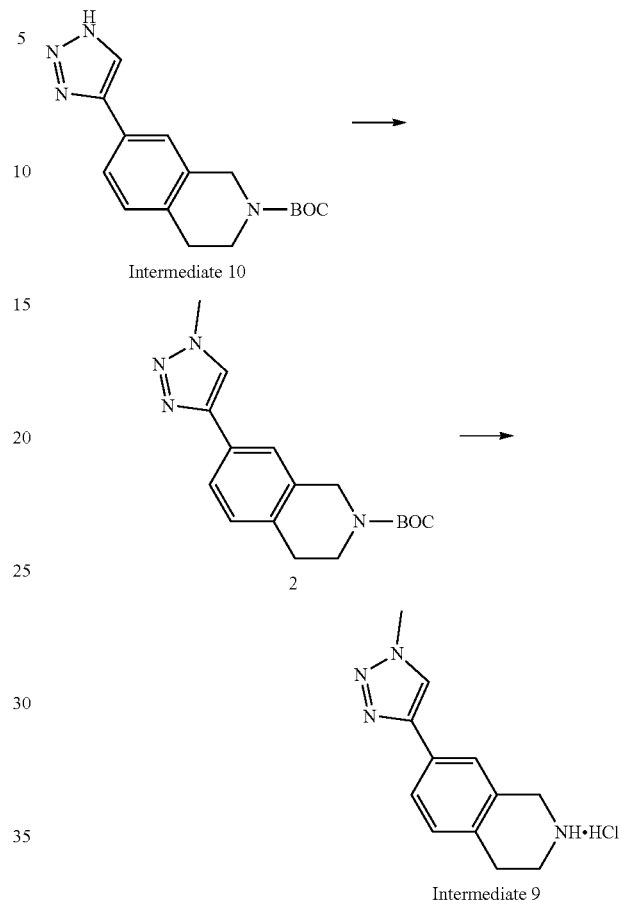

1. To a solution of Intermediate 10 (2.5 g, 8.3 mmol) in DMF (20 mL) at 0° C. was added K₂CO₃ (2.3 g, 16.6 mmol). The resulting mixture was stirred at 0° C. for 2 h and MeI (2.6 mL) was added and the mixture stirred at RT for 4 h. The mixture was treated with water and extracted with EA. The combined extracts were washed with water, brine, dried over anhydrous Na₂SO₄, filtered and concentrated to give a crude oil. The crude product was purified by silica gel to afford 2 (1.4 g, 54%).

2. To a solution of 2 (1.4 g) in dry DCM (20 mL) at 0° C. was added HCl/Ether (5 mL, 3 M). The resulting solution was allowed to slowly warm to RT and stirred overnight. The reaction was concentrated to afford Intermediate 9 (1 g, 78%)

Preparation of Intermediate 10

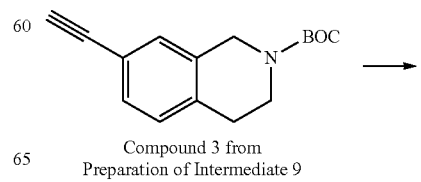

Compound 3 from
Preparation of Intermediate 9

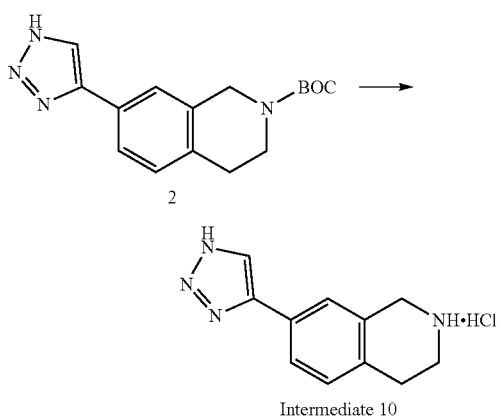

Intermediate 10

1. To a solution of compound 3 from Preparation of Intermediate 9 (4.6 g, 17.9 mmol) in DMSO (40 mL) was added NaN$_3$ (1.4 g, 21.5 mmol) and NH$_4$Cl (1.44 g, 26.8 mmol). The resulting solution was stirred at 70° C. overnight. The mixture was treated with water and extracted with EA. The combined extracts were washed with water, brine, dried over anhydrous Na$_2$SO$_4$, filtered and concentrated to give a crude oil. The crude product was purified by silica gel to afford 2 (3.4 g, 62.2%).

2. To a solution of 2 (3.4 g) in dry DCM (20 mL) at 0° C. was added HCl/Ether (10 mL, 3 M). The resulting solution was allowed to slowly warm to RT and stirred overnight. The reaction was concentrated to afford Intermediate 10 (1.76 g, 57.1%).

Preparation of Intermediate 11

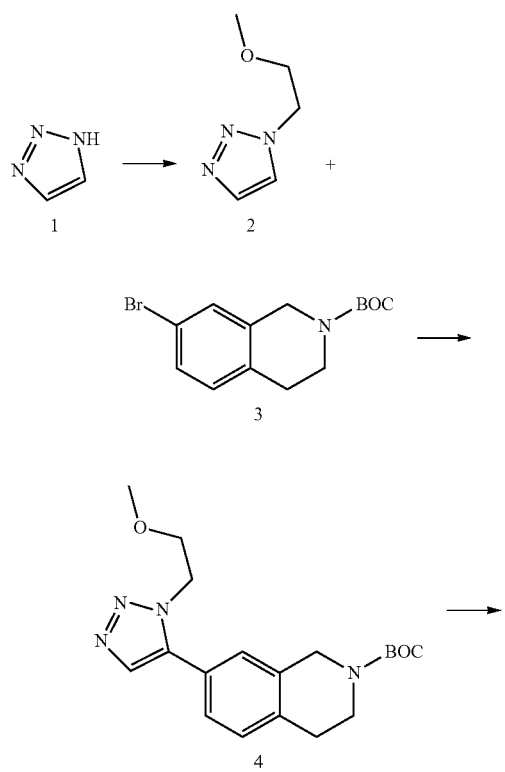

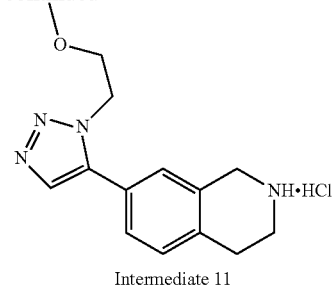

Intermediate 11

1. To a slurry of 1 (1 g, 15 mmol) and K$_2$CO$_3$ (3.1 g, 22.5 mmol) in MeCN (10 mL) was added a solution of 1-bromo-2-methoxyethane (2.5 g, 18 mmol) in MeCN (10 mL) over 3 min. The reaction mixture was stirred at RT for 2 h. The mixture was filtered and the filtrate was concentrated. The residue was purified by silica gel chromatography to afford 2 as yellow oil (0.66 g, 35%).

2. To a solution of 3 (Key Organics, 312 mg, 1 mmol) in DMF (6 mL) was added 2 (127 mg, 1 mmol), Pd(OAc)$_2$ (11 mg, 0.05 mmol), XPhos (48 mg, 0.1 mmol) and K$_2$CO$_3$ (276 mg, 2 mmol). The mixture was heated to 100° C. under N$_2$ and stirred for 20 h. The reaction was quenched with water and extracted with EtOAc. The combined extracts were concentrated and the residue was purified by silica gel chromatography to afford 4 as yellow oil (0.108 g, 30%).

3. To a solution of 4 (108 mg, 0.3 mmol) in MeOH (10 mL) was added HCl/Dioxane (4 mL, 16 mmol). The mixture was stirred at RT for 3 h. The mixture was concentrated to give Intermediate 11 (100 mg, 100%).

Preparation of Intermediate 12

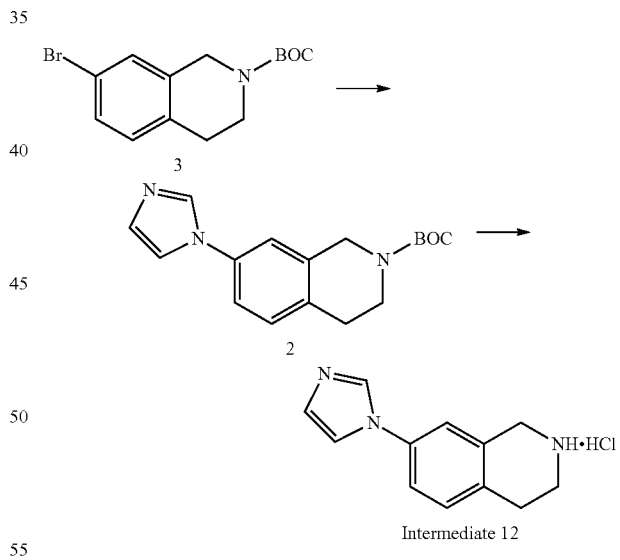

Intermediate 12

1. To a solution of 1 (Key Organics, 160 mg, 0.5 mmol) in DMF (3 mL) was added Cs$_2$CO$_3$ (165 mg, 0.5 mmol), imidazole (68 mg, 1 mmol), CuI (10 mg, 0.05 mmol). The mixture was heated to 100° C. and stirred for 20 h under N$_2$. The mixture was poured into water and extracted with EtOAc. The extracts were washed with water, brine, and dried over Na$_2$SO$_4$, filtered and concentrated to give 2 (168 mg, 90%).

2. A mixture of 2 (160 mg, 0.53 mmol) and HCl/Dioxane (3 mL, 12 mmol) was stirred at RT for 2 h. The mixture was concentrated to afford Intermediate 12 (106 mg, 90%).

Preparation of Intermediate 13

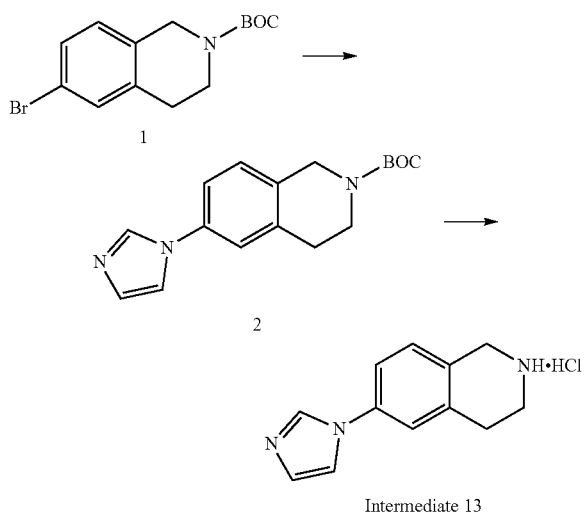

Intermediate 13

1. Intermediate 13 was prepared following the procedure described for Intermediate 12 except 2-N-BOC-6-bromo-1,2,3,4-tetrahydroisoquinoline 1 (Bioorg. & Med. Chem. Lett. 2018, 28, 3050) was used in place of 2-N-BOC-7-bromo-1,2,3,4-tetrahydroisoquinoline.

Preparation of Intermediate 14

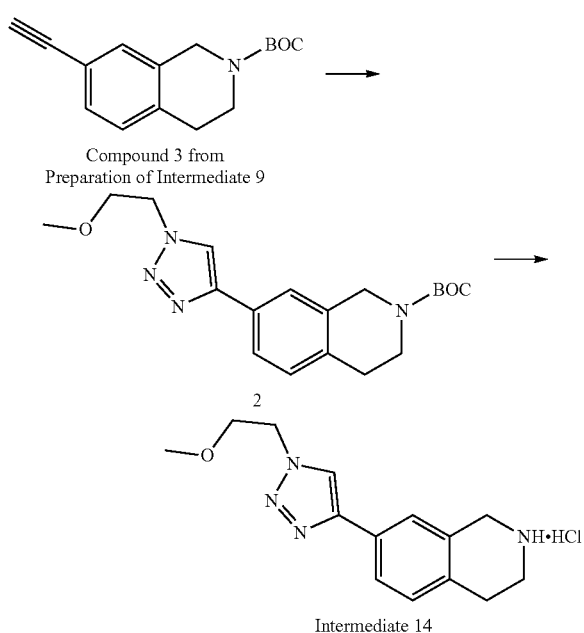

Intermediate 14

1. A mixture of compound 3 from Preparation of Intermediate 9 (650 mg, 2.53 mmol), 1-iodo-2-methoxyethane (471 mg, 2.53 mmol), NaN$_3$ (164 mg, 2.53 mmol), CuI (482 mg, 2.53 mmol), t-BuOH (748 mg, 10.1 mmol) and H$_2$O (5.00 g, 278 mmol) was stirred at 100° C. in a sealed tube overnight. The mixture was cooled to RT and extracted with EtOAc. The combined organic layers were washed with water, brine, dried over Na$_2$SO$_4$ and concentrated to give a crude product which was purified by silica gel chromatography to afford 2 (350 mg, 39%) as an off-white solid.

2. A mixture of 2 (350 mg, 0.98 mmol), HCl-dioxane (4 M, 5 mL, 20.0 mmol) and CH$_2$Cl$_2$ (10 mL) was stirred at RT for 2 h. The mixture was concentrated to give Intermediate 14 (260 mg, 90%) as a white solid Preparation of Intermediate 15

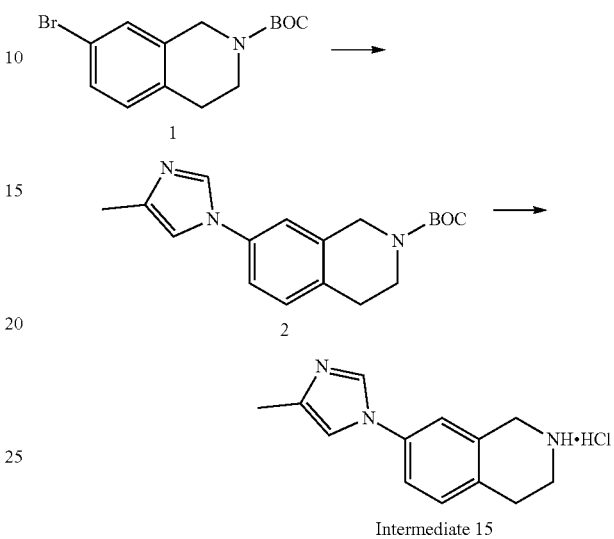

Intermediate 15

1. A mixture of 1 (Key Organics, 1.00 g, 3.20 mmol), (S,S)—N,N'-dimethyl-1,2-diaminocyclohexane (91.0 mg, 0.64 mmol), 4-methyl-1H-imidazole (525 mg, 6.39 mmol), CuI (304 mg, 1.60 mmol) and t-BuOK (1.07 g, 9.60 mmol) in DMF (5 mL) was stirred at 120° C. for 4 h. After cooling to RT, the mixture was directly purified by prep-HPLC to give 2 (320 mg, 31% yield) as an off-white solid.

2. A mixture of 2 (220 mg, 0.70 mmol), HCl-dioxane (4 M, 3.00 mL, 12.0 mmol) and CH$_2$Cl$_2$ (3 mL) was stirred at RT for 2 h. The mixture was concentrated to give Intermediate 15 (150 mg, 86% yield) as an off-white solid.

Preparation of Intermediate 16

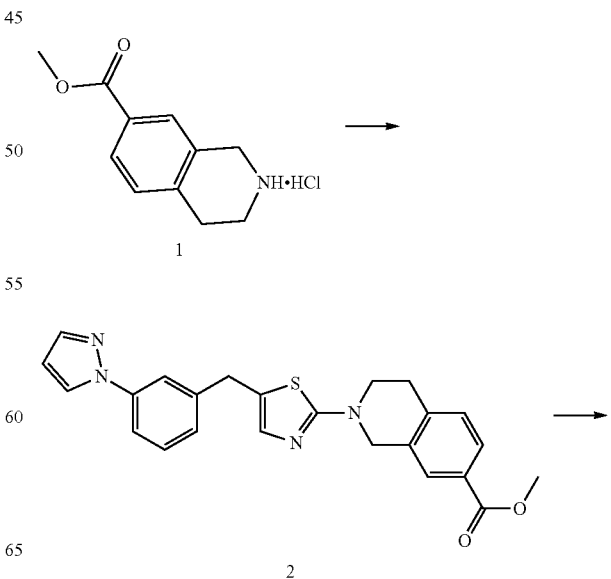

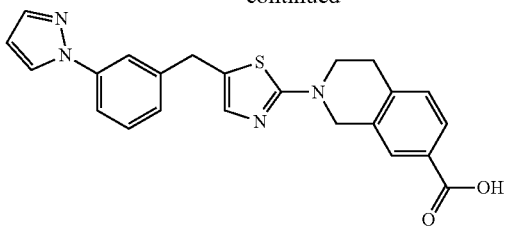

3

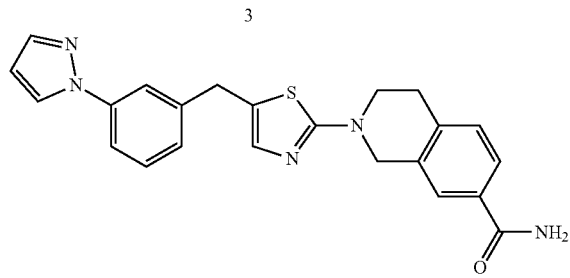

Intermediate 16

1. A mixture of 1 (J. Med. Chem. 42, 1, 118-134, 750 mg), Intermediate 2 (908 mg, 3.29 mmol), Pd$_2$(dba)$_3$ (290 mg, 0.33 mmol), SPhos (132 mg, 0.33 mmol), t-BuOK (750 mg, 6.70 mmol) and dioxane (10 mL) was stirred at 100° C. for 4 h. The mixture was quenched with water and extracted with EtOAc. The combined organic extracts were washed with water and brine, dried over Na$_2$SO$_4$, and concentrated. The residue was purified by column chromatography to give 2 (550 mg, 37% yield for 2 steps) as a yellow solid.

2. A mixture of 2 (550 mg, 1.28 mmol), LiOH (61.0 mg, 2.56 mmol), MeOH (3 mL) and H$_2$O (3 mL) was stirred at RT for 3 h. The mixture was acidified with 2 N HCl to pH 4-5 which resulted in a precipitate. The precipitate was filtered, washed with water and dried to give 3 (170 mg, 32% yield) as an off-white solid.

3. A mixture of 3 (170 mg, 0.41 mmol), HATU (250 mg, 0.62 mmol), DIEA (280 mg, 2.17 mmol), NH$_4$Cl (134 mg, 2.5 mmol) and DMF (2 mL) was stirred at RT for 4 h. The mixture was quenched with water and extracted with EtOAc. The combined organic extracts were washed with water and brine, dried over Na$_2$SO$_4$, and concentrated. The residue was purified by prep-TLC to give Intermediate 16 (130 mg, 76% yield) as a yellow solid.

Preparation of Intermediate 17

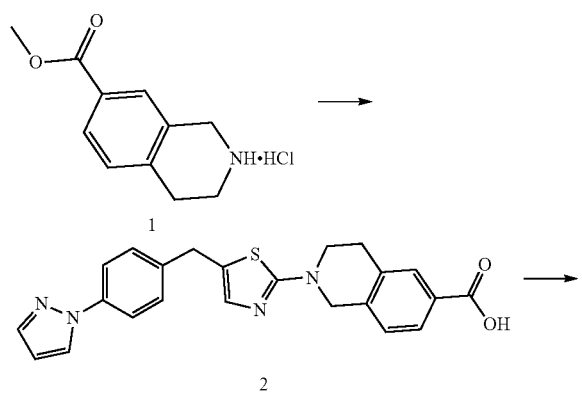

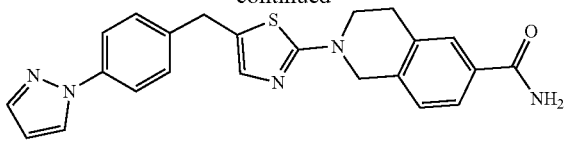

Intermediate 17

1. To a solution of 1 (J. Med. Chem. 42, 1, 118-134, 227 mg, 1 mmol) in dioxane (20 mL) was added Intermediate 3 (300 mg, 1.1 mmol), Pd$_2$(dba)$_3$ (72 mg, 0.08 mmol), SPhos (65 mg, 0.16 mmol) and t-KOBu (340 mg, 3 mmol). The mixture was heated to 100° C. and stirred for 20 h under N$_2$. the mixture was cooled to RT and LiOH (0.4 g, 10 mmol) and water (4 mL) were added. The resulting mixture was stirred at 60° C. for 2 h, cooled, acidified with 1 N HCl to pH 5. The resulting mixture was extracted with EtOAc and the organic extracts were concentrated to give a crude oil. The crude product was purified by silica gel chromatography to afford 2 as pale yellow solid (0.31 g, 74%).

2. To a solution of 2 (50 mg, 0.12 mmol) in DMF (2 mL) was added DIEA (25 mg, 0.18 mmol), HATU (0.69 g, 0.18 mmol) and NH$_4$Cl (7.1 mg, 0.13 mmol). The mixture was stirred at RT for 1 h. The mixture was treated with water and extracted with EtOAc. The organic extracts were washed with water, brine, dried over anhydrous Na$_2$SO$_4$, filtered and concentrated to give a crude oil. The crude product was purified by silica gel chromatography to afford Intermediate 17 as white solid (11.2 mg, 22.4%).

Preparation of Intermediate 18

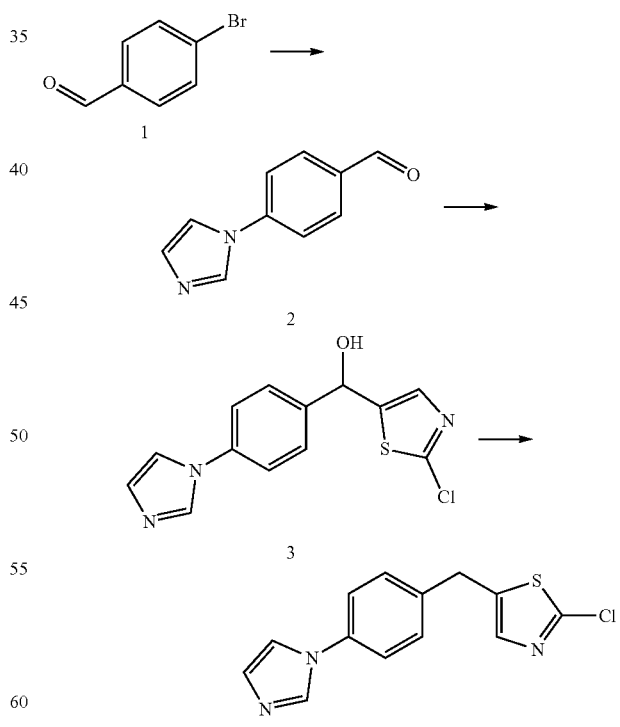

Intermediate 18

1. To a solution of 1 (20 g, 108.1 mmol) in dry DMF (200 mL) were added 1H-imidazole (8.1 g, 118.9 mmol), Cs$_2$CO$_3$ (38.7 g, 118.9 mmol), CuI (2 g), 18-Crown-6 (2 g). The resulting solution was stirred at 80° C. for 24 h. The mixture was cooled to RT, treated with water and extracted with EA. The combined extracts were washed with water, brine, dried over anhydrous Na$_2$SO$_4$, filtered and concentrated to give a crude oil. The crude product was purified by recrystallization to afford 2 (11 g, 59.2%).

2. To a solution of 2-chlorothiazole (3.8 g, 32 mmol) in dry THF (50 mL) was added n-BuLi (14 mL, 34.9 mmol) dropwise at −78° C. under N$_2$. After 1 h a solution of 2 (5 g, 29.1 mmol) was added dropwise at −78° C. The resulting solution was allowed to slowly warm to RT. The reaction was quenched with NH$_4$Cl solution and extracted with EA. The combined extracts were concentrated to give a crude oil. The crude product was purified by silica gel chromatography to afford 3 (3.5 g, 41.4%).

3. To a solution of 3 (3.5 g, 12.0 mmol) in DCE (60 mL) at 0° C. was slowly added TFA (9 mL, 120 mmol) and TES (5.8 mL, 36 mmol). The resulting solution was stirred at RT for 3 h. The reaction was quenched with H$_2$O and extracted with DCM. The organic layer was concentrated to give a crude oil and purified by silica gel chromatography to afford Intermediate 18 (1.8 g, 54.4%).

Preparation of Intermediate 19

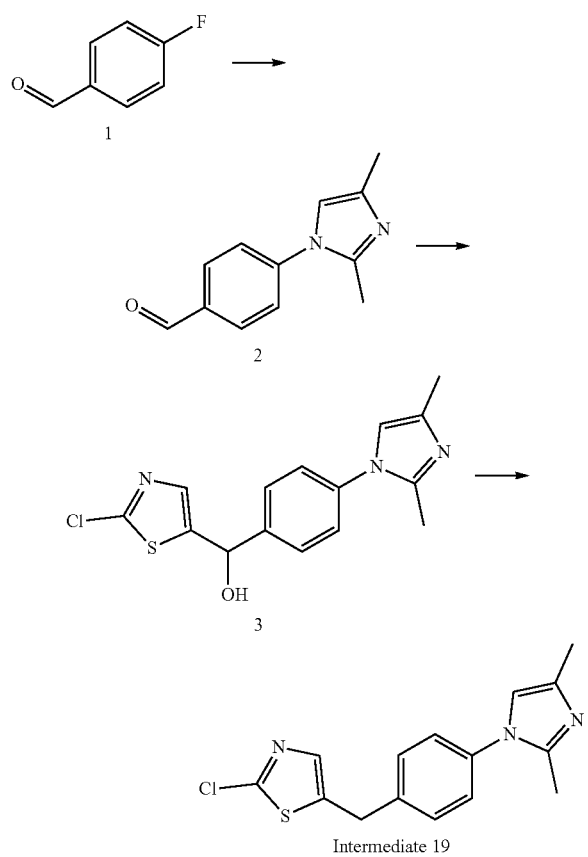

Intermediate 19

1. To a solution of 1 (6.20 g, 50 mmol) and 2,4-dimethyl-1H-imidazole (7.20 g, 75 mmol) in DMF (100 mL) was added Cs$_2$CO$_3$ (48.70 g, 150 mmol). The resulting mixture was stirred at 120° C. for 2 hrs. It was cooled to RT, filtered and the filtrate was poured into water, extracted with CH$_2$Cl$_2$, the combined organic phase was washed with brine, dried over Na$_2$SO$_4$, filtered, concentrated. The residue was purified by chromatography on silica gel, to give 2 (1.80 g, 18% yield) as a brown oil. MS (ESI): mass calcd. for C$_{12}$H$_{12}$N$_2$O 200.24, m/z found 200.9 [M+H]$^+$.

2. To a solution of 2-chlorothiazole (1.20 g, 10 mmol) in THF (20 mL) at −78° C. was added n-BuLi (2.4 M, 5.5 mL) under N$_2$ dropwise. After 1 h, a solution of 2 (1.80 g, 9 mmol) in THF (20 mL) was added dropwise. The reaction was slowly warmed to RT and stirred overnight. The mixture was quenched with sat. aq. NH$_4$Cl and extracted with EtOAc, the combined organic phase was washed with brine, dried over Na$_2$SO$_4$, filtered, concentrated. The residue was purified by chromatography on silica gel to give 3 (1.83 g, 64% yield) as a yellow oil. MS (ESI): mass calcd. for C$_{15}$H$_{14}$ClN$_3$OS 319.81, m/z found 319.8 [M+H]$^+$.

3. A mixture of 3 (1.83 g, 5.7 mmol), TES (9 mL) in TFA (18 mL) was stirred at 60° C. for 3 hrs. Then it was concentrated and the residue was diluted with sat. aq. NaHCO$_3$ and extracted with CH$_2$Cl$_2$, the combined organic phase was washed with brine, dried over Na$_2$SO$_4$, filtered, concentrated and the residue purified by chromatography on silica gel to give Intermediate 19 (1.20 g, 69.0% yield) as a brown oil. MS (ESI): mass calcd. for C$_{15}$H$_{14}$ClN$_3$S 303.81, m/z found 303.8 [M+H]$^+$.

Preparation of Intermediate 20

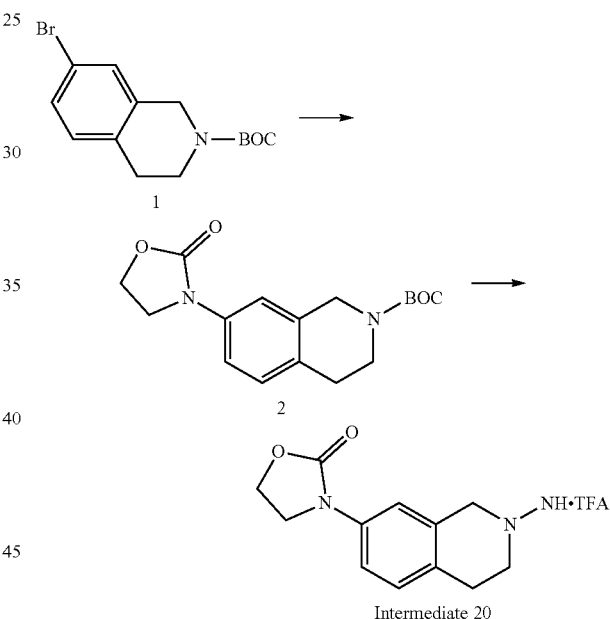

Intermediate 20

1. A mixture of 1 (Key Organics, 5.68 g, 0.018 mol), oxazolidin-2-one (4.7 g, 0.054 mol), Pd$_2$(dba)$_3$ (8.23 g, 0.009 mol), S-phos (3.69 g, 0.009 mol) and t-BuOK (6.0 g, 0.054 mol) in dried 1,4-dioxane (150 mL) was stirred at 100° C. overnight. The reaction mixture was cooled to RT, filtered and concentrated to afford crude product. The residue was purified by silica gel chromatography to afford 2 (5.02 g, 88% yield) as a yellow solid. MS (ESI): mass calcd. for C$_{17}$H$_{22}$N$_2$O$_4$ 318.37, m/z found 340.8 [M+H]$^+$.

2. To a solution of 2 (5.02 g, 16 mmol) in DCM (100 mL) was added TFA (25 mL). The reaction was stirred at RT for 6 h. Then the reaction concentrated to afford a crude product. It was dissolved with DCM and diluted with petroleum ether. The resulting suspension was filtered and the filter cake was washed with petroleum ether and dried to afford Intermediate 20 (3.50 g, 70%), MS (ESI): mass calcd. for C$_{14}$H$_{15}$F$_3$N$_2$O$_3$ 316.28, m/z found 218.9 [M+H]$^+$.

Preparation of Intermediate 21

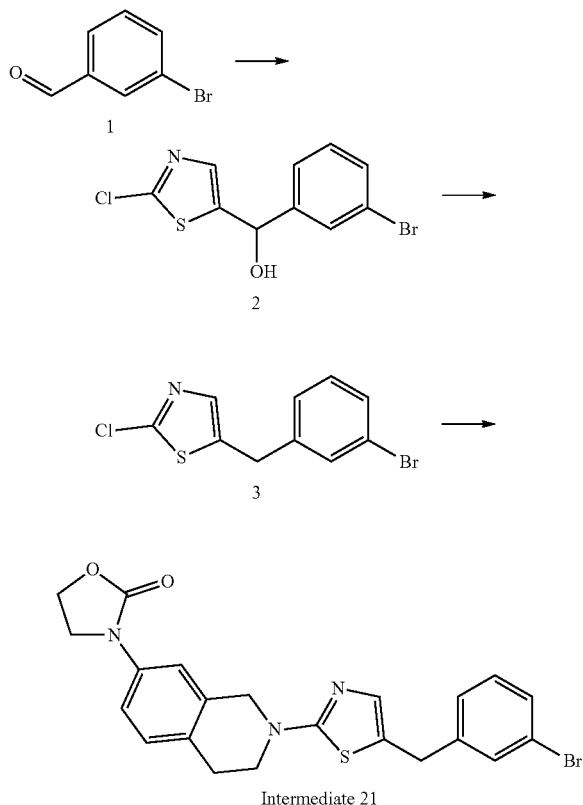

Intermediate 21

1. To a solution of 2-chlorothiazole (5.76 g, 48 mmol) in dry THF (200 mL) at −78° C. was added n-BuLi (2.4M, 25.0 mL, 60 mmol) dropwise under $N_2$. After 0.5 h, a solution of 1 (8.00 g, 43 mmol) in THF (50 mL) was added dropwise. The reaction was slowly warmed up to RT. The mixture was quenched with sat. aq. $NH_4Cl$ and extracted with EtOAc and the combined organic phase was washed with brine, dried over $Na_2SO_4$, filtered, concentrated to give a crude product which was purified by chromatography on silica gel to afford 2 (8.50 g, 64% yield) as a yellow oil. MS (ESI): mass calcd. for $C_{10}H_7BrClNOS$ 304.59, m/z found 305.7 $[M+H]^+$.

2. A mixture of 2 (8.50 g, 27.9 mmol) in TES (20 mL) and TFA (60 mL) was stirred at 60° C. for 2 h. The mixture was concentrated and the residue was diluted with sat. aq. $NaHCO_3$ and extracted with DCM and the combined organic phase was washed with brine, dried over $Na_2SO_4$, filtered, concentrated to give a crude product which was purified by chromatography on silica gel to afford 3 (7.00 g, 86.9% yield) as a brown oil. MS (ESI): mass calcd. for $C_{10}H_7BrClNS$ 288.59, m/z found 289.6 $[M+H]^+$.

3. To a solution of 3 (3.00 g, 10.4 mmol) in DMSO (30 mL) was added Intermediate 20 (3.45 g, 10.4 mmol) and $K_2CO_3$ (4.31 g, 31.2 mmol). The reaction mixture was stirred at 140° C. for 3 hrs. The reaction was cooled to RT, poured into ice-water, extracted with $CH_2Cl_2$, the combined organic phase was washed with brine, dried over $Na_2SO_4$, filtered, concentrated and purified by chromatography on silica gel to afford Intermediate 21 (2.10 g, 42.9% yield) as a yellow solid. MS (ESI): mass calcd. for $C_{22}H_{20}BrN_3O_2S$ 470.39, m/z found 470.5 $[M+H]^+$.

Preparation of Intermediate 22

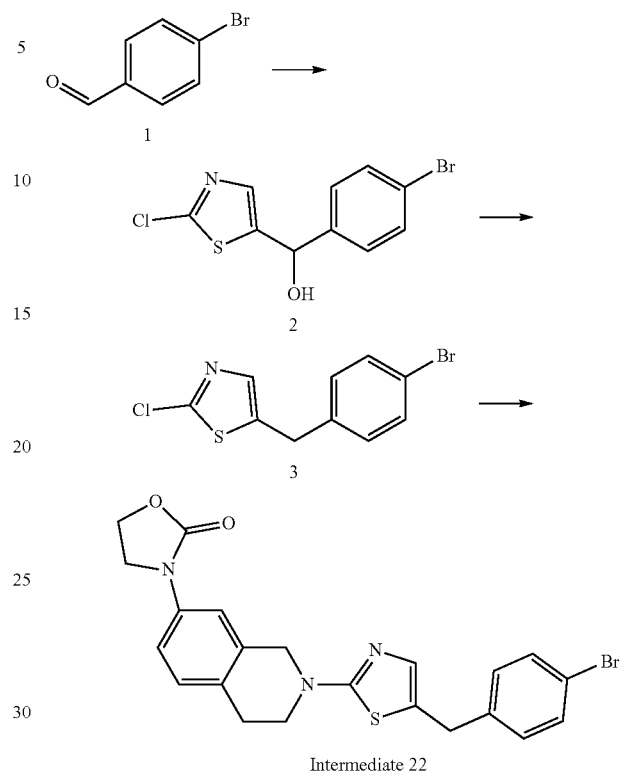

Intermediate 22

1. To a solution of 2-chlorothiazole (5.76 g, 48 mmol) in dry THF (40 mL) was added n-BuLi (2.4M, 20.0 mL, 48 mmol) at −78° C. under $N_2$ dropwise. After 1 h, the solution of 1 (7.40 g, 40 mmol) in THF (40 mL) was added dropwise. The reaction mixture was slowly warmed up to RT and stirred overnight. Then it was quenched with sat. aq. $NH_4Cl$ and extracted with EtOAc and the combined organic phase was washed with brine, dried over $Na_2SO_4$, filtered, concentrated and purified by chromatography on silica gel to give 2 (8.00 g, 66% yield) as a yellow oil. MS (ESI): mass calcd. for $C_{10}H_7BrClNOS$ 304.59, m/z found 305.7 $[M+H]^+$.

2. A mixture of (4-bromophenyl)(2-chlorothiazol-5-yl) methanol (8.00 g, 26.4 mmol) and TES (18 mL) in TFA (50 mL) was stirred at RT for 2 hrs. Then it was concentrated and the residue was diluted with sat. aq. $NaHCO_3$, extracted with DCM and the combined organic phase was washed with brine, dried over $Na_2SO_4$, filtered, concentrated and purified by chromatography on silica gel to give 3 (7.20 g, 94.7% yield) as a brown oil. MS (ESI): mass calcd. for $C10H_7BrClNS$ 288.59, m/z found 289.6 $[M+H]^+$.

3. To a solution of 3 (3.10 g, 11 mmol) in DMSO (30 mL) were added Intermediate 20 (3.5 g, 11 mmol) and $K_2CO_3$ (4.56 g, 33 mmol). The reaction was stirred at 140° C. for 3 hrs. The reaction was cooled to RT and then poured into ice-water, extracted with $CH_2Cl_2$, dried over $Na_2SO_4$. The combined organic layers were concentrated to afford a crude product which was purified by silica gel chromatography to afford the Intermediate 22 (4.78 g, 92% yield) as a yellow solid. MS (ESI): mass calcd. for $C_{22}H_{20}BrN_3O_2S$ 470.39, m/z found 470.7 $[M+H]^+$.

Preparation of Intermediate 23

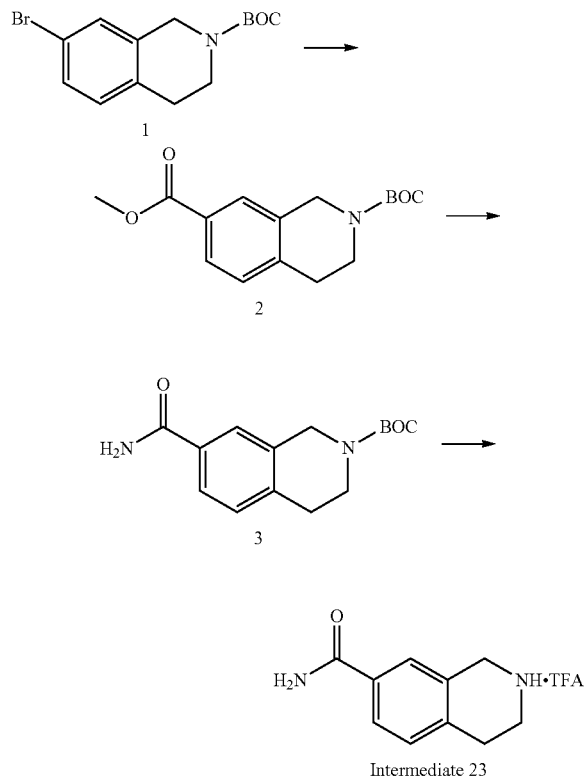

Intermediate 23

1. A mixture of 1 (Key Organics, 15 g, 48 mmol), TEA (9.7 g, 96 mmol), and Pd(dppf)Cl$_2$ (2.8 g, 3.84 mmol) in MeOH (200 ml) and MeCN (50 ml) in a bomb was purged 3× with CO, then heated at 100° C. for 24 h under 120 atm pressure of CO. The mixture was cooled, filtered through Celite, the filter cake was washed with EA and the filtrate concentrated to give a crude product which was purified by silica gel chromatography to afford 2 (11.5 g, 82.1% yield) as an oil. MS (ESI): mass calcd. for C$_{16}$H$_{21}$NO$_4$ 291.15, m/z found 313.9 [M+Na]t NMR (400 MHz, CDCl$_3$) δ ppm 7.84 (d, J=8.2 Hz, 1H), 7.82 (s, 1H), 7.22 (d, J=7.9 Hz, 1H), 4.63 (s, 2H), 3.93 (s, 3H), 3.68 (t, J=5.4 Hz, 2H), 2.90 (t, J=5.5 Hz, 2H), 1.51 (s, 9H).

2. To a solution of 2 (10.8 g, 37 mmol) in MeOH (20 ml) was added MeOH saturated with NH$_3$ (250 ml). The reaction was stirred at 120° C. for 60 h in a bomb, cooled to RT and concentrated to afford a crude product which was purified by silica gel chromatography to afford 3 (8.4 g, 81.9% yield) as a yellow solid. MS (ESI): mass calcd. for C$_{15}$H$_{20}$N$_2$O$_3$ 276.34, m/z found 298.9 [M+Na]$^+$. NMR (400 MHz, DMSO) δ ppm 7.89 (s, 1H), 7.69-7.67 (m, 2H), 7.30 (s, 1H), 7.23 (d, J=8.0 Hz, 1H), 4.54 (s, 2H), 3.56 (t, J=5.8 Hz, 2H), 2.81 (t, J=5.8 Hz, 2H), 1.44 (s, 9H).

3. To a solution of 3 (8.4 g, 30.3 mmol) in DCM (20 ml) was added TFA (12 ml). The reaction was stirred at RT for 6 h, concentrated to afford a crude product. It was dissolved with DCM and diluted with PE which resulted in a precipitate which was collected by filtration. The filter cake was washed with EA and dried in vacuum to afford Intermediate 23 (6.3 g, 71.4%), MS (ESI): mass calcd. for C$_{12}$K$_3$F$_3$N$_2$O$_3$ 290.24, m/z found 177.0 [M+H]$^+$.

Preparation of Intermediate 24

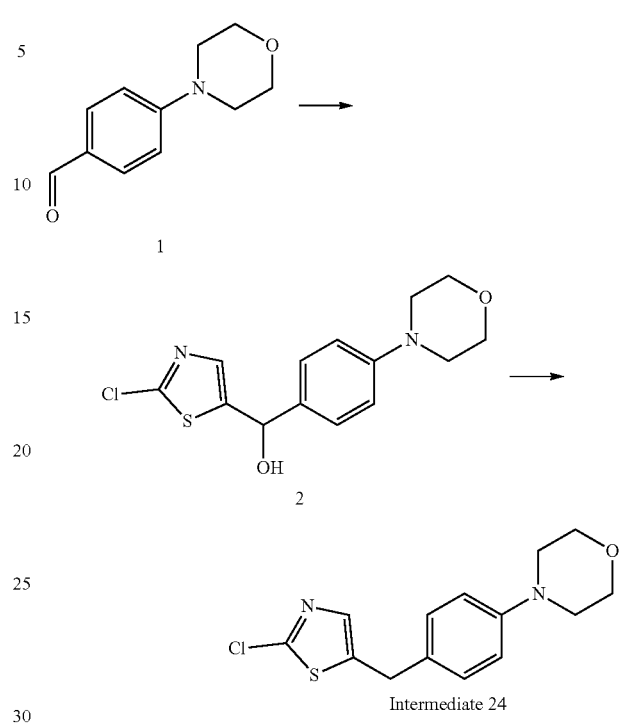

Intermediate 24

1. To a solution of 2-chlorothiazole (1.24 g, 10.35 mmol) in dry THF (50 mL) at −78° C. under N$_2$ was added n-BuLi (2.4 M, 4.8 mL) dropwise. After 0.5 h, a solution of 1 (Sigma-Aldrich, 1.80 g, 9.41 mmol) in dried THF (10 mL) was added dropwise. The reaction was slowly warmed to RT. The mixture was quenched with aq. NH$_4$Cl and extracted with DCM and dried over Na$_2$SO$_4$. The combined organic layers were concentrated to give a crude product which was purified by silica gel chromatography to afford 2 (2.00 g, 68.36% yield) as a white solid. MS (ESI): mass calcd. for C$_{14}$H$_{15}$ClN$_2$O$_2$S 310.80, m/z found 311.4 [M+H]$^+$.

2. A mixture of 2 (2.0 g, 6.44 mmol), TES (10 mL) and TFA (30 mL) was stirred at 80° C. for 2 h. The mixture was concentrated and the residue was washed with aq. NaHCO$_3$ and extracted with DCM (30 mL×3) and dried over Na$_2$SO$_4$. The combined extracts were concentrated to give a crude product which was purified by silica gel chromatography to afford the Intermediate 24 (1.1 g, 57.94% yield) as a white solid. MS (ESI): mass calcd. for C$_{14}$H$_{15}$ClN$_2$OS 294.8, m/z found 295.4 [M+H]$^+$.

Preparation of Intermediate 25

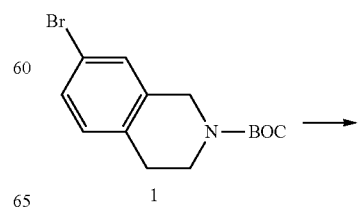

-continued

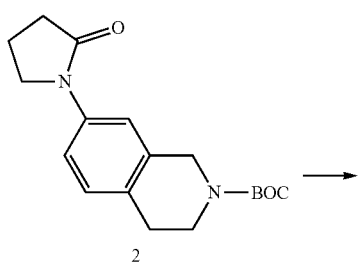

2

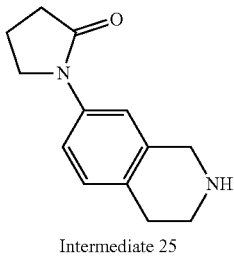

Intermediate 25

1. A mixture of 1 (Key Organics, 5.0 g, 16.01 mmol), pyrrolidin-2-one (4.09 g, 48.03 mmol), Pd$_2$(dba)$_3$ (1.17 g, 1.6 mmol), S-Phos (1.31 g, 3.2 mmol) and t-BuOK (5.38 g, 48.03 mmol) in dried 1,4-dioxane (200 mL) was stirred at 100° C. overnight. The mixture was poured into water and extracted with DCM, dried over Na$_2$SO$_4$, filtered and concentrated. The resulting residue was purified by silica gel chromatography to afford 2 (3.2 g, 63.17%) as a white solid. mass calcd. for C$_{18}$H$_{24}$N$_2$O$_3$ 316.40, m/z found 316.8 [M+H]$^+$.

2. A mixture of 2 (3.2 g, 10.11 mmol), DCM (40 mL) and TFA (20 mL) was stirred at room temperature for 5 h. The mixture was concentrated and the residue was washed with aq. NaHCO$_3$ and extracted with DCM, dried over Na$_2$SO$_4$. The combined extracts were concentrated to give a crude product, which was purified by silica gel chromatography to afford Intermediate 25 (1.05 g, 48.02% yield) as a white solid. MS (ESI): mass calcd. for C$_{13}$H$_{16}$N$_2$O 216.28, m/z found 216.8 [M+H]$^+$.

Preparation of Intermediate 26

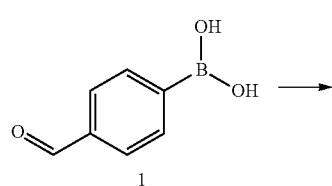

1

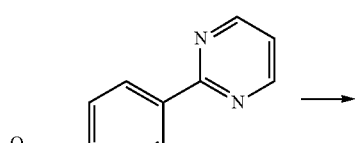

2

-continued

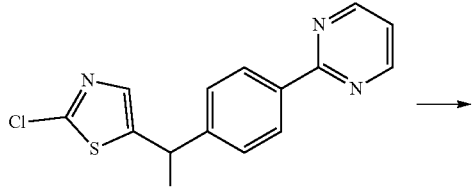

3

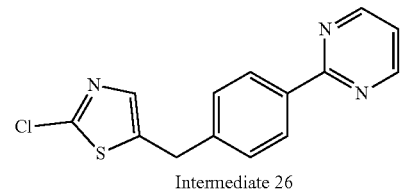

Intermediate 26

1. A mixture of 1 (Sigma-Aldrich, 4 g, 26.7 mmol), 2-bromopyrimidine (3.51 g, 22.1 mmol), NaHCO$_3$ (6.73 g, 80.1 mmol), Pd(PPh$_3$)$_4$ (766 mg, 0.663 mmol) in DMF/H$_2$O (100 mL/50 mL) was stirred at 90° C. for 18 hrs under N$_2$ atmosphere. The mixture was filtered through Celite and the filter cake washed with EA and the filtrate was concentrated. The resulting mixture was extracted with EA and the combined extracts were washed with brine, water, and dried with Na$_2$SO$_4$. The mixture was filtered and the filtrate concentrated to give residue which was purified by silica gel chromatography to afford 2 (3.84 g, 78.1% yield) as a white solid. MS (ESI): mass calcd. for C$_{11}$H$_8$N$_2$O 184.20, m/z found 185.0 [M+H]$^+$.

2. To a solution of 2-chlorothiazole (2.69 g, 22.7 mmol) in dry THF (80 mL) at −78° C. under N$_2$ was added dropwise n-BuLi (2.4 M, 9.9 mL, 23.75 mmol). After 1 h a solution of 2 (3.8 g, 20.6 mmol, 106 mL THF) was added dropwise to the mixture. The reaction was slowly warmed to RT and stirred for 18 hrs. The resulting mixture was quenched with aq. NH$_4$Cl and extracted with EtOAc and the combined extracts were dried over Na$_2$SO$_4$. The organic solution was concentrated to give a crude product which was purified by silica gel chromatography to afford 3 (4.65 g, 74.2% yield) as a white solid. MS (ESI): mass calcd. for C$_{14}$H$_{10}$ClN$_3$OS 303.76, m/z found 303.8 [M+H]$^+$.

3. To a solution of 3 (3 g, 9.87 mmol) and TFA (11.3 g, 98.7 mmol) in dry DCE at 0° C. was added dropwise TES (3.42 g, 29.6 mmol) and the reaction was stirred for 8 hrs at 60° C. The mixture was cooled and concentrated. The resulting residue was treated with saturated NaHCO$_3$, extracted with EA and the combined extracts were washed with brine, water and dried with Na$_2$SO$_4$. The solvent was removed to afford the crude product which was purified by flash chromatography to afford Intermediate 26 (1.2 g, 42.2% yield) as a white solid. MS (ESI): mass calcd. for C$_{14}$H$_{10}$ClN$_3$S 287.77, m/z found 287.8 [M+H]$^+$.

Preparation of Intermediate 27

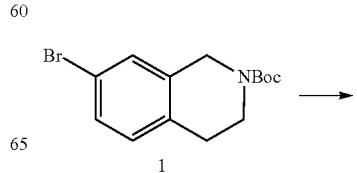

1

-continued

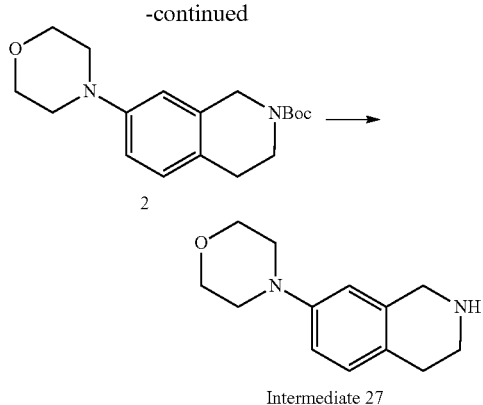

Intermediate 27

1. A mixture of 1 (2.00 g, 6.4 mmol), morpholine (1.80 g, 20.6 mmol), Pd$_2$(dba)$_3$ (2.0 g, 2.2 mmol), S-Phos (1.20 g, 3.0 mmol) and K$_2$CO$_3$ (2.80 g, 20 mmol) in dried 1,4-dioxane (80 mL) was stirred at 100° C. overnight. The reaction mixture was cooled to RT, filtered and the filtrate concentrated. The resulting residue was purified by silica gel chromatography to afford 2 (1.30 g, 64%) as a yellow oil. mass calcd. for C$_{18}$H$_{26}$N$_2$O$_3$ 318.19, m/z found 319.0[M+H]$^+$.

2. A mixture of 2 (1.30 g, 5 mmol) and TES (5 mL) in TFA (10 mL) was stirred at 50° C. for 2 hrs. The mixture was cooled, concentrated and the residue treated with sat. aq. NaHCO$_3$, extracted with CH$_2$Cl$_2$ and the combined organic phase was washed with brine, dried over Na$_2$SO$_4$, filtered and the filtrate concentrated to give Intermediate 27 (1.4 g, crude product) as a brown oil. MS (ESI): mass calcd. for C$_{13}$H$_{18}$N$_2$O 218.14, m/z found 219.0[M+H]t Preparation of Intermediate 28

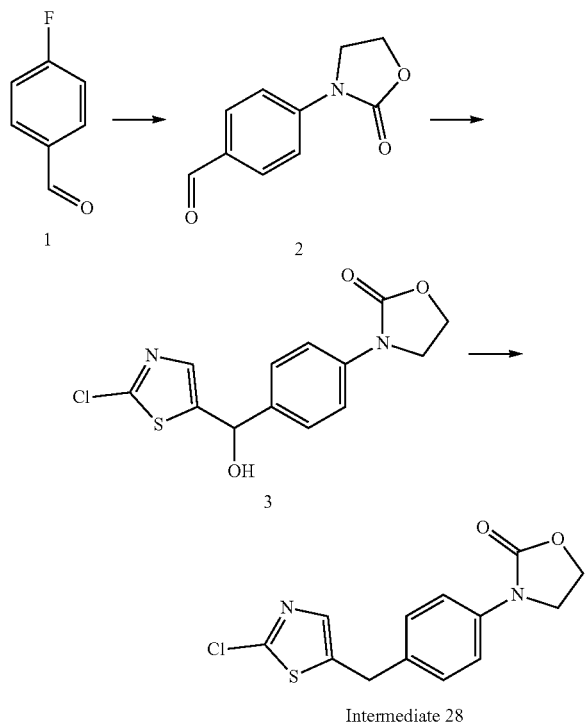

Intermediate 28

1. To a solution of 1 (4.46 g, 36 mmol) in DMF (100 mL) was added oxazolidin-2-one (2.61 g, 30 mmol) and Cs$_2$CO$_3$ (11.74 g, 36 mmol). The resulting mixture was stirred at 120° C. overnight. The mixture was cooled to RT, filtered, the filtrate poured into water and the mixture extracted with EA. The combined extracts were washed with brine, dried with Na$_2$SO$_4$, concentrated and purified by chromatography on silica gel to give 2 (4.17 g, 70% yield) as a white solid. MS (ESI): mass calcd. for C$_{10}$H$_9$NO$_3$ 191.19, m/z found 192.0 [M+H]$^+$.

2. To a solution of 2-chlorothiazole (0.86 g, 7.2 mmol) in THF (25 mL) at −78° C. was added n-BuLi (3 mL, 7.2 mmol) dropwise. After 1 h, a solution of 2 (1.06 g, 5.5 mmol) in THF (15 mL) was added dropwise. The reaction mixture was stirred 2 hrs, quenched with sat. aq. NH$_4$Cl and extracted with EtOAc. The combined extracts were washed with brine, dried over Na$_2$SO$_4$, filtered, concentrated to give 3 (crude, 1.8 g) as a yellow oil. MS (ESI): mass calcd. for C$_{14}$H$_{12}$ClN$_3$O$_2$S 310.75, m/z found 311.21[M+H]$^+$.

3. A mixture of 3 (0.1 g, 0.32 mmol) and TES (0.5 mL) in TFA (1 mL) was stirred at RT for 2 hrs. The mixture was concentrated and the residue was purified by chromatography on silica gel to give Intermediate 28 (78 mg, 82% yield) as a white solid. MS (ESI): mass calcd. for C$_{13}$H$_{11}$ClN$_2$O$_2$S 294.75, m/z found 295.19[M+H]$^+$.

Preparation of Intermediate 29

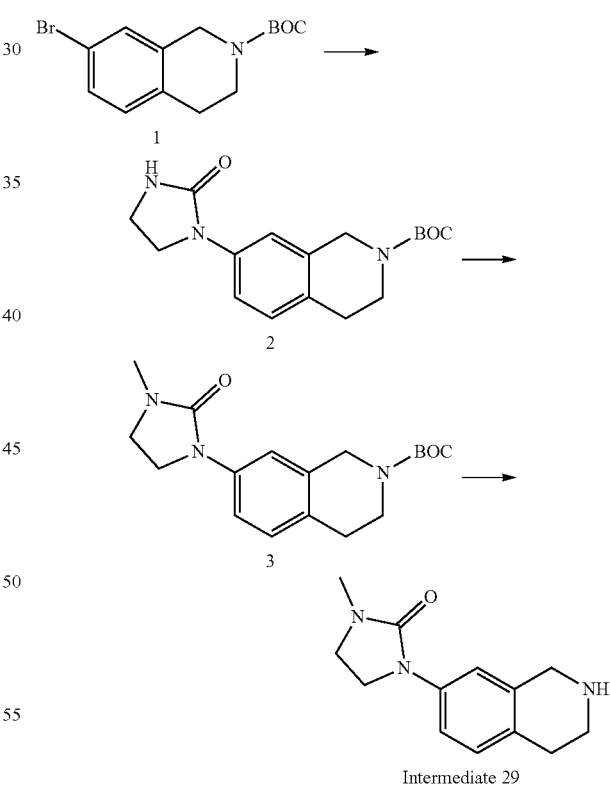

Intermediate 29

1. A mixture of compound 1 (Key Organics, 5.40 g, 17.4 mmol), imidazolidin-2-one (4.50 g, 52.3 mmol), t-BuOK (5.75 g, 51.3 mmol), CuI (2.52 g, 13.2 mmol) and (S,S)—N,N'-dimethyl-1,2-diaminocyclohexane (0.83 g, 6.5 mmol) in DMF (200 mL) was stirred at 120° C. overnight. The reaction mixture was cooled to RT, filtered and concentrated to afford 2 (5.1 g, 92%) as a yellow oil. mass calcd. for C$_{17}$H$_{23}$N$_3$O$_3$ 317.39, m/z found 317.9[M+H]$^+$.

2. To a solution of 2 (1.50 g, 4.7 mmol) in THF at 0° C. (40 mL) was added NaH (200 mg, 13.8 mmol). After 0.5 h, a solution of iodomethane (1.41 g, 9.9 mmol) in THF (10 mL) was added dropwise. The reaction mixture was slowly warmed to RT and stirred at 60° C. for 4 h. The reaction was quenched with water and extracted with EA, the combined extracts washed with brine, dried over anhydrous $Na_2SO_4$ and concentrated to give 3 (1 g, 64%). mass calcd. for $C_{18}H_{25}N_3O_3$ 331.42. m/z found 332.0 $[M+H]^+$.

3. A mixture of 3 (2 g, 6 mmol) and TFA (9 mL) in DCM (40 mL) was stirred at RT for 2 hrs.

Then it was concentrated and the residue was diluted with sat. aq. of $NaHCO_3$, extracted with $CH_2Cl_2$ and the combined organic phase was washed with brine, dried over $Na_2SO_4$, filtered, concentrated to give Intermediate 29 (1.1 g) as a brown oil. MS (ESI): mass calcd. for $C_{13}H_{17}N_3O$ 231.3, m/z found 231.9 $[M+H]^+$.

Preparation of Intermediate 30

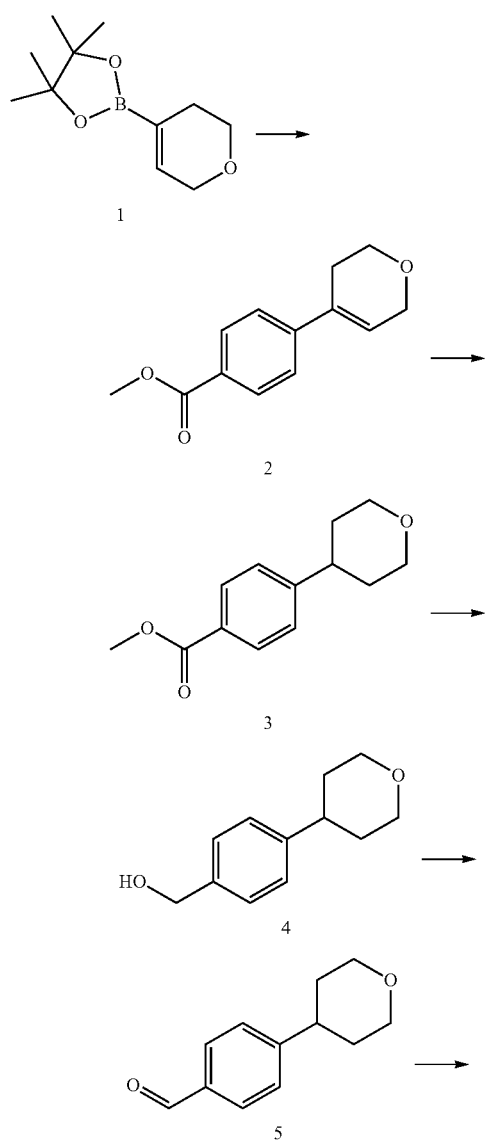

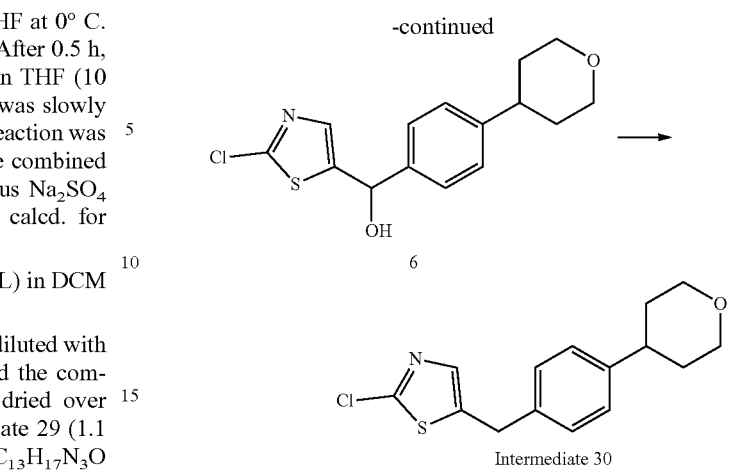

Intermediate 30

1. A vessel containing a mixture of methyl 4-bromobenzoate (1.1 g, 5.12 mmol), 1 (Sigma-Aldrich, 1.1 g, 5.24 mmol), Pd(dppf)Cl$_2$ (299 mg, 0.41 mmol) and $K_2CO_3$ (1.412 g, 10 mmol) in 1,4-dioxane (15 mL) and $H_2O$ (1 mL) was purged with $N_2$ three times and the resulting mixture was heated to 100° C. for 16 h. It was cooled to RT, concentrated and the residue purified by chromatography on silica gel to give 2 (940 mg, 93% yield) as a white solid. MS (ESI): mass calcd. for $C_{13}H_{14}O_3$ 218.25, m/z found 219.0 $[M+H]^+$.

2. A mixture of 2 (940 mg, 4.31 mmol) and Pd/C (250 mg) in EtOAc (40 mL) was stirred at RT for 16 h under $H_2$. The mixture was filtered and concentrated to give 3 (948 mg, 100% yield) as a colorless oil. MS (ESI): mass calcd. for $C_{13}H_{16}O_3$ 220.27, m/z found 221.0 $[M+H]^+$.

3. LiAlH$_4$ (160 mg, 4.09 mmol) was added to a solution of 3 (900 mg, 4.09 mmol) in dry THF (15 mL) at 0° C. The mixture was warmed to RT and stirred for 2 h, cooled to 0° C. and quenched with sat. aq. NH$_4$Cl and extracted with EtOAc. The combined extracts were washed with brine, dried over $Na_2SO_4$, filtered, concentrated to give 4 (765 mg, 97% yield) as a yellow oil. MS (ESI): mass calcd. for $C_{12}H_{16}O_2$ 192.26, m/z found 175.0 $[M-OH]^+$.

4. To a solution of 4 in DCM (8 mL) was added Dess-Martin reagente (70 mg, 0.12 mmol). The resulting mixture was stirred at RT for 1 h, concentrated and the residue purified by chromatography on silica gel to give 5 (15.5 mg, 78% yield) as a yellow oil. MS (ESI): mass calcd. for $C_{12}H_{14}O_2$ 190.24, m/z found 191.0 $[M+H]^+$.

5. n-BuLi (1.45 mL, 3.47 mmol, 2.4 M) was added dropwise to the solution of 2-chlorothiazole (416 mg, 3.47 mmol) in THF (3 mL) at −78° C. After 30 min. a solution of 5 (600 mg, 3.16 mmol) in THF (6 mL) was added dropwise and the resulting mixture warmed to RT and stirred overnight. The mixture was quenched with sat. aq. NH$_4$Cl, extracted with EtOAc. The combined extracts were washed with brine, dried over $Na_2SO_4$, filtered, concentrated and purified by chromatography on silica gel to give 6 (860 mg, 88% yield) as a white solid. MS (ESI): mass calcd. for $C_{15}H_{16}ClNO_2S$ 309.81, m/z found 309.8 $[M+H]^+$.

6. A mixture of 6 (690 mg, 2.23 mmol), TES (2 mL) and TFA (2 mL) was stirred at RT for 2 h under $N_2$. The mixture was concentrated and the residue diluted with sat. aq. NaHCO$_3$, extracted with DCM. The combined extracts were washed with brine, dried over $Na_2SO_4$, filtered, concentrated and the residue purified by chromatography on silica gel to give Intermediate 30 (566.6 mg, 87% yield) as a yellow oil. MS (ESI): mass calcd. for $C_{15}H_{16}ClNOS$ 293.81, m/z found 294.1 $[M+H]^+$.

Preparation of Intermediate 31

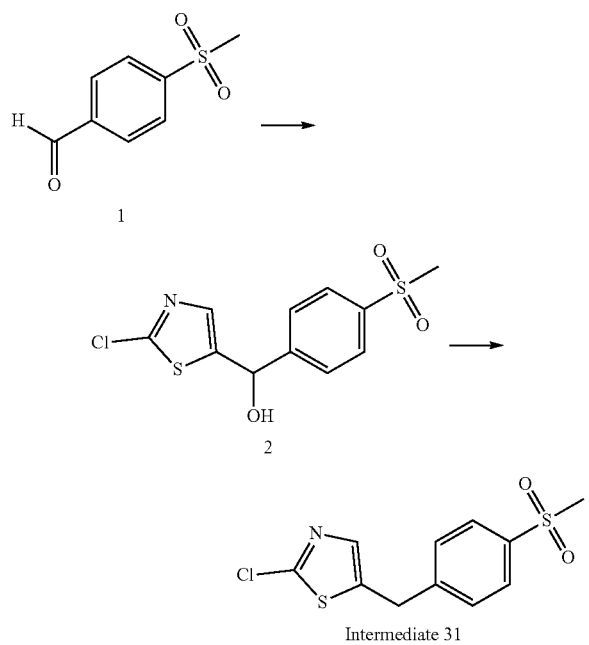

1. To a solution of 2-chlorothiazole (3.59 g, 29.9 mmol) in dry THF (94 mL) at −78° C. under $N_2$ was added dropwise n-BuLi (2.4 M in Hex, 13.0 mL, 31.2 mmol). After 1 h, a solution of 1 (Enamine, 5 g, 27.2 mmol) in dried THF (200 mL) was added dropwise. The reaction was warmed to RT and stirred for 18 hrs. The mixture was quenched with saturated aq. $NH_4Cl$ and extracted with EtOAc. The combined extracts were dried over $Na_2SO_4$ and concentrated to give a crude product which was purified by silica gel chromatography to afford 2 (1.6 g, 19.4% yield) as a white solid. MS (ESI): mass calcd. for $C_{11}H_{10}ClNO_3S_2$ 303.78, m/z found 303.7 $[M+H]^+$.

2. To a solution of 2 (1.6 g, 5.26 mmol) in TFA (12 mL) was added dropwise TES (3 g, 26.3 mmol) over 15 min. The reaction was stirred at 70° C. for 2 hrs, quenched with saturated $NaHCO_3$ and extracted with EtOAc. The combined extracts were washed with water, dried over $Na_2SO_4$ and concentrated to give a crude product which was purified by silica gel chromatography to afford Intermediate 31 (1.3 g, 85.8% yield) as a white solid. MS (ESI): mass calcd. for $C_{11}H_{10}ClNO_2S_2$ 287.78, m/z found 287.7 $[M+H]^+$.

Preparation of Intermediate 34

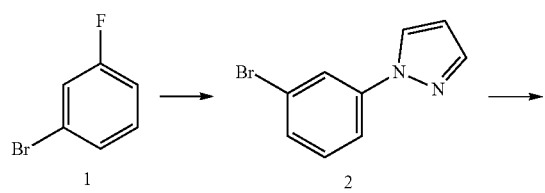

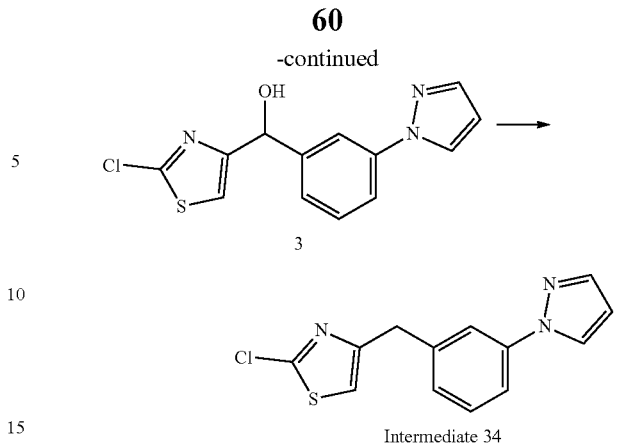

1. To a solution of 1H-pyrazole (5.86 g, 86.2 mmol) in anhydrous DMF (50.0 mL) was added NaH (60%, 10.3 g, 258.6 mmol) under $N_2$ and the reaction mixture was stirred at 60° C. for 1 h. Then 1 (15.1 g, 86.2 mmol) was added, and the resulting mixture was stirred at 120° C. for 3 h. The reaction was quenched with water and extracted with EtOAc. The combined organic layers were washed with water, brine, dried over $Na_2SO_4$ and concentrated to give a crude product which was purified by silica gel chromatography to afford 2 (4.0 g, 21% yield) as a colorless oil.

2. To a solution of 2 (2.66 g, 18.0 mmol) in dry THF (50 mL) was added n-BuLi (2.5 M in hexane, 7.2 mL, 18.0 mmol) dropwise at −78° C. under $N_2$. After 1 h, a solution of 2-chloro-4-thiazolecarboxaldehyde (Sigma-Aldrich, 4.00 g, 18.02 mmol) in THF (10 mL) was added dropwise. The resulting mixture was warmed to room temperature. The reaction was quenched with saturated $NH_4Cl$ and extracted with EtOAc. The combined organic extracts were concentrated to give a crude oil which was purified by silica gel chromatography to afford 3 (420 mg, 8% yield) as a yellow oil.

3. To a solution of 3 (400 mg, 1.44 mmol) in TFA (10 mL) was added TES (3 mL), and the resulting mixture was stirred at 100° C. for 2 h. The reaction was concentrated and the residue was purified by silica gel chromatography to afford Intermediate 34 (250 mg, 63% yield) as a yellow solid.

Preparation of Intermediate 35

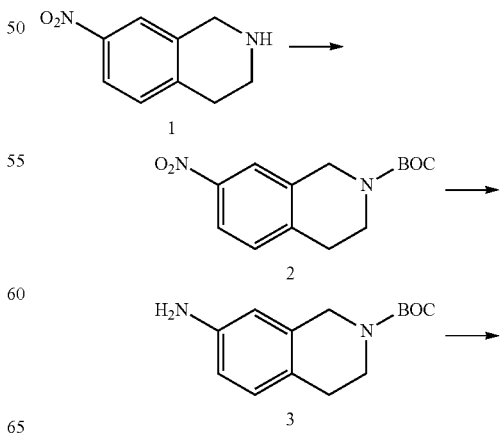

-continued

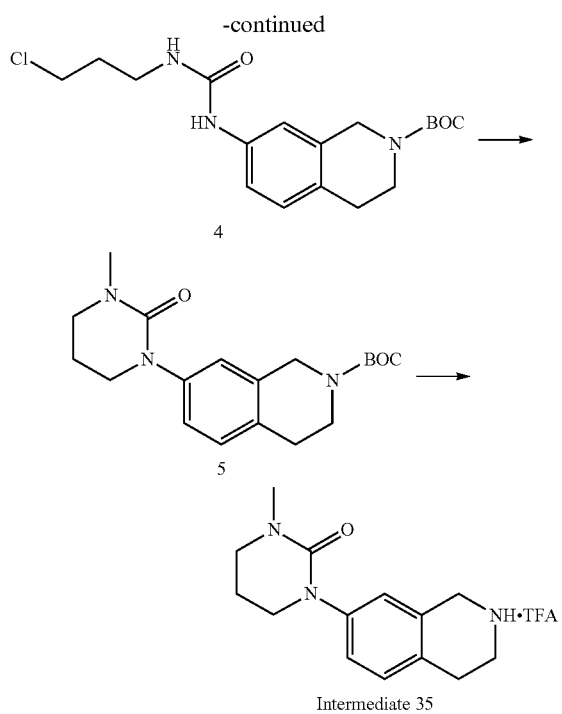

Intermediate 35

1. To the mixture of 1 (4 g, 22.5 mmol) in sat. aq. NaHCO₃ (50 mL) and THF (50 mL) was added BOC₂O (5.63 g, 25.8 mmol) and the resulting mixture was stirred at RT for 16 h. The mixture was concentrated and the residue was extracted with EtOAc, and the combined organic phase was washed with brine, dried over Na₂SO₄, filtered, concentrated and purified by chromatography on silica gel to give 2 (5.8 g, 93.5% yield) as a brown solid. MS (ESI): mass calcd. for $C_{14}H_{18}N_2O_4$ 278.31, m/z found 301.0 [M+Na]⁺.

2. A mixture of 2 (5.8 g, 20.9 mmol) and Pd/C (1.2 g) in EtOAc (60 mL) was stirred at RT for 16 h under H₂. The mixture was filtered and concentrated to give 3 (5 g, 96.7% yield) as a brown oil. MS (ESI): mass calcd. for $C_{14}H_{20}N_2O_2$ 248.33, m/z found 271.0 [M+Na]⁺.

3. A mixture of 3 (2 g, 8.06 mmol) and 3-chloropropyl isocyanate (1.16 g, 9.68 mmol) in dry DCM (20 mL) was stirred at RT for 16 h. Then it was concentrated and the residue was washed with a mixture of EA/PE (1/50), filtered and the solid obtained was dried in vacuum to give 4 (2.8 g, 95% yield) as a brown solid. MS (ESI): mass calcd. for $C_{18}H_{26}ClN_3O_3$ 367.87, m/z found 368.0 [M+H]⁺.

4. To the solution of 4 (2.7 g, 7.4 mmol) in THF (270 mL) at 0° C. was added NaH (888 mg, 22.2 mmol) portion wise. Then it was warmed to RT and stirred for 16 h. The volume was reduced to approximately 40 mL and it was cooled to 0° C. and MeI (1.58 g, 11.1 mmol) was added and the resulting mixture was warmed to RT and stirred for 16 h. The mixture was quenched with water, extracted with EtOAc, the combined organic extracts were washed with brine, dried over Na₂SO₄, filtered, concentrated. The resulting residue was purified by chromatography on silica gel, eluting to give 5 (2.4 g, 96% yield) as a yellow oil. MS (ESI): mass calcd. for $C_{19}H_{27}N_3O_3$ 345.44, m/z found 346.0 [M+H]⁺.

5. To the solution of 5 (2.4 g, 6.96 mmol) in DCM (15 mL) was added TFA (15 mL). After stirring for 16 h, it was concentrated and the residue was washed with EtOAc, filtered and dried in vacuum to give the desired product Intermediate 35 (2.2 g, 88% yield) as a white solid. MS (ESI): mass calcd. for $C_{16}H_{20}F_3N_3O_3$ 359.35, m/z found 246.0 [M-TFA+H]⁺.

EXAMPLES

Example 1

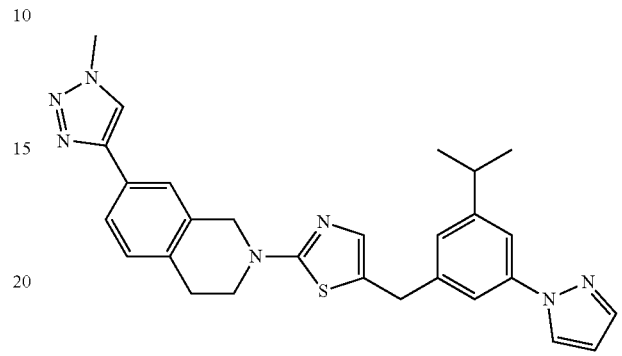

1. To a solution of Intermediate 7 (346 mg, 1.09 mmol) in DMSO (10 mL) were added Intermediate 9 (329 mg, 1.31 mmol) and K₂CO₃ (300 mg, 2.18 mmol). The mixture was stirred at 120° C. overnight, cooled to RT. The mixture was treated with water and extracted with EA. The combined organic extracts were washed with water, brine, dried over anhydrous Na₂SO₄, filtered and concentrated to give a crude oil. The crude product was purified by silica gel chromatography to afford 90.36 mg Example 1. ¹HNMR (CDCl₃, 300 MHz) δ: δ: 1.3-1.4 (d, 6H), 3.0-3.1 (m, 2H), 3.6-3.8 (m, 2H), 4.1 (s, 2H), 4.2-4.3 (s, 2H), 4.8-4.9 (s, 2H), 6.5 (s, 1H), 7.0-7.1 (s, 1H), 7.1-7.2 (s, 1H), 7.4-7.5 (s, 1H), 7.5-7.6 (s, 1H), 7.7.6-7.7 (d, 1H), 7.7-7.8 (s, 1H), 7.8-7.9 (s, 1H), 7.9-8.0 (s, 1H). LC-MS: m/z=496.5 (M+1)+.

Example 2

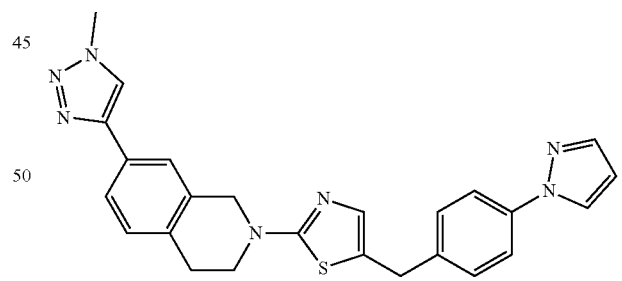

1. A mixture of Intermediate 9 (100 mg, 0.40 mmol), Intermediate 3 (121 mg, 0.44 mmol), Pd₂(dba)₃ (36.6 mg, 0.04 mmol), SPhos (16.4 mg, 0.04 mmol) and t-BuOK (123 mg, 1.10 mmol) in dioxane (2.00 mL) was stirred at 95° C. for 2 h. The reaction was quenched with water and extracted with EtOAc. The combined organic extracts were washed with water and brine, dried over Na₂SO₄, and concentrated. The residue was purified by prep-HPLC to give Example 2 (45.9 mg, 25% yield) as a yellow solid. ¹H NMR (400 MHz, DMSO-d₆) δ 2.91 (2H, t, J=5.6 Hz), 3.67 (2H, t, J=5.6 Hz), 4.04 (2H, s), 4.08 (3H, s), 4.60 (2H, s), 6.53 (1H, t, J=2.0 Hz), 7.03 (1H, s), 7.25 (1H, d, J=8.0 Hz), 7.36 (2H, d, J=8.4

Hz), 7.63-7.73 (3H, m), 7.77 (2H, d, J=8.4 Hz), 8.46 (2H, d, J=2.0 Hz). MS Calcd.: 453.2; MS Found: 454.2 [M+H]⁺.

Example 3

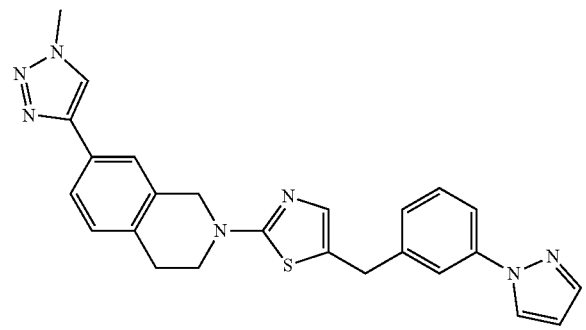 [SMILES: Cn1cc(-c2ccc3c(c2)CN(c2ncc(Cc4cccc(-n5cccn5)c4)s2)CC3)nn1]

1. Following the procedure described for Example 1, Intermediate 9 and Intermediate 2 were reacted to afford 11.03 mg of Example 3. (9.58 mg) ¹HNMR (CDCl₃, 300 MHz) δ: 3.0-3.1 (m, 2H), 3.7-3.8 (m, 2H), 4.1 (s, 2H), 4.4.3 (s, 2H), 4.6 (s, 2H), 6.5 (s, 1H), 7.0-7.1 (s, 1H), 7.1-7.3 (m, 2H), 7.3 (s, 1H), 7.4 (m, 1H), 7.5-7.7 (m, 4H), 7.7-7.8 (s, 1H), 7.8-7.9 (s, 1H), 7.9-8.0 (s, 1H). LC-MS: m/z=454.4 (M+1)⁺.

Example 4

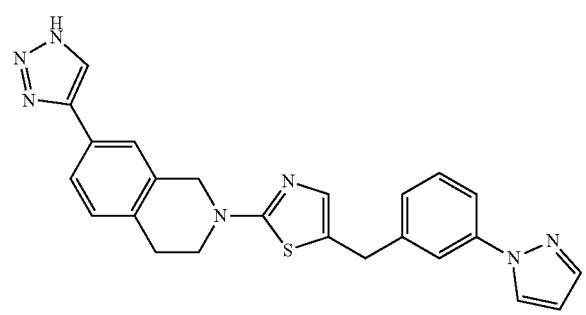 [SMILES: c1cc(Cc2cnc(N3CCc4ccc(-c5c[nH]nn5)cc4C3)s2)cc(-n2cccn2)c1]

1. Following the procedure described for Example 1, Intermediate 10 and Intermediate 2 were reacted to afford 11.03 mg of Example 4. ¹HNMR (CDCl₃, 300 MHz) δ: 3.0-3.1 (m, 2H), 3.6-3.8 (m, 2H), 4.1 (s, 2H), 4.8 (s, 2H), 6.5 (s, 1H), 7.7.1-7.3 (m, 5H), 7.4-7.5 (m, 1H), 7.6-7.7 (m, 3H), 7.7-7.8 (s, 1H), 7.8-7.9 (s, 1H), 7.9-8.0 (s, 1H). LC-MS: m/z=440.4 (M+1)⁺.

Example 5

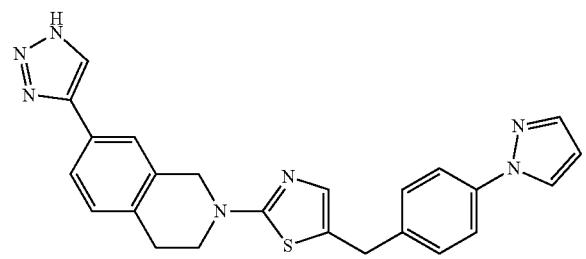 [SMILES: c1cnn(-c2ccc(Cc3cnc(N4CCc5ccc(-c6c[nH]nn6)cc5C4)s3)cc2)c1]

1. Following the procedure described for Example 1, Intermediate 10 and Intermediate 3 were reacted to afford 30.02 mg of Example 5. ¹HNMR (CDCl₃, 300 MHz) δ: 3.0-3.1 (m, 4H), 3.6-3.8 (m, 2H), 4.1 (s, 2H), 4.8-4.9 (s, 2H), 6.4-6.5 (s, 1H), 7.1-7.3 (m, 5H), 7.4 (m, 1H), 7.5-7.6 (m, 3H), 7.7 (s, 1H), 7.7.8 (s, 1H), 7.9-8.0 (s, 1H). LC-MS: m/z=440.4 (M+1)⁺.

Example 6

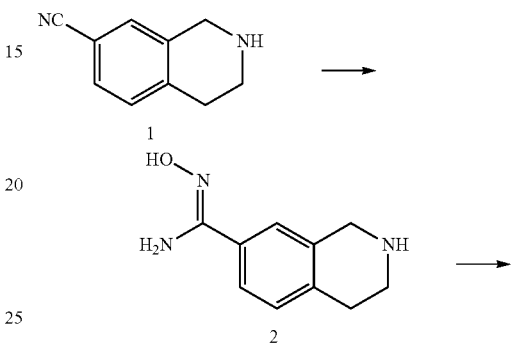

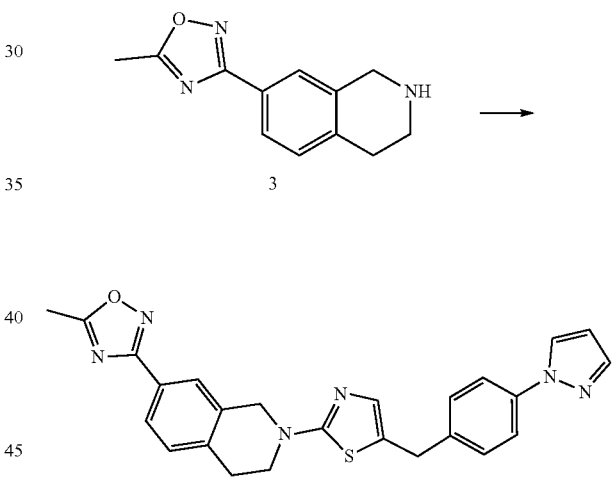

1. To a solution of 1 (Sigma-Aldrich, 158 mg, 1 mmol) in EtOH (20 mL) was added NH₂OH (1.5 mL). The mixture was heated to reflux for 20 h. The mixture was cooled and concentrated to give 2 as white solid (0.19 g, 100%).

2. A mixture of 2 (0.19 g, 1 mmol) in Ac₂O (10 mL) was heated to reflux for 2 h. The mixture was cooled and concentrated and the residue dissolved in conc. HCl (10 mL) and the mixture was heated to reflux overnight. The mixture was concentrated to give 3 as white solid (0.4 g, 100%).

3. To a solution of 3 (20 mg, 0.5 mmol) in dioxane (10 mL) was added Intermediate 3 (250 mg, 0.9 mmol), Pd₂(dba)₃ (32 mg, 0.04 mmol), SPhos (30 mg, 0.07 mmol) and t-BuOK (165 mg, 0.75 mmol). The resulting mixture was heated to 100° C. and for 20 h under N₂. The mixture was quenched with water and extracted with EtOAc. The combined extracts were concentrated to give a crude oil which was purified by silica gel chromatography to afford Example 6 as yellow solid (40 mg, 20%). LC-MS: m/z=455.1 (M+1)⁺.

Example 7

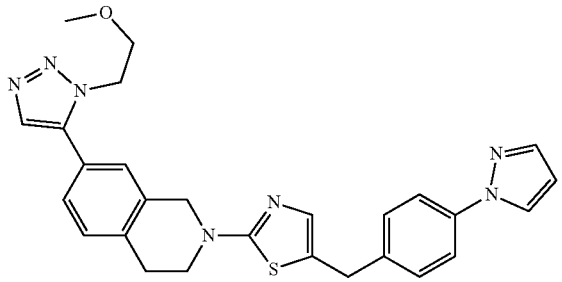 [SMILES: COCCn1nncc1-c1ccc2c(c1)CN(c1ncc(Cc3ccc(-n4cccn4)cc3)s1)CC2]

Figure 2:
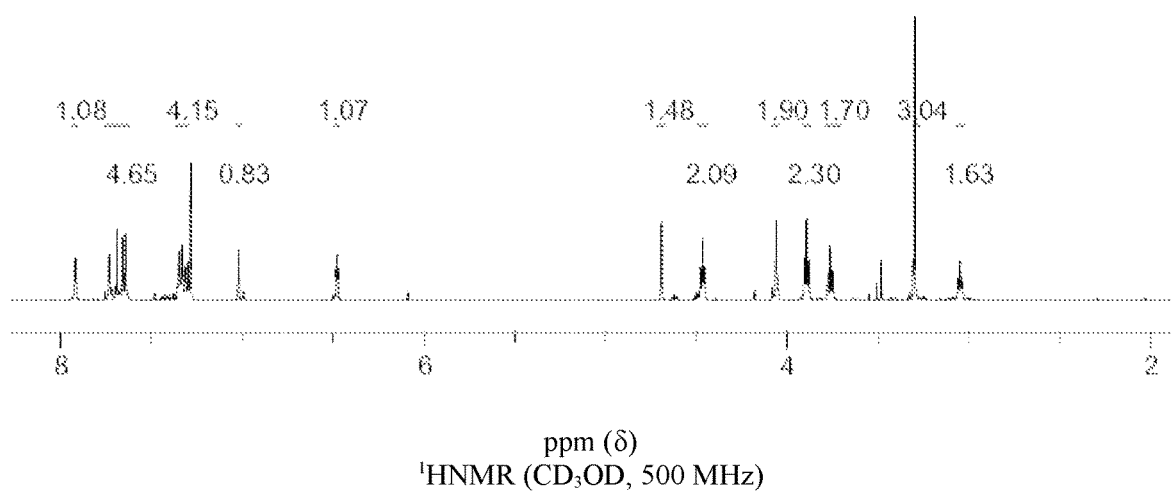
FIG. 2 presents the proton (1H) NMR Spectrum of Example 7 in CD$_3$OD at 500 MHz.

1. To a solution of Intermediate 11 (82 mg, 0.3 mmol, 1 eq.) in Dioxane (20 mL) was added Intermediate 3 (137 mg, 0.5 mmol, 1.6 eq.), Pd$_2$(dba), (18 mg, 0.027 mmol, 0.09 eq), SPhos (18 mg, 0.04 mmol, 0.13 eq) and t-BuOK (330 mg, 3 mmol, 10 eq). The mixture was heated to 100° C. and stirred for 20 h under N$_2$. The mixture was quenched with water and extracted with EtOAc. The combined extracts were concentrated to give a crude oil which was purified by silica gel chromatography to afford Example 7 as yellow solid (40 mg, 27%). LC-MS: m/z=498.2 (M+1)$^+$. An $^1$HNMR Spectrum of Example 7 product is presented in FIG. 2.

Example 8

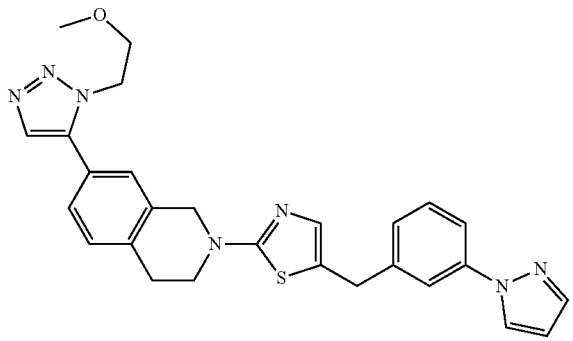 [SMILES: COCCn1nncc1-c1ccc2c(c1)CN(c1ncc(Cc3cccc(-n4cccn4)c3)s1)CC2]

Figure 3:
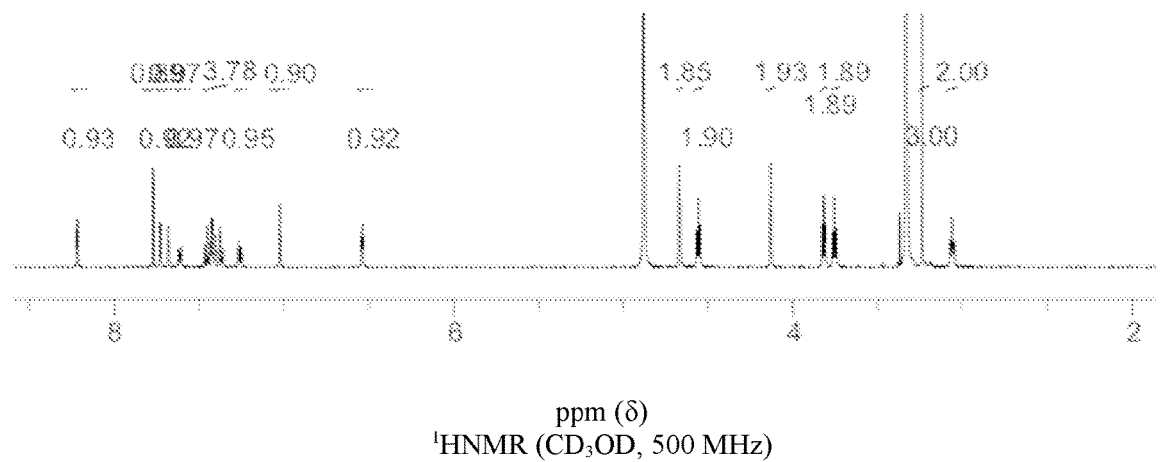
FIG. 3 presents the proton (1H) NMR Spectrum of Example 8 in CD$_3$OD at 500 MHz.

1. The title compound was prepared following the procedure described for Example 7 using Intermediate 2 in place of Intermediate 3 and 5 eq. of t-BuOK to afford Example 8 as yellow solid (90 mg, 27%). LC-MS: m/z=498.2 (M+1). An $^1$HNMR Spectrum of Example 8 product is presented in FIG. 3.

Example 9

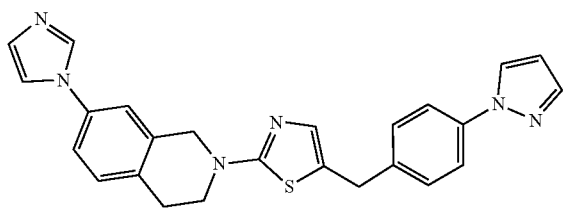 [SMILES: c1cnn(-c2ccc(Cc3cnc(N4CCc5ccc(-n6ccnc6)cc5C4)s3)cc2)c1]

Figure 4:
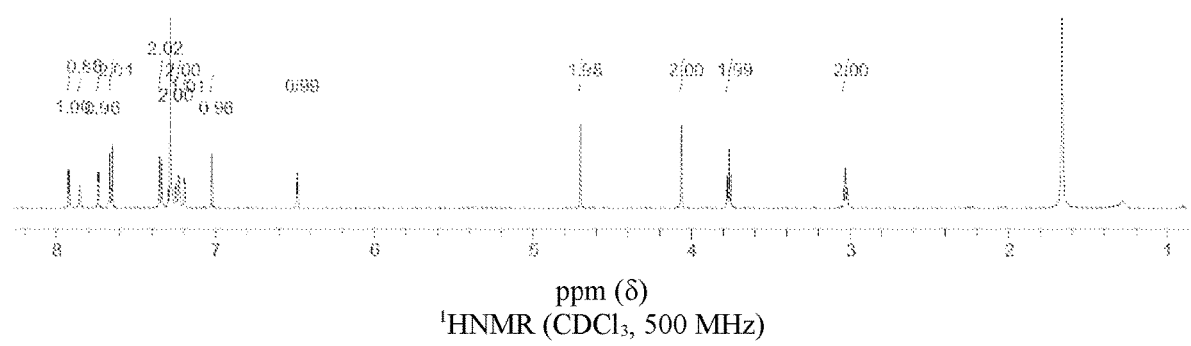
FIG. 4 presents the proton (1H) NMR Spectrum of Example 9 in CDCl$_3$ at 500 MHz.

1. The title compound was prepared following the procedure described for Example 7 using Intermediate 12 in place of Intermediate 11, 1 eq. of Intermediate 3, 0.06 eq. of Pd$_2$(dba)$_3$, 0.07 eq. SPhos and 2.4 eq. of t-BuOK to afford Example 9 as white solid (100 mg, 45.6%). LC-MS: m/z=439.2 (M+1)$^+$. An $^1$HNMR Spectrum of Example 9 product is presented in FIG. 4.

Example 10

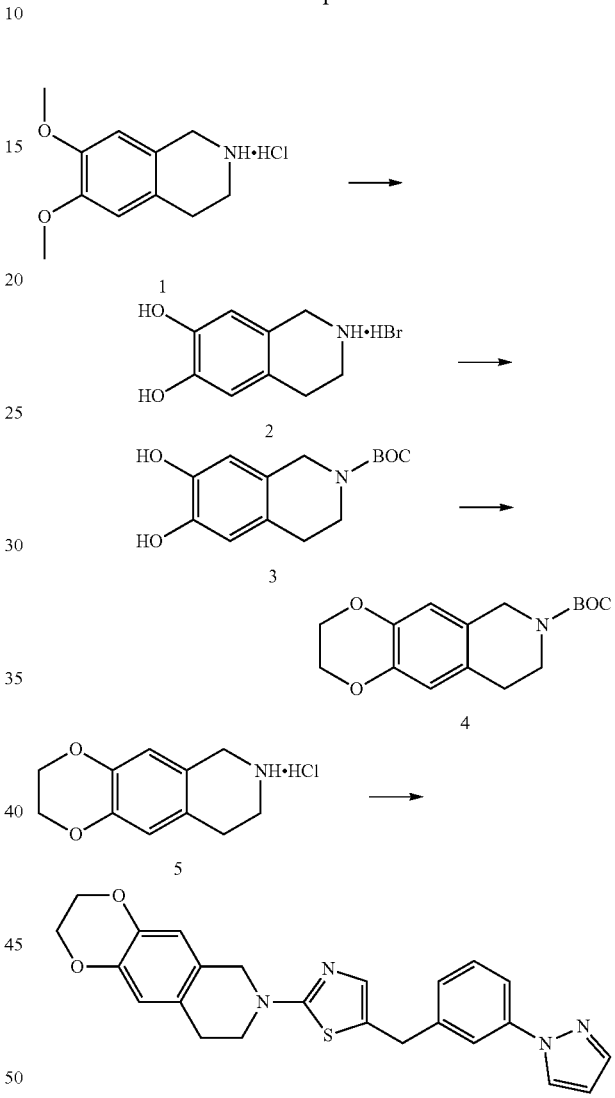

1. A mixture of 1 (Sigma-Aldrich, 2.03 g, 8.86 mmol) in 45% HBr in HOAC (15 mL) was heated to 110° C. and stirred for 5 h. After cooling to RT, the precipitate was filtered to afford 2 as white solid (1.92 g, 88%).

2. BOC$_2$O (1.88 g, 8.61 mmol) and TEA (2.8 mL, 16.45 mmol) in THF (20 mL) was added dropwise to a suspension of 2 (1.92 g, 7.83 mmol) in water (6 mL). The mixture was stirred at RT overnight. After concentration, the residue was dissolved in EtOAc was washed with water. The organic mixture was dried over Na$_2$SO$_4$ and concentrated. The residue was purified by flash column chromatography to give 3 (1.8 g, 86.9%).

3. To a solution of 3 (0.4 g, 1.5 mmol) in dioxane (20 mL) was added 1,2-dibromoethane (0.31 g, 1.66 mmol), 2 N aq. NaOH (5 mL, 10 mmol) and TBAB (20 mg, 0.16 mmol).

The mixture was heated to 90° C. and stirred overnight. The reaction was quenched with water and extracted with EtOAc. The organic extracts were dried over Na₂SO₄, filtered and concentrated to give 4 (210 mg, 47.8%).

4. To a solution of 4 (210 mg, 0.72 mmol) in DCM (20 mL) was added 4 M HCl/Dioxane (3 mL, 12 mmol). The mixture was stirred at RT overnight, then concentrated to afford 5 (150 mg, 92%).

Figure 5:
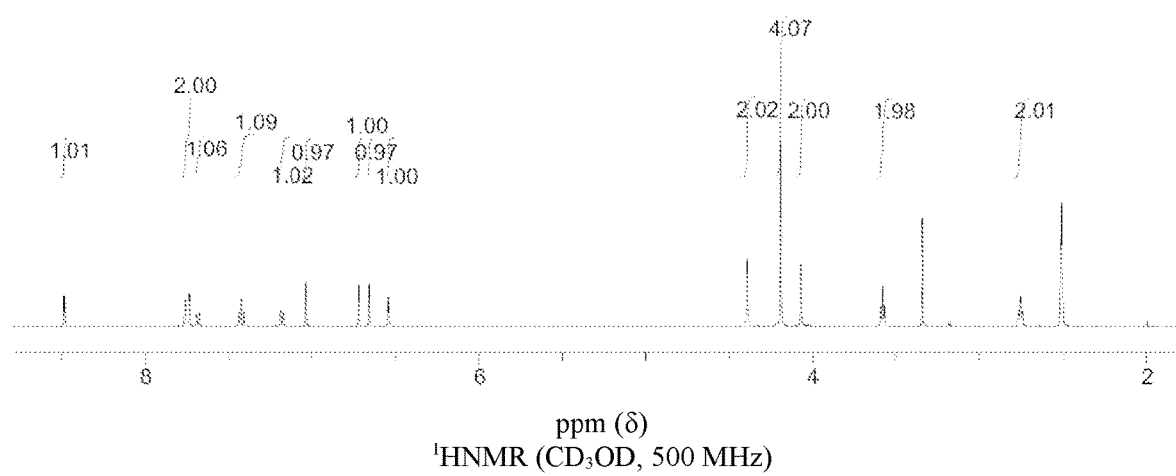
FIG. 5 presents the proton (1H) NMR Spectrum of Example 10 in CD$_3$OD at 500 MHz.

5. To a solution of 5 (137 mg, 0.6 mmol) in D5oxane (10 mL) was added Intermediate 2 (170 mg, 0.62 mmol), Pd2(dba)3 (55 mg, 0.06 mmol), SPhos (50 mg, 0.12 mmol) and t-KOBu (135 mg, 1.2 mmol). The mixture was heated to 100° C. and stirred for 20 h under N2. The mixture was quenched with water and extracted with EtOAc. The combined organic extracts were concentrated. The resulting material was purified by silica gel chromatography to afford Example 10 as white solid (80 mg, 30%). m/z=431.1 (M+H)⁺. An ¹HNMR Spectrum of Example 10 product is presented in FIG. 5.

Example 11

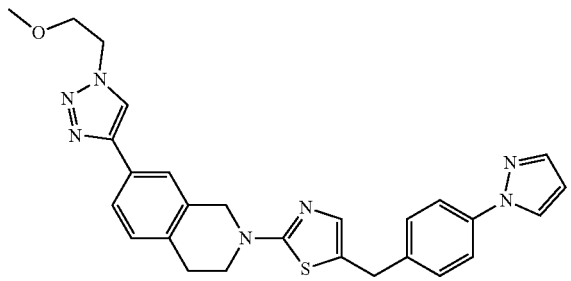 [SMILES: COCCn1cc(-c2ccc3c(c2)CN(c2ncc(Cc4ccc(-n5cccn5)cc4)s2)CC3)nn1]

1. The title compound was prepared following the procedure described for Example 7 using Intermediate 14 in place of Intermediate 11, 1 eq. of Intermediate 3, 0.09 eq. of Pd₂(dba)₃, 0.16 eq. SPhos and 3 eq. of t-BuOK to afford Example 11 (75.9 mg, 35%) as a white solid. ¹H NMR (400 MHz, DMSO-d₆) δ 2.92 (2H, t, J=6.0 Hz), 3.26 (3H, s), 3.67 (2H, t, J=6.0 Hz), 3.77 (2H, t, J=5.2 Hz), 4.04 (2H, s), 4.56 (2H, t, J=5.6 Hz), 4.60 (2H, s), 6.52-6.53 (1H, m), 7.03 (1H, s), 7.25 (1H, d, J=8.0 Hz), 7.36 (2H, d, J=8.8 Hz), 7.65-7.67 (1H, m), 7.70-7.72 (2H, m), 7.76-7.78 (2H, m), 8.45 (1H, d, J=2.4 Hz), 8.48 (1H, s). MS Calcd.: 497.2; MS Found: 498.2 [M+H]⁺.

Example 12

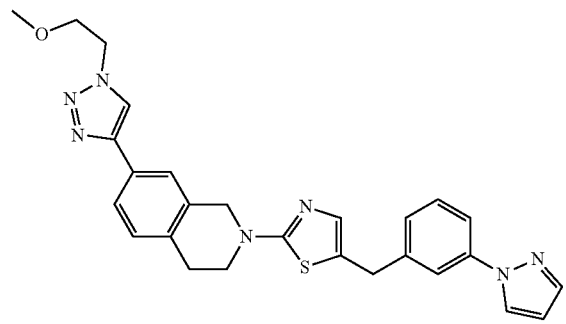 [SMILES: COCCn1cc(-c2ccc3c(c2)CN(c2ncc(Cc4cccc(-n5cccn5)c4)s2)CC3)nn1]

1. The title compound was prepared following the procedure described for Example 7 using Intermediate 14 in place of Intermediate 11, 1 eq. of Intermediate 2 in place of Intermediate 3, 0.09 eq. of Pd₂(dba)₃, 0.18 eq. SPhos and 3 eq. of t-BuOK to afford Example 12 (51.5 mg, 23%) as a white solid. ¹H NMR (400 MHz, DMSO-d₆) δ 2.91 (2H, t, J=6.0 Hz), 3.26 (3H, s), 3.67 (2H, t, J=6.0 Hz), 3.77 (2H, t, J=5.2 Hz), 4.08 (2H, s), 4.56 (2H, t, J=5.2 Hz), 4.59 (2H, s), 6.54 (1H, t, J=2.0 Hz), 7.06 (1H, s), 7.19 (1H, d, J=7.6 Hz), 7.25 (1H, d, J=8.0 Hz), 7.43 (1H, t, J=8.0 Hz), 7.65-7.77 (5H, m), 8.48-8.49 (2H, m). MS Calcd.: 497.2; MS Found: 498.2 [M+H]⁺.

Example 13

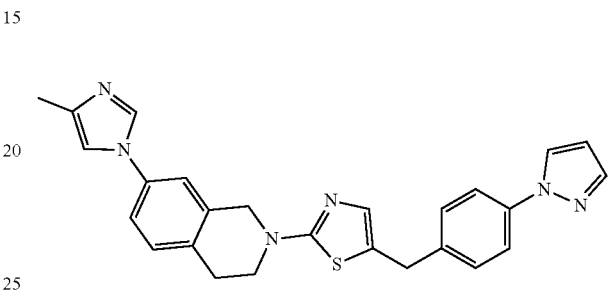

1. The title compound was prepared following the procedure described for Example 7 using Intermediate 15 in place of Intermediate 11, 1 eq. of Intermediate 3, 0.09 eq. of Pd₂(dba)₃, 0.2 eq. SPhos and 2.8 eq. of t-BuOK to afford Example 13 (33.4 mg, 15% yield) as a white solid. ¹H NMR (400 MHz, DMSO-d₆) δ 2.15 (3H, s), 2.91 (2H, t, J=5.6 Hz), 3.66 (2H, t, J=6.0 Hz), 4.04 (2H, s), 4.60 (2H, s), 6.53 (1H, t, J=2.0 Hz), 7.03 (1H, s), 7.29 (1H, d, J=8.0 Hz), 7.35-7.43 (4H, m), 7.51 (1H, d, J=2.0 Hz), 7.72 (1H, d, J=1.6 Hz), 7.77 (2H, d, J=8.8 Hz), 8.08 (1H, d, J=1.2 Hz), 8.46 (1H, d, J=2.4 Hz). MS Calcd.: 452.2; MS Found: 453.2 [M+H]⁺.

Example 14

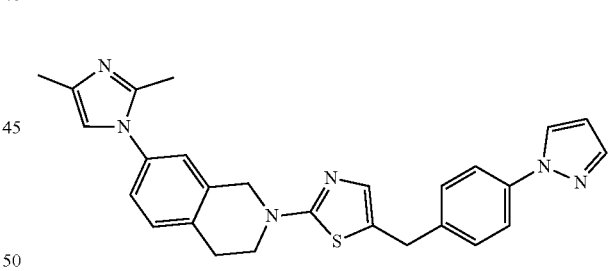

1. A mixture of Intermediate 1 (100 mg, 0.38 mmol), Intermediate 3, (115 mg, 0.42 mmol), Pd₂(dba)₃ (36.6 mg, 0.04 mmol), SPhos (32.9 mg, 0.08 mmol) and t-BuOK (128 mg, 1.14 mmol) in dry dioxane (4.00 mL) was stirred at 90° C. for 4 h. When the reaction was completed, it was quenched with water and extracted with EtOAc. The combined organic layers were washed with water, brine, dried over Na₂SO₄ and concentrated to give a crude product which was purified by prep-HPLC to afford Example 14 (33.5 mg, 19% yield) as a white solid. ¹H NMR (400 MHz, DMSO-d₆) δ 2.08 (3H, s), 2.22 (3H, s), 2.94 (2H, t, J=5.6 Hz), 3.67 (2H, d, J=5.6 Hz), 4.04 (2H, s), 4.59 (2H, s), 6.53 (1H, t, J=2.0 Hz), 6.92 (1H, d, J=8.0, 2.0 Hz), 7.03 (1H, s), 7.21 (1H, d, J=8.0, 2.0 Hz), 7.30-7.32 (2H, m), 7.36 (2H, d, J=8.4 Hz), 7.72 (1H, d, J=2.0 Hz), 7.77 (2H, d, J=8.8 Hz), 8.46 (1H, d, J=2.4 Hz). MS Calcd.: 466.2; MS Found: 467.2 [M+H]⁺.

Alternate Preparation of Example 14

1. To a solution of Intermediate 1 (25 g, 110 mmol) in DMSO (500 mL) was added Intermediate 3 (40 g, 145 mmol) and $K_2CO_3$ (45.54 g, 330 mmol). The flask was purged with $N_2$ three times and stirred at 140° C. for 2 hrs, cooled to RT, diluted with EA, filtered, concentrated and the residue purified by chromatography on silica gel, eluting to give a material that was recrystallized with EtOAc to give Example 14 (21.8 g, 42.5% yield) as an off-white solid. MS (ESI): mass calcd. for $C_{27}H_{26}N_6S$ 466.61, m/z found 466.8 $[M+H]^+$. $^1H$ NMR (400 MHz, DMSO) δ ppm 8.46 (d, J=2.3 Hz, 1H), 7.78 (d, J=8.4 Hz, 2H), 7.73 (s, 1H), 7.37 (d, J=8.4 Hz, 2H), 7.33-7.31 (m, 2H), 7.22 (d, J=8.1 Hz, 1H), 7.03 (s, 1H), 6.94 (s, 1H), 6.53 (s, 1H), 4.60 (s, 2H), 4.05 (s, 2H), 3.68 (t, J=5.9 Hz, 2H), 2.95 (t, J=5.8 Hz, 2H), 2.23 (s, 3H), 2.09 (s, 3H).

Example 15

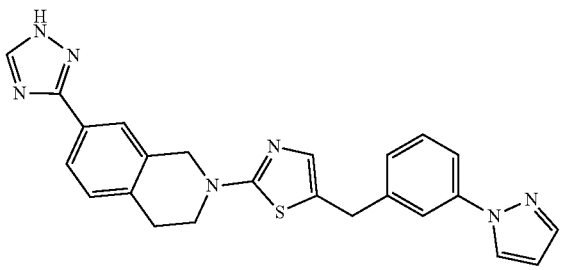 [SMILES: c1cc(Cc2cnc(N3CCc4ccc(-c5nc[nH]n5)cc4C3)s2)cc(-n2cccn2)c1]

1. A mixture of Intermediate 16 (130 mg, 0.31 mmol) and DMF-DMA (10 mL) was stirred at 100° C. for 1 h. The mixture was concentrated and the residue was dissolved in the mixture of EtOH (10 mL) and $N_2H_4 \cdot H_2O$ (2 mL), and the resulting mixture was stirred at RT for 0.5 h. The mixture was quenched with water and extracted with EtOAc. The combined organic layers were washed with water and brine, dried over $Na_2SO_4$, and concentrated. The residue was purified by prep-HPLC to give Example 15 (11.0 mg, 8% yield) as a white solid. $^1H$ NMR (400 MHz, DMSO-$d_6$) δ 2.92-2.94 (2H, m), 3.68 (2H, t, J=6.0 Hz), 4.08 (2H, s), 4.61 (2H, s), 6.54 (1H, t, J=2.0 Hz), 7.06 (1H, s), 7.18 (1H, d, J=8.0 Hz), 7.25-7.30 (1H, m), 7.43 (1H, t, J=7.6 Hz), 7.67-7.69 (1H, m), 7.73 (1H, d, J=1.6 Hz), 7.77 (1H, s), 7.81-7.84 (2H, m), 8.49 (1H, d, J=2.8 Hz), 8.58-8.62 (1H, m), 14.09-14.40 (1H, m). MS Calcd.: 439.2; MS Found: 440.1 $[M+H]^+$.

Example 16

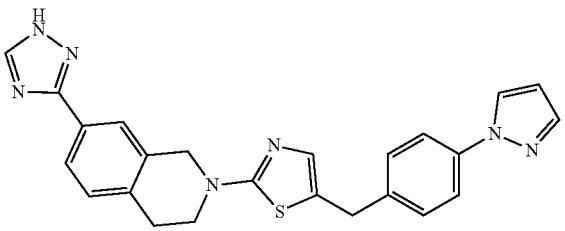 [SMILES: c1cnn(-c2ccc(Cc3cnc(N4CCc5ccc(-c6nc[nH]n6)cc5C4)s3)cc2)c1]

Figure 6:
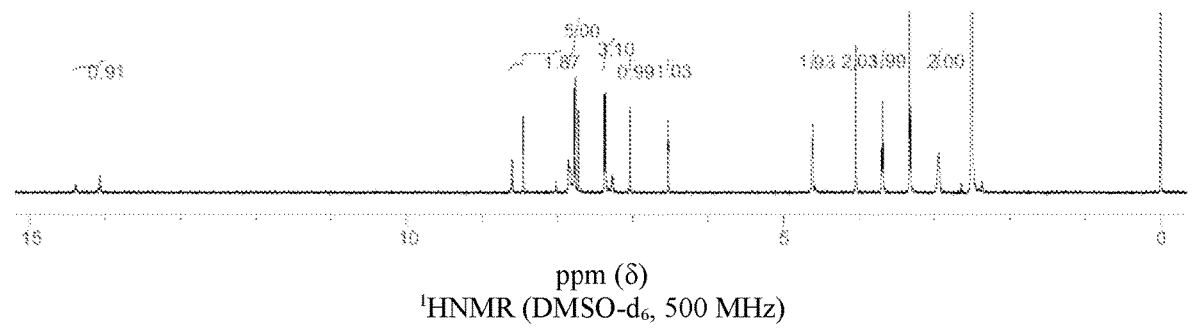
FIG. 6 presents the proton (1H) NMR Spectrum of Example 16 in DMSO-d$_6$ at 500 MHz.

1. Following the procedure described for Example 15, Intermediate 17 (0.18 g, 0.43 mmol) was converted to Example 16 as white solid (60 mg, 31%). LC-MS: m/z=440.2 (M+1)+. An $^1HNMR$ Spectrum of Example 17 product is presented in FIG. 6.

Example 17

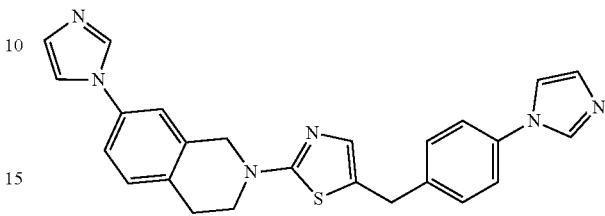

1. Following the procedure described for Example 1, Intermediate 18 and Intermediate 12 were reacted to afford 19.6 mg of Example 17. $^1HNMR$ (CDCl$_3$, 300 MHz) δ: 3.0-3.1 (m, 2H), 3.7-3.8 (m, 2H), 4.1 (m, 2H), 4.7-4.8 (s, 2H), 7.0-7.1 (s, 1H), 7.2-7.5 (m, 14H), 7.8-7.9 (s, 2H). LC-MS: m/z=439.4 $(M+1)^+$.

Example 18

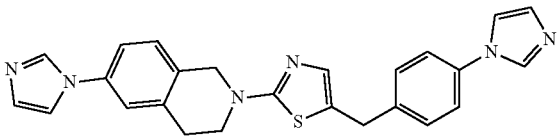 [SMILES: c1cn(-c2ccc(Cc3cnc(N4CCc5cc(-n6ccnc6)ccc5C4)s3)cc2)cn1]

1. Following the procedure described for Example 1, 300 mg of Intermediate 3 and 350 mg of Intermediate 13 were converted to Example 18 (24.62 mg). $^1HNMR$ (CDCl$_3$, 300 MHz) δ: 3.0-3.1 (m, 2H), 3.7-3.8 (m, 2H), 4.0-4.1 (m, 2H), 4.6-4.7 (s, 2H), 6.4-6.5 (s, 1H), 6.9-7.0 (s, 1H), 7.2 (s, 1H), 7.3-7.4 (d, 2H), 7.6-7.7 (d, 1H), 7.7-7.8 (s, 1H), 7.8-7.9 (s, 1H) 7.9-8.0 (s, 1H). LC-MS: m/z=439.3 $(M+1)^+$.

Example 19

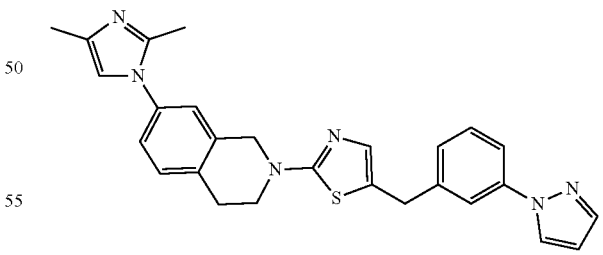

1. Following the procedure described for Example 7 using Intermediate 1 in place of Intermediate 11, 1.2 eq. of Intermediate 2 in place of Intermediate 3, 0.11 eq. of Pd$_2$(dba)$_3$, 0.22 eq. SPhos and 3 eq. of t-BuOK provided Example 19 (33.5 mg, 20% yield) as a white solid. $^1H$ NMR (400 MHz, DMSO-$d_6$) δ 2.08 (3H, s), 2.21 (3H, s), 2.94 (2H, t, J=5.6 Hz), 3.67 (2H, t, J=2.0 Hz), 4.09 (2H, d, J=4.8 Hz), 4.59 (2H, s), 6.54 (1H, t, J=2.4 Hz), 6.91 (1H, s), 7.06-7.07 (1H, m), 7.20 (2H, t, J=8.0 Hz), 7.29-7.35 (2H, m), 7.40-

7.44 (1H, m), 7.69 (1H, d, J=8.4 Hz), 7.73 (1H, d, J=1.2 Hz), 7.76 (1H, s), 8.48 (1H, d, J=2.8 Hz). MS Calcd.: 466.2; MS Found: 467.3 [M+H]⁺.

Example 20

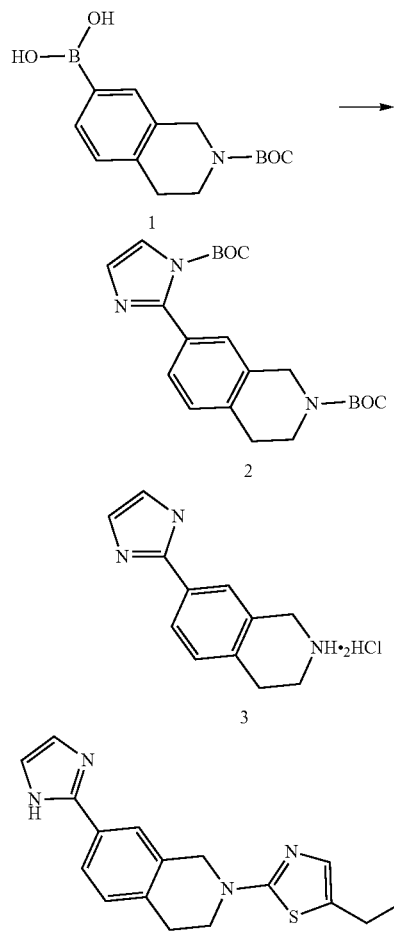

1. To a mixture of 1 (PCT Int. Appl. (2008), WO 2008079277 A, 4 g, 14 mmol) tert-butyl 2-bromo-1H-imidazole-1-carboxylate (FCH Group, 1.8 g, 7 mmol) and NaOH (3 mL, 1.5 M) in toluene (20 mL) and ethanol (2 mL) was added Pd(PPh₃)₄ (0.084 g, 0.14 mmol) under N₂. The resulting mixture was stirred at 120° C. for 24 h. The mixture was cooled to RT, treated with water and extracted with EA. The combined organic extracts were washed with water, brine, dried over anhydrous Na₂SO₄, filtered and concentrated to give a crude oil. The crude product was purified by recrystallization to afford 2 (1.1 g, 38%).

2. A mixture of 2 (1.1 g, 2.76 mmol) in HCl/Et₂O (3 M, 20 ml) was stirred at RT overnight. The mixture was filtered the filter cake washed with Et₂O to give 3 (0.4 g, 80%).

3. To a mixture of 3 (0.3 g, 1.6 mmol) in DMSO (5 mL) were added Intermediate 3 (0.3 g, 1.1 mmol)) and K₂CO₃ (0.3 g, 2.2 mmol). The mixture was stirred at 140° C. overnight. The mixture was cooled to RT, treated with water and extracted with EA. The combined organic extracts were washed with water, brine, dried over anhydrous Na₂SO₄, filtered and concentrated to give a crude oil which was purified by silica gel chromatography to afford Example 20 (15 mg). ¹HNMR (CDCl₃, 300 MHz) δ: 2.9-3.1 (m, 2H), 3.7-3.8 (m, 2H), 4.0-4.1 (m, 2H), 4.6-4.7 (s, 2H), 6.4-6.5 (s, 1H), 6.9-7.0 (s, 1H), 7.1-7.2 (m, 3H), 7.6-7.8 (m, 4H), 7.9-8.0 (s, 1H). LC-MS: m/z=439.4 (M+23)⁺

Example 21

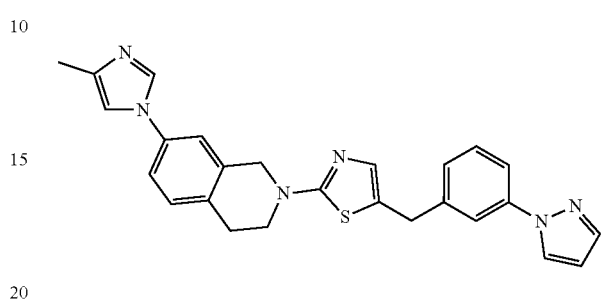

1. A mixture of Intermediate 4 (190 mg, 0.42 mmol), 4-methyl-1H-imidazole (104 mg, 1.26 mmol), (S,S)—N,N'-dimethyl-1,2-diaminocyclohexane (12 mg, 0.08 mmol), t-BuOK (141 mg, 1.26 mmol) and CuI (40 mg, 0.21 mmol) in NMP (5 mL) was stirred at 140° C. overnight under N₂. The mixture was cooled to RT, diluted with MeOH, filtered, the filtrate concentrated and purified by Prep-HPLC to give Example 21 (20 mg, 10.5% yield) as a yellow-white solid. MS (ESI): mass calcd. for C₂₆H₂₄N₆S 452.58, m/z found 452.8 [M+H]⁺. ¹H NMR (400 MHz, DMSO) δ ppm 8.49 (d, J=2.3 Hz, 1H), 8.08 (s, 2H), 7.77 (s, 1H), 7.74 (s, 1H), 7.69 (d, J=8.3 Hz, 1H), 7.51 (s, 1H), 7.44-7.41 (m, 2H), 7.29 (d, J=8.2 Hz, 1H), 7.20 (d, J=7.6 Hz, 1H), 7.07 (s, 1H), 6.55 (s, 1H), 4.60 (s, 2H), 4.09 (s, 2H), 3.66 (t, J=5.9 Hz, 2H), 2.92 (t, J=5.8 Hz, 2H), 2.16 (s, 2H).

Example 22

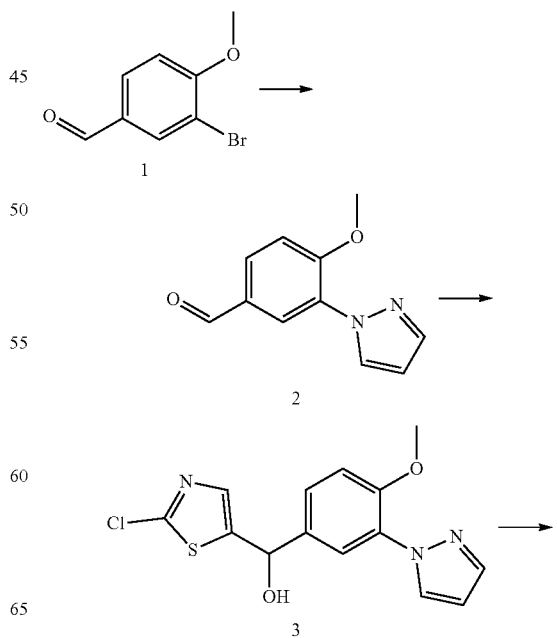

73

-continued

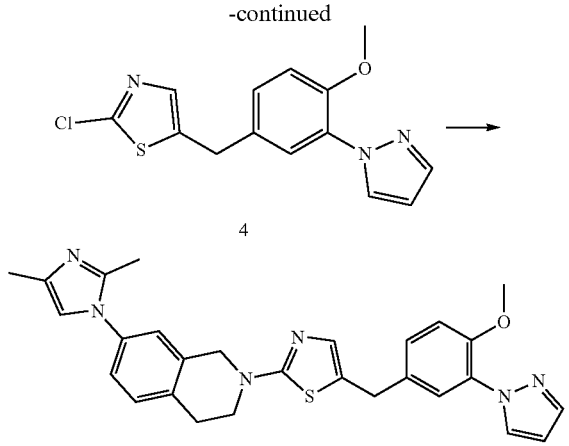

1. To a solution of 1 (4.50 g, 20.93 mmol) in DMF (30 mL) was added (R,R)—N,N'-dimethyl-1,2-diaminocyclohexane (0.30 g, 2.09 mmol), 1H-pyrazole (1.42 g, 20.93 mmol), CuI (0.40 g, 2.09 mmol) and K$_2$CO$_3$ (5.75 g, 41.7 mmol). The reaction mixture was stirred at 150° C. for 18 h. The reaction was cooled to RT, poured into ice-water, extracted with CH$_2$Cl$_2$, dried over Na$_2$SO$_4$. The combined organic extracts were concentrated under reduce pressure and purified by chromatography on silica gel to afford 2 (1.80 g, 42.6% yield) as a yellow solid. MS (ESI): mass calcd. for C$_{20}$H$_{18}$BrN$_3$OS 202.21, m/z found 202.7 [M+H]$^+$.

2. To a solution of 2-chlorothiazole (1.07 g, 8.9 mmol) in dry THF (40 mL) at −78° C. was added n-BuLi (2.4M, 4.0 mL, 9.6 mmol) dropwise. After 1 h, a solution of 2 (1.80 g, 8.9 mmol) in THF (40 mL) was added dropwise. The reaction was slowly warmed to RT. The mixture was quenched with sat. aq. of NH$_4$Cl and extracted with EtOAc and the combined organic extracts were washed with brine, dried over Na$_2$SO$_4$, filtered and concentrated. The resulting residue was purified by chromatography on silica gel to afford 3 (1.4 g, 48.9% yield) as a yellow oil. MS (ESI): mass calcd. for C$_{10}$H$_7$BrClNOS 321.78, m/z found 322.4 [M+H]$^+$.

3. A mixture of 3 (1.40 g, 4.35 mmol) in TES (5 mL) and TFA (15 mL) was stirred at 60° C. for 2 hrs. The mixture was concentrated and the residue was washed with sat. aq. NaHCO$_3$ and extracted with CH$_2$Cl$_2$, dried over Na$_2$SO$_4$. The organic extracts were concentrated to give a crude product which was purified by chromatography on silica gel to afford 4 (1.2 g, 90.2% yield) as a yellow oil. MS (ESI): mass calcd. for C$_{10}$H$_7$BrClNS 305.78, m/z found 306.2 [M+H]$^+$.

4. To a solution of 4 (0.2 g, 0.65 mmol) in 1,4-dioxane (30 mL) was added Intermediate 1 (0.148 g, 0.65 mmol) and K$_2$CO$_3$ (0.27 g, 1.95 mmol). The reaction was stirred at 120° C. for 5 h. The mixture was cooled to RT, poured into ice-water, extracted with CH$_2$Cl$_2$ and the combined organic extracts were washed with brine, dried over Na$_2$SO$_4$, filtered, concentrated under reduce pressure. The resulting residue was purified by Prep-HPLC to afford the Example 22 (18.5 mg, 5.7% yield) as a yellow solid. MS (ESI): mass calcd. for C$_{28}$H$_{28}$N$_6$OS 496.63, m/z found 496.7 [M+H]$^+$. $^1$H NMR (400 MHz, DMSO-d6) δ ppm 8.16 (d, J=2.4 Hz, 1H), 7.68 (s, 1H), 7.53 (d, J=1.6 Hz, 1H), 7.32 (d, J=8.4 Hz, 2H), 7.28-7.15 (m, 3H), 7.03 (s, 1H), 6.93 (s, 1H), 6.47 (s, 1H), 4.59 (s, 2H), 4.02 (s, 2H), 3.67 (s, 2H), 2.67 (t, J=5.8 Hz, 2H), 2.95 (t, J=5.8 Hz, 2H), 2.23 (s, 3H), 2.09 (s, 3H).

74

Example 23

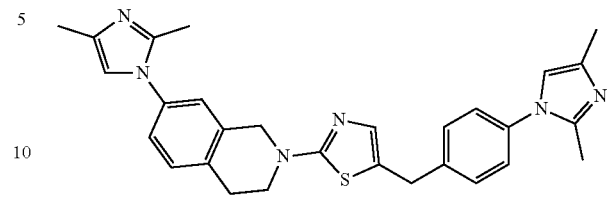

1. Following the procedure described for Example 1, Intermediate 19 (225 mg) and Intermediate 1 (202 mg) were converted to Example 23 as a white solid. MS (ESI): mass calcd. for C$_{29}$H$_{30}$N$_6$S 494.66, m/z found 494.8 [M+H]$^+$. NMR (400 MHz, DMSO) δ ppm 7.44 (s, 4H), 7.39 (d, J=8.8 Hz, 2H), 7.31 (d, J=8.1 Hz, 1H), 7.21 (d, J=8.3 Hz, 2H), 7.07 (s, 1H), 4.63 (s, 2H), 4.10 (s, 2H), 3.69 (t, J=5.7 Hz, 2H), 2.98 (t, J=5.6 Hz, 2H), 2.35 (d, J=5.2 Hz, 6H), 2.19 (s, 6H).

Example 24

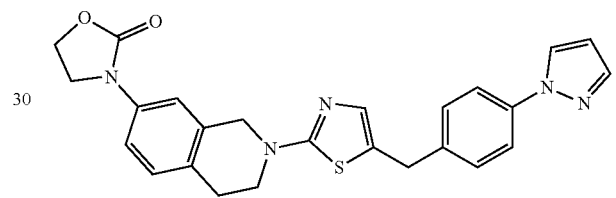

1. The title compound was prepared following the procedure described for Example 21 using Intermediate 5 (100 mg) in place of Intermediate 4, oxazolidin-2-one (1.15 eq.) in place of 4-methyl-1H-imidazole, t-BuOK (3 eq.), CuI (0.6 eq), (S,S)—N,N'-dimethyl-1,2-diaminocyclohexane (0.2 eq) to give Example 24 (40 mg, 14.8% yield) as a yellow solid. MS (ESI): mass calcd. for C$_{25}$H$_{23}$N$_5$O$_2$S 457.55, m/z found 457.7 [M+H]$^+$. NMR (400 MHz, DMSO-d6) δ ppm 8.46 (d, J=2.0 Hz, 1H), 7.78 (d, J=8.4 Hz, 2H), 7.73 (s, 1H), 7.45 (d, J=8.4 Hz, 1H), 7.39-7.36 (m, 3H), 7.21 (d, J=8.4 Hz, 1H), 7.08 (s, 1H), 6.54 (s, 1H), 4.57 (s, 2H), 4.44 (t, J=7.6 Hz, 2H), 4.08-4.00 (m, 4H), 3.67 (t, J=5.6 Hz, 2H), 2.89 (t, J=6.0 Hz, 2H).

Example 25

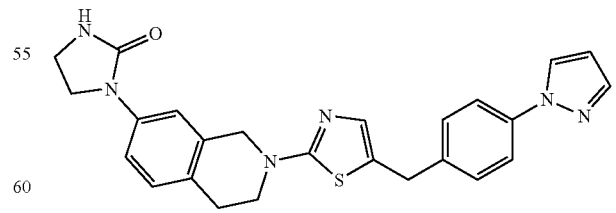

1. The title compound was prepared following the procedure described for Example 21 using Intermediate 5 (200 mg) in place of Intermediate 4, imidazolidin-2-one (1 eq.) in place of 4-methyl-1H-imidazole, t-BuOK (3 eq.), CuI (0.5 eq), (S,S)—N,N'-dimethyl-1,2-diaminocyclohexane (0.2 eq)

to give Example 25 (30 mg, 14.8% yield) as a yellow solid. MS (ESI): mass calcd. for $C_{25}H_{24}N_6OS$ 456.56, m/z found 456.8 [M+H]$^+$. $^1$H NMR (400 MHz, DMSO-d6) δ ppm 8.45 (d, J=2.4 Hz, 1H), 7.76 (d, J=8.4 Hz, 2H), 7.72 (s, 1H), 7.44 (dd, J=8.4, 1.6 Hz, 1H), 7.38-7.31 (m, 3H), 7.09 (d, J=8.4 Hz, 1H), 7.01 (s, 1H), 6.91 (s, 1H), 6.52 (s, 1H), 4.51 (s, 2H), 4.03 (s, 2H), 3.80 (t, J=7.6 Hz, 2H), 3.63 (t, J=6.0 Hz, 2H), 3.38 (t, J=8.4 Hz, 2H), 2.82 (t, J=6.0 Hz, 2H).

Example 26

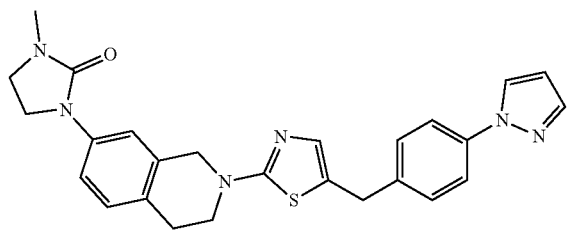 [SMILES: CN1CCN(c2ccc3c(c2)CN(c2ncc(Cc4ccc(-n5cccn5)cc4)s2)CC3)C1=O]

1. A mixture of Intermediate 5 (100 mg, 0.22 mmol), 1-methylimidazolidin-2-one (66 mg, 0.66 mmol), (Pd$_2$(dba)$_3$) (100 mg, 0.11 mmol), t-BuOK (74 mg, 0.66 mmol) and SPhos (44 mg, 0.11 mmol) in dioxane (10 mL) was stirred under nitrogen atmosphere at 100° C. for 16 h. The solvent was removed under reduce pressure and the residue was purified by prep-HPLC to give Example 26 (50 mg, 48.1% yield) as a yellow solid. MS (ESI): mass calcd. for $C_{26}H_{26}N_6OS$ 470.59, m/z found 470.8 [M+H]$^+$. $^1$H NMR (400 MHz, DMSO-d6) δ ppm 8.45 (d, J=2.4 Hz, 1H), 7.76 (d, J=8.4 Hz, 2H), 7.72 (s, 1H), 7.47 (dd, J=8.4, 2.0 Hz, 1H), 7.38-7.31 (m, 3H), 7.10 (d, J=8.4 Hz, 1H), 7.01 (s, 1H), 6.52 (s, 1H), 4.51 (s, 2H), 4.03 (s, 2H), 3.74 (t, J=7.2 Hz, 2H), 3.63 (t, J=5.6 Hz, 2H), 3.41 (t, J=8.4 Hz, 2H), 2.83 (t, J=6.0 Hz, 2H), 2.75 (s, 3H).

Example 27

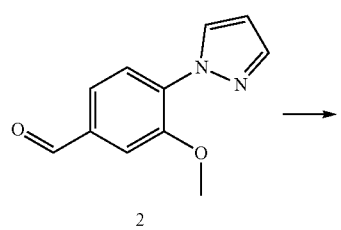

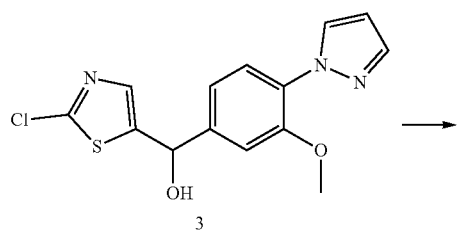

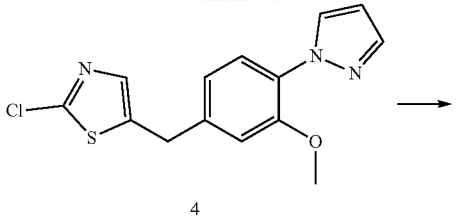

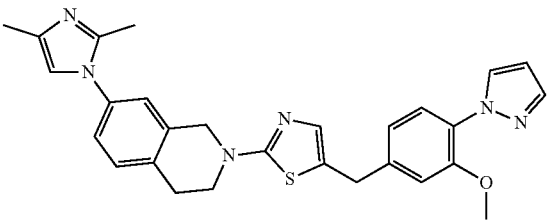

1. A mixture of 4-fluoro-3-methoxy-benzaldehyde (5.0 g, 32.4 mmol), 1H-pyrazole (3.3 g, 48.6 mmol), K$_2$CO$_3$ (6.8 g, 48.6 mmol) in DMF (30 mL) was stirred under N$_2$ at 120° C. for 20 h. After cooling to RT, ice-water was added to the mixture which was then extracted with EA. The combined organic extracts were washed with water, brine and dried over Na$_2$SO$_4$, filtered and concentrated. The resulting residue was purified by column chromatography on silica gel to give 2 (3.0 g, 53.4% yield) as a pale yellow solid. MS (ESI): mass calcd. for $C_{11}H_{10}N_2O_2$ 202.21, m/z found 202.9 [M+H]$^+$.

2. To a solution of 2-chlorothiazole (3.0 g, 25.1 mmol) in dry THF (100 mL) at −78° C. was added n-BuLi (11.3 mL, 2.4 M, 27.2 mmol) dropwise and stirred at this temperature for 1 h. A solution of 2 (4.2 g, 20.9 mmol) was added dropwise at −78° C. The resulting solution was slowly warmed to RT. The reaction mixture was quenched with NH$_4$Cl solution and extracted with EA. The combined organic extracts were washed with brine and dried over Na$_2$SO$_4$, filtered and concentrated. The resulting residue was purified by column chromatography on silica gel to give 3 (5.6 g, 83.8% yield) as a yellow solid. MS (ESI): mass calcd. for $C_{14}H_{12}ClN_3O_2S$ 321.78, m/z found 321.8 [M+H]$^+$.

3. To a RT solution of 3 (5.6 g, 17.4 mmol) in TFA (20 mL) was added TES (11.4 g, 69.6 mmol). The reaction mixture was stirred at reflux for 1 h. The mixture was evaporated, and ice-water was added to the mixture which was then extracted with EA. The combined organic extracts were washed with saturated NaHCO$_3$ solution, brine and dried over Na$_2$SO$_4$, filtered and concentrated. The resulting residue was purified by column chromatography on silica gel 4 (4.8 g, 90.2% yield) as a clear liquid. MS (ESI): mass calcd. for $C_{14}H_{12}ClN_3OS$ 305.78, m/z found 305.8 [M+H]$^+$.

4. Following the procedure described for Example 1, 4 (200 mg) and Intermediate 1 (148 mg) were converted to Example 27 (10 mg, 57.3% yield) as a white solid. MS (ESI): mass calcd. for $C_{28}H_{28}N_6OS$ 496.63, m/z found 496.8 [M+H]$^+$. $^1$H NMR (400 MHz, DMSO-d6) δ ppm 8.11 (d, J=2.4 Hz, 1H), 7.66 (s, 1H), 7.53 (d, J=8.4 Hz, 1H), 7.36 (m, 2H), 7.28 (d, J=8.0 Hz, 1H), 7.16 (s, 1H), 7.13 (s, 1H), 7.05 (s, 1H), 6.93 (d, J=8.0 Hz, 1H), 6.45 (s, 1H), 4.61 (s, 2H), 4.06 (s, 2H), 3.83 (s, 3H), 3.68 (t, J=6.0 Hz, 2H), 2.96 (t, J=6.0 Hz, 2H), 2.31 (s, 3H), 2.15 (s, 3H).

Example 28

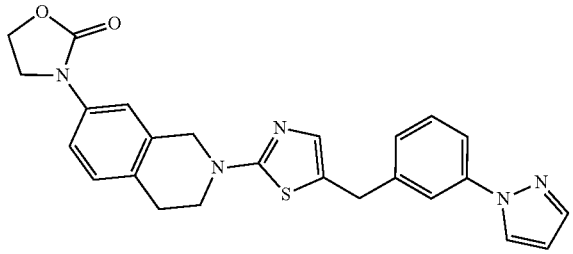 [SMILES: O=C1OCCN1c1ccc2c(c1)CN(c1ncc(Cc3cccc(-n4cccn4)c3)s1)CC2]

1. Following the procedure described for Example 1, Intermediate 20 and Intermediate 2 were reacted to afford Example 28 (43.2 mg, 26.2% yield) as a white solid. MS (ESI): mass calcd. for $C_{25}H_{23}N_5O_2S$ 457.55, m/z found 457.8 [M+H]$^+$. $^1$H NMR (400 MHz, DMSO-d6) δ ppm 8.48 (d, J=2.0 Hz, 1H), 7.75 (d, J=12.4 Hz, 2H), 7.69 (d, J=8.0 Hz, 1H), 7.44 (dd, J=15.8, 7.8 Hz, 2H), 7.36 (s, 1H), 7.19 (d, J=8.0 Hz, 2H), 7.05 (s, 1H), 6.54 (s, 1H), 4.54 (s, 2H), 4.43 (t, J=7.8 Hz, 2H), 4.08 (s, 2H), 4.03 (t, J=8.0 Hz, 2H), 3.64 (t, J=5.8 Hz, 2H), 2.86 (t, J=5.6 Hz, 2H).

Example 29

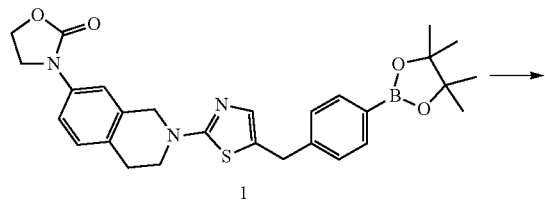

1. A mixture of Intermediate 22 (329 mg, 0.48 mmol), 4,4,4',4',5,5,5',5'-octamethyl-2,2'-bi(1,3,2-dioxaborolane) (203 mg, 0.8 mmol), Pd(dppf)Cl$_2$ (102 mg, 0.14 mmol) and AcOK (206 mg, 2.1 mmol) in dry 1,4-dioxane (20 mL) was stirred at 100° C. overnight. The mixture was cooled to RT, concentrated and the residue purified by chromatography on silica gel to afford 1 (250 mg, 69.0%). mass calcd. for $C_{28}H_{32}BN_3O_4S$ 517.45, m/z found 517.6 [M+H]$^+$.

2. To a mixture of 1 (100 mg, 0.19 mmol) and 2-chloropyrimidine (23 mg, 0.20 mmol) in 1,4-dioxane (8 mL) and H$_2$O (2 mL) were added K$_2$CO$_3$ (80 mg, 0.57 mmol), Pd(dppf)Cl$_2$ (14 mg, 0.02 mmol). The resulting mixture was stirred at 100° C. overnight. The mixture was cooled to room temperature, poured into ice-water, extracted with EA, the combined organic phase was washed with brine, dried over Na$_2$SO$_4$, filtered and concentrated. The resulting residue was purified by Prep-TLC to give Example 29 (9 mg, 10%) as a white solid. mass calcd. For $C_{26}H_{23}N_5O_2S$ 469.16. m/z found 469.7 [M+H]$^+$, $^1$H NMR (400 MHz, DMSO) δ ppm 8.90 (d, J=4.8 Hz, 2H), 8.34 (d, J=8.1 Hz, 2H), 7.51-7.32 (m, 5H), 7.20 (d, J=8.4 Hz, 1H), 7.05 (s, 1H), 4.55 (s, 2H), 4.43 (t, J=7.9 Hz, 2H), 4.09 (s, 2H), 4.03 (t, J=8.0 Hz, 2H), 3.65 (t, J=5.8 Hz, 2H), 2.87 (t, J=5.7 Hz, 2H).

Example 30

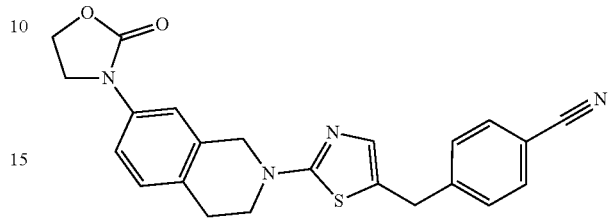

1. To a solution of Intermediate 22 (180 mg, 0.38 mmol) in DMI (6 mL) were added CuCN (70 mg, 0.78 mmol) and CuI (90 mg, 0.46 mmol). The resulting mixture was heated to 190° C. for 1 h in a microwave. The reaction mixture was cooled to RT, poured into water and extracted with CH$_2$Cl$_2$. The combined extracts were dried over Na$_2$SO$_4$, filtered and the filtrate concentrated. The resulting residue was purified by Prep-TLC to afford Example 30 (11 mg, 7%) as a white solid. mass calcd. for $C_{23}H_{20}N_4O_2S$ 416.5, m/z found 416.8 [M+H]$^+$, $^1$H NMR (400 MHz, DMSO-d6) δ ppm 7.78 (d, J=8.1 Hz, 2H), 7.46 (d, J=8.1 Hz, 2H), 7.37 (s, 1H), 7.20 (d, J=8.5 Hz, 1H), 7.04 (s, 1H), 4.55 (s, 2H), 4.46-4.41 (m, 2H), 4.11 (s, 2H), 4.06-4.01 (m, 2H), 3.65 (t, J=5.9 Hz, 2H), 2.86 (t, J=5.8 Hz, 2H).

Example 31

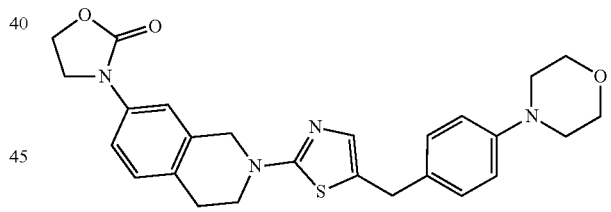

1. A mixture of Intermediate 22 (240 mg, 0.5 mmol), morpholine (131 mg, 1.5 mmol), Pd$_2$(dba)$_3$ (229 mg, 0.25 mmol), SPhos (103 mg, 0.25 mmol) and K$_2$CO$_3$ (207 mg, 1.5 mmol) in 1,4-dioxane (15 mL) was stirred at 100° C. overnight. The mixture was cooled to RT, poured into water and extracted with CH$_2$Cl$_2$. The combined extracts were dried over Na$_2$SO$_4$, filtered and the filtrate concentrated. The resulting residue was purified by Prep-TLC to afford Example 31 (10 mg, 4.2%) as a white solid. mass calcd. for $C_{26}H_{28}N_4O_3S$ 476.6, m/z found 476.8 [M+H]$^+$, $^1$H NMR (400 MHz, DMSO-d6) δ ppm 7.45 (d, J=9.9 Hz, 1H), 7.37 (s, 1H), 7.19 (d, J=8.4 Hz, 1H), 7.09 (d, J=8.4 Hz, 2H), 6.95 (s, 1H), 6.87 (d, J=8.5 Hz, 2H), 4.53 (s, 2H), 4.48-4.34 (m, 2H), 4.12-3.95 (m, 2H), 3.88 (s, 2H), 3.75-3.67 (m, 4H), 3.64 (t, J=5.8 Hz, 2H), 3.08-3.01 (m, 4H), 2.87 (t, J=5.9 Hz, 2H).

Example 32

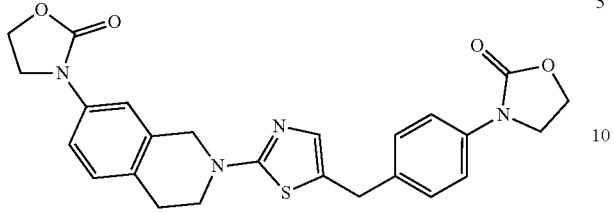

1. Following the procedure described for Example 31 using t-BuOK (170 mg) instead of $K_2CO_3$, Intermediate 22 (240 mg) and oxazolidin-2-one (170 mg) were converted to Example 32 (10 mg, 4%) as a white solid. mass calcd. for $C_{25}H_{24}N_4O_4S$ 476.55, m/z found 476.7 [M+H]$^+$, $^1$H NMR (400 MHz, DMSO) δ ppm 7.50 (d, J=8.4 Hz, 2H), 7.45 (d, J=8.2 Hz, 1H), 7.37 (s, 1H), 7.26 (d, J=8.4 Hz, 2H), 7.20 (d, J=8.3 Hz, 1H), 6.98 (s, 1H), 4.54 (s, 2H), 4.43 (t, J=7.0 Hz, 4H), 4.04 (t, J=7.1 Hz, 4H), 3.98 (s, 2H), 3.64 (t, J=5.9 Hz, 2H), 2.86 (t, J=5.9 Hz, 2H).

Example 33

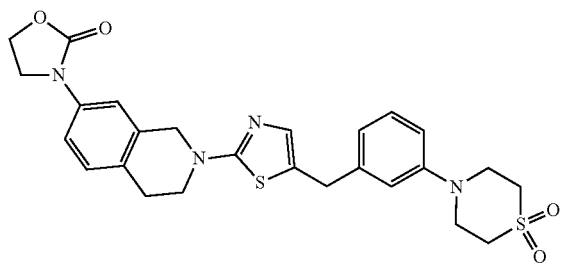 [SMILES: O=C1OCCN1c1ccc2c(c1)CN(c1ncc(Cc3cccc(N4CCS(=O)(=O)CC4)c3)s1)CC2]

1. Following the procedure described for Example 31 using $Cs_2CO_3$ (488 mg) instead of $K_2CO_3$, Intermediate 21 (220 mg) and thiomorpholine 1,1-dioxide (270 mg) were converted to Example 33 (7.8 mg, 2.9%) as a white solid. mass calcd. For $C_{26}H_{28}N_4O_4S_2$ 524.65, m/z found 524.7 [M+H]$^+$, $^1$H NMR (400 MHz, CDCl$_3$) δ ppm 7.38 (d, J=8.8 Hz, 2H), 7.25 (d, J=7.8 Hz, 1H), 7.19 (d, J=8.4 Hz, 1H), 7.00 (s, 1H), 6.87-6.77 (m, 3H), 4.64 (s, 2H), 4.51 (dd, J=8.8, 7.0 Hz, 2H), 4.16 (t, J=8.0 Hz, 2H), 3.98 (s, 2H), 3.85 (t, J=5.2 Hz, 4H), 3.76 (t, J=5.8 Hz, 2H), 3.11 (t, J=5.0 Hz, 4H), 2.96 (t, J=5.8 Hz, 2H).

Example 34

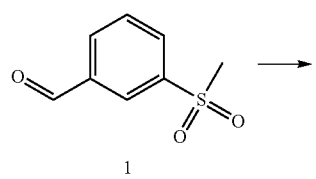

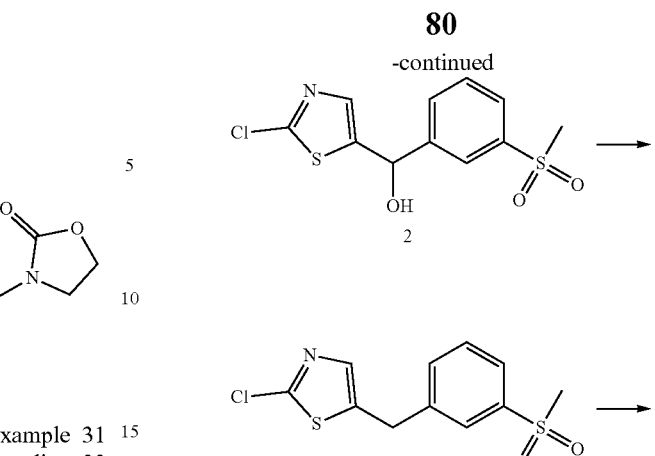

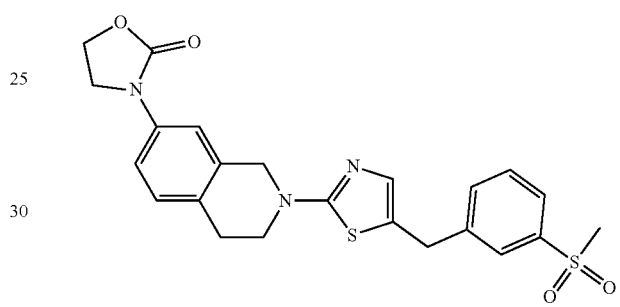

1. To a solution of 2-chlorothiazole (0.72 g, 6.00 mmol) in dry THF (50 mL) at –78° C. under $N_2$ was added n-BuLi (2.4M, 2.5 mL, 6 mmol) dropwise. After 0.5 h a solution of 1 (1.00 g, 5.43 mmol) in dry THF (5 mL) was added dropwise. The reaction was slowly warmed to RT. The reaction was quenched with saturated $NH_4Cl$ and extracted with EtOAc. The combined organic extracts were washed with brine, dried over $Na_2SO_4$, filtered and the filtrate concentrated to give a crude product which was purified by silica gel chromatography to afford 2 (0.60 g, 36% yield) as a yellow oil. MS (ESI): mass calcd. for $C_{11}H_{10}ClNO_3S_2$ 303.78, m/z found 304.1 [M+H]$^+$.

2. A mixture of 2 (600 mg, 1.97 mmol) in TES 3 mL) and TFA (10 mL) was stirred at 60° C. for 2 h. The mixture was concentrated and the residue was diluted with saturated $NaHCO_3$, extracted with DCM and the combined organic extracts were washed with brine, dried over $Na_2SO_4$, filtered and concentrated. The resulting residue was purified by silica gel chromatography to afford the 3 (400 mg, 70.5% yield) as a brown oil. MS (ESI): mass calcd. for $C_{11}H_{10}ClNO_2S_2$ 287.78, m/z found 288.0 [M+H]$^+$.

3. Following the procedure described for Example 1, Intermediate 20 (229 mg) and 3 (200 mg) were converted to Example 34 (30 mg, 9.26% yield) as a yellow solid. MS (ESI): mass calcd. for $C_{23}H_{23}N_3O_4S_2$ 469.57, m/z found 469.7 [M+H]$^+$. $^1$H NMR (301 MHz, DMSO-d6) δ ppm 7.80 (d, J=7.5 Hz, 2H), 7.61 (s, 2H), 7.45 (d, J=7.2 Hz, 1H), 7.37 (s, 1H), 7.19 (d, J=8.1 Hz, 1H), 7.05 (s, 1H), 4.54 (s, 2H), 4.42 (t, J=7.8 Hz, 2H), 4.14 (s, 2H), 4.02 (t, J=7.8 Hz, 2H), 3.64 (t, J=5.4 Hz, 2H), 3.18 (s, 3H), 2.86 (t, J=5.1 Hz, 2H).

Example 35

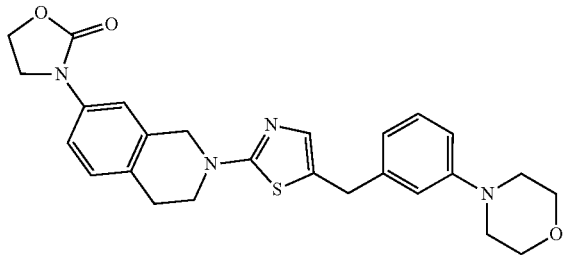 [SMILES: O=C1OCCN1c1ccc2c(c1)CN(c1ncc(Cc3cccc(N4CCOCC4)c3)s1)CC2]

1. Following the procedure described for Example 31 using Cs$_2$CO$_3$ (488 mg) instead of K$_2$CO$_3$, Intermediate 21 (235 mg) and morpholine (130 mg) were converted to Example 35 (10.6 mg, 4.4%) as a white solid. mass calcd. for C$_{26}$H$_{28}$N$_4$O$_3$S 476.60, m/z found 476.8 [M+H]$^+$, $^1$H NMR (400 MHz, DMSO-d6) δ ppm 7.45 (d, J=6.0 Hz, 1H), 7.37 (s, 1H), 7.23-7.12 (m, 2H), 6.98 (s, 1H), 6.84 (s, 1H), 6.79 (d, J=7.6 Hz, 1H), 6.68 (d, J=7.6 Hz, 1H), 4.54 (s, 2H), 4.43 (t, J=7.8 Hz, 2H), 4.03 (t, J=7.8 Hz, 2H), 3.92 (s, 2H), 3.72 (t, J=4.6 Hz, 4H), 3.64 (t, J=6.0 Hz, 2H), 3.08 (t, J=4.6 Hz, 4H), 2.86 (t, J=5.8 Hz, 2H).

Example 36

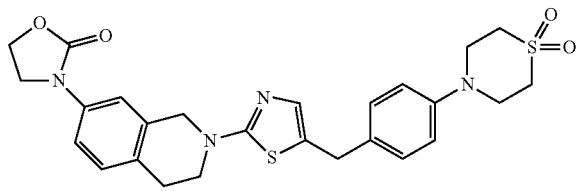 [SMILES: O=C1OCCN1c1ccc2c(c1)CN(c1ncc(Cc3ccc(N4CCS(=O)(=O)CC4)cc3)s1)CC2]

1. Following the procedure described for Example 31 using Cs$_2$CO$_3$ (371 mg) instead of K$_2$CO$_3$, Intermediate 22 (180 mg) and thiomorpholine 1,1-dioxide (154 mg) were converted to Example 36 (9 mg, 4%) as a white solid. mass calcd. for C$_{26}$H$_{28}$N$_4$O$_4$S$_2$ 524.65, m/z found 524.7 [M+H]$^+$, $^1$H NMR (300 MHz, DMSO-d6) δ ppm 7.40 (d, J=8.7 Hz, 1H), 7.32 (s, 1H), 7.14 (d, J=8.4 Hz, 1H), 7.07 (d, J=8.3 Hz, 2H), 6.92 (d, J=4.6 Hz, 3H), 4.50 (s, 2H), 4.39 (t, J=7.8 Hz, 2H), 3.99 (t, J=7.8 Hz, 2H), 3.85 (s, 2H), 3.69 (s, 4H), 3.60 (t, J=5.7 Hz, 2H), 3.07 (s, 4H), 2.83 (s, 2H).

Alternate Preparation of Example 36

1. A mixture of Intermediate 22 (50 g, 0.106 mol), thiomorpholine 1,1-dioxide (71.8 g, 0.531 mol), Pd(OAc)$_2$ (12 g, 0.053 mol), SPhos (23.4 g, 0.053 mol) and Cs$_2$CO$_3$ (43.3 g, 0.133 mol) in dried 1,4-dioxane (2.8 L) was stirred at 100° C. for 6 hrs under N$_2$. The mixture was diluted with DCM:MeOH 10:1 (1 L) and the resulting suspension filtered. The filter cake was washed twice with DCM:MeOH=10:1 and the combined filtrate concentrated. The resulting residue was dissolved with DCM:MeOH 10:1 (200 mL), the mixture was heated at reflux for 30 min. and MeOH (300 mL) was added and the mixture heated at reflux for 20 min. and the suspension was filtered through Celite. The filtrate was concentrated and the residue was treated as described above four times. After the fourth filtration, the combined filtrate was concentrated to afford the crude product as an orange solid which was slurried twice with MeCN (300 mL) to afford Example 36 (25.9 g, 46.4%) as a white solid. MS (ESI): mass calcd. for C$_{26}$H$_{28}$N$_4$O$_4$S$_2$ 524.65 m/z found 524.8 [M+H]$^+$. $^1$H NMR (400 MHz, DMSO-d6) δ ppm 7.45 (dd, J=8.4, 2.4, 1H), 7.37 (d, J=2.1, 1H), 7.19 (d, J=8.4, 1H), 7.12 (d, J=8.7, 2H), 6.99-6.94 (m, 3H), 4.54 (s, 2H), 4.43 (dd, J=8.9, 7.1, 2H), 4.03 (dd, J=8.9, 7.2, 2H), 3.89 (s, 2H), 3.76-3.70 (m, 4H), 3.64 (t, J=6.0 Hz, 2H), 3.16-3.07 (m, 4H), 2.86 (t, J=5.9, 2H).

Example 37

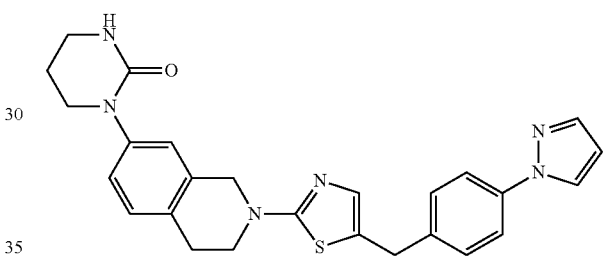

1. A mixture of Intermediate 5 (225 mg, 0.50 mmol), tetrahydropyrimidin-2(1H)-one (150 mg, 1.50 mmol), Pd$_2$(dba)$_3$ (92 mg, 0.1 mmol), SPhos (82 mg, 0.2 mmol) and t-BuOK (168 mg, 1.5 mmol) in 1,4-dioxane (20 mL) was stirred at 100° C. overnight. The mixture was cooled, poured into water and extracted with DCM, dried over Na$_2$SO$_4$, filtered and the filtrate concentrated. The resulting residue was purified by Prep-TLC to afford Example 37 (3.4 mg, 1.4%) as a white solid. mass calcd. for C$_{26}$H$_{26}$N$_6$OS 470.60, m/z found 470.8 [M+H]$^+$, $^1$H NMR (400 MHz, CD$_3$OD) δ ppm 8.20 (d, J=2.8 Hz, 1H), 7.72 (d, J=1.6 Hz, 2H), 7.70 (s, 1H), 7.68 (s, 1H), 7.40 (d, J=8.8 Hz, 2H), 7.20 (d, J=9.2 Hz, 1H), 7.14 (s, 1H), 4.58 (s, 2H), 4.09 (s, 2H), 3.70 (m, 1H), 3.40 (t, J=5.8 Hz, 4H), 2.97 (t, J=5.8 Hz, 2H), 2.1 (t, J=6.0 Hz, 2H).

The compounds listed in Table 2 below were prepared in a similar manner to that described in Example 37.

TABLE 2

| Example | Final Product | [M + H]$^+$ | $^1$H NMR | Yield |
|---|---|---|---|---|
| Example 69 | | 471.8 | $^1$H NMR (300 MHz, DMSO-d6) δ ppm 8.42 (s, 1H), 7.72 (t, J = 9.1 Hz, 3H), 7.33 (d, J = 8.1 Hz, 2H), 7.16 (d, J = 8.8 Hz, 2H), 6.99 (s, 1H), 6.50 (s, 1H), 4.52 (s, 2H), 4.30 (t, J = 5.1 Hz, 2H), 4.02 (s, 2H), 3.62 (m, 4H), 2.87 (t, J = 5.5 Hz, 1H), 2.15-1.99 (m, 2H). | 3.9% |

TABLE 2-continued

| Example | Final Product | [M + H]⁺ | ¹H NMR | Yield |
|---|---|---|---|---|
| Example 70 | 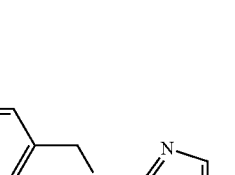 | 484.8 | ¹H NMR (300 MHz, DMSO-d6) δ ppm 8.42 (d, J = 1.8 Hz, 1H), 7.83-7.61 (m, 3H), 7.33 (d, J = 8.1 Hz, 2H), 7.11-6.91 (m, 2H), 6.78 (s, 2H), 6.50 (s, 1H), 4.47 (s, 2H), 4.01 (s, 2H), 3.69 (s, 2H), 3.60 (t, J = 5.7 Hz, 2H), 3.40 (s, 4H), 2.87 (s, 3H), 2.77 (t, J = 5.1 Hz, 2H). | 9.6% |
| Example 71 | 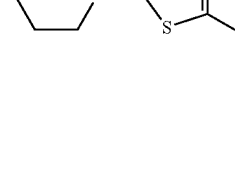 | 470.8 | ¹H NMR (400 MHz, DMSO-d6) δ ppm 8.46 (d, J = 2.4 Hz, 1H), 7.77 (d, J = 8.4 Hz, 2H), 7.73 (d, J = 1.6 Hz, 1H), 7.36 (d, J = 8.8 Hz, 2H), 7.08-6.98 (m, 2H), 6.81-6.78 (m, 2H), 6.53 (t, J = 2.2 Hz, 2H), 4.49 (s, 2H), 4.04 (s, 2H), 3.66 (s, 2H), 3.62 (t, J = 6.0 Hz, 2H), 3.35-3.34 (m, 2H), 3.29 (d, J = 2.8 Hz, 2H), 2.79 (t, J = 6.0 Hz, 2H). | 3.4% |
| Example 72 | 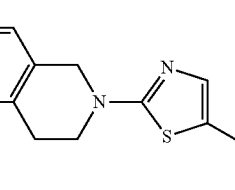 | 457.8 | ¹H NMR (400 MHz, DMSO-d6) δ ppm 8.45 (d, J = 2.4 Hz, 1H), 7.77 (d, J = 8.8 Hz, 2H), 7.72 (d, J = 1.6 Hz, 1H), 7.36 (d, J = 8.4 Hz, 2H), 7.09-6.98 (m, 2H), 6.84-6.76 (m, 2H), 6.53 (t, J = 2.2 Hz, 1H), 4.49 (s, 2H), 4.04 (s, 2H), 3.72 (t, J = 4.8 Hz, 4H), 3.62 (t, J = 6.0 Hz, 2H), 3.05 (t, J = 4.8 Hz, 4H), 2.79 (t, J = 5.8 Hz, 2H). | 4.7% |
| Example 73 | 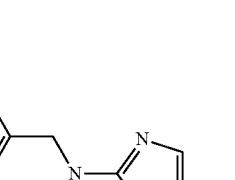 | 455.8 | ¹H NMR (400 MHz, DMSO-d6) δ ppm 8.45 (d, J = 2.4 Hz, 1H), 7.76 (d, J = 8.4 Hz, 2H), 7.72 (d, J = 1.6 Hz, 1H), 7.52 (dd, J = 8.4, 2.4 Hz, 1H), 7.45 (d, J = 2.4 Hz, 1H)), 7.35 (d, J = 8.4 Hz, 2H), 7.16 (d, J = 8.4 Hz, 1H), 7.01 (s, 1H), 6.52 (t, J = 2.4 Hz, 1H), 4.53 (s, 2H), 4.03 (s, 2H), 3.79 (t, J = 6.0 Hz, 2H), 3.64 (t, J = 6.0 Hz, 2H), 2.86 (t, J = 6.0 Hz, 2H), 2.47 (t, J = 6.0 Hz, 2H), 2.04 (m, 2H). | 39.6% |

Example 38

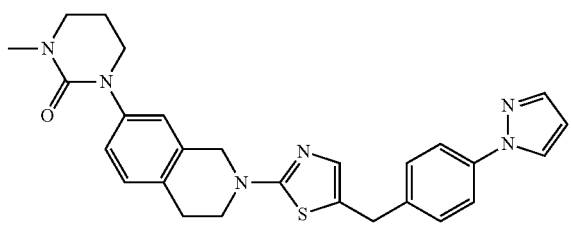 [SMILES: CN1CCCN(c2ccc3c(c2)CN(c2ncc(Cc4ccc(-n5cccn5)cc4)s2)CC3)C1=O]

1. A solution of Example 37 (30 mg, 0.064 mmol) in dried DMF (3 mL) was cooled to 0° C., NaH (24 mg, 1 mmol) was added and after 0.5 h CH₃I was added. The reaction was warmed to RT and stirred overnight. The mixture was poured into water and extracted with DCM. The combined extracts were dried over Na₂SO₄, filtered and the filtrate concentrated. The resulting residue was purified by Prep-TLC to afford Example 38 (10.06 mg, 34.22%) as a white solid. mass calcd. for $C_{27}H_{28}N_6OS$ 484.62, m/z found 484.8 [M+H]⁺. ¹H NMR (400 MHz, CDCl₃) δ=7.92 (d, J=2.1 Hz, 1H), 7.74 (d, J=1.5 Hz, 1H), 7.66 (d, J=8.5 Hz, 2H), 7.34 (d, J=8.5 Hz, 2H), 7.13 (s, 2H), 7.08 (s, 1H), 7.01 (s, 1H), 6.54-6.45 (m, 1H), 4.61 (s, 2H), 4.05 (s, 2H), 3.75 (d, J=5.8 Hz, 2H), 3.71-3.64 (m, 2H), 3.40 (t, J=6.1 Hz, 2H), 2.95 (t, J=5.8 Hz, 2H), 2.13 (dt, J=11.9 Hz, 6.0 Hz, 2H).

Example 39

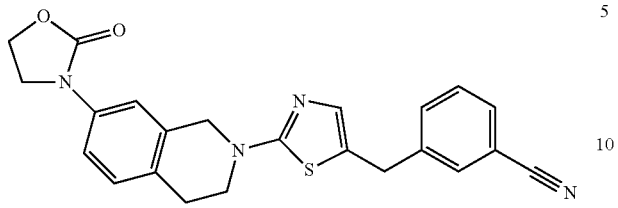

1. To a mixture of Intermediate 21 (170 mg, 0.36 mmol), CuCN (39 mg, 0.72 mmol) and CuI (168 mg, 1.44 mmol) in DMI (2 mL) was heated to 190° C. in a microwave for 50 minutes. The mixture was cooled, filtered and the solids washed with DCM/MeOH (10:1) and water, the water layer was extracted with DCM/MeOH (10:1). The combined organic extracts were washed with water, brine and dried over $Na_2SO_4$, filtered and the filtrate concentrated. The resulting residue was purified by prep-TLC to give Example 39 (8.5 mg, 5.7% yield) as a white solid. MS (ESI): mass calcd. for $C_{23}H_{20}N_4O_2S$ 416.50, m/z found 416.8 $[M+H]^+$. $^1H$ NMR (400 MHz, $CDCl_3$) δ ppm 7.59-7.53 (m, 2H), 7.50 (d, J=7.9 Hz, 1H), 7.45 (d, J=7.8 Hz, 1H), 7.42-7.37 (m, 2H), 7.20 (d, J=9.0 Hz, 1H), 7.00 (s, 1H), 4.64 (s, 2H), 4.51 (dd, J=8.8 Hz, 7.0 Hz, 2H), 4.06 (t, J=8.0 Hz, 4H), 3.75 (t, J=5.9 Hz, 2H), 2.97 (t, J=5.8 Hz, 2H).

Example 40

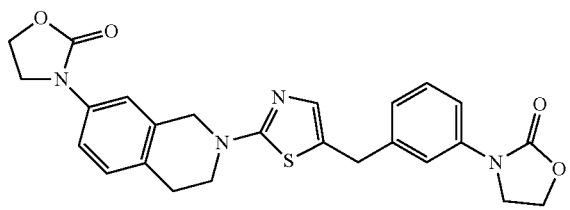 [SMILES: O=C1OCCN1c1cccc(Cc2cnc(N3CCc4ccc(N5CCOC5=O)cc4C3)s2)c1]

1. Following the procedure described for Example 31 using $Cs_2CO_3$ (488 mg) instead of $K_2CO_3$, Intermediate 21 (235 mg) and oxazolidin-2-one (200 mg) were converted to Example 40 (5 mg, 2%) as a white solid. mass calcd. for $C_{25}H_{24}N_4O_4S$ 476.55, m/z found 476.8 $[M+H]^+$. $^1H$ NMR (400 MHz, $CDCl_3$) δ ppm 7.47-7.39 (m, 3H), 7.38-7.32 (m, 2H), 7.19 (d, J=8.4 Hz, 1H), 7.05 (d, J=7.6 Hz, 1H), 7.00 (s, 1H), 4.64 (s, 2H), 4.53-4.48 (m, 4H), 4.10-4.03 (m, 6H), 3.75 (t, J=5.6 Hz, 2H), 2.96 (t, J=5.8 Hz, 2H).

Example 41

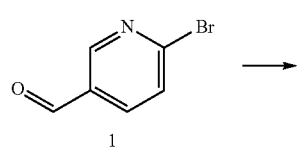

1. To a solution of 1 (2.00 g, 10.75 mmol) in DMF (30 mL) were added 1H-pyrazole (1.10 g, 16.13 mmol) and $K_2CO_3$ (4.46 g, 32.25 mmol). The reaction was stirred at 100° C. for 18 h. The reaction was cooled to RT and then poured into ice-water, extracted with $CH_2Cl_2$ and the extracts dried over $Na_2SO_4$. The organic extracts were concentrated to afford a residue which was purified by silica gel chromatography to afford 2 (1.00 g, 53.7% yield) as a yellow solid. MS (ESI): mass calcd. for $C_9H_7N_3O$ 173.18, m/z found 173.8 $[M+H]^+$.

2. To a solution of 2-chlorothiazole (762 mg, 6.35 mmol) in dry THF (50 mL) at −78° C. under $N_2$ was added n-BuLi (2.4 M, 2.89 mL) dropwise. After 0.5 h, a solution of 2 (1.00 g, 5.77 mmol) in dried THF (10 mL) was added dropwise. The reaction was slowly warmed to RT. The mixture was quenched with aq. $NH_4Cl$ and extracted with EtOAc and the extracts dried over $Na_2SO_4$. The organic extracts were concentrated to give a residue which was purified by silica gel chromatography to afford 3 (800 mg, 47.36% yield) as a white solid. MS (ESI): mass calcd. for $C_{12}H_9ClN_4OS$ 292.74, m/z found 292.8 $[M+H]^+$.

3. A mixture of 3 (800 mg, 2.73 mmol), TES (5 mL) and TFA (15 mL) was stirred at 70° C. for 2 h. The mixture was concentrated and the residue was diluted with aq. $NaHCO_3$ and extracted with DCM and the extracts dried over $Na_2SO_4$. The extracts were concentrated to give a crude product which was purified by silica gel chromatography to afford 4 (400 mg, 52.9% yield) as a white solid. MS (ESI): mass calcd. for $C_{12}H_9ClN_4S$ 276.74, m/z found 276.8 $[M+H]^+$.

4. To a solution of 4 (400 mg, 1.46 mmol) in DMSO (10 mL) were added 7-bromo-1,2,3,4-tetrahydroisoquinoline (Key Organics, 335 mg, 1.58 mmol) and $Cs_2CO_3$ (1.54 g, 4.74 mmol). The reaction was stirred at 140° C. for 5 h, cooled to RT and poured into ice-water, extracted with DCM. The combined extracts dried over $Na_2SO_4$ and the extracts were concentrated under reduce pressure to afford a crude product. The crude product was purified by silica gel chromatography to afford 5 (300 mg, 45.42% yield) as a white solid. MS (ESI): mass calcd. for $C_{21}H_{18}BrN_5S$ 452.37, m/z found 452.8 $[M+H]^+$.

5. A mixture of 5 (300 mg, 0.45 mmol), oxazolidin-2-one (136 mg, 1.36 mmol), $Pd_2(dba)_3$ (66 mg, 0.09 mmol), SPhos (92 mg, 0.225 mmol) and t-BuOK (162 mg, 1.35 mmol) in dried 1,4-dioxane was stirred at 100° C. overnight. The mixture was cooled, poured into water and extracted with $CH_2Cl_2$, dried over $Na_2SO_4$, filtered and the filtrate concentrated to afford a residue. The residue was purified by Prep-HPLC to afford Example 41 (39.6 mg, 19.19%) as a white solid. mass calcd. for $C_{24}H_{22}N_6O_2S$ 458.54, m/z found 458.8 $[M+H]^+$, $^1$H NMR (400 MHz, DMSO-$d_6$) δ ppm 8.59 (dd, J=2.8, 0.6 Hz, 1H), 8.39 (d, J=1.6 Hz, 1H), 7.90-7.84 (m, 2H), 7.82-7.79 (m, 1H), 7.45 (dd, J=8.4 Hz, 2.4, 1H), 7.37 (d, J=2.2 Hz, 1H), 7.20 (d, J=8.4 Hz, 1H), 7.04 (s, 1H), 6.57 (dd, J=2.5 Hz, 1.7 Hz, 1H), 4.56 (s, 2H), 4.43 (dd, J=9.6 Hz, 6.4 Hz, 2H), 4.09 (s, 2H), 4.03 (dd, J=8.4 Hz, 7.0 Hz, 2H), 3.65 (t, J=6.0 Hz, 2H), 2.87 (t, J=6.0 Hz, 2H).

Example 42

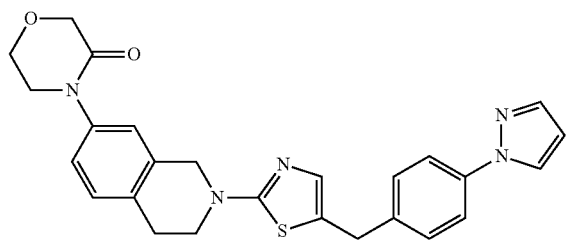

1. To a solution of Intermediate 5 (225 mg, 0.50 mmol), morpholin-3-one (171 mg, 1.50 mmol) in dried 1,4-dioxane (15 mL) were added $K_2CO_3$ (209 mg, 1.51 mmol), CuI (10 mg, 0.05 mmol) and (S,S)—N,N'-dimethyl-1,2-diaminocyclohexane (8 mg, 0.05 mmol). The resulting solution was stirred at 150° C. for 1.5 h in microwave. The mixture was cooled to RT, filtered and the filtrate concentrated. The resulting residue was purified by Prep-TLC to afford Example 42 (20.8 mg, 5.6%) as a white solid. mass calcd. for $C_{26}H_{25}N_5O_2S$ 471.58, m/z found 471.8 $[M+H]^+$, $^1$H NMR (400 MHz, DMSO-d6) δ ppm 8.45 (d, J=2.4 Hz, 1H), 7.77 (d, J=8.8 Hz, 2H), 7.73 (d, J=1.6 Hz, 1H), 7.36 (d, J=8.4 Hz, 2H), 7.25 (s, 1H), 7.21 (s, 2H), 7.02 (s, 1H), 6.53 (t, J=2.2 Hz, 1H), 4.55 (s, 2H), 4.19 (s, 2H), 4.04 (s, 2H), 3.96 (t, J=5.0 Hz, 2H), 3.70 (t, J=5.0 Hz, 2H), 3.66 (t, J=6.0 Hz, 2H), 2.90 (t, J=6.0 Hz, 2H).

Example 43

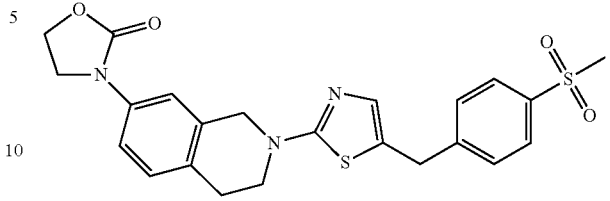

1. Following the procedure described for Example 1, Intermediate 20 (357 mg) and Intermediate 31 (270 mg) were converted to Example 43 (55 mg, 13% yield) as a white solid. MS (ESI): mass calcd. for $C_{23}H_{23}N_3O_4S_2$ 469.11, m/z found 69.7 $[M+H]^+$, 1H NMR (400 MHz, DMSO) δ ppm 7.87 (d, J=8.3 Hz, 2H), 7.52 (d, J=8.3 Hz, 2H), 7.45 (dd, J=8.4, 2.3 Hz, 1H), 7.38 (d, J=2.0 Hz, 1H), 7.20 (d, J=8.4 Hz, 1H), 7.06 (s, 1H), 4.55 (s, 2H), 4.48-4.35 (m, 2H), 4.13 (s, 2H), 4.09-3.98 (m, 2H), 3.65 (t, J=5.9 Hz, 2H), 3.19 (s, 3H), 2.87 (t, J=5.9 Hz, 2H).

Example 44

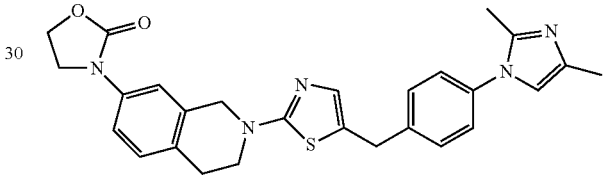

1. Following the procedure described for Example 1, Intermediate 20 (227 mg) and Intermediate 19 (200 mg) were converted to a crude product that was purified by Prep-TLC to afford Example 44 (12 mg, 4% yield) as a white solid. MS (ESI): mass calcd. for $C_{27}H_{27}N_5O_2S$ 485.19. m/z found 486.9 $[M+H]^+$. $^1$HNMR (400 MHz, DMSO-d6) δ ppm 7.46 (d, J=8.7 Hz, 1H), 7.36 (dd, J=14.2, 7.2 Hz, 5H), 7.20 (d, J=8.4 Hz, 1H), 7.05 (s, 1H), 6.97 (s, 1H), 4.56 (s, 2H), 4.44 (t, J=7.9 Hz, 2H), 4.06 (d, J=5.5 Hz, 2H), 4.03 (d, J=7.7 Hz, 2H), 3.66 (t, J=5.9 Hz, 2H), 2.88 (t, J=5.6 Hz, 2H), 2.23 (s, 3H), 2.09 (s, 3H).

Example 45

1.

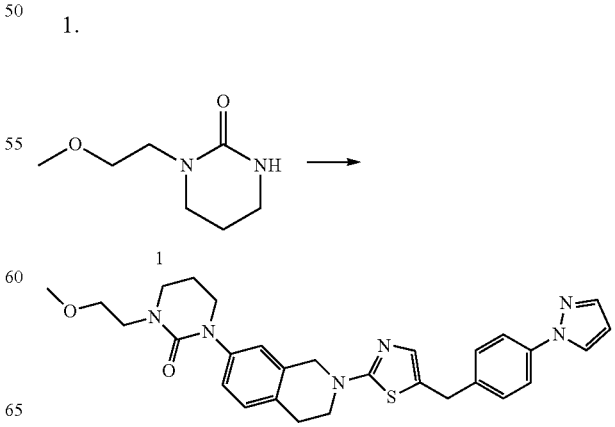

To a mixture of 2-methoxyethan-1-amine (1 g, 13.3 mmol) in DMF (100 mL) was added 3-chloropropyl isocyanate (1.9 g, 16 mmol), then t-BuOK (2.23 g, 20 mmol) was added and the resulting mixture was stirred at RT for 16 h. The mixture was concentrated and the residue purified by chromatography on silica gel to give 1 (630 mg, 30% yield) as a white solid. MS (ESI): mass calcd. for $C_7H_{14}N_2O_2S$ 158.20, m/z found 159.0 [M+H]$^+$.

2. A mixture of 1 (245 mg, 1.55 mmol), Intermediate 5 (140 mg, 0.31 mmol), t-BuONa (104 mg, 1.1 mmol), Pd(OAc)$_2$ (43 mg, 0.19 mmol) and SPhos (78 mg, 0.19 mmol) in 1,4-dioxane (8 mL) was purged 3× with N$_2$. The resulting mixture was stirred at 100° C. for 15 h, cooled to RT, diluted with a mixture (DCM/MeOH, 10/1, 20 mL), filtered and the filtrate was concentrated. The resulting residue was purified by chromatography on silica gel to give Example 45 (13 mg, 8% yield) as a white solid. MS (ESI): mass calcd. for $C_{29}H_{32}N_6O_2S$ 528.68, m/z found 528.8 [M+H]$^+$. NMR (400 MHz, DMSO) δ ppm 8.46 (s, 1H), 7.77 (d, J=8.3 Hz, 2H), 7.72 (s, 1H), 7.36 (d, J=8.3 Hz, 2H), 7.00-7.06 (m, 3H), 7.02 (s, 1H), 6.53 (s, 1H), 4.50 (s, 2H), 4.04 (s, 2H), 3.66-3.58 (m, 4H), 3.45-3.40 (m, 6H), 3.26 (s, 3H), 2.85 (t, J=5.8 Hz, 1H), 2.01-1.96 (m, 2H).

Example 46

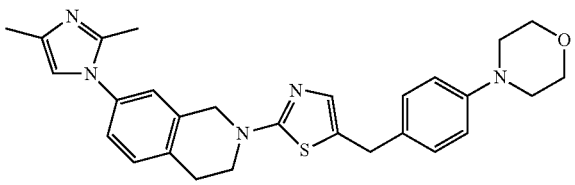

Example 46

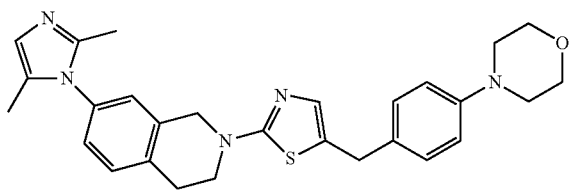

Example 47

Example 47

1. A mixture of Intermediate 1 (150 mg, 0.66 mmol), Intermediate 24 (233 mg, 0.79 mmol) and K$_2$CO$_3$ (273 mg, 1.98 mmol) in DMSO (6 mL) was evacuated and refilled with N$_2$ three times and was stirred at 130° C. for 3 h. The mixture was cooled to RT, diluted with a mixture of DCM/MeOH 20/1 (20 mL), filtered and the filtrate was concentrated and purified by chromatography on silica gel to give the curede product, The crude product was purified by SFC (chiralpak-IB, CO$_2$-EtOH(DEA)) to give Example 46 (56.38 mg, 17.6% yield) as a white solid. MS (ESI): mass calcd. for $C_{28}H_{31}N_5OS$ 485.65, m/z found 485.9 [M+H]$^+$. $^1$H NMR (400 MHz, DMSO) δ ppm 7.32-7.30 (m, 2H), 7.21 (d, J=7.7 Hz, 1H), 7.10 (d, J=8.2 Hz, 2H), 6.96 (s, 1H), 6.92 (s, 1H), 6.88 (d, J=8.4 Hz, 2H), 4.58 (s, 2H), 3.89 (s, 2H), 3.74-3.71 (m, 4H), 3.66 (t, J=5.7 Hz, 2H), 3.09-3.01 (m, 4H), 2.94 (t, J=5.7 Hz, 2H), 2.23 (s, 3H), 2.08 (s, 3H) and Example 47 (15 mg) as a yellow/white solid MS (ESI): mass calcd. for $C_{28}H_{31}N_5OS$ 485.65, m/z found 485.9 [M+H]$^+$. $^1$H NMR (400 MHz, DMSO) δ ppm 7.35 (d, J=8.2 Hz, 1H), 7.25 (s, 1H), 7.15 (d, J=7.9 Hz, 1H), 7.10 (d, J=8.4 Hz, 2H), 6.96 (s, 1H), 6.88 (d, J=8.5 Hz, 2H), 6.62 (s, 1H), 4.60 (s, 2H), 3.89 (s, 2H), 3.74-3.67 (m, 6H), 3.07-3.05 (m, 4H), 2.98 (t, J=5.4 Hz, 2H), 2.09 (s, 3H), 1.95 (s, 3H).

Example 48

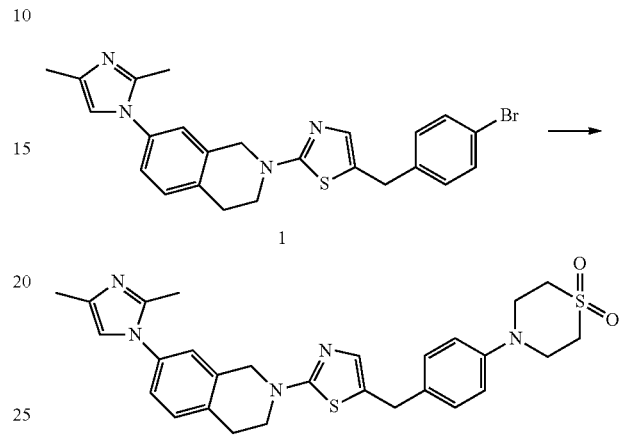

1. Following the procedure described for Example 1 except the mixture was heated at 100° C. for 2 h, Intermediate 1 (280 mg) and Intermediate 6 (403 mg) were converted to a crude product which was purified by Combi-Flash to give 1 (380 mg, 66% yield) as a white solid. MS (ESI): mass calcd. for $C_{24}H_{23}BrN_4S$ 479.4, m/z found 479 [M+H]$^+$.

2. A mixture 1 (240 mg, 0.5 mmol), thiomorpholine 1,1-dioxide (135 mg, 1 mmol), Pd$_2$(dba)$_3$ (41 mg, 0.05 mmol), SPhos (20 mg, 0.05 mmol), t-BuOK (122 mg, 1 mmol) in toluene (10 mL) was stirred at 100° C. for 2 h. The mixture was cooled and diluted with EA, washed with water, brine and dried over Na$_2$SO$_4$, filtered and concentrated. The resulting residue was purified by Prep-HPLC to give Example 48 (50 mg, 22% yield) as a white solid. MS (ESI): mass calcd. for $C_{28}H_{31}N_5O_2S_2$ 533.7, m/z found 534 [M+H]$^+$. $^1$H NMR (400 MHz, DMSO-d6) δ 8.16 (s, 1H), 7.31 (d, J=8.4 Hz, 2H), 7.22 (d, J=8.3 Hz, 1H), 7.12 (d, J=8.4 Hz, 2H), 6.97 (d, J=7.4 Hz, 3H), 6.92 (s, 1H), 4.59 (s, 2H), 3.90 (s, 2H), 3.73 (s, 5H), 3.67 (t, J=5.7 Hz, 2H), 3.11 (s, 4H), 2.94 (t, J=5.5 Hz, 2H), 2.23 (s, 3H), 2.08 (s, 3H).

Example 49

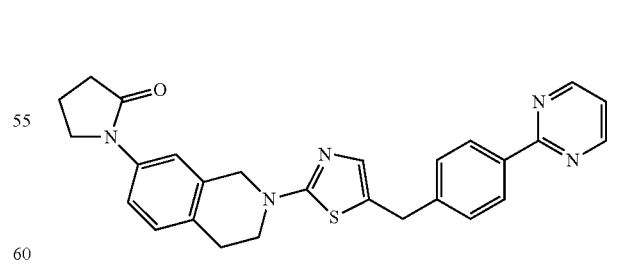

1. Following the procedure described for Example 1 except the mixture was heated at 100° C. for 5 h, Intermediate 25 (200 mg) and Intermediate 26 (266 mg) were converted to a crude product which was purified by Prep-HPLC to afford Example 49 (82.6 mg, 19.20%) as a white solid. mass calcd. for $C_{27}H_{25}N_5OS$ 467.59, m/z found 467.8

[M+H]+, 1H NMR (400 MHz, DMSO-d6) δ ppm 8.90 (d, J=4.8 Hz, 2H), 8.34 (d, J=8.0 Hz, 2H), 7.52 (d, J=8.4 Hz, 1H), 7.42 (m, 4H), 7.17 (d, J=8.4 Hz, 1H), 7.04 (s, 1H), 4.54 (s, 2H), 4.09 (s, 2H), 3.80 (t, J=7.0 Hz, 2H), 3.65 (t, J=5.8 Hz, 2H), 2.86 (t, J=5.4 Hz, 2H), 2.47 (d, J=7.8 Hz, 2H), 2.05 (dt, J=14.7 Hz, 7.3 Hz, 1H).

Example 50

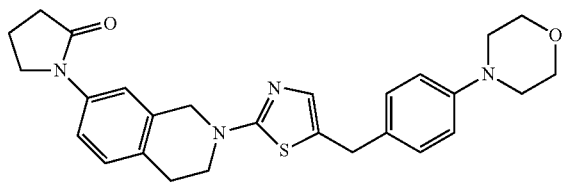 [SMILES: O=C1CCCN1c1ccc2c(c1)CN(c1ncc(Cc3ccc(N4CCOCC4)cc3)s1)CC2]

1. Following the procedure described for Example 1 except the mixture was heated at 100° C. for 5 h and Cs2CO3 (663 mg) was used in place of K2CO3, Intermediate 25 (235 mg) and Intermediate 24 (200 mg) were converted to a crude product which was purified by Prep-HPLC to afford Example 50 (66.2 mg, 20.51%) as a white solid. mass calcd. for $C_{27}H_{30}N_4O_2S$ 474.62, m/z found 474.8 [M+H]+, NMR (400 MHz, DMSO-d6) δ ppm 7.52 (d, J=8.4 Hz, 1H), 7.45 (s, 1H), 7.17 (d, J=8.4 Hz, 1H), 7.09 (d, J=8.4 Hz, 2H), 6.95 (s, 1H), 6.88 (d, J=8.4 Hz, 2H), 4.52 (s, 2H), 3.88 (s, 2H), 3.80 (t, J=7.0 Hz, 2H), 3.73 (t, J=7.0 Hz, 4H), 3.63 (t, J=5.8 Hz, 2H), 3.01 (t, J=4.6 Hz, 4H), 2.86 (t, J=5.8 Hz, 2H), 2.47 (t, J=4.0 Hz, 2H), 2.09-1.99 (m, 2H).

Example 51

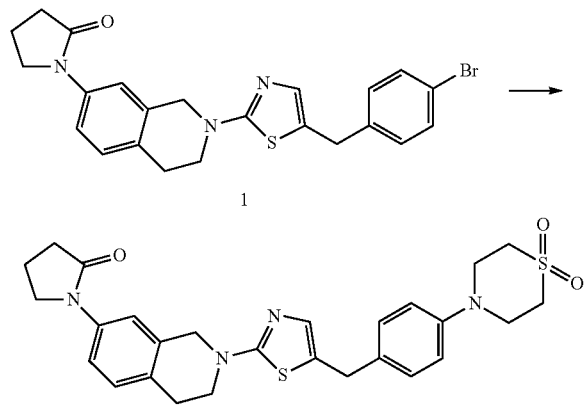

1. Following the procedure described for Example 1 except the mixture was heated at 100° C. for 2 h, Intermediate 25 (380 mg) and Intermediate 6 (366 mg) were converted to a crude product which was purified by combi-flash to give 1 (280 mg, 52% yield) as a white solid. MS (ESI): mass calcd. for $C_{23}H_{22}BrN_3OS$ 468.4, m/z found 468 [M+H]+.

2. A mixture 1 (235 mg, 0.5 mmol), thiomorpholine 1,1-dioxide (135 mg, 1 mmol), Pd2(dba)3 (41 mg, 0.05 mmol), SPhos (20 mg, 0.05 mmol), t-BuOK (122 mg, 1 mmol) in toluene (10 mL) was stirred at 100° C. for 2 h. The mixture was cooled and diluted with EA, washed with water, brine and dried over Na2SO4, filtered, concentrated. The resulting residue was purified by Prep-HPLC to give Example 51 (110 mg, 42% yield) as a white solid. MS (ESI): mass calcd. for $C_{27}H_{30}N_4O_3S_2$ 522.7, m/z found 523 [M+H]+. TI NMR (400 MHz, CDCl3) δ ppm 7.51 (d, J=8.2 Hz, 1H), 7.45 (s, 1H), 7.16 (d, J=8.3 Hz, 1H), 7.11 (d, J=8.2 Hz, 2H), 6.99-6.93 (m, J=4.9 Hz, 3H), 4.52 (s, 2H), 3.89 (s, 2H), 3.80 (t, J=6.9 Hz, 2H), 3.72 (s, 4H), 3.66-3.59 (m, 2H), 3.10 (s, 4H), 2.85 (t, J=5.6 Hz, 2H), 2.47 (d, J=8.0 Hz, 2H), 2.07-1.99 (m, 2H).

Example 52

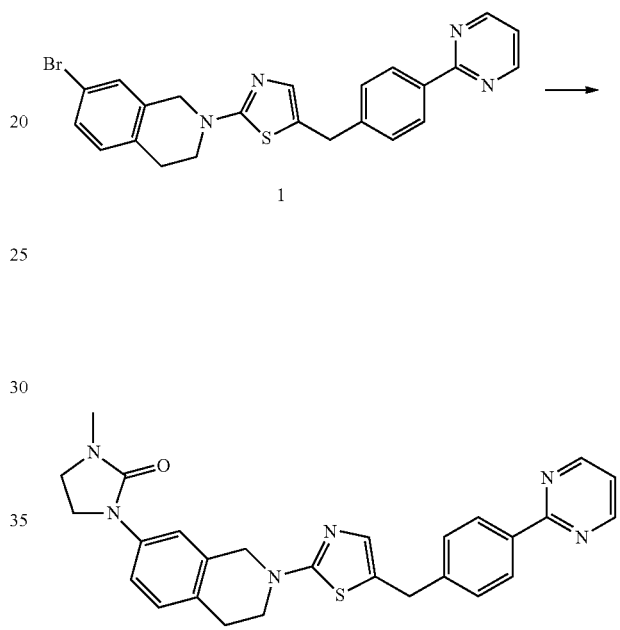

1. Following the procedure described for Example 1 except the mixture was heated at 100° C. for 4 h, Intermediate 26 (300 mg) and 7-bromo-1,2,3,4-tetrahydroisoquinoline hydrochloride (Key Organics, 270 mg) were converted to a crude product that was purified by purified by flash chromatography to afford 1 (380 mg 78.7% yield) as a white solid. MS (ESI): mass calcd. for $C_{23}H_{19}BrN_4S$ 463.40, m/z found 462.8 [M+H]+.

2. A mixture of 1 (150 mg, 0.324 mmol), 1-methylimidazolidin-2-one (162 mg, 1.62 mmol), Pd2(dba)3 (148 mg, 0.162 mmol), SPhos (67 mg, 0.162 mmol) and t-BuOK (109 mg, 0.972 mol) in dried 1,4-dioxane (21 mL) was stirred at 100° C. for 6 hrs. The mixture was diluted with DCM: MeOH 10:1 and filtered and the filter cake washed twice with DCM:MeOH 10:1. The combined the filtrate was concentrated and the residue was purified by flash chromatography to afford a product which was purified by Prep-HPLC to give Example 52 (69 mg, 44.2%, 99.1% purity 214 nm) as a white solid. MS (ESI): mass calcd. for $C_{27}H_{26}N_6OS$ 482.61 m/z found 482.8 [M+H]+. 1H NMR (400 MHz, DMSO-d6) δ ppm 8.90 (d, J=4.6 Hz, 2H), 8.34 (d, J=7.6 Hz, 2H), 7.48 (d, J=8.2 Hz, 1H), 7.42 (dd, J=14.3, 6.4, 3H), 7.33 (s, 1H), 7.11 (d, J=8.4 Hz, 1H), 7.04 (s, 1H), 4.52 (s, 2H), 4.09 (s, 2H), 3.74 (t, J=7.9 Hz, 2H), 3.64 (t, J=5.8 Hz, 2H), 3.42 (t, J=7.7 Hz, 2H), 2.83 (t, J=5.5 Hz, 2H), 2.75 (s, 3H).

Example 53

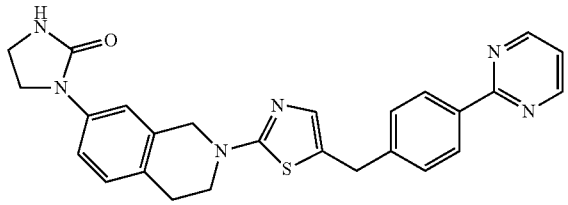 [SMILES: O=C1NCCN1c1ccc2c(c1)CN(c1ncc(Cc3ccc(-c4ncccn4)cc3)s1)CC2]

1. A mixture of the product of Example 52 Step 1 (150 mg, 0.324 mmol) and imidazolidin-2-one (139 mg, 1.62 mmol) were treated as described in Example 52 Step 2 to give a crude product that was purified by purified by flash chromatography. The resulting material was slurried with PE:Hexane 1:1 to afford Example 53 (54.3 mg, 35.8%, 99.8% purity 214 nm) as a white solid. MS (ESI): mass calcd. for $C_{26}H_{24}N_6OS$ 468.58 m/z found 468.8 [M+H]$^+$. $^1$H NMR (400 MHz, DMSO-d6) δ ppm 8.90 (d, J=4.8, 2H), 8.34 (d, J=8.0, 2H), 7.43 (dd, J=16.4, 8.5, 4H), 7.34 (s, 1H), 7.10 (d, J=8.4, 1H), 7.05 (s, 1H), 6.92 (s, 1H), 4.52 (s, 2H), 4.09 (s, 2H), 3.82 (t, J=5.8, 2H), 3.64 (t, J=5.8, 2H), 3.43-3.36 (m, 4H), 2.84 (t, J=5.7, 2H).

Example 54

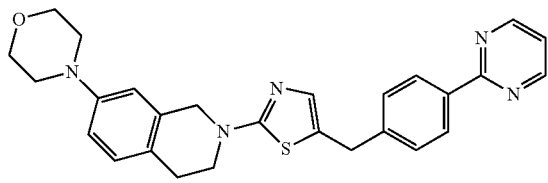 [SMILES: c1cnc(-c2ccc(Cc3cnc(N4CCc5ccc(N6CCOCC6)cc5C4)s3)cc2)nc1]

1. Following the procedure described for Example 1 except the mixture was heated at 100° C. for 5 h, Intermediate 26 (170 mg) and Intermediate 27 (224 mg) were converted to a crude product. The crude product was purified by Prep-HPLC to afford Example 54 (64.7 mg, 23.35%) as a white solid. mass calcd. for $C_{27}H_{27}N_5OS$ 469.61, m/z found 469.8 [M+H]$^+$, $^1$H NMR (400 MHz, DMSO-d6) δ ppm 8.90 (d, J=4.8 Hz, 2H), 8.34 (d, J=7.6 Hz, 2H), 7.51-7.36 (m, 3H), 7.10-6.98 (m, 2H), 6.86-6.75 (m, 2H), 4.49 (s, 2H), 4.08 (s, 2H), 3.72 (t, J=4.4 Hz, 2H), 3.61 (t, J=5.6 Hz, 2H), 3.05 (t, J=4.8 Hz, 4H), 2.79 (t, J=5.8 Hz, 2H).

Example 55

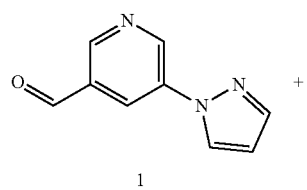

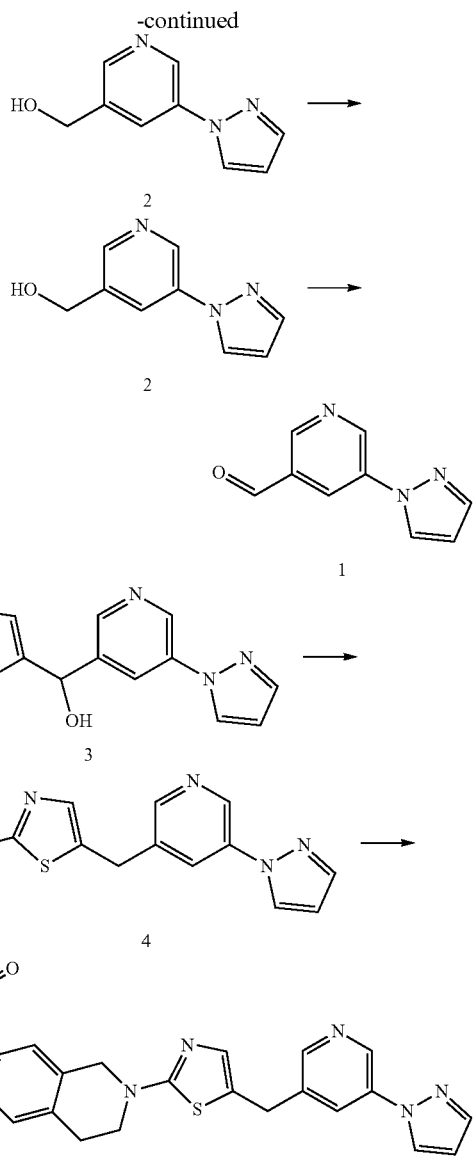

1. A mixture of 5-bromonicotinaldehyde (2 g, 10.8 mmol), 1H-pyrazole (1.46 g, 21.5 mmol), CuI (1.03 g, 5.4 mmol), (S,S)—N,N'-dimethyl-1,2-diaminocyclohexane (307 mg, 2.16 mmol) and Cs$_2$CO$_3$ (10.6 g, 32.4 mmol) in DMF (40 mL) was purged with N$_2$ three times and the mixture was heated to 120° C. for 16 h. The mixture was cooled to RT, diluted with EtOAc, filtered and the filtrate concentrated. The resulting residue was purified by chromatography on silica gel to give a mixture of 1 and 2 (1 g, impure) as a brown solid. MS (ESI): mass calcd. for $C_9H_7N_3O$ 173.18, m/z found 174.0 [M+H]$^+$.

2. To the mixture of 1 and 2 (1 g, 5.78 mmol) in MeOH (10 mL) at 0° C. was added NaBH$_4$ (330 mg, 8.67 mmol) and the mixture warmed up RT and stirred for 2 h. The mixture was concentrated and the residue purified by chromatography on silica gel to give 2 (470 mg, 25% yield) as a white solid. MS (ESI): mass calcd. for $C_9H_9N_3O$ 175.19, m/z found 176.1 [M+H]$^+$.

3. To 2 (470 mg, 2.69 mmol) in DCM (15 mL) was added Dess-Martin reagent (1.48 g, 3.49 mmol). The resulting mixture was stirred at RT for 30 min., concentrated and the residue purified by chromatography on silica gel to give 1

(420 mg, 90% yield) as a white solid. MS (ESI): mass calcd. for $C_9H_7N_3O$ 173.18, m/z found 174.0 $[M+H]^+$.

4. n-BuLi (1.32 mL, 3.16 mmol, 2.4 M) was added to the solution of 2-chlorothiazole (378 mg, 3.16 mmol) in THF (2 mL) dropwise under $N_2$ at −70° C. After a stirring 30 min, a solution of 1 (420 mg, 2.43 mmol) in THF (15 mL) was added dropwise and the resulting mixture was warmed to RT and stirred overnight. The mixture was quenched with sat. aq. $NH_4Cl$ (20 mL), extracted with EtOAc and the combined organic extracts were washed with brine, dried over $Na_2SO_4$, filtered and the filtrate concentrated. The resulting residue was purified by chromatography on silica gel to give 3 (490 mg, 69% yield) as a yellow white solid. MS (ESI): mass calcd. for $C_{12}H_9ClN_4OS$ 292.74, m/z found 292.8 $[M+H]^+$.

5. To the solution of 3 (490 mg, 1.68 mmol) in DCM (8 mL) was added $SOCl_2$ (240 mg, 2.01 mmol) dropwise. After a stirring of 2 h, the mixture was concentrated to give a yellow white solid. The solid was dissolved in AcOH (10 mL) and Zn powder (546 mg, 8.4 mmol) was added and the resulting mixture was stirred at RT for 1 h, neutralized with sat. aq. $NaHCO_3$ and extracted with EtOAc. The combined organic phase was washed with brine, dried over $Na_2SO_4$, filtered and the filtrate concentrated. The resulting residue was purified by chromatography on silica gel to give 4 (350 mg, 75% yield) as a white oil. MS (ESI): mass calcd. for $C_{12}H_9ClN_4S$ 276.74, m/z found 277.0 $[M+H]^+$.

6. A mixture of 4 (100 mg, 0.36 mmol), Intermediate 20 (140 mg, 0.44 mmol) and $K_2CO_3$ (150 mg, 1.08 mmol) in DMSO (10 mL) was stirred under nitrogen atmosphere at 120° C. for 2 h, cooled to RT and ice-water was added to the mixture which was then extracted with EA. The combined organic extracts were washed with water, brine and dried over $Na_2SO_4$, filtered and the filtrate concentrated. The resulting residue was purified by prep-TLC to give Example 55 (75 mg, 45.5% yield) as a yellow solid. MS (ESI): mass calcd. for $C_{24}H_{22}N_6O_2S$ 458.54, m/z found 458.9 $[M+H]^+$. $^1H$ NMR (400 MHz, DMSO-d6) δ ppm 8.97 (d, J=2.0 Hz, 1H), 8.60 (d, J=2.0 Hz, 1H), 8.44 (s, 1H), 8.12 (s, 1H), 7.80 (s, 1H), 7.45 (d, J=8.4 Hz, 1H), 7.36 (s, 1H), 7.18 (d, J=8.4 Hz, 1H), 7.07 (s, 1H), 6.60 (s, 1H), 4.54 (s, 2H), 4.42 (t, J=8.0 Hz, 2H), 4.14 (s, 2H), 4.02 (t, J=8.0 Hz, 2H), 3.64 (t, J=5.6 Hz, 2H), 2.86 (t, J=5.6 Hz, 2H).

Example 56

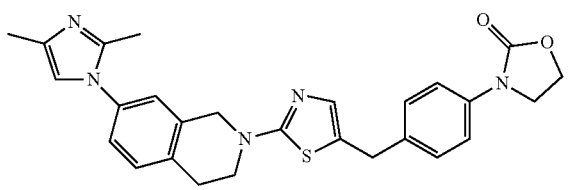 [SMILES: Cc1cn(-c2ccc3c(c2)CN(c2ncc(Cc4ccc(N5CCOC5=O)cc4)s2)CC3)c(C)n1]

1. Following the procedure described for Example 1 except the mixture was heated at 120° C. for 3 h, Intermediate 1 (100 mg) and Intermediate 28 (156 mg) were converted to a crude product that was purified by prep-HPLC to obtain Example 56 (60 mg, 0.124 mmol, yield 28%) as a white solid. MS (ESI): mass calcd. for $C_9H_9BrO_2$ 485.19, m/z found 485.9 $[M+H]^+$. $^1H$ NMR (400 MHz, $CD_3OD$) δ 7.51 ppm (d, J=8.4 Hz, 2H), 7.36 (d, J=8.0 Hz, 1H), 7.27 (d, J=8.7 Hz, 3H), 7.22 (d, J=8.1 Hz, 1H), 6.96 (s, 1H), 6.93 (s, 1H), 4.63 (s, 2H), 4.47 (t, J=8.2 Hz, 2H), 4.09 (t, J=8.0 Hz, 2H), 4.00 (s, 2H), 3.72 (t, J=5.9 Hz, 2H), 3.03 (t, J=5.8 Hz, 2H), 2.33 (s, 3H), 2.22 (s, 3H).

Example 57

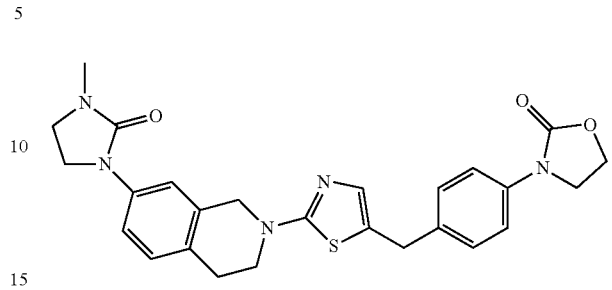

1. Following the procedure described for Example 1 except the mixture was heated at 120° C. for 2 h, Intermediate 29 (135 mg) and Intermediate 28 (100 mg) were converted to a crude product that was purified by prep-TLC to give Example 57 (35 mg, 35.3% yield) as a white solid. MS (ESI): mass calcd. for $C_{26}H_{27}N_5O_3S$ 489.59, m/z found 489.9 $[M+H]^+$. $^1H$ NMR (400 MHz, DMSO-d6) δ ppm 7.50-7.45 (m, 3H), 7.32 (s, 1H), 7.25 (d, J=8.0 Hz, 2H), 7.10 (d, J=8.4 Hz, 1H), 6.97 (s, 1H), 4.51-4.48 (m, 2H), 4.42 (t, J=8.0 Hz, 2H), 4.03 (t, J=8.4 Hz, 2H), 3.96 (s, 2H), 3.74 (t, J=8.0 Hz, 2H), 3.62 (t, J=5.6 Hz, 2H), 3.42 (t, J=8.4 Hz, 2H), 2.82 (t, J=5.6 Hz, 2H), 2.75 (s, 3H).

Example 58

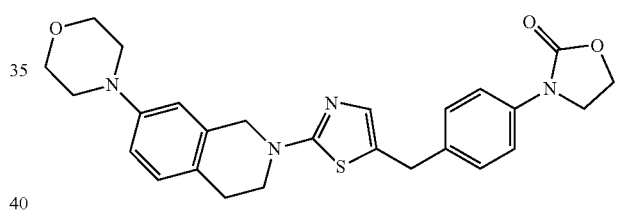

1. Following the procedure described for Example 1 except the mixture was heated at 120° C. for 3 h, Intermediate 27 (300 mg) and Intermediate 28 (307 mg) were converted to a crude product that was purified by prep-TLC to give Example 58 (38 mg, 8% yield) as a white solid. MS (ESI): mass calcd. for $C_{26}H_{28}N_4O_3S$, 476.19. m/z found 476.9 $[M+H]^+$, $^1H$ NMR (400 MHz, DMSO-d6) δ ppm 7.49 (d, J=8.3 Hz, 2H), 7.26 (d, J=8.4 Hz, 2H), 7.03 (d, J=8.1 Hz, 1H), 6.97 (s, 1H), 6.80 (d, J=10.1 Hz, 2H), 4.44 (dd, J=17.0, 9.1 Hz, 4H), 4.04 (t, J=7.9 Hz, 2H), 3.97 (s, 2H), 3.78-3.64 (m, 4H), 3.60 (t, J=5.7 Hz, 2H), 3.06 (d, J=5.1 Hz, 4H), 2.78 (t, J=5.7 Hz, 2H).

Example 59

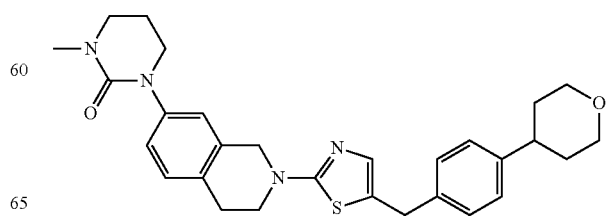

1. Following the procedure described for Example 1, Intermediate 35 (351 mg) and Intermediate 30 (250 mg) were heated at 130° C. for 2 h. The mixture was cooled to RT, diluted with a mixture of DCM/MeOH 20/1 (20 mL), filtered and the filtrate concentrated. The resulting residue was purified by chromatography on silica gel to give Example 59 (37.5 mg, 9% yield) as a yellow white solid. MS (ESI): mass calcd. for $C_{29}H_{34}N_4O_2S$ 502.68, m/z found 502.9 [M+H]$^+$. $^1$H NMR (400 MHz, DMSO) δ ppm 7.20-7.16 (m, 4H), 7.10-7.04 (m, 3H), 6.98 (s, 1H), 4.49 (s, 2H), 3.95-3.92 (m, 4H), 3.64-3.59 (m, 4H), 3.44-3.38 (m, 2H), 3.32-3.31 (m, 2H), 2.84 (s, 5H), 2.76-2.68 (m, 1H), 2.04-1.98 (m, 2H), 1.67-1.61 (m, 4H).

Example 60

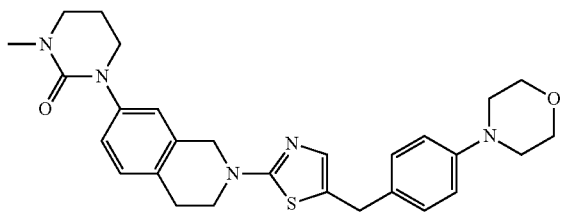

1. Following the procedure described for Example 1 using $Cs_2CO_3$ (313 mg) instead of $K_2CO_3$ and heating the mixture at 130° C. for 4 h, Intermediate 35 (100 mg) and Intermediate 24 (106 mg) were converted to a crude product that was purified by Prep-TLC to give Example 60 (20 mg, 13% yield) as a white solid. MS (ESI): mass calcd. $C_{28}H_{33}N_5O_2S$ 503.24. $^1$H NMR (400 MHz, DMSO) δ ppm 7.21 (s, 1H), 7.13 (dd, J=9.4, 5.6 Hz, 5H), 6.92 (d, J=8.5 Hz, 2H), 4.56 (s, 2H), 3.93 (s, 2H), 3.79-3.70 (m, 4H), 3.68 (t, J=5.9 Hz, 2H), 3.64-3.54 (m, 2H), 3.33 (t, J=6.0 Hz, 2H), 3.17-3.00 (m, 4H), 2.91 (t, J=5.7 Hz, 2H), 2.85 (s, 3H), 2.18-1.93 (m, 2H).

Example 61

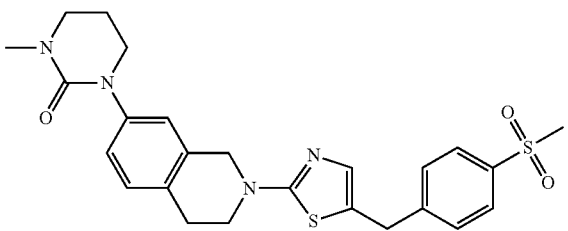

1. Following the procedure described for Example 1 except the mixture was heated at 100° C. for 3 h, Intermediate 35 (170 mg) and Intermediate 31 (200 mg) were converted to a crude product that was purified by prep-TLC to give Example 61 (27 mg, 8% yield) as a white solid. MS (ESI): mass calcd. for $C_{25}H_{28}N_4O_3S_2$, 496.16. m/z found 497.0 [M+H]$^+$, $^1$H NMR (400 MHz, DMSO-d6) δ ppm 7.87 (d, J=8.0 Hz, 2H), 7.52 (d, J=8.2 Hz, 2H), 7.08 (dd, J=15.4, 7.2 Hz, 4H), 4.51 (s, 2H), 4.14 (t, J=5.6 Hz, 4H), 3.32 (d, J=9.1 Hz, 2H), 3.19 (s, 3H), 2.92-2.77 (m, 5H), 2.08-1.95 (m, 2H).

Example 62

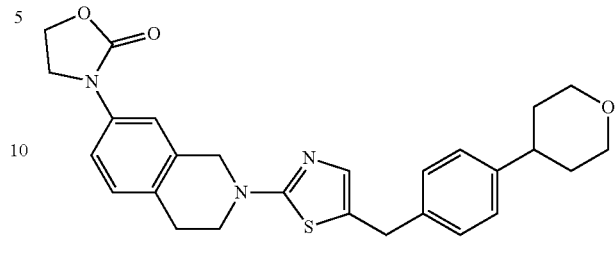

1. Following the procedure described for Example 59 except the mixture was heated at 130° C. for 4.5 h, Intermediate 20 (204 mg) and Intermediate 30 (150 mg) were converted to Example 62 (56 mg, 23% yield) as a yellow white solid. MS (ESI): mass calcd. for $C_{24}H_{29}N_3O_3S$ 475.61, m/z found 475.8 [M+H]$^+$. $^1$H NMR (400 MHz, DMSO) δ ppm 7.45 (d, J=8.1 Hz, 1H), 7.37 (s, 1H), 7.20-7.17 (m, 5H), 6.99 (s, 1H), 4.54 (s, 2H), 4.45-4.41 (m, 2H), 4.05-4.01 (m, 2H), 3.95-3.92 (m, 4H), 3.64 (t, J=5.7 Example 61 Hz, 2H), 3.45-3.39 (m, 2H), 2.86 (t, J=5.7 Hz, 2H), 2.75-2.71 (m, 1H), 1.67-1.61 (m, 4H).

Example 63

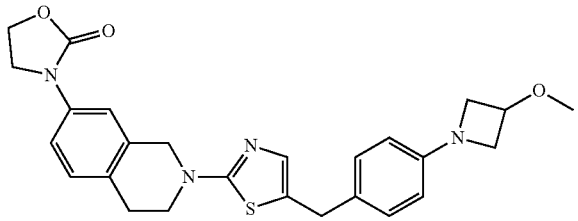 [SMILES: COC1CN(c2ccc(Cc3cnc(N4CCc5ccc(N6CCOC6=O)cc5C4)s3)cc2)C1]

1. Following the procedure described for Example 31 using $Cs_2CO_3$ (833 mg) instead of $K_2CO_3$ and the vessel was purged 3× with $N_2$, Intermediate 22 (200 mg) and 3-methoxyazetidine hydrochloride (159 mg) were heated at 100° C. for 5 h and the mixture was cooled to RT, diluted with a mixture (DCM/MeOH, 10/1, 20 mL), filtered and the filtrate was concentrated. The resulting residue was purified by chromatography on silica gel to give the Example 63 (35.7 mg, 17.7% yield) as a yellow white solid. MS (ESI): mass calcd. for $C_{26}H_{28}N_4O_3S$ 476.60, m/z found 476.8 [M+H]$^+$. $^1$H NMR (400 MHz, DMSO) δ ppm 7.45 (d, J=8.3 Hz, 1H), 7.37 (s, 1H), 7.19 (d, J=8.7 Hz, 1H), 7.04 (d, J=8.1 Hz, 2H), 6.93 (s, 1H), 6.38 (d, J=8.2 Hz, 2H), 4.53 (s, 2H), 4.43 (t, J=7.8 Hz, 2H), 4.32-4.27 (m, 1H), 4.05-3.99 (m, 4H), 3.85 (s, 2H), 3.64 (t, J=5.8 Hz, 2H), 3.55-3.52 (m, 2H), 3.23 (s, 3H), 2.86 (t, J=5.8 Hz, 2H).

Example 64

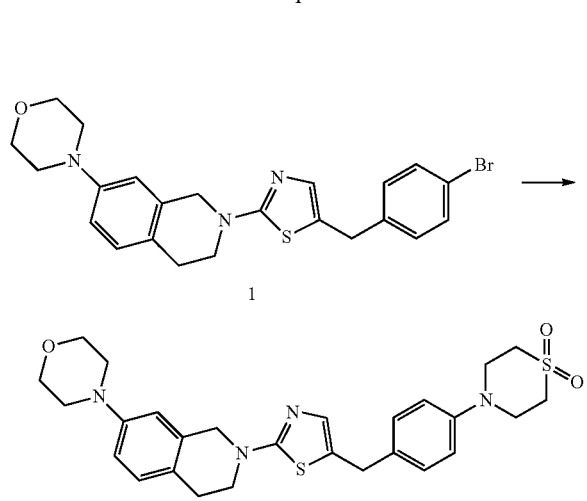

1. Following the procedure described for Example 1 except the mixture was heated at 130° C. for 3 h, Intermediate 27 (900 mg) and Intermediate 6 (1.1 g) were converted to 1 (400 mg, 23% yield) as a yellow solid. MS (ESI): mass calcd. for $C_{23}H_{24}BrN_3OS$ 469.08, m/z found 469.7 $[M+H]^+$.

2. A mixture of 1 (150 mg, 0.32 mmol), thiomorpholine 1,1-dioxide (180 mg, 1.3 mmol), $Pd_2(dba)_3$ (90 mg, 0.1 mmol), SPhos (80 mg, 0.2 mmol) and t-BuONa (170 mg, 1.8 mmol) in dried 1,4-dioxane (25 mL) was stirred at 100° C. overnight. The reaction mixture was cooled to RT, filtered and the filtrate concentrated to afford a residue which was purified by Prep-TLC to afford Example 64 (35 mg, 21%) as a white solid. mass calcd. for $C_{24}H_{32}N_4O_3S_2$ 524.19, m/z found 524.8 $[M+H]^+$, $^1H$ NMR (400 MHz, DMSO) δ ppm 7.08 (d, J=8.4 Hz, 2H), 7.00 (d, J=8.2 Hz, 1H), 6.94 (d, J=5.5 Hz, 3H), 6.77 (d, J=9.1 Hz, 2H), 4.45 (s, 2H), 3.87 (s, 2H), 3.69 (m, 8H), 3.58 (t, J=5.7 Hz, 2H), 3.04 (m, 8H), 2.76 (t, J=5.6 Hz, 1H).

Example 65

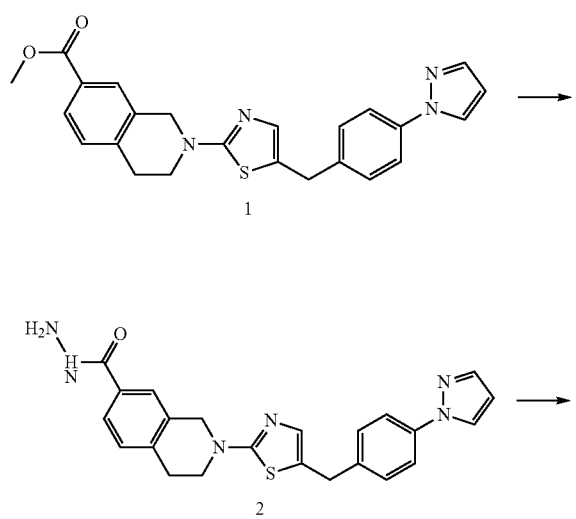

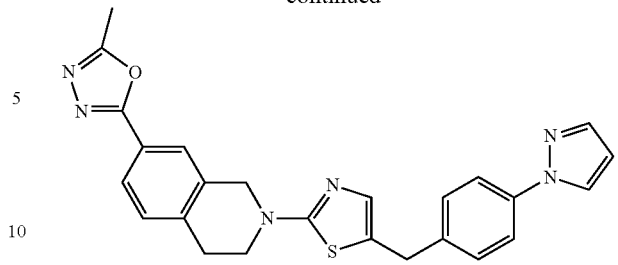

1. A mixture of Intermediate 5 (200 mg, 0.44 mmol), TEA (134 mg, 1.33 mmol), and $Pd(dppf)Cl_2$ (32.4 mg, 0.044 mmol) in MeOH (2 mL) and MeCN (1 mL) in a bomb under CO atmosphere was heated at 100° C. for 24 hrs. The mixture was filtered through Celite, the filter cake was washed with EA and the combined filtrate was concentrated to give a crude product which was purified by silica gel chromatography to afford 1 (140 mg, 73.4% yield) as a white solid. MS (ESI): mass calcd. for $C_{24}H_{22}N_4O_2S$ 430.53, m/z found 430.8 $[M+H]^+$.

2. A mixture of 1 (140 mg, 0.33 mmol), $N_2H_4$—$H_2O$ (130 mg, 2.60 mmol) in EtOH (1 mL) and THF (1 mL) were put in a bomb which was was heated at 80° C. for 5 days. The mixture was concentrated to give a crude product which was purified by silica gel chromatography to afford 2 (125 mg, 89.3% yield) as a white solid. MS (ESI): mass calcd. for $C_{23}H_{22}N_6OS$ 430.53, m/z found 430.8 $[M+H]^+$.

3. A mixture of 2 (120 mg, 0.28 mmol), trimethyl orthoacetate (132 mg, 0.70 mmol), $NH_4Cl$ (4.5 mg, 0.08 mmol) in EtOH (1 mL) and THF (1 mL) was put in sealed tube which was heated at 80° C. for 18 hrs. The mixture was cooled and trimethyl orthoacetate (132 mg, 0.70 mmol) and $NH_4Cl$ (4.5 mg, 0.08 mmol) was added and the mixture heated at 80° C. for 18 hrs. The mixture was cooled and trimethyl orthoacetate (132 mg, 0.70 mmol) and $NH_4Cl$ (4.5 mg, 0.08 mmol) was added and the mixture heated at 80° C. for 18 hrs. The mixture was cooled and concentrated. The resulting residue was purified by Prep-HPLC to afford Example 65 (30 mg, 23.7% yield, 96.2% purity 214 nm) as a white solid. MS (ESI): mass calcd. for $C_{25}H_{22}N_6OS$ 454.55 m/z found 454.8 $[M+H]^+$. NMR (400 MHz, DMSO-d6) δ ppm 8.46 (d, J=2.2, 1H), 7.85 (s, 1H), 7.80-7.76 (m, 3H), 7.73 (d, J=1.5, 1H), 7.40 (d, J=8.0, 1H), 7.36 (d, J=8.6, 2H), 7.04 (s, 1H), 6.53 (dd, J=2.4, 1.8, 1H), 4.65 (s, 2H), 4.05 (s, 2H), 3.70 (t, J=5.9, 2H), 2.98 (t, J=5.8, 2H), 2.58 (s, 3H).

Example 66

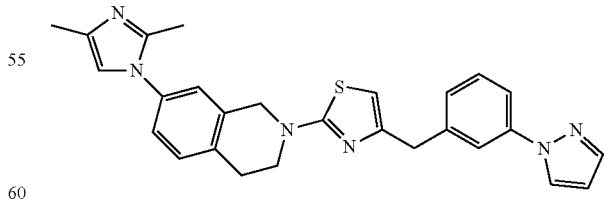

1. A mixture of Intermediate 1 hydrochloride salt (55 mg, 0.21 mmol), Intermediate 34 (57.7 mg, 0.21 mmol), $Pd_2(dba)_3$ (27.5 mg, 0.03 mmol), SPhos (24.7 mg, 0.06 mmol) and t-BuOK (84 mg, 0.75 mmol) in dry dioxane (4 mL) was stirred at 90° C. for 4 h under $N_2$. The mixture was cooled to RT, poured into water and extracted with EtOAc. The combined organic layers were washed with water, brine, dried over Na$_2$SO$_4$ and concentrated to give a crude product which was purified by Prep-HPLC to afford Example 66 (1.9 mg, 2% yield) as a white solid. MS Calcd.: 467.2; MS Found: 468.3 [M+H]$^+$. NMR (400 MHz, DMSO-d$_6$) δ 2.08 (3H, s), 2.23 (3H, s), 2.96 (2H, t, J=6.4 Hz), 3.68 (2H, t, J=6.0 Hz), 3.95 (2H, s), 4.61 (2H, s), 6.29 (1H, d, J=1.6 Hz), 6.38 (1H, s), 6.93 (1H, s), 7.22 (1H, d, J=7.6 Hz), 7.31-7.34 (2H, m), 7.42-7.44 (2H, m), 7.50-7.60 (5H, m).

Example 67

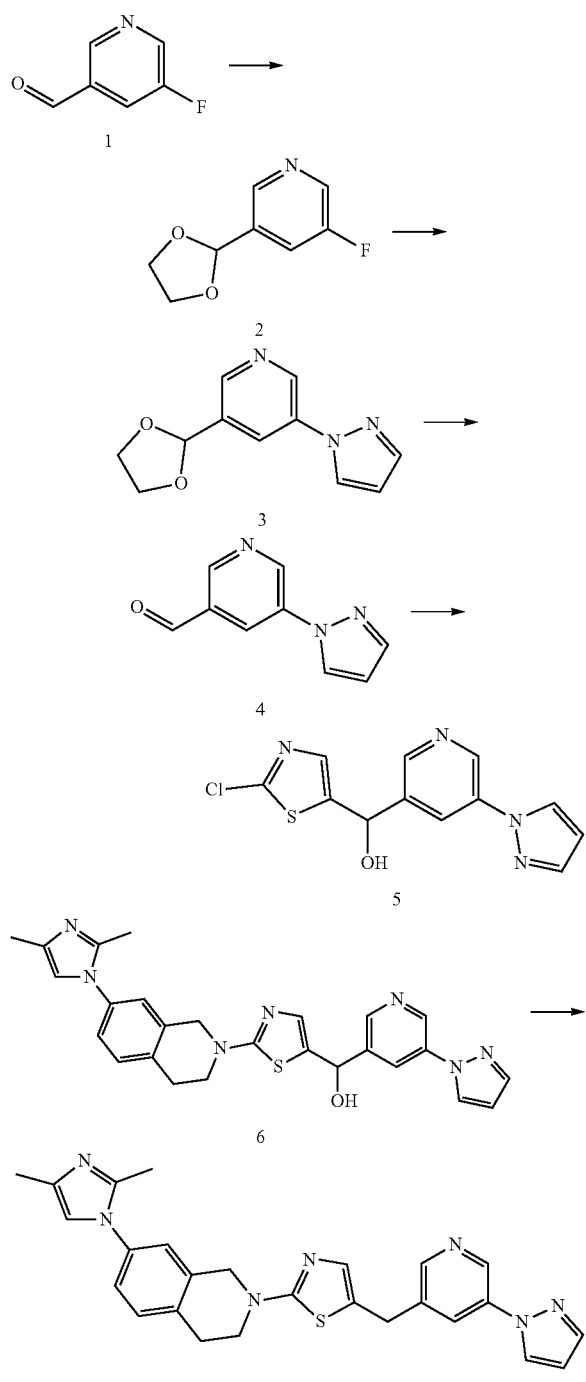

1. A mixture of 1 (2.00 g, 16.0 mmol), ethanediol (1.12 g, 18.0 mmol) and TsOH (100 mg, 0.53 mmol) in benzene (10 mL) was refluxed for 18 h and concentrated. The residue was dissolved in Et$_2$O and the solution washed with 10% NaHCO$_3$. The organic mixture was dried over Na$_2$SO$_4$ and filtered, and the filtrate was evaporated to give 2 (1.45 g, 54%) as a colorless oil.

2. To a solution of 1H-pyrazole (1.16 g, 17.0 mmol) in anhydrous DMF (10.0 mL) was added NaH (60% dispersion in mineral oil, 3.50 g, 87.0 mmol) under N$_2$, and the resulting mixture was stirred at 60° C. for 2 h. Then a solution of 2 (1.45 g, 8.57 mmol) in DMF (3.0 mL) was added dropwise and the resulting mixture was stirred at 80° C. for 3 h. The mixture was cooled to RT, poured into water and extracted with EtOAc. The combined organic extracts were washed with water, brine, dried over Na$_2$SO$_4$ and concentrated to give a crude product which was purified by silica gel chromatography to afford 3 (862 mg, 58% yield) as a colorless oil.

3. A mixture of 3 (862 mg, 3.97 mmol), CuSO$_4$ (64.0 mg, 0.40 mmol), H$_2$O (5.00 mL) and HCO$_2$H (20.0 mL) was stirred at 80° C. for 4 h. The mixture was cooled, poured into water and basified with aqueous K$_2$CO$_3$ to pH 8. The mixture was extracted with EtOAc. The combined organic extracts were washed with water, brine, dried over Na$_2$SO$_4$ and concentrated to give a crude product which was purified by silica gel chromatography to afford 4 (320 mg, 46% yield) as a colorless oil.

4. To a solution of 2-chlorothiazole (221 mg, 1.85 mmol) in dry THF (10 mL) at −78° C. under N$_2$ was added n-BuLi (2.5 M, 0.8 mL, 2.00 mmol) dropwise. After 1 h, a solution of 4 (320 mg, 1.85 mmol) in dry THF (3 mL) was added dropwise. The resulting solution was slowly warmed to RT. The mixture was diluted with NH$_4$Cl solution and extracted with EtOAc. The organic extracts were concentrated to give a residue which was purified by silica gel chromatography to afford 5 (173 mg, 32% yield) as a yellow oil.

5. A mixture of 5 (388 mg, 1.33 mmol), Intermediate 1 hydrochloride salt (350 mg, 1.33 mmol), Pd$_2$(dba)$_3$ (91.5 mg, 0.1 mmol), SPhos (82.3 mg, 0.2 mmol) and t-BuOK (446 mg, 3.99 mmol) in dry dioxane (6 mL) was stirred at 90° C. for 4 h under N$_2$. The mixture was cooled to RT, poured into water and extracted with EtOAc. The combined organic extracts were washed with water, brine, dried over Na$_2$SO$_4$ and concentrated to give a crude product, which was purified by prep-HPLC to afford 6 (170 mg, 26% yield) as a white solid.

6. To a solution of 6 (170 mg, 0.35 mmol) in TFA (10 mL) was added TES (3 mL), and the resulting mixture was stirred at 100° C. for 1 h. The mixture was concentrated and the residue was purified by prep-HPLC to afford Example 67 (5.20 mg, 3% yield) as a white solid. $^1$H NMR (400 MHz, DMSO-d$_6$) δ 2.08 (3H, s), 2.22 (3H, s), 2.94 (2H, t, J=5.6 Hz), 3.67 (2H, t, J=5.6 Hz), 4.15 (2H, s), 4.60 (2H, s), 6.60 (1H, t, J=2.0 Hz), 6.91 (1H, s), 7.08 (1H, s), 7.22 (1H, s), 7.30 (2H, d, J=8.0 Hz), 7.81 (1H, d, J=1.2 Hz), 8.13 (1H, s), 8.45 (1H, d, J=1.6 Hz), 8.60 (1H, d, J=2.0 Hz), 8.97 (1H, d, J=2.4 Hz).

Example 68

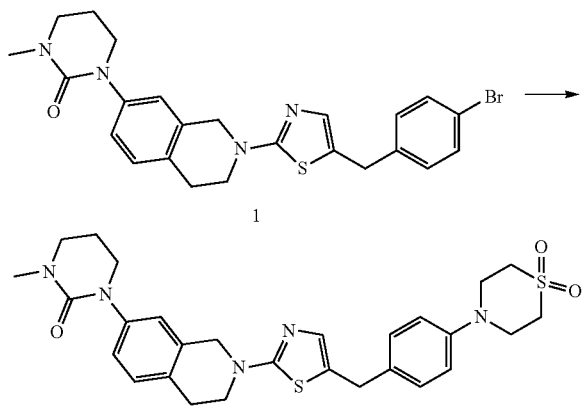

1. Following the procedure described for Example 1 except $Cs_2CO_3$ (1.37 mg) was used instead of $K_2CO_3$ and the mixture was heated at 110° C. for 2 h, Intermediate 6 (400 mg) and Intermediate 35 (580 mg) were converted to 1 (600 mg, 85%) as brown oil. MS (ESI): mass calcd. for $C_{24}H_{25}BrN_4OS$ 496.09. m/z found 496.8 $[M+H]^+$.

2. A mixture of 1 (500 mg, 1 mmol), thiomorpholine 1,1-dioxide (405 mg, 3 mmol), $Pd(dba)_2$ (288 mg, 0.5 mmol), SPhos (205 mg, 0.5 mmol) and t-BuONa (290 mg, 3.0 mmol) in dried 1,4-dioxane (30 mL) was stirred at 100° C. overnight. The mixture was cooled to RT, filtered and concentrated. The resulting residue was purified by silica gel chromatography. The resulting material was purified by Prep-TLC to afford Example 68 (50 mg, 9%) as a white solid. mass calcd. for $C_{28}H_{33}N_5O_3S_2$ 551.2, m/z found 551.72 $[M+H]^+$. $^1H$ NMR (400 MHz, DMSO-d6) δ ppm 7.17-7.03 (m, 5H), 7.00-6.92 (m, 3H), 4.49 (s, 2H), 3.90 (s, 2H), 3.77-3.69 (m, 4H), 3.62 (m, 4H), 3.19-3.03 (m, 4H), 2.86 (m, 5H), 2.07-1.94 (m, 2H), 1.24 (s, 2H).

Assessing Antiviral Activity Against Human Cytomegalovirus (HCMV)

To assess their antiviral activity, some compounds were tested against human cytomegalovirus (HCMV) in vitro. Human MRCS cells were grown to confluency (~1.0×10^4 cells/well) in 96-well plate format in Dulbecco's Modified Eagle Medium (DMFM) supplemented with 10% fetal bovine serum (FBS) 2 mM L-glutamine, 0.1 mM non-essential amino acids, 10 mM HEPES, and 100 U/ml each of penicillin and streptomycin and infected with an HCMV variant expressing mCherry tagged pUL99 (the product of late viral UL99 gene) at a multiplicity of 0.01 infectious unit (IU) per cell. Assays were performed in triplicate. One hour later, medium of the cells was replaced with fresh medium containing the indicated compounds at 25, 12.5, 6.25, 3.13, 1.56, 0.78, 0.39 μM or the carrier in which the compounds are dissolved (DMSO). Final concentration of DMSO was 0.5% in each treatment. Virus yield in the culture was determined at 7 days post infection by quantification of fluorescent (mCherry positive) cells in each well by fluorescent microscopy. Results were plotted using CDD Vault (CDD Vault was developed by Collaborative Drug Discovery, Inc., 1633 Bayshore Hwy, Suite 342, Burlingame, Calif. 94010) in order to calculate IC50s. Results of compounds tested with this assay are provided in Table 1.

Assessing Antiviral Activity Against Influenza

To assess their antiviral activity, some compounds were tested against murine adapted human influenza (PR8) in vitro. Canine MDCK cells were grown to confluency (~1.0× 10^4 cells/well) in 96-well plate format in Eagle's Minimal Essential Medium (EMEM) supplemented with 10% fetal bovine serum (FBS) and 100 U/ml each of penicillin and streptomycin. Wells were washed in 1×PBS and infected with an PR8 variant expressing mCherry downstream and separated by a 2A autocleavage site from the NS-1 protein at a multiplicity of 0.01 infectious unit (IU) per cell in serum free EMEM. Assays were performed in triplicate. One hour later, virus containing medium in the cells was replaced with fresh complete medium containing the indicated compounds at 25, 12.5, 6.25, 3.13, 1.56, 0.78, 0.39 μM or the carrier in which the compounds are dissolved (DMSO) and supplemented with 2.5 μg/ml TPCK trypsin. Final concentration of DMSO was 0.5% in each treatment. Virus yield in the culture was determined at 3 days post infection by quantification of fluorescent (mCherry positive) cells in each well by fluorescent microscopy. Results were plotted using CDD Vault (CDD Vault was developed by Collaborative Drug Discovery, Inc., 1633 Bayshore Hwy, Suite 342, Burlingame, Calif. 94010) in order to calculate IC50s. Results of compounds tested with this assay are provided in Table 1.

TABLE 1

| Example | Structure | HCMV IC50 (μM) | Flu IC50 (μM) |
|---|---|---|---|
| 4 | 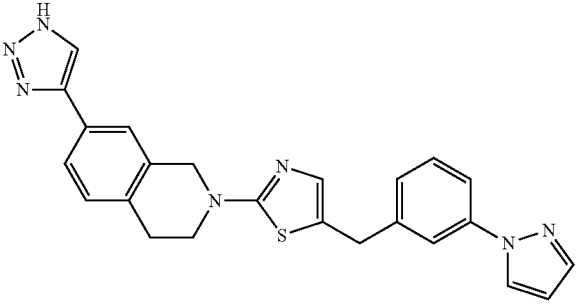 [SMILES: c1cc(Cc2cnc(N3CCc4ccc(-c5c[nH]nn5)cc4C3)s2)cc(-n2cccn2)c1] | 0.758 | >25 |

TABLE 1-continued

| Example | Structure | HCMV IC50 (μM) | Flu IC50 (μM) |
|---|---|---|---|
| 2 | 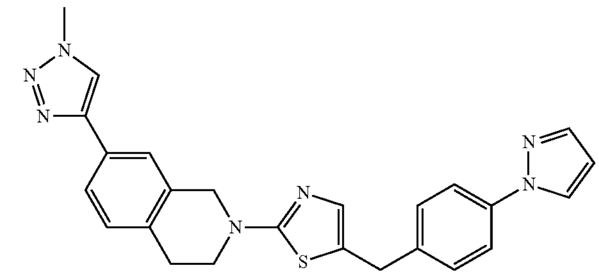 [SMILES: Cn1cc(-c2ccc3c(c2)CN(c2ncc(Cc4ccc(-n5cccn5)cc4)s2)CC3)nn1] | 1.17 | 6.017 |
| 3 | 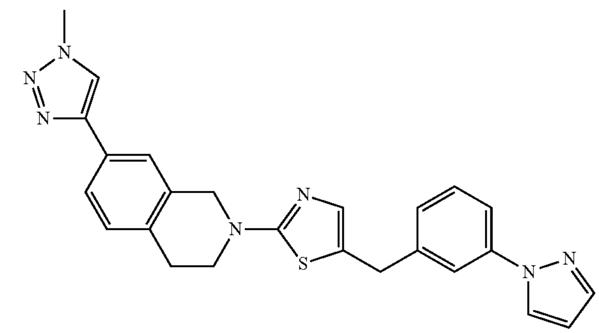 [SMILES: Cn1cc(-c2ccc3c(c2)CN(c2ncc(Cc4cccc(-n5cccn5)c4)s2)CC3)nn1] | 1.91 | >25 |
| 5 | 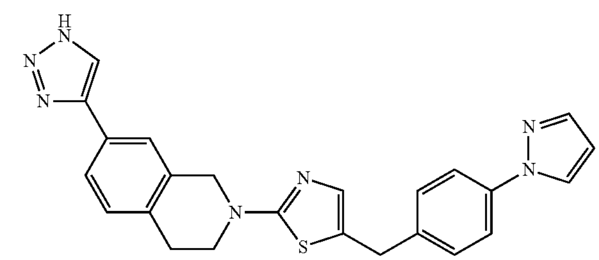 [SMILES: c1cnn(-c2ccc(Cc3cnc(N4CCc5ccc(-c6c[nH]nn6)cc5C4)s3)cc2)c1] | 0.807 | >25 |
| 1 | 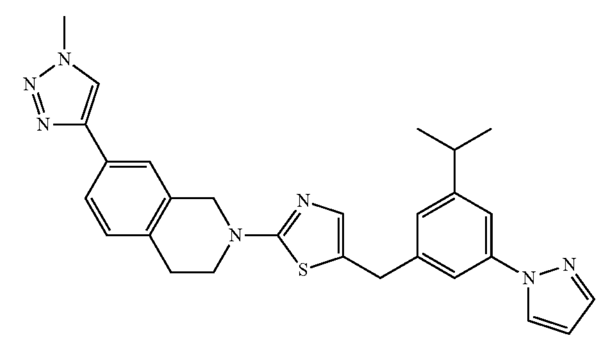 [SMILES: CC(C)c1cc(Cc2cnc(N3CCc4ccc(-c5cn(C)nn5)cc4C3)s2)cc(-n2cccn2)c1] | 11.7 | ND |
| 6 | 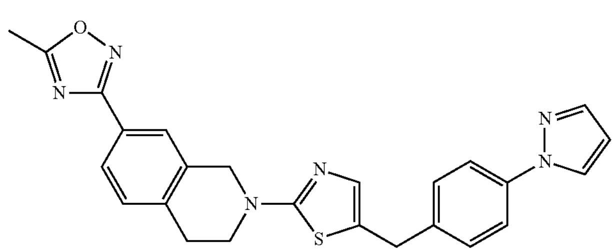 [SMILES: Cc1nc(-c2ccc3c(c2)CN(c2ncc(Cc4ccc(-n5cccn5)cc4)s2)CC3)no1] | 3.367 | ND |

TABLE 1-continued

| Example | Structure | HCMV IC50 (μM) | Flu IC50 (μM) |
|---|---|---|---|
| 7 | 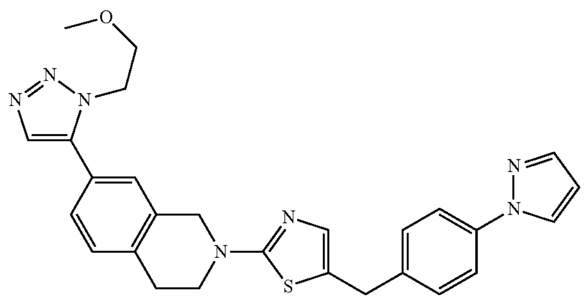 [SMILES: COCCn1nncc1-c1ccc2c(c1)CN(c1ncc(Cc3ccc(-n4cccn4)cc3)s1)CC2] | 1.695 | >25 |
| 8 | 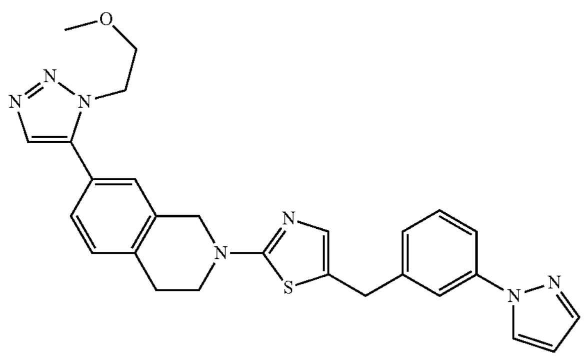 [SMILES: COCCn1nncc1-c1ccc2c(c1)CN(c1ncc(Cc3cccc(-n4cccn4)c3)s1)CC2] | 2.008 | >25 |
| 9 | 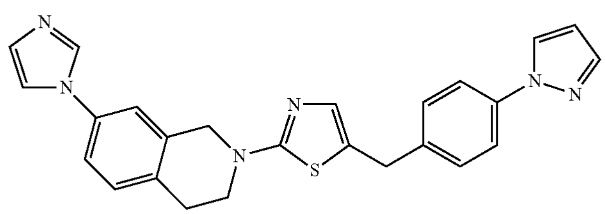 [SMILES: c1cnn(-c2ccc(Cc3cnc(N4CCc5ccc(-n6ccnc6)cc5C4)s3)cc2)c1] | 0.479 | 1.25 |
| 16 | 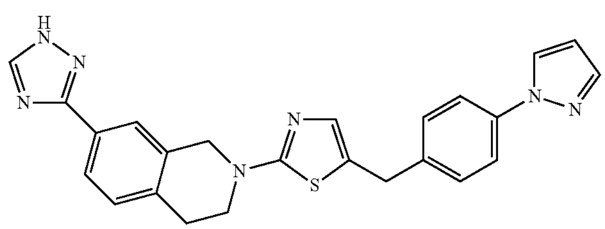 [SMILES: c1cnn(-c2ccc(Cc3cnc(N4CCc5ccc(-c6nc[nH]n6)cc5C4)s3)cc2)c1] | 0.2 | >25 |
| 11 | 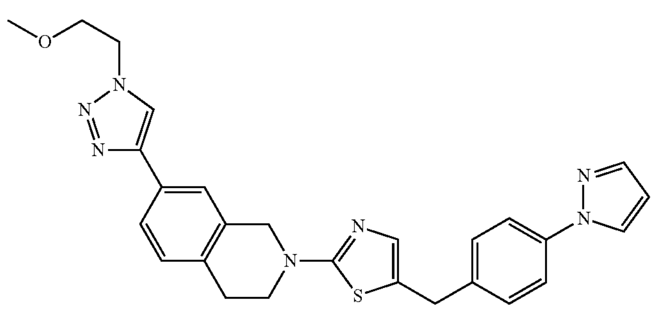 [SMILES: COCCn1cc(-c2ccc3c(c2)CN(c2ncc(Cc4ccc(-n5cccn5)cc4)s2)CC3)nn1] | 1.695 | >25 |

TABLE 1-continued

| Example | Structure | HCMV IC50 (μM) | Flu IC50 (μM) |
|---|---|---|---|
| 12 | 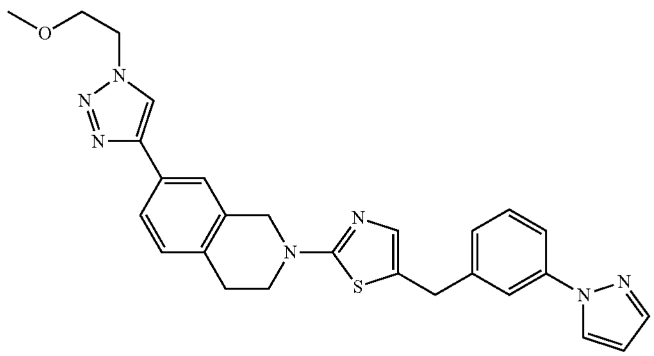 [SMILES: COCCn1cc(-c2ccc3c(c2)CN(c2ncc(Cc4cccc(-n5cccn5)c4)s2)CC3)nn1] | 5.977 | >25 |
| 15 | 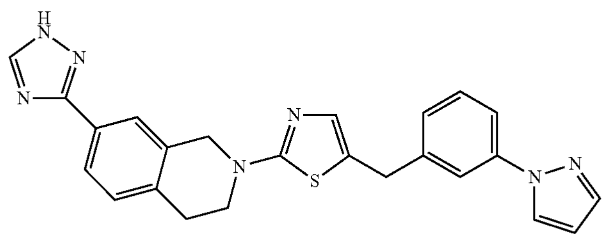 [SMILES: c1cc(Cc2cnc(N3CCc4ccc(-c5nc[nH]n5)cc4C3)s2)cc(-n2cccn2)c1] | 1.847 | >25 |
| 13 | 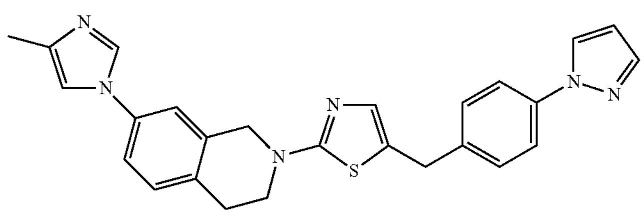 [SMILES: Cc1cn(-c2ccc3c(c2)CN(c2ncc(Cc4ccc(-n5cccn5)cc4)s2)CC3)cn1] | 1.056 | 22.9 |
| 14 | 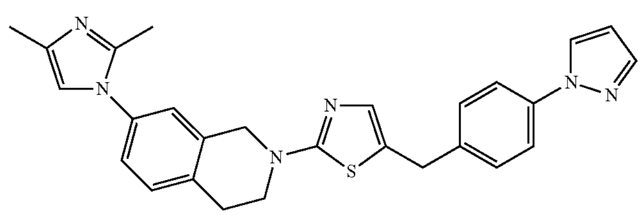 [SMILES: Cc1cn(-c2ccc3c(c2)CN(c2ncc(Cc4ccc(-n5cccn5)cc4)s2)CC3)c(C)n1] | 0.453 | 2.11 |
| 17 | 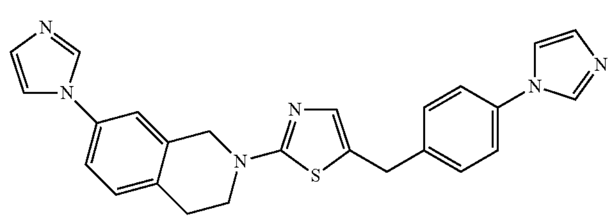 [SMILES: c1cn(-c2ccc(Cc3cnc(N4CCc5ccc(-n6ccnc6)cc5C4)s3)cc2)cn1] | 0.748 | 0.672 |
| 18 | 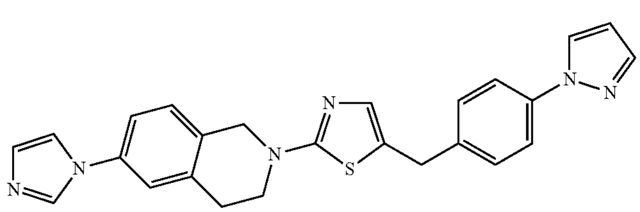 [SMILES: c1cnn(-c2ccc(Cc3cnc(N4CCc5cc(-n6ccnc6)ccc5C4)s3)cc2)c1] | 1.078 | >25 |

TABLE 1-continued

| Example | Structure | HCMV IC50 (μM) | Flu IC50 (μM) |
|---|---|---|---|
| 19 | 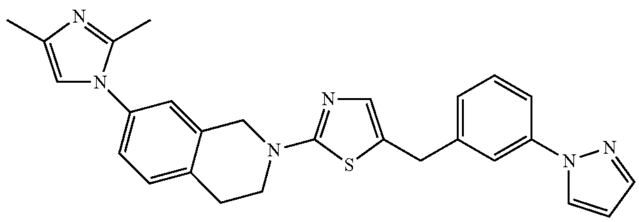 [SMILES: Cc1cn(-c2ccc3c(c2)CN(c2ncc(Cc4cccc(-n5cccn5)c4)s2)CC3)c(C)n1] | 1.302 | 6.917 |
| 66 | 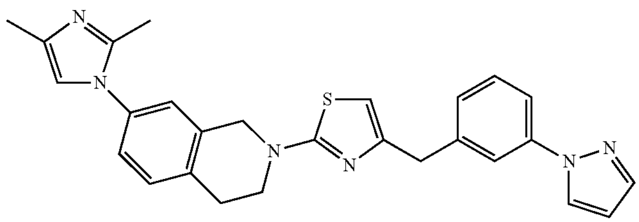 [SMILES: Cc1cn(-c2ccc3c(c2)CN(c2nc(Cc4cccc(-n5cccn5)c4)cs2)CC3)c(C)n1] | 4.482 | ND |
| 67 | 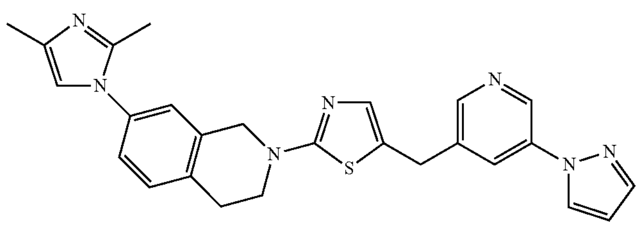 [SMILES: Cc1cn(-c2ccc3c(c2)CN(c2ncc(Cc4cncc(-n5cccn5)c4)s2)CC3)c(C)n1] | 1.189 | 12.467 |
| 20 | 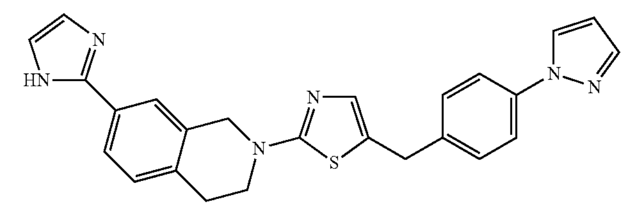 [SMILES: c1cnn(-c2ccc(Cc3cnc(N4CCc5ccc(-c6ncc[nH]6)cc5C4)s3)cc2)c1] | 5.271 | ND |
| 21 | 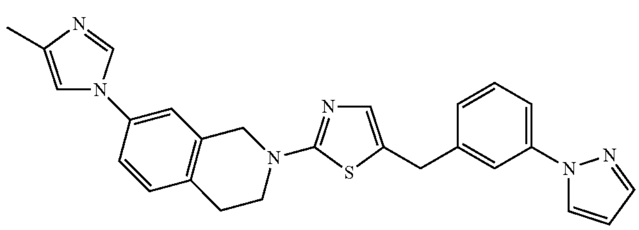 [SMILES: Cc1cn(-c2ccc3c(c2)CN(c2ncc(Cc4cccc(-n5cccn5)c4)s2)CC3)cn1] | 2.625 | ND |
| 22 | 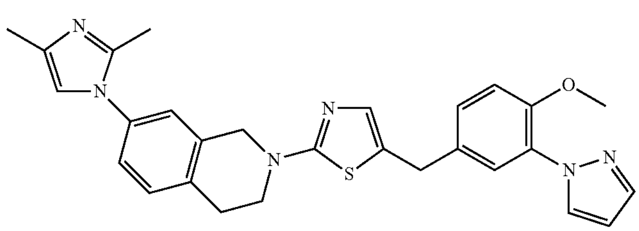 [SMILES: COc1ccc(Cc2cnc(N3CCc4ccc(-n5cc(C)nc5C)cc4C3)s2)cc1-n1cccn1] | 0.306 | 1.602 |

TABLE 1-continued

| Example | Structure | HCMV IC50 (μM) | Flu IC50 (μM) |
|---|---|---|---|
| 23 | 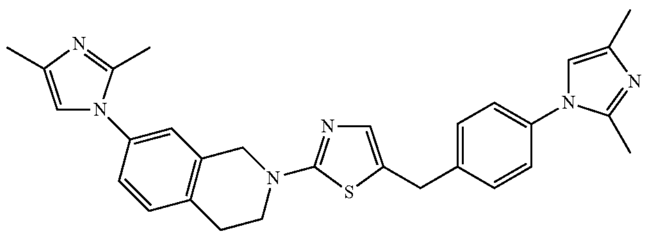 [SMILES: Cc1cn(-c2ccc(Cc3cnc(N4CCc5ccc(-n6cc(C)nc6C)cc5C4)s3)cc2)c(C)n1] | 0.707 | 2.961 |
| 24 | 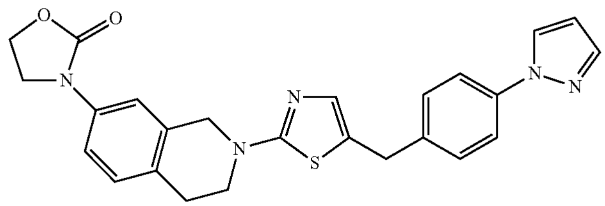 [SMILES: O=C1OCCN1c1ccc2c(c1)CN(c1ncc(Cc3ccc(-n4cccn4)cc3)s1)CC2] | 0.353 | 0.663 |
| 25 | 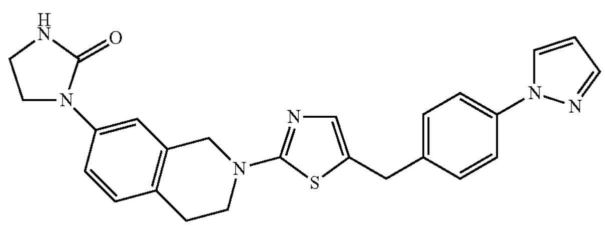 [SMILES: O=C1NCCN1c1ccc2c(c1)CN(c1ncc(Cc3ccc(-n4cccn4)cc3)s1)CC2] | 0.911 | >25 |
| 26 | 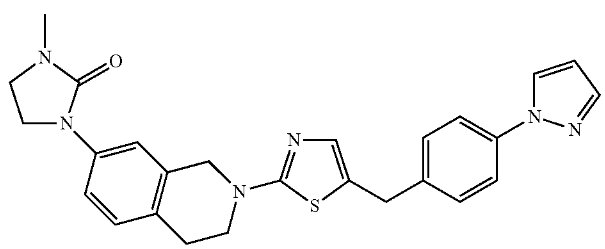 [SMILES: CN1CCN(c2ccc3c(c2)CN(c2ncc(Cc4ccc(-n5cccn5)cc4)s2)CC3)C1=O] | 0.637 | >25 |
| 27 | 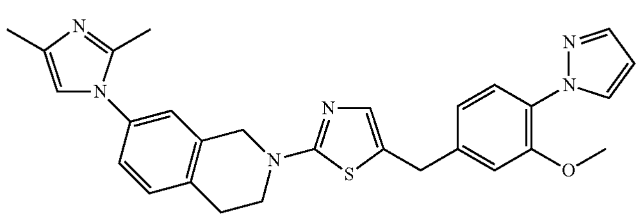 [SMILES: COc1cc(Cc2cnc(N3CCc4ccc(-n5cc(C)nc5C)cc4C3)s2)ccc1-n1cccn1] | 0.345 | 2.229 |
| 28 | 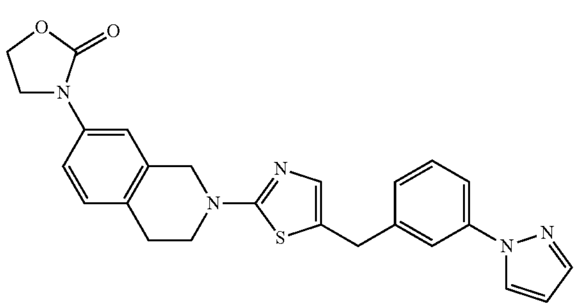 [SMILES: O=C1OCCN1c1ccc2c(c1)CN(c1ncc(Cc3cccc(-n4cccn4)c3)s1)CC2] | 1.888 | 1.324 |

TABLE 1-continued

| Example | Structure | HCMV IC50 (μM) | Flu IC50 (μM) |
|---|---|---|---|
| 30 | 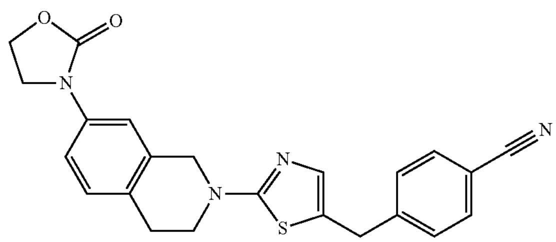 [SMILES: N#Cc1ccc(Cc2cnc(N3CCc4ccc(N5CCOC5=O)cc4C3)s2)cc1] | 4.425 | ND |
| 31 | 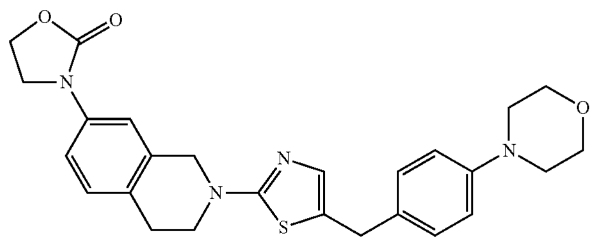 [SMILES: O=C1OCCN1c1ccc2c(c1)CN(c1ncc(Cc3ccc(N4CCOCC4)cc3)s1)CC2] | 0.803 | 2 |
| 32 | 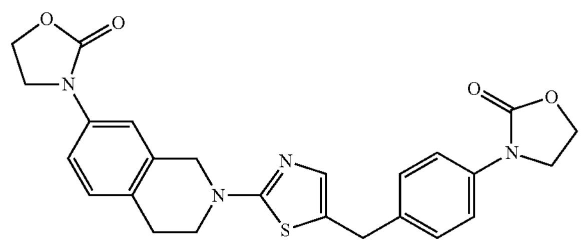 [SMILES: O=C1OCCN1c1ccc(Cc2cnc(N3CCc4ccc(N5CCOC5=O)cc4C3)s2)cc1] | 0.979 | 0.716 |
| 33 | 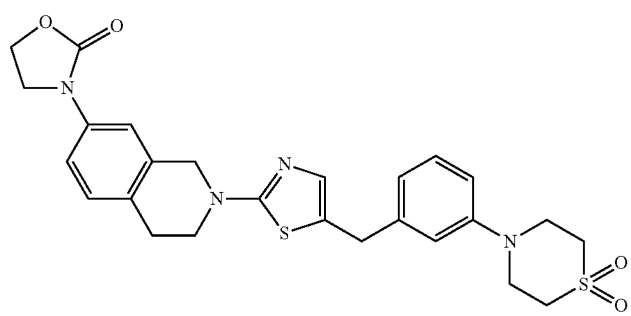 [SMILES: O=C1OCCN1c1ccc2c(c1)CN(c1ncc(Cc3cccc(N4CCS(=O)(=O)CC4)c3)s1)CC2] | 0.903 | 4.151 |
| 34 | 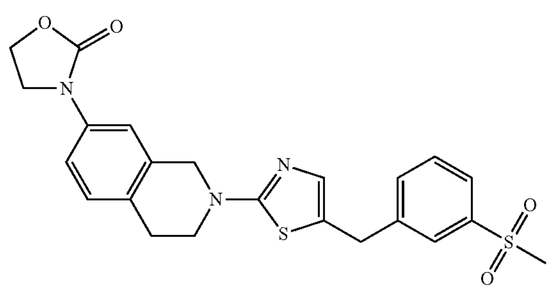 [SMILES: CS(=O)(=O)c1cccc(Cc2cnc(N3CCc4ccc(N5CCOC5=O)cc4C3)s2)c1] | 0.633 | 3.474 |

TABLE 1-continued

| Example | Structure | HCMV IC50 (μM) | Flu IC50 (μM) |
|---|---|---|---|
| 35 | 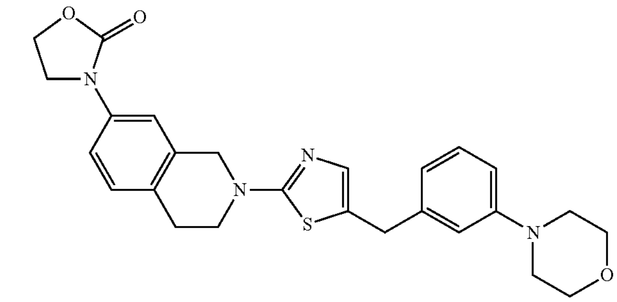 [SMILES: O=C1OCCN1c1ccc2c(c1)CN(c1ncc(Cc3cccc(N4CCOCC4)c3)s1)CC2] | 0.891 | 3.492 |
| 36 | 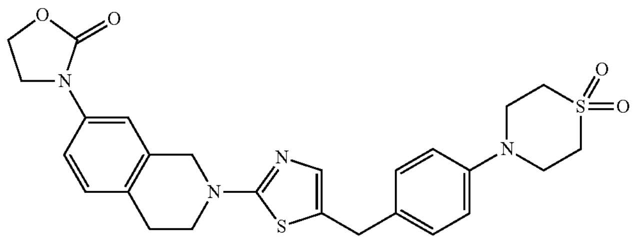 [SMILES: O=C1OCCN1c1ccc2c(c1)CN(c1ncc(Cc3ccc(N4CCS(=O)(=O)CC4)cc3)s1)CC2] | 0.666 | 1.094 |
| 73 | 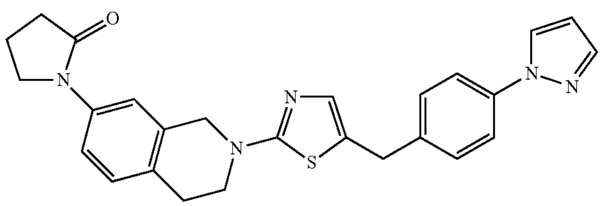 [SMILES: O=C1CCCN1c1ccc2c(c1)CN(c1ncc(Cc3ccc(-n4cccn4)cc3)s1)CC2] | 0.423 | 10.3 |
| 39 | 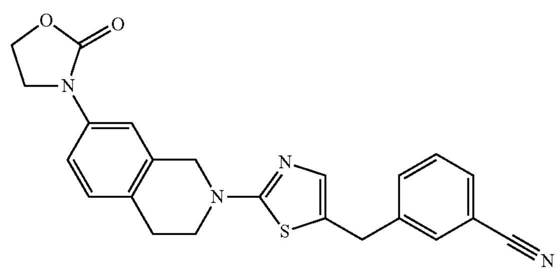 [SMILES: N#Cc1cccc(Cc2cnc(N3CCc4ccc(N5CCOC5=O)cc4C3)s2)c1] | 2.745 | 12.386 |
| 40 | 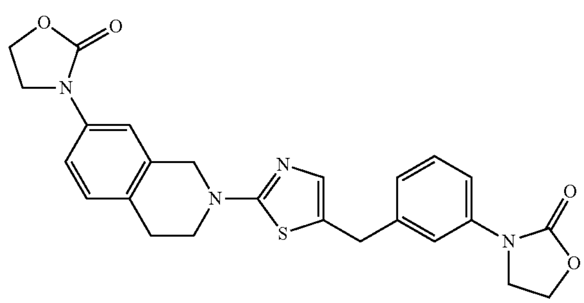 [SMILES: O=C1OCCN1c1cccc(Cc2cnc(N3CCc4ccc(N5CCOC5=O)cc4C3)s2)c1] | 0.956 | 2.483 |
| 29 | 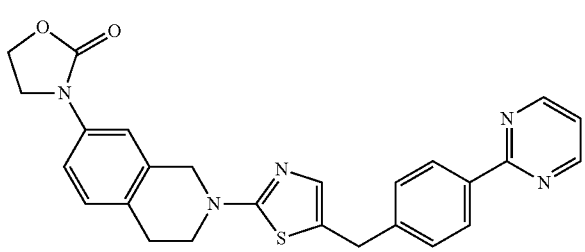 [SMILES: O=C1OCCN1c1ccc2c(c1)CN(c1ncc(Cc3ccc(-c4ncccn4)cc3)s1)CC2] | 0.858 | 0.289 |

TABLE 1-continued

| Example | Structure | HCMV IC50 (μM) | Flu IC50 (μM) |
|---|---|---|---|
| 41 | 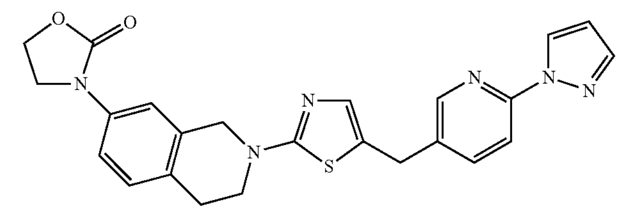 | 0.553 | 0.982 |
| 69 | 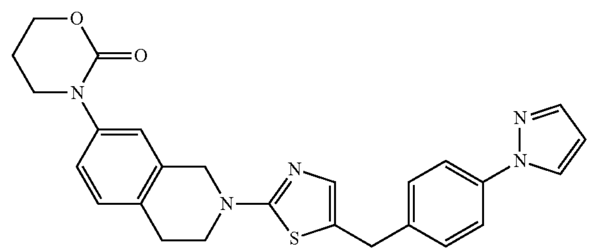 [SMILES: O=C1OCCCN1c1ccc2c(c1)CN(c1ncc(Cc3ccc(-n4cccn4)cc3)s1)CC2] | 4.899 | >25 |
| 42 | 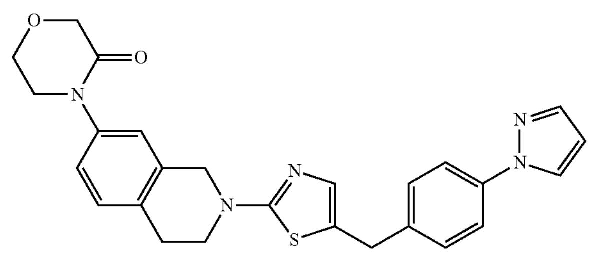 | 2.468 | >25 |
| 70 | 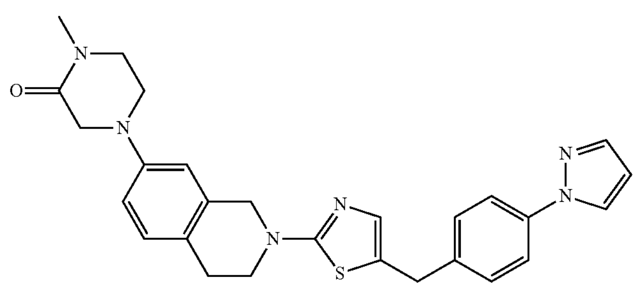 [SMILES: CN1CCN(c2ccc3c(c2)CN(c2ncc(Cc4ccc(-n5cccn5)cc4)s2)CC3)CC1=O] | 2.139 | 10.539 |
| 71 | 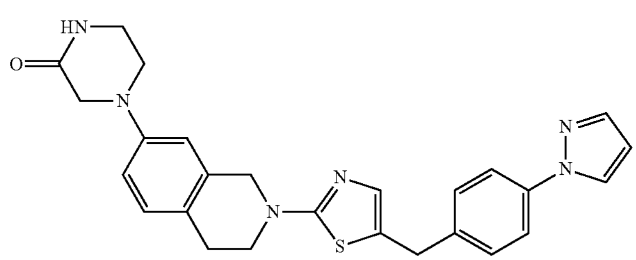 [SMILES: O=C1CN(c2ccc3c(c2)CN(c2ncc(Cc4ccc(-n5cccn5)cc4)s2)CC3)CCN1] | 10 | >25 |
| 72 | 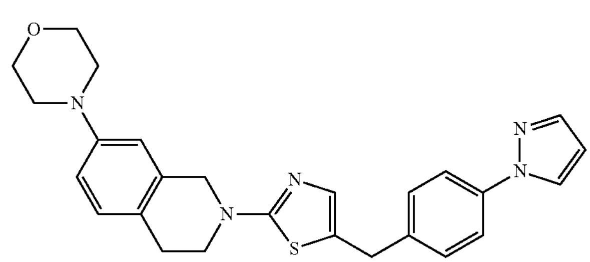 [SMILES: c1cnn(-c2ccc(Cc3cnc(N4CCc5ccc(N6CCOCC6)cc5C4)s3)cc2)c1] | 0.537 | >25 |

TABLE 1-continued

| Example | Structure | HCMV IC50 (μM) | Flu IC50 (μM) |
|---|---|---|---|
| 37 | 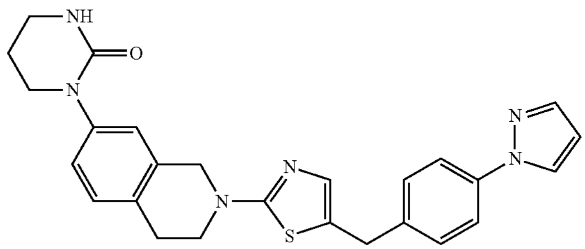 [SMILES: O=C1NCCCN1c1ccc2c(c1)CN(c1ncc(Cc3ccc(-n4cccn4)cc3)s1)CC2] | 9.96 | >25 |
| 43 | 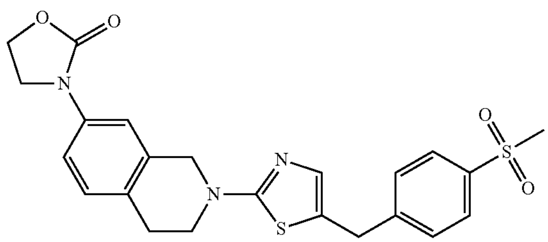 [SMILES: CS(=O)(=O)c1ccc(Cc2cnc(N3CCc4ccc(N5CCOC5=O)cc4C3)s2)cc1] | 0.617 | 1.163 |
| 38 | 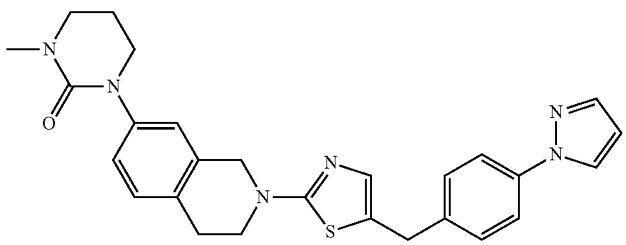 [SMILES: CN1CCCN(c2ccc3c(c2)CN(c2ncc(Cc4ccc(-n5cccn5)cc4)s2)CC3)C1=O] | 3.489 | 3.681 |
| 44 | 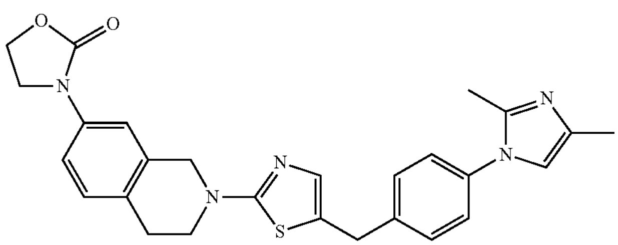 [SMILES: Cc1cn(-c2ccc(Cc3cnc(N4CCc5ccc(N6CCOC6=O)cc5C4)s3)cc2)c(C)n1] | 0.552 | 1.58 |
| 55 | 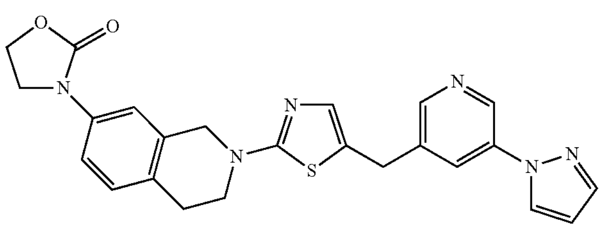 [SMILES: O=C1OCCN1c1ccc2c(c1)CN(c1ncc(Cc3cncc(-n4cccn4)c3)s1)CC2] | 3.826 | 2.393 |
| 56 | 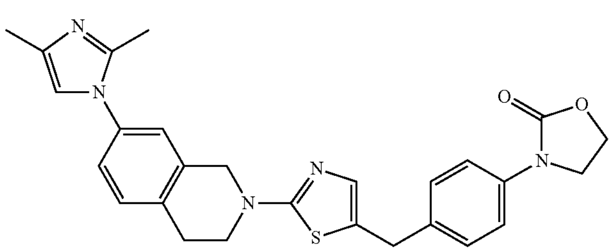 [SMILES: Cc1cn(-c2ccc3c(c2)CN(c2ncc(Cc4ccc(N5CCOC5=O)cc4)s2)CC3)c(C)n1] | 0.317 | 2.254 |

TABLE 1-continued

| Example | Structure | HCMV IC50 (μM) | Flu IC50 (μM) |
|---|---|---|---|
| 46 | 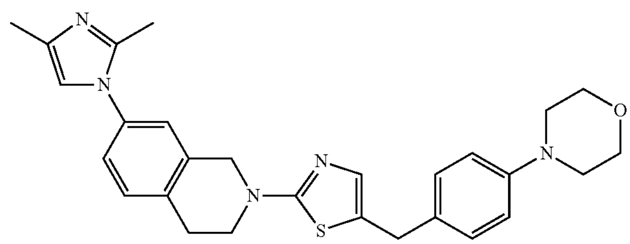 [SMILES: Cc1cn(-c2ccc3c(c2)CN(c2ncc(Cc4ccc(N5CCOCC5)cc4)s2)CC3)c(C)n1] | 0.605 | 3.324 |
| 47 | 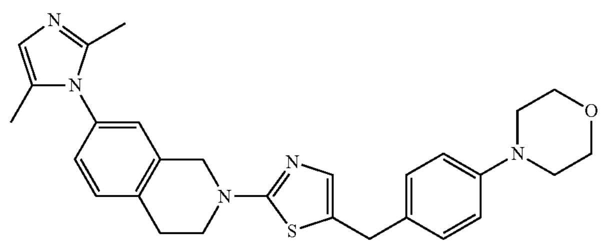 [SMILES: Cc1cnc(C)n1-c1ccc2c(c1)CN(c1ncc(Cc3ccc(N4CCOCC4)cc3)s1)CC2] | 0.796 | 4.01 |
| 48 | 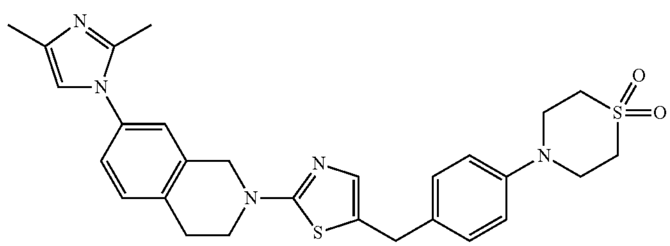 [SMILES: Cc1cn(-c2ccc3c(c2)CN(c2ncc(Cc4ccc(N5CCS(=O)(=O)CC5)cc4)s2)CC3)c(C)n1] | 0.195 | 1.517 |
| 49 | 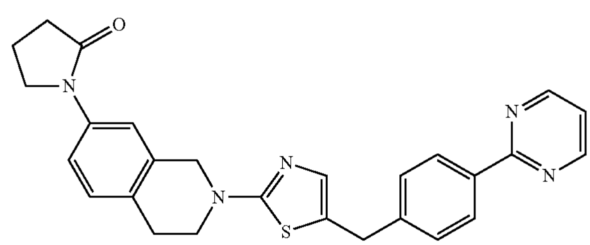 [SMILES: O=C1CCCN1c1ccc2c(c1)CN(c1ncc(Cc3ccc(-c4ncccn4)cc3)s1)CC2] | 0.516 | ND |
| 50 | 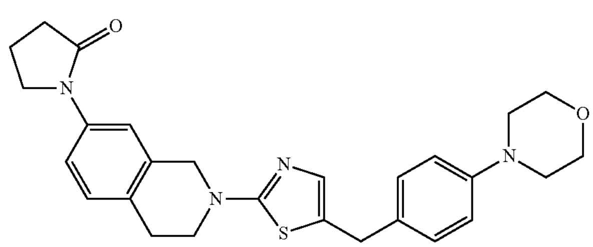 [SMILES: O=C1CCCN1c1ccc2c(c1)CN(c1ncc(Cc3ccc(N4CCOCC4)cc3)s1)CC2] | 0.613 | 4.719 |
| 51 | 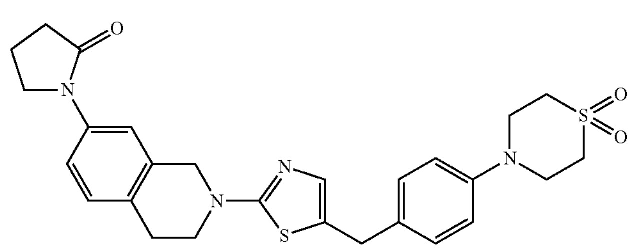 [SMILES: O=C1CCCN1c1ccc2c(c1)CN(c1ncc(Cc3ccc(N4CCS(=O)(=O)CC4)cc3)s1)CC2] | 0.737 | 2.41 |

TABLE 1-continued

| Example | Structure | HCMV IC50 (µM) | Flu IC50 (µM) |
|---|---|---|---|
| 53 | 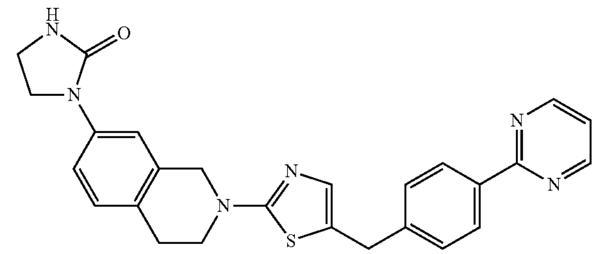 [SMILES: O=C1NCCN1c1ccc2c(c1)CN(c1ncc(Cc3ccc(-c4ncccn4)cc3)s1)CC2] | >4.167 | 11.241 |
| 57 | 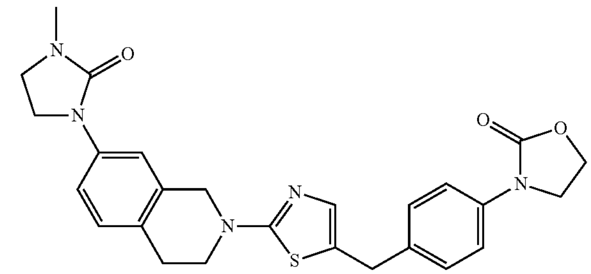 [SMILES: CN1CCN(c2ccc3c(c2)CN(c2ncc(Cc4ccc(N5CCOC5=O)cc4)s2)CC3)C1=O] | 0.742 | 10.443 |
| 52 | 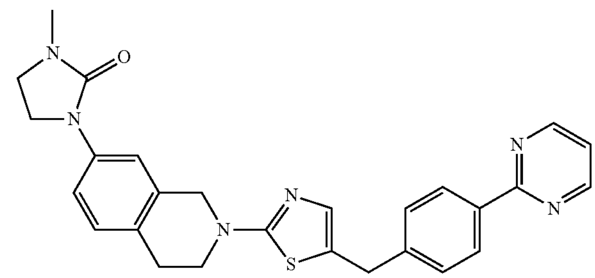 [SMILES: CN1CCN(c2ccc3c(c2)CN(c2ncc(Cc4ccc(-c5ncccn5)cc4)s2)CC3)C1=O] | 1.357 | >25 |
| 58 | 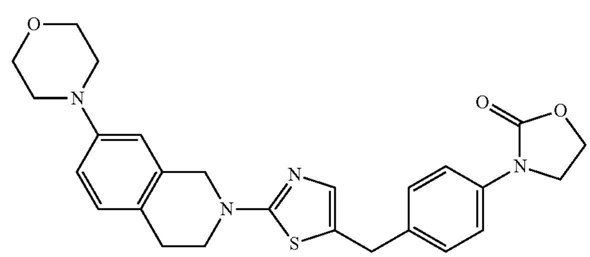 [SMILES: O=C1OCCN1c1ccc(Cc2cnc(N3CCc4ccc(N5CCOCC5)cc4C3)s2)cc1] | 1.128 | 3.543 |
| 54 | 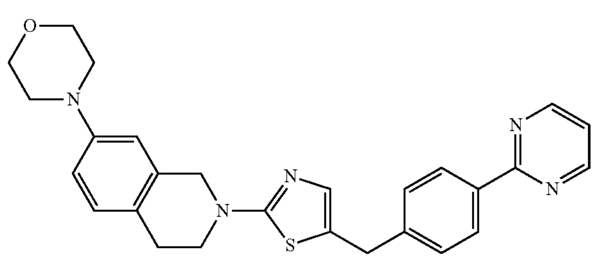 [SMILES: c1cnc(-c2ccc(Cc3cnc(N4CCc5ccc(N6CCOCC6)cc5C4)s3)cc2)nc1] | 1.095 | ND |
| 61 | 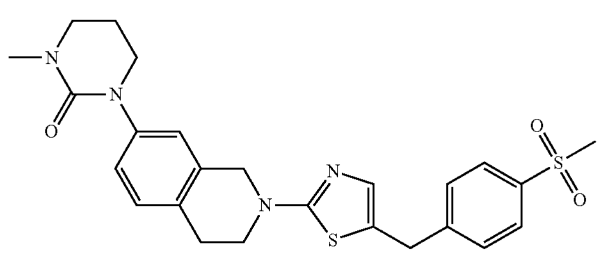 | 4.708 | >25 |

TABLE 1-continued

| Example | Structure | HCMV IC50 (μM) | Flu IC50 (μM) |
|---|---|---|---|
| 62 | 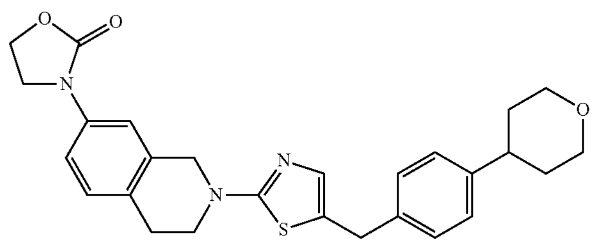 | 0.362 | 1.412 |
| 45 | 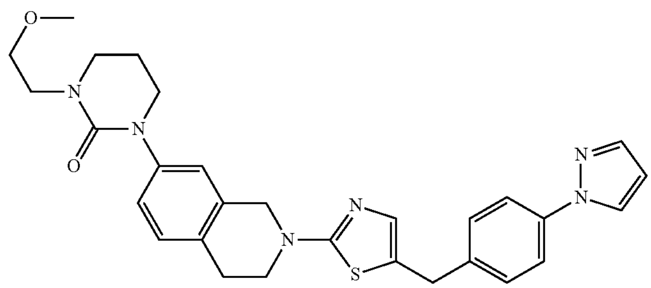 [SMILES: COCCN1CCCN(c2ccc3c(c2)CN(c2ncc(Cc4ccc(-n5cccn5)cc4)s2)CC3)C1=O] | 1.777 | ND |
| 60 | 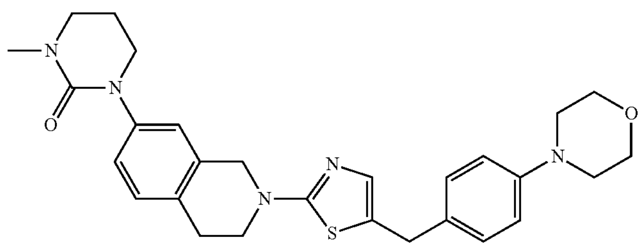 | 9.842 | >25 |
| 59 | 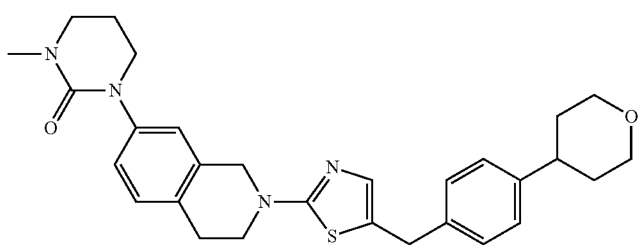 | 0.73 | 1.29 |
| 63 | 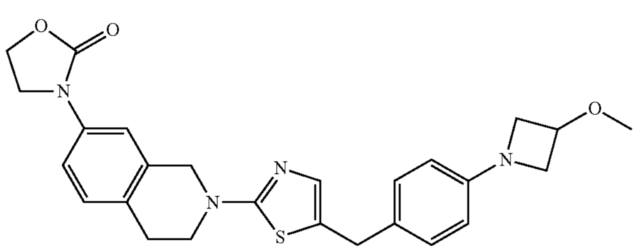 [SMILES: COC1CN(c2ccc(Cc3cnc(N4CCc5ccc(N6CCOC6=O)cc5C4)s3)cc2)C1] | ND | 7.451 |
| 64 | 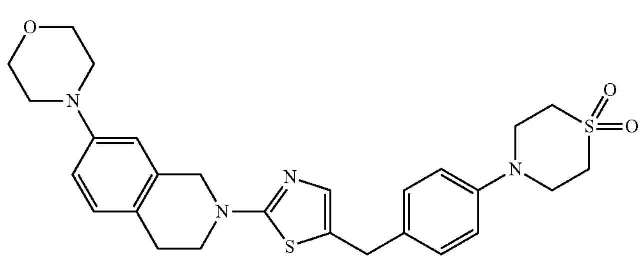 [SMILES: O=S1(=O)CCN(c2ccc(Cc3cnc(N4CCc5ccc(N6CCOCC6)cc5C4)s3)cc2)CC1] | ND | 0.639 |

TABLE 1-continued

| Example | Structure | HCMV IC50 (μM) | Flu IC50 (μM) |
|---|---|---|---|
| 65 | 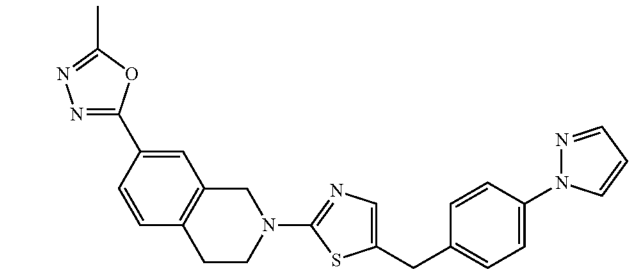 [SMILES: Cc1nnc(-c2ccc3c(c2)CN(c2ncc(Cc4ccc(-n5cccn5)cc4)s2)CC3)o1] | ND | 1.787 |
| 68 | 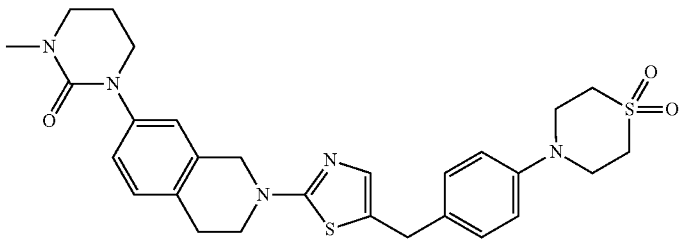 [SMILES: CN1CCCN(c2ccc3c(c2)CN(c2ncc(Cc4ccc(N5CCS(=O)(=O)CC5)cc4)s2)CC3)C1=O] | ND | ND |
| 10 | 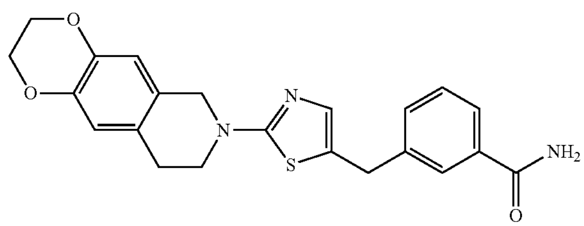 [SMILES: NC(=O)c1cccc(Cc2cnc(N3CCc4cc5c(cc4C3)OCCO5)s2)c1] | 8.63 | ND |

ND = not done

Some compounds in Table 1 have also been tested and found to inhibit the replication of RSV, Zika Virus strain MR776, and BK Virus in cell culture.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A composition comprising a compound of Formula I:

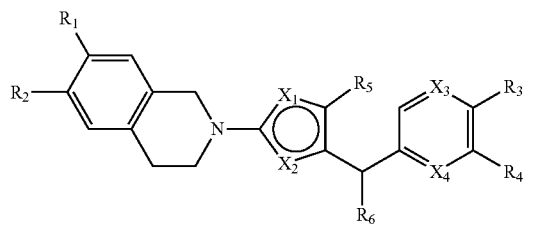

wherein:
one of $X_1$ and $X_2$ is N and the other is S;
$X_3$ and $X_4$ are independently selected from C and N; and when $X_3$ is C it is optionally substituted with methyl, ethyl, propyl, i-propyl or n-propyl;
one of $R_1$ and $R_2$ is H and the other is a 5- or 6-membered aryl or cycloalkyl with 0 to 3 ring heteroatoms independently selected from N and O and substituted with 0 to 3 groups independently selected from:
=O, $C_{1-6}$ straight or branched alkyl optionally substituted with —$OR_{12}$ or $NR_7R_8$, $C_{1-6}$ straight or branched alkoxy optionally substituted with $NR_7R_8$ or —$OR_{12}$, and $C_{3-6}$ cycloalkyl optionally substituted with —$R_{12}$, —$OR_{12}$ or —$NR_7R_8$,
or $R_1$ and $R_2$ together form a 5- or 6-membered aryl or cycloalkyl with 0 to 3 ring heteroatoms independently selected from N and O and substituted with 0 to 3 groups independently selected from:
=O, $C_{1-6}$ straight or branched alkyl optionally substituted with —$OR_{12}$ or $NR_7R_8$, $C_{1-6}$ straight or branched alkoxy optionally substituted with $NR_7R_8$ or —$OR_{12}$, and $C_{3-6}$ cycloalkyl optionally substituted with —$R_{12}$, —$OR_{12}$ or —$NR_7R_8$;
$R_3$ is selected from H, halo, —C≡CH, —CN=N, —OH, —$OCF_3$, —$OCHF_2$, $C_{1-4}$ straight or branched alkoxy, —$SO_2(C_{1-6}alkyl)$, —$N(CH_3)_2$, —$C(O)NH_2$, —$NHSO_2R_7$, —$C(O)NR_7R_8$, and a ring structure comprising a 5- or 6-membered aryl or a 4-, 5-, or 6-membered cycloalkyl with 0 to 3 ring heteroatoms independently selected from N, O and S and substituted with 0 to 2 groups independently selected from =O, halo, $C_{1-6}$ straight or branched alkyl optionally substituted with —$OR_{12}$ or —$NR_7R_8$, $C_{1-6}$ straight or branched alkoxy optionally substituted with —$NR_7R_8$ or —$OR_{12}$, —C(O)—$C_{1-6}$ alkyl and —C(O)O—$C_{1-6}$ alkyl;

$R_4$ is selected from H, halo, —C≡CH, —C≡N, —OH, —$OCF_3$, —$OCHF_2$, $C_{1-4}$ straight or branched alkoxy, —$SO_2(C_{1-6}alkyl)$, —$N(CH_3)_2$, —$C(O)NH_2$, —$NHSO_2R_7$, —$C(O)NR_7R_8$, a ring structure comprising a 5- or 6-membered aryl or a 4-, 5-, or 6-membered cycloalkyl with 0 to 3 ring heteroatoms independently selected from N, O and S and substituted with 0 to 2 groups independently selected from =O, halo, $C_{1-6}$ straight or branched alkyl optionally substituted with —$OR_{12}$ or —$NR_7R_8$, $C_{1-6}$ straight or branched alkoxy optionally substituted with —$NR_7R_8$ or —$OR_{12}$, —C(O)—$C_{1-6}$ alkyl and —C(O)O—$C_{1-6}$ alkyl, or the $R_4$ group bonds to $X_4$ to form a 5- or 6-membered aryl or cycloalkyl with 0 to 3 ring heteroatoms independently selected from N, O and S and substituted with 0 to 2 groups independently selected from =O, halo, $C_{1-6}$ straight or branched alkyl optionally substituted with —$OR_{12}$ or —$NR_7R_8$, $C_{1-6}$ straight or branched alkoxy optionally substituted with —$NR_7R_8$ or —$OR_{12}$, —C(O)—$C_{1-6}$ alkyl and —C(O)O—$C_{1-6}$ alkyl;

provided that:
at least one of $R_3$ and $R_4$ is selected from the group consisting of: H, halo, —C≡CH, —C≡N, —OH, —$OCF_3$—$OCHF_2$, $C_{1-4}$ straight or branched alkoxy, —$SO_2(C_{1-6}$ alkyl), —$N(CH_3)_2$, —$C(O)NH_2$, —$NHSO_2R_7$, and —$C(O)NR_7R_8$, and $R_3$ and $R_4$ are not both H;

$R_5$ is selected from the group consisting of H, methyl, ethyl, n-propyl, isopropyl, n-butyl, $CF_3$, $CH_2CF_3$ and halo;

$R_6$ is selected from the group consisting of H, methyl, ethyl, n-propyl, isopropyl, n-butyl, $CF_3$, $CH_2CF_3$, halo, cyclopropylmethyl and $C_{1-4}$ alkoxy;

$R_7$ and $R_8$ are independently selected, in each instance, from H, $C_{1-6}$ straight or branched alkyl, $C_{3-6}$ cycloalkyl, cyclopropylmethyl and cyclobutylmethyl; and $R_{12}$ is independently selected, in each instance, from H and $C_{1-4}$ straight or branched alkyl;

or a pharmaceutically acceptable salt or solvate thereof.

2. The composition of claim 1, wherein:
$R_3$ is selected from the group consisting of:

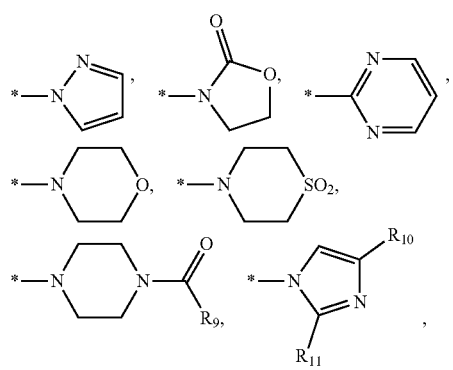

and —$SO_2(C_{1-6}$ alkyl);

wherein:

$R_9$ is selected from the group consisting of: H, cyclopropyl, cyclopropylmethyl, cyclobutyl, cyclopentyl, cyclohexyl, $C_{1-6}$ straight or branched alkyl optionally substituted with —$OR_{12}$ or —$NR_7R_8$, and $C_{1-6}$ straight or branched alkoxy optionally substituted with —$NR_7R_8$; and $R_{10}$ and $R_{11}$ are independently selected from the group consisting of: H, cyclopropyl, cyclopropylmethyl, cyclobutyl, $C_{1-4}$ straight or branched alkyl optionally substituted with —$OR_{12}$ or —$NR_7R_8$, $C_{1-4}$ straight or branched alkoxy optionally substituted with —$NR_7R_8$.

3. The composition of claim 1, wherein:
$R_4$ is selected from the group consisting of:

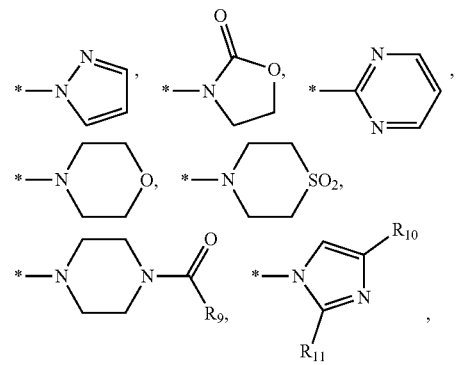

and —$SO_2(C_{1-6}$ alkyl);

wherein:

$R_9$ is selected from the group consisting of: H, cyclopropyl, cyclopropylmethyl, cyclobutyl, cyclopentyl, cyclohexyl, $C_{1-6}$ straight or branched alkyl optionally substituted with —$OR_{12}$ or —$NR_7R_8$, and $C_{1-6}$ straight or branched alkoxy optionally substituted with —$NR_7R_8$; and $R_{10}$ and $R_{11}$ are independently selected from the group consisting of: H, cyclopropyl, cyclopropylmethyl, cyclobutyl, $C_{1-4}$ straight or branched alkyl optionally substituted with —$OR_{12}$ or —$NR_7R_8$, $C_{1-4}$ straight or branched alkoxy optionally substituted with —$NR_7R_8$.

4. The composition of claim 1, wherein:
one of $R_1$ and $R_2$ is H and the other is a 5- or 6-membered aryl or cycloalkyl with 1 to 3 ring heteroatoms independently selected from N and O and substituted with 0 to 2 groups independently selected from:
=O, $C_{1-6}$ straight or branched alkyl optionally substituted with —$OR_{12}$ or —$NR_7R_8$, $C_{1-6}$ straight or branched alkoxy optionally substituted with —$NR_7R_8$ or —$OR_{12}$, cyclopropyl, cyclopropylmethyl, cyclobutyl, cyclopentyl, and cyclohexyl, or $R_1$ and $R_2$ together form a 5- or 6-membered aryl, cycloalkyl or cycloalkenyl with 1 to 3 ring heteroatoms independently selected from N and O and substituted with 0 to 2 groups independently selected from:
=O, $C_{1-6}$ straight or branched alkyl optionally substituted with —$OR_{12}$ or —$NR_7R_8$, $C_{1-6}$ straight or branched alkoxy optionally substituted with —$NR_7R_8$ or —$OR_{12}$, cyclopropyl, cyclopropylmethyl, cyclobutyl, cyclopentyl, and cyclohexyl.

5. The composition of claim 4, wherein:
R$_3$ is selected from the group consisting of:

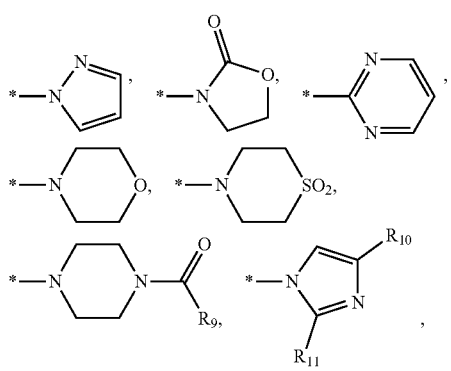

and —SO$_2$(C$_{1-6}$ alkyl);
wherein:
R$_9$ is selected from the group consisting of: H, cyclopropyl, cyclopropylmethyl, cyclobutyl, cyclopentyl, cyclohexyl, C$_{1-6}$ straight or branched alkyl optionally substituted with —OR$_{12}$ or —NR$_7$R$_8$, and C$_{1-6}$ straight or branched alkoxy optionally substituted with —NR$_7$R$_8$; and
R$_{10}$ and R$_{11}$ are independently selected from the group consisting of: H, cyclopropyl, cyclopropylmethyl, cyclobutyl, C$_{1-4}$ straight or branched alkyl optionally substituted with —OR$_{12}$ or —NR$_7$R$_8$, C$_{1-4}$ straight or branched alkoxy optionally substituted with —NR$_7$R$_8$.

6. The composition of claim 4, wherein:
R$_4$ is selected from the group consisting of:

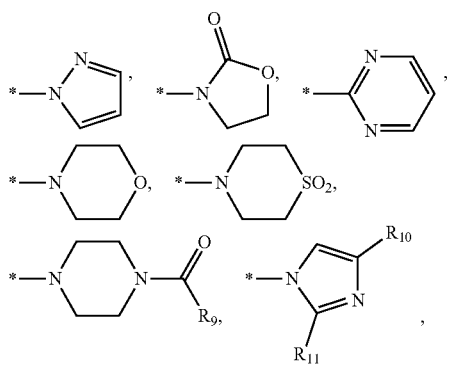

and —SO$_2$(C$_{1-6}$ alkyl);
wherein:
R$_9$ is selected from the group consisting of: H, cyclopropyl, cyclopropylmethyl, cyclobutyl, cyclopentyl, cyclohexyl, C$_{1-6}$ straight or branched alkyl optionally substituted with —OR$_{12}$ or —NR$_7$R$_8$, and C$_{1-6}$ straight or branched alkoxy optionally substituted with —NR$_7$R$_8$; and
R$_{10}$ and R$_{11}$ are independently selected from the group consisting of: H, cyclopropyl, cyclopropylmethyl, cyclobutyl, C$_{1-4}$ straight or branched alkyl optionally substituted with —OR$_{12}$ or —NR$_7$R$_8$, C$_{1-4}$ straight or branched alkoxy optionally substituted with —NR$_7$R$_8$.

7. The composition of claim 4, wherein:
one of R$_1$ and R$_2$ is H and the other is a 5- or 6-membered aryl or cycloalkyl with at least one N ring heteroatom and 0 to 2 additional ring heteroatoms independently selected from N and O and substituted with 0 to 2 groups independently selected from:
=O, C$_{1-6}$ straight or branched alkyl optionally substituted with —OR$_{12}$ or NR$_7$R$_8$, C$_{1-6}$ straight or branched alkoxy optionally substituted with —NR$_7$R$_8$ or —OR$_{12}$, and C$_{3-6}$ cycloalkyl optionally substituted with —R$_{12}$, —OR$_{12}$ or —NR$_7$R$_8$.

8. The composition of claim 7, wherein the compound of Formula I is:

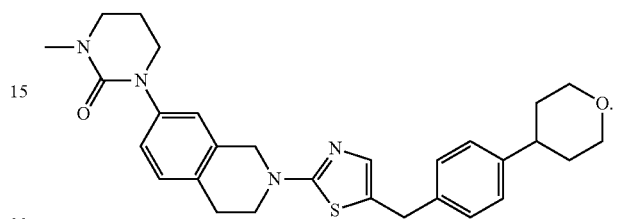

9. The composition of claim 7, wherein:
R$_3$ is selected from the group consisting of:

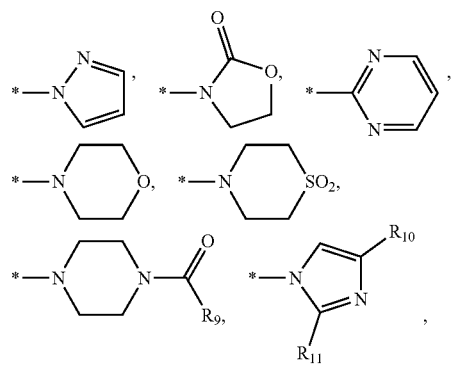

and —SO$_2$(C$_{1-6}$ alkyl);
wherein:
R$_9$ is selected from the group consisting of: H, cyclopropyl, cyclopropylmethyl, cyclobutyl, cyclopentyl, cyclohexyl, C$_{1-6}$ straight or branched alkyl optionally substituted with —OR$_{12}$ or —NR$_7$R$_8$, and C$_{1-6}$ straight or branched alkoxy optionally substituted with —NR$_7$R$_8$; and
R$_{10}$ and R$_{11}$ are independently selected from the group consisting of: H, cyclopropyl, cyclopropylmethyl, cyclobutyl, C$_{1-4}$ straight or branched alkyl optionally substituted with —OR$_{12}$ or —NR$_7$R$_8$, C$_{1-4}$ straight or branched alkoxy optionally substituted with —NR$_7$R$_8$.

10. The composition of claim 9, wherein the compound of Formula I is selected from the group consisting of:

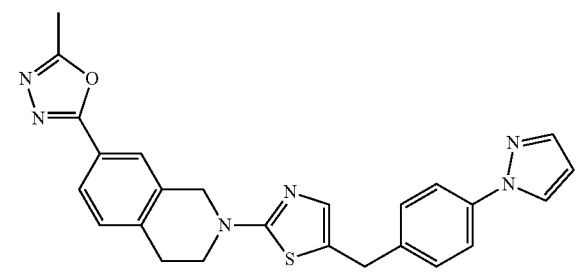

-continued

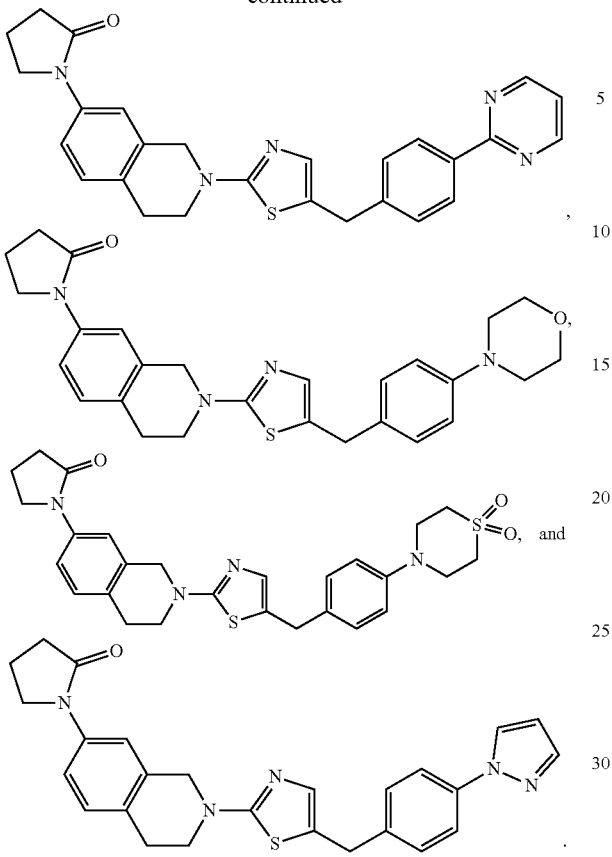

11. The composition of claim 7, wherein:
R₄ is selected from the group consisting of:

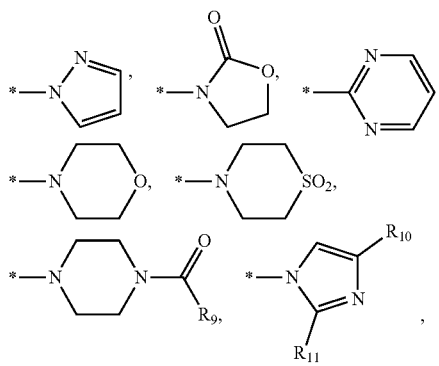

and —SO₂(C₁₋₆ alkyl);
wherein:
R₉ is selected from the group consisting of: H, cyclopropyl, cyclopropylmethyl, cyclobutyl, cyclopentyl, cyclohexyl, C₁₋₆ straight or branched alkyl optionally substituted with —OR₁₂ or —NR₇R₈, and C₁₋₆ straight or branched alkoxy optionally substituted with —NR₇R₈; and
R₁₀ and R₁₁ are independently selected from the group consisting of: H, cyclopropyl, cyclopropylmethyl, cyclobutyl, C₁₋₄ straight or branched alkyl optionally substituted with —OR₁₂ or —NR₇R₈, C₁₋₄ straight or branched alkoxy optionally substituted with —NR₇R₈.

12. The composition of claim 7, wherein:
one of R₁ and R₂ is H and the other is selected from the group consisting of:
wherein:

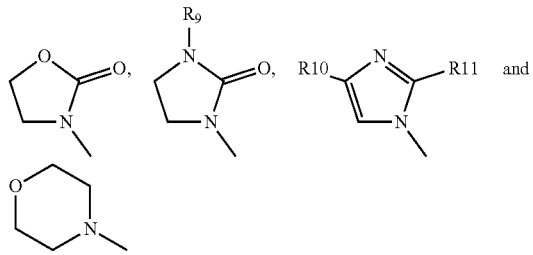

R₉ is selected from the group consisting of: H, cyclopropyl, cyclopropylmethyl, cyclobutyl, cyclopentyl, cyclohexyl, C₁₋₆ straight or branched alkyl optionally substituted with —OR₁₂ or —NR₇R₈, and C₁₋₆ straight or branched alkoxy optionally substituted with —NR₇R₈;
R₁₀ and R₁₁ are independently selected from the group consisting of: H, cyclopropyl, cyclopropylmethyl, cyclobutyl, C₁₋₄ straight or branched alkyl optionally substituted with —OR₁₂ or —NR₇R₈, C₁₋₄ straight or branched alkoxy optionally substituted with —NR₇R₈.

13. The composition of claim 12, wherein the compound of Formula I is:

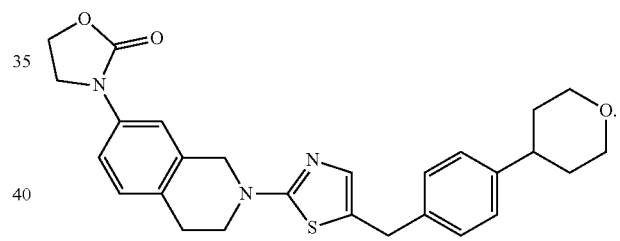

14. The composition of claim 12, wherein:
R₃ is selected from the group consisting of:

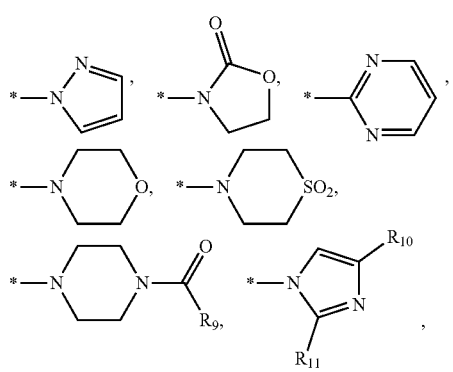

and —SO₂(C₁₋₆ alkyl);
wherein:
R₉ is selected from the group consisting of: H, cyclopropyl, cyclopropylmethyl, cyclobutyl, cyclopentyl, cyclohexyl, C₁₋₆ straight or branched alkyl optionally substituted with —OR$_{12}$ or —NR$_7$R$_8$, and C$_{1-6}$ straight or branched alkoxy optionally substituted with —NR$_7$R$_8$; and R$_{10}$ and R$_{11}$ are independently selected from the group consisting of: H, cyclopropyl, cyclopropylmethyl, cyclobutyl, C$_{1-4}$ straight or branched alkyl optionally substituted with —OR$_{12}$ or —NR$_7$R$_8$, C$_{1-4}$ straight or branched alkoxy optionally substituted with —NR$_7$R$_8$.

15. The composition of claim 14, wherein the compound of Formula I is selected from the group consisting of:

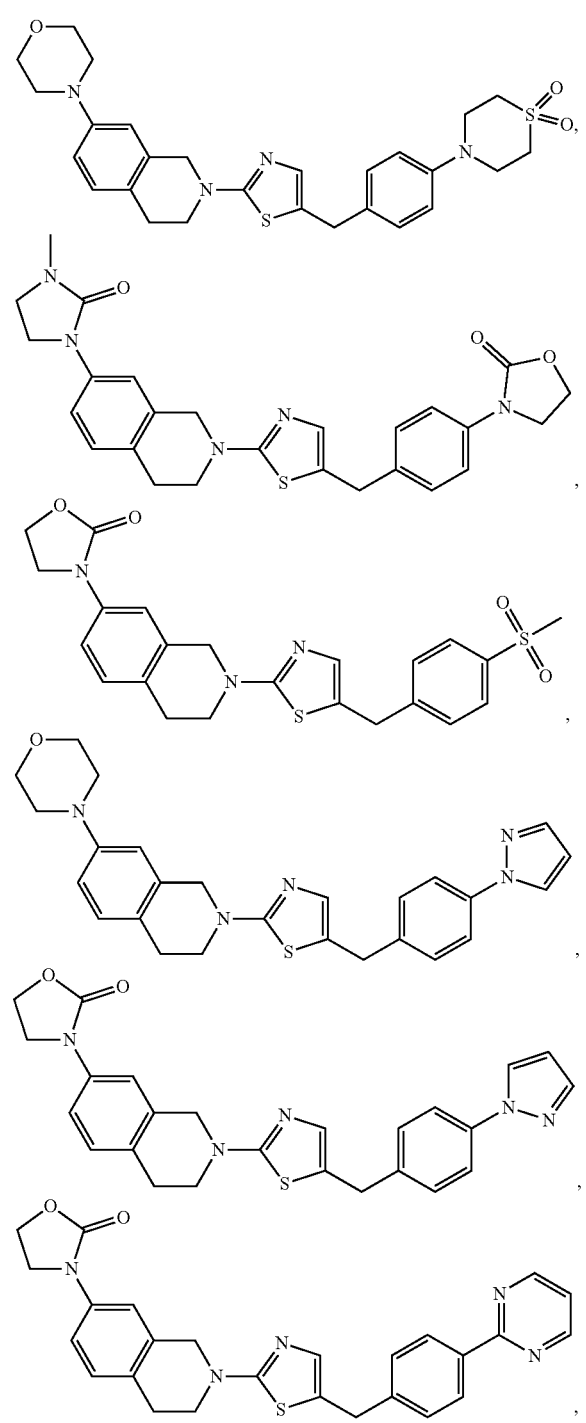

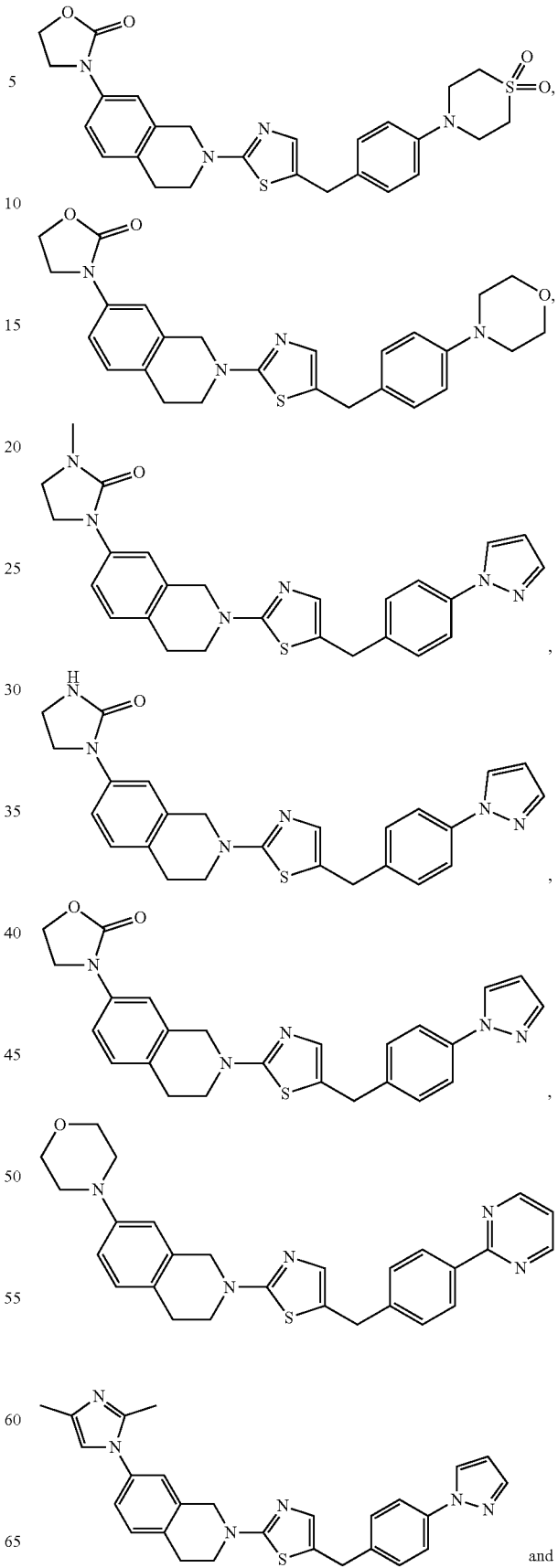

and

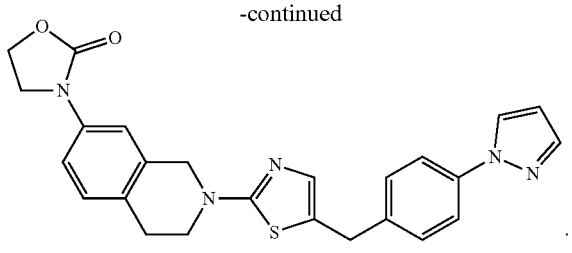

16. The composition of claim 12, wherein:
R$_4$ is selected from the group consisting of:

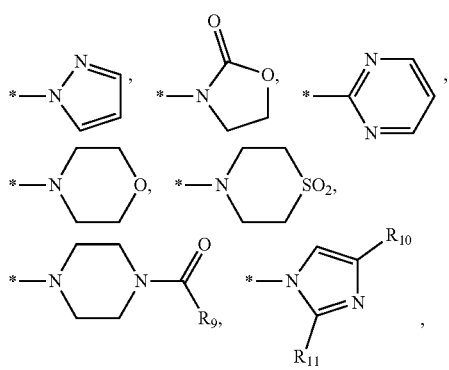

and —SO$_2$(C$_{1-6}$ alkyl);
wherein:
R$_9$ is selected from the group consisting of: H, cyclopropyl, cyclopropylmethyl, cyclobutyl, cyclopentyl, cyclohexyl, C$_{1-6}$ straight or branched alkyl optionally substituted with —OR$_{12}$ or —NR$_7$R$_8$, and C$_{1-6}$ straight or branched alkoxy optionally substituted with —NR$_7$R$_8$; and
R$_{10}$ and R$_{11}$ are independently selected from the group consisting of: H, cyclopropyl, cyclopropylmethyl, cyclobutyl, C$_{1-4}$ straight or branched alkyl optionally substituted with —OR$_{12}$ or —NR$_7$R$_8$, C$_{1-4}$ straight or branched alkoxy optionally substituted with —NR$_7$R$_8$.

17. The composition of claim 16, wherein the compound of Formula I is:

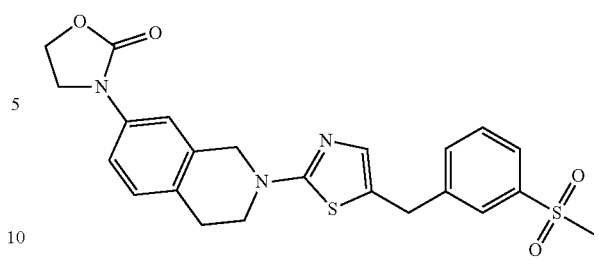

18. A method for treating or preventing a viral infection in a subject, the method comprising administering to the subject a therapeutically effective amount of a composition of claim 1.

19. The method of claim 18, wherein the method further comprises administering a therapeutically effective amount of an antiviral agent.

20. The method of claim 19, wherein the antiviral agent is selected from the group consisting of: acyclovir, docosanol, ribarivin, interferons, and the like; cellulose acetate, carbopol and carrageenan, pleconaril, amantidine, rimantidine, fomivirsen, zidovudine, lamivudine, zanamivir, oseltamivir, brivudine, abacavir, adefovir, amprenavir, arbidol, atazanavir, atripla, cidofovir, combivir, edoxudine, efavirenz, emtricitabine, enfuvirtide, entecavir, famciclovir, fosamprenavir, foscarnet, fosfonet, ganciclovir, gardasil, ibacitabine, imunovir, idoxuridine, imiquimod, indinavir, inosine, integrase inhibitor, lamivudine, lopinavir, loviride, mk-0518, maraviroc, moroxydine, nelfinavir, nevirapine, nexavir, nucleotide and/or nucleoside analogues, oseltamivir, penciclovir, peramivir, podophyllotoxin, rimantadine, ritonavir, saquinavir, stavudine, tenofovir, tenofovir disoproxil, tipranavir, trifluridine, trizivir, tromantadine, truvada, valaciclovir, valganciclovir, vicriviroc, vidarabine, viramidine, zalcitabine, morpholino oligonucleotides, ribozyme, protease inhibitors, an assembly inhibitor, zidovudine, brincidofovir, favipiravir, nitoxanide, letermovir, maribavir, CMX157 or a combination thereof.

21. A method for treating or preventing a viral infection in a subject, the method comprising administering to the subject a therapeutically effective amount of a composition of claim 7.

* * * * *